US007595339B2

(12) United States Patent
Allen et al.

(10) Patent No.: US 7,595,339 B2
(45) Date of Patent: Sep. 29, 2009

(54) CB1 MODULATOR COMPOUNDS

(75) Inventors: Jennifer Rebecca Allen, Indianapolis, IN (US); Albert Kudzovi Amegadzie, Indianapolis, IN (US); Kevin Matthew Gardinier, Indianapolis, IN (US); George Stuart Gregory, Fishers, IN (US); Stephen Andrew Hitchcock, Westlake Village, CA (US); Paul J. Hoogestraat, Indianapolis, IN (US); Winton Dennis Jones, Jr., Carmel, IN (US); Daryl Lynn Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 91 days.

(21) Appl. No.: 11/840,417

(22) Filed: Aug. 17, 2007

(65) Prior Publication Data
US 2008/0287504 A1    Nov. 20, 2008

Related U.S. Application Data

(63) Continuation of application No. 10/596,495, filed as application No. PCT/US2004/039763 on Dec. 13, 2004, now Pat. No. 7,276,516.

(60) Provisional application No. 60/532,247, filed on Dec. 23, 2003.

(51) Int. Cl.
    *A61K 31/40*    (2006.01)
(52) U.S. Cl. ..................................... 514/418
(58) Field of Classification Search .................. 514/418
    See application file for complete search history.

(56) References Cited

U.S. PATENT DOCUMENTS

| | | | |
|---|---|---|---|
| 4,973,587 | A | 11/1990 | Ward et al. |
| 5,013,837 | A | 5/1991 | Ward et al. |
| 5,081,122 | A | 1/1992 | Ward |
| 5,112,820 | A | 5/1992 | Ward |
| 5,292,736 | A | 3/1994 | Kumar et al. |
| 5,532,237 | A | 7/1996 | Gallant et al. |
| 5,624,941 | A | 4/1997 | Barth et al. |
| 6,028,084 | A | 2/2000 | Barth et al. |
| 2002/0119972 | A1 | 8/2002 | Leftheris et al. |
| 2003/0114495 | A1 | 6/2003 | Finke et al. |
| 2003/0119810 | A1 | 6/2003 | Achard et al. |

FOREIGN PATENT DOCUMENTS

| | | |
|---|---|---|
| EP | 0 658 546 B1 | 5/2001 |
| EP | 1 506 960 A1 | 2/2005 |
| WO | WO 96/25397 | 8/1996 |
| WO | WO 97/29079 | 8/1997 |
| WO | WO 98/31227 | 7/1998 |
| WO | WO 98/37061 | 8/1998 |
| WO | WO 98/41519 | 9/1998 |
| WO | WO 98/43635 | 10/1998 |
| WO | WO 98/43636 | 10/1998 |
| WO | WO 99/02499 | 1/1999 |
| WO | WO 00/10967 | 3/2000 |
| WO | WO 00/10968 | 3/2000 |
| WO | WO 03/026648 A1 | 4/2003 |
| WO | WO 03/027076 | 4/2003 |

OTHER PUBLICATIONS

Harrold et al., Brain research, (Oct. 18, 2002) vol. 952, No. 2, pp. 232-238.*
Kuster, et al., "Aminoalkylindole Binding in Rat Cerebellum : Selective Displacement by Natural and Synthetic Cannabinoids" *The J. Pharmacology and Experimental Therapeutics*, vol. 264., 3, 1352-1363 (1993).
Little, et al., "Pharmacology and Stereoselectivity of Structurally Novel Cannabinoids in Mice[1]", *The J. Pharmacology and Experimental Therapeutics*, vol. 247., 3, 1046-1051 (1988).
Rinaldi-Carmona, et al "SR141716A, a potent and selective antagonist of the brain cannabinoid receptor", *FEBS Letter*, vol. 350, 240-244 (1994).
Portier, et al., "SR 144528, an Antagonist for the Peripheral Cannabinoid Receptor that Behaves as an Inverse Agonist" *The J. Pharmacology and Experimental Therapeutics* vol. 288, 2 (1999).
Rinaldi-Carmona, et al., "Biochemical and Pharmacological Charcterisation of SR141716A, The First Potent and Selective Brain Cannabinoid Receptor Antagonist", *Life Sciences*, vol. 56, 23/24, 1941-1947 (1995).
STN File Registry, RN394228-83-2 (2000) STN File Registry, RN394228-85-4 (2000) STN File Registry, RN439128-75-3 (2000).

* cited by examiner

*Primary Examiner*—D. Margaret Seaman
*Assistant Examiner*—Niloofar Rahmani
(74) *Attorney, Agent, or Firm*—R. Craig Tucker

(57) ABSTRACT

Novel compounds of structural formula (I) are disclosed. As modulators of the Cannabinoid-1 (CB1) receptor, these compounds are useful in the treatment, prevention and suppression of diseases mediated by the CB1 receptor. As such, compounds of the present invention are useful as in the treatment, prevention and suppression of psychosis, memory deficits, cognitive disorders, migraine, neuropathy, neuro-inflammatory disorders (e.g., multiple sclerosis, Guillain-Barre syndrome and the inflammatory sequelae of viral encephalitis), cerebral vascular accidents, head trauma, anxiety disorders, stress, epilepsy, Parkinson's disease, and schizophrenia. The compounds are also useful for the treatment of substance abuse disorders, particularly to opiates, alcohol, and nicotine. The compounds are also useful for the treatment of obesity or eating disorders associated with excessive food intake and complications associated therewith.

(I)

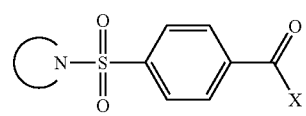

2 Claims, No Drawings

CB1 MODULATOR COMPOUNDS

CROSS REFERENCE TO RELATED APPLICATIONS

This application is a continuation of application U.S. Ser. No. 10/596,495, filed on Jun. 15, 2006, now U.S. Pat. No. 7,276,516 which is the 35 U.S.C. 371 National Stage Entry under of PCT/US2004/039763 filed Dec. 13, 2004 which claims benefit of U.S. Provisional Application Ser. No. 60/532,247 filed Dec. 23, 2003.

BACKGROUND OF THE INVENTION

Marijuana (*Cannabis sativa* L.) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed $CB_1$ and $CB_2$. The $CB_1$ receptor is primarily found in the central and peripheral nervous systems and to a lesser extent in several peripheral organs. The $CB_2$ receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046-1051); WIN55212-2 (J. Pharmacol. Exp. Ther. 1993, 264, 1352-1363); SR141716A (FEBS Lett. 1994, 350, 240-244; Life Sci. 1995, 56, 1941-1947); and SR144528 (J. Pharmacol. Exp. Ther. 1999, 288, 582-589). The pharmacology and therapeutic potential for cannabinoid receptor ligands has been reviewed (Exp. Opin. Ther. Patents 1998, 8, 301-313; Ann. Rep. Med. Chem., A. Doherty, Ed.; Academic Press, NY 1999, Vol. 34, 199-208; Exp. Opin. Ther. Patents 2000, 10, 1529-1538; Trends in Pharma. Sci. 2000, 21, 218-224). There is at least one $CB_1$ modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders.

Hitherto, several classes of $CB_1$ modulators are known. U.S. Pat. Nos. 5,624,941 and 6,028,084, PCT Publication Nos. WO98/43636 and WO98/43635, and European Patent Application No. EP-658546 disclose substituted pyrazoles having activity against the cannabinoid receptors. PCT Publication Nos. WO98/31227 and WO98/41519 also disclose substituted pyrazoles having activity against the cannabinoid receptors. PCT Publication Nos. WO98/37061, WO00/10967, and WO00/10968 disclose diaryl ether sulfonamides having activity against the cannabinoid receptors. PCT Publication Nos. WO97/29079 and WO99/02499 disclose alkoxy-isoindolones and alkoxy-quinolones as having activity against the cannabinoid receptors. U.S. Pat. No. 5,532,237 discloses N-benzoyl-indole derivatives having activity against the cannabinoid receptors. U.S. Pat. No. 4,973,587, U.S. Pat. No. 5,013,837, U.S. Pat. No. 5,081,122, U.S. Pat. No. 5,112,820, and U.S. Pat. No. 5,292,736 disclose aminoalkylindole derivatives as having activity against the cannabinoid receptors. PCT Publication No. WO03/027076 discloses 1H-imidazole derivatives having $CB_1$ agonist, $CB_1$ partial agonist or $CB_1$ antagonist activity. PCT Publication No. WO03/026648 discloses 4,5-dihydro-1H-pyrazole derivatives having potent $CB_1$-antagonist activity. US Publication No. US 2003/0114495 discloses substituted imidazoles as cannabinoid receptor modulators. US Publication No. US 2003/0119810 discloses pharmaceutical compositions containing 3-aminoazetidine derivatives possessing a high affinity for $CB_1$ receptors.

[4-(2,3-dihydro-indole-1-sulfonyl)-phenyl]-(4-phenyl-piperazin-1-yl)-methanone RN 439128-75-3, [4-(2,3-dihydro-indole-1-sulfonyl)-phenyl]-morpholin-4-yl-methanone RN394228-83-2, and [4-(2,3-dihydro-indole-1-sulfonyl)-phenyl]-piperidin-1-yl-methanone RN 394228-85-4 are found in the CA database.

There still remains a need for potent low molecular weight $CB_1$ modulators that have pharmacokinetic and pharmacodynamic properties suitable for use as human pharmaceuticals.

SUMMARY OF THE INVENTION

In one aspect, the present invention provides compounds of formula I

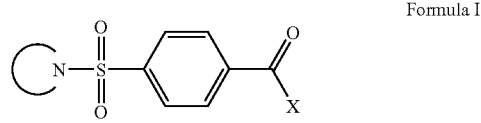

Formula I wherein:

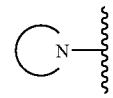

is a 6,5-bicyclic ring selected from the group consisting of:

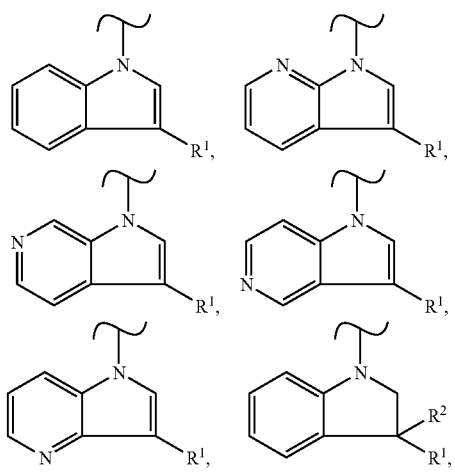

-continued

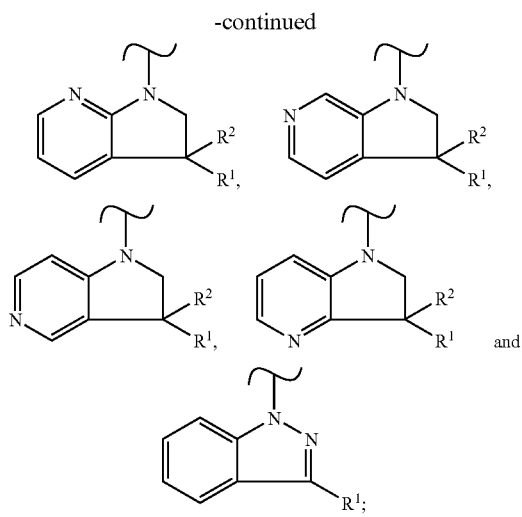

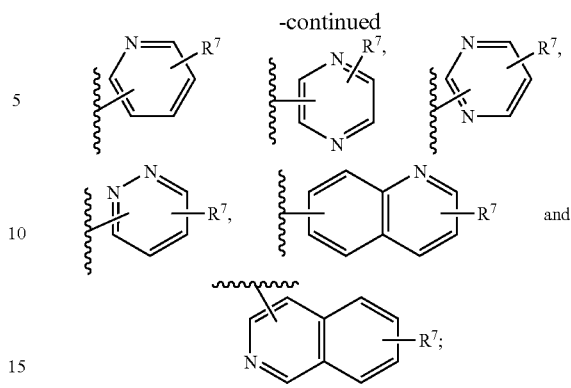

R² is hydrogen, alkyl, heterocyclyl or, together with R¹ and the carbon to which they are attached, forms a saturated ring substituent selected from the group consisting of:
(a) cycloalkyl, and
(b) heterocyclyl selected from the group consisting of: tetrahydrofuranyl, tetrahydropyranyl and piperidinyl optionally N-substituted with alkyl, acetyl or aryl, X is —NR¹³R³ or

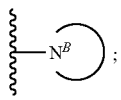

R³ is selected from the group consisting of:
(a) hydrogen,
(b) alkyl optionally substituted with one or two substituents independently selected from the group consisting of hydroxy, alkoxy, halogen, amino, alkylamino, and dialkylamino,
(c) cycloalkyl optionally substituted with one or two substituents independently selected from the group consisting of hydroxy, alkoxy, halo, amino, alkylamino, and dialkylamino,
(d) heterocyclyl selected from the group consisting of:

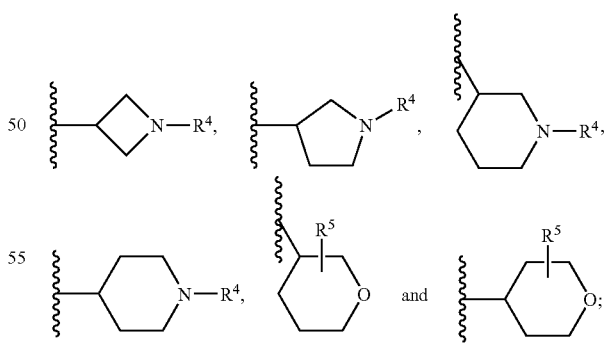

(e) cycloalkylalkyl selected from the group consisting of:

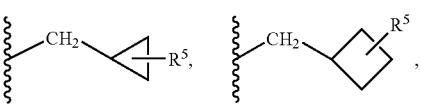

R¹ is selected from the group consisting of:
(a) hydrogen,
(b) alkylcarbonyl optionally substituted with heterocyclyl,
(c) heterocyclylcarbonyl optionally substituted with alkyl or acetyl,
(d) alkyl or haloalkyl,
(e) cycloalkyl optionally substituted with one or two substituents independently selected from the group consisting of alkyl, halo, oxo, hydroxy, alkoxy, amino, alkylamino and dialkylamino,
(f) heterocyclyl selected from the group consisting of:

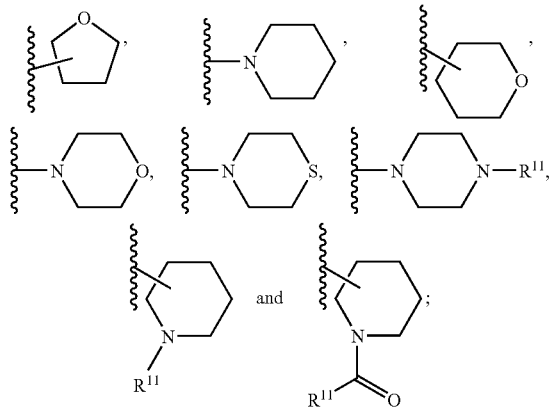

(g) aryl optionally substituted with halo, alkyl, alkoxy, cyano, amino, alkylamino, or dialkylamino, and
(h) heteroaryl selected from the group consisting of:

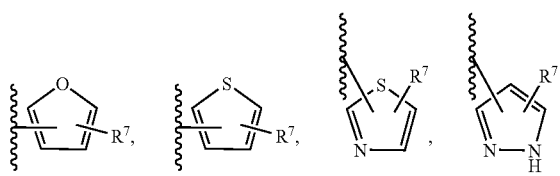

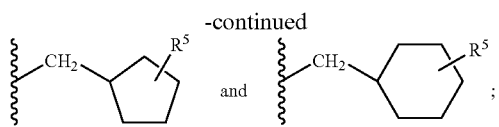

(f) heterocyclylalkyl selected from the group consisting of:

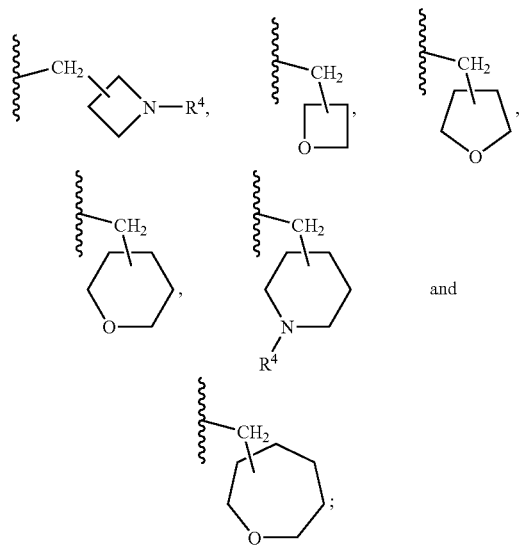

(g) arylalkyl selected from the group consisting of:

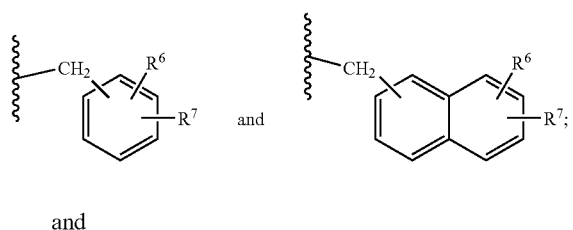

and (h) heteroarylalkyl selected from the group consisting of:

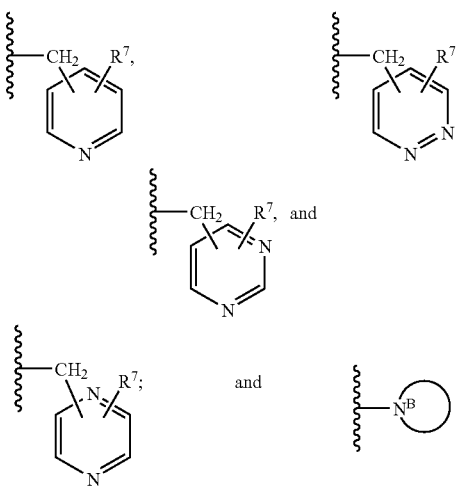

is a heterocyclic ring selected from the group consisting of:

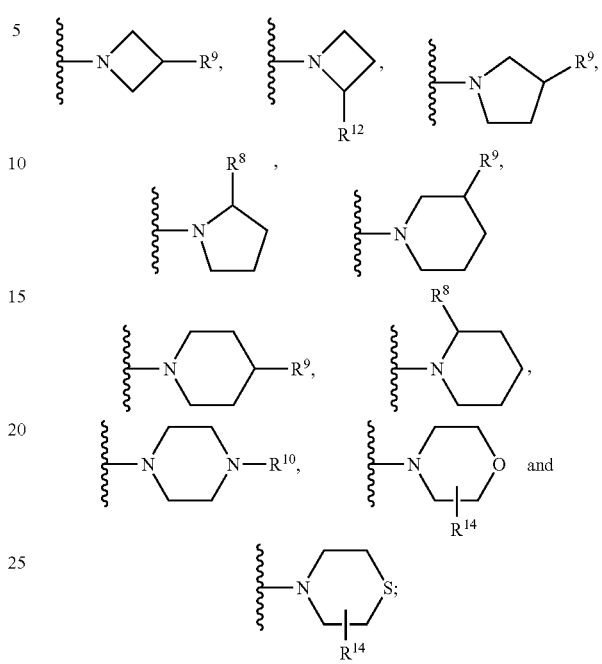

$R^4$ is hydrogen, phenyl, halophenyl, acyl, or alkoxycarbonyl;

$R^5$ is hydrogen, hydroxy or alkoxy;

each of $R^6$ and $R^7$ is independently selected from hydrogen, halo, cyano, alkyl, alkoxy, haloalkyl, haloalkoxy, amino, alkylamino, dialkylamino, alkoxycarbonyl, dialkylaminocarbonyl, aryl, and aryloxy;

$R^8$ is hydrogen, hydroxyalkyl, acyl, oxo, aryl, pyridinyl, alkyl-$SO_2$—O—, $R^b$—NH—$CH_2$—, arylalkyl, or $R^c{}_2$N—CO—O—;

$R^9$ is hydrogen, hydroxy, hydroxyalkyl, acyl, halo, dihalo, oxo, aryl, haloarylalkyl, pyridinyl, alkyl-$SO_2$—O—, $R^a$—NH—, $R^b$—NH—$CH_2$—, arylalkyl,

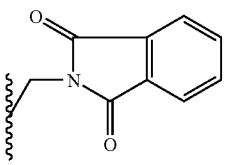

or $R^c{}_2$N—CO—O—;

$R^{10}$ is hydrogen, alkyl, alkoxycarbonyl, aryl or haloaryl;

$R^{11}$ is hydrogen, alkyl or aryl;

$R^{12}$ is hydrogen or aryl;

$R^{13}$ is hydrogen or alkyl;

$R^{14}$ is hydrogen, allyl, aryl or acyl;

$R^a$ is hydrogen, alkoxycarbonyl or halophenyl;

$R^b$ is hydrogen, alkoxy, phenyl, halophenyl, halophenylalkyl, halopyridinyl, pyrimidinyl, alkoxycarbonyl, diallylaminocarbonyl or dialkylaminothiocarbonyl; and $R^c$ is hydrogen or alkyl;

and all salts, solvates, optical and geometric isomers, and crystalline forms thereof with the proviso that the compound of formula (I) is other than [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, and [4-(2,3-dihydro-indole-1 sulfonyl)-phenyl]-piperidin-1-yl-methanone.

In a preferred embodiment,

is a 6,5-bicyclic ring selected from the group consisting of:

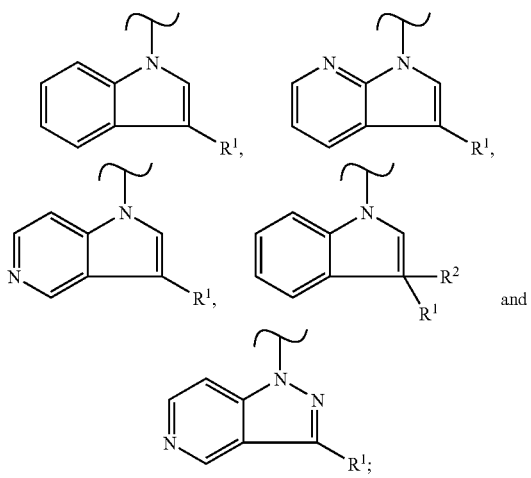

$R^1$ is selected from the group consisting of:
(a) hydrogen,
(b) alkylcarbonyl optionally substituted with heterocyclyl,
(c) heterocyclylcarbonyl optionally substituted with alkyl or acetyl,
(d) methyl, propyl, t-butyl or trifluoromethyl,
(e) cycloalkyl optionally substituted with oxo, hydroxy, methoxy, difluoro or methyl,
(f) heterocyclyl selected from the group consisting of:

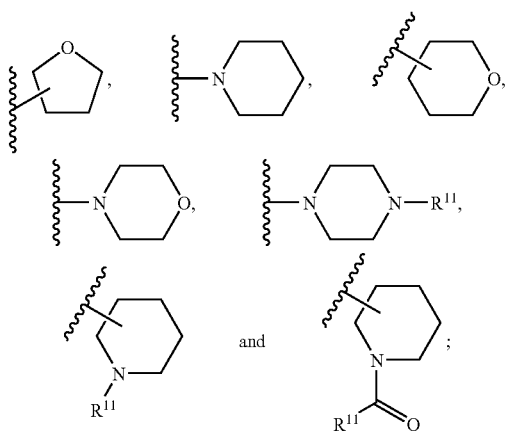

(g) phenyl optionally substituted with halo, methyl, methoxy, cyano or dimethylamino, and
(h) heteroaryl selected from the group consisting of:

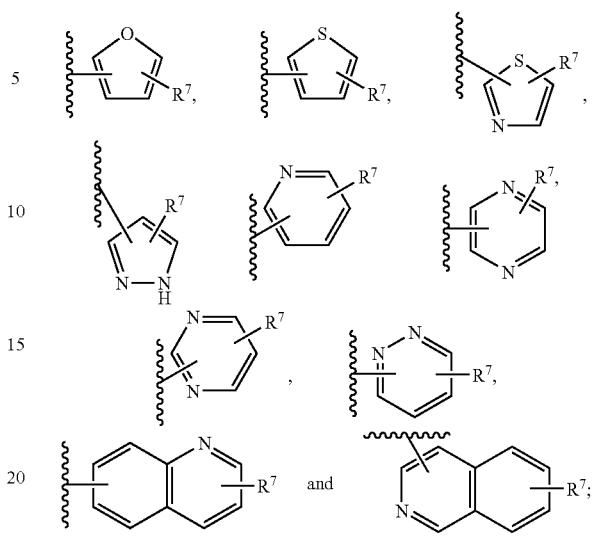

$R^2$ is H, methyl, ethyl, or together with $R^1$ and the carbon to which they are attached, forms a saturated ring substituent selected from the group consisting of:
(a) cycloalkyl, and
(b) heterocyclyl selected from the group consisting of: tetrahydropyranyl and N-methylpiperidin-4-yl;
X is —NR$^{13}$R$^3$ or

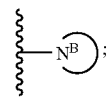

$R^3$ is selected from the group consisting of:
(a) hydrogen,
(b) $(C_1-C_2)$ alkyl optionally substituted with $(C_1-C_2)$ alkoxy,
(c) $(C_4-C_6)$ cycloalkyl optionally substituted with one or two substitutes independently selected from hydroxy, methoxy, amino, alkylamino, and dialkylamino,
(d) heterocyclyl selected from the group consisting of:

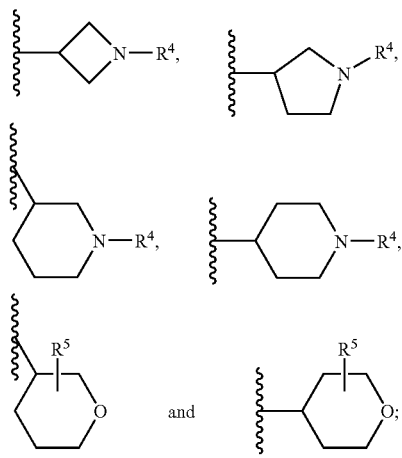

(e) cycloalkylalkyl selected from the group consisting of:

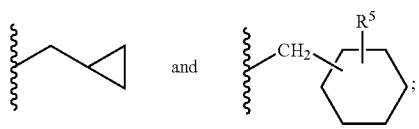

(f) heterocyclylalkyl selected from the group consisting of:

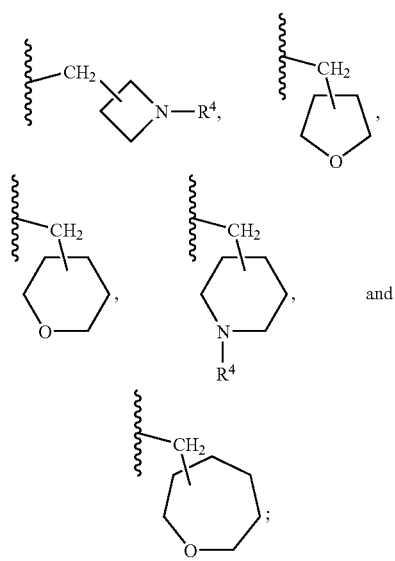

(g) arylalkyl which is

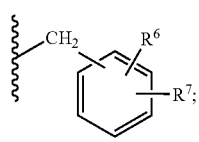

and
(h) heteroarylalkyl selected from the group consisting of:

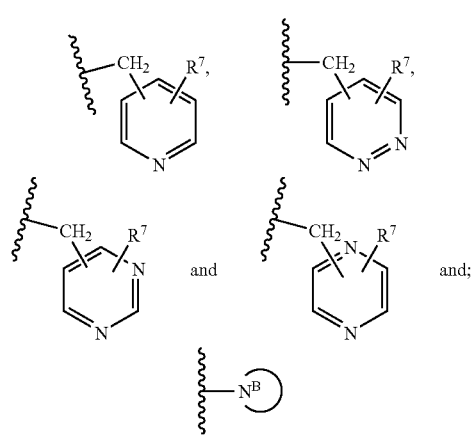

is a heterocyclic ring selected from the group consisting of:

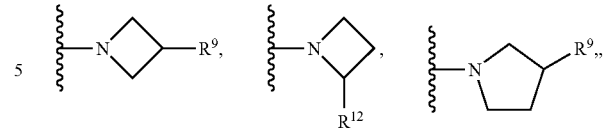

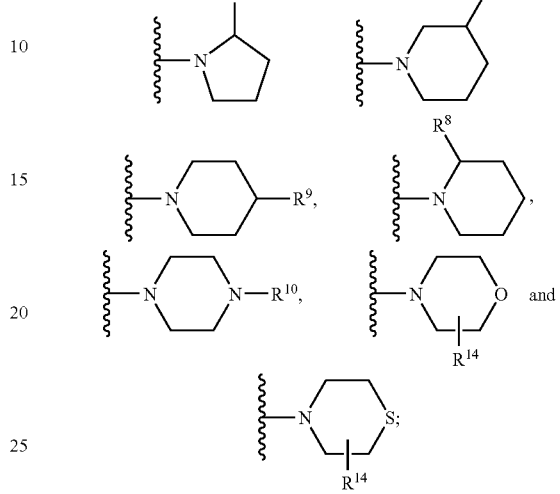

$R^4$ is hydrogen, phenyl, fluorophenyl, t-butyloxycarbonyl or methoxycarbonyl;

$R^5$ is hydrogen, hydroxy or methoxy;

each of $R^6$ and $R^7$ is independently selected from the group consisting of hydrogen, alkyl, fluoro, chloro, trifluoromethyl, cyano, methoxy, amino, monomethylamino, dimethylamino, methoxycarbonyl and dimethylaminocarbonyl;

$R^8$ is hydrogen, hydroxyalkyl, acyl, oxo, aryl, pyridinyl, alkyl-$SO_2$—O—, $R^b$—NH—$CH_2$—, arylalkyl or $(CH_3)_2$N—CO—O—;

$R^9$ is hydrogen, hydroxy, hydroxymethyl, acetyl, fluoro, difluoro, oxo, phenyl, benzyl, pyridinyl, $CH_3$—$SO_2$—O—, $R^a$—NH—, $R^b$—NH—$CH_2$—,

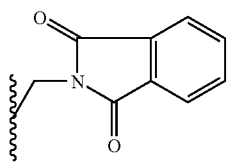

or $(CH_3)_2$N—CO—O—;

$R^{10}$ is hydrogen or alkyl;

$R^{11}$ is hydrogen or alkyl;

$R^{12}$ is hydrogen or phenyl;

$R^{13}$ is hydrogen or methyl;

$R^{14}$ is hydrogen, methyl, phenyl, or acetyl;

$R^a$ is hydrogen, methoxycarbonyl, t-butyloxycarbonyl, or fluorophenyl; and $R^b$ is hydrogen, methoxy, phenyl, phenylalkyl, fluorophenylalkyl, fluorophenyl, pyridinyl, fluoropyridinyl, pyrimidinyl, methoxycarbonyl, t-butyloxycarbonyl, dimethylaminocarbonyl or dimethylaminothiocarbonyl.

In another preferred embodiment,

is selected from the group consisting of:

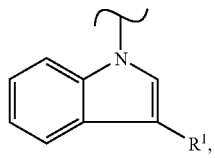 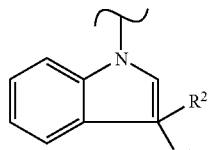 and

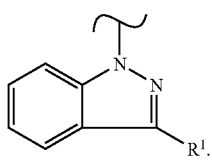

In another preferred embodiment,

 is 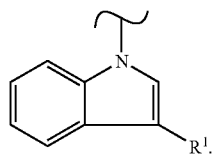.

In another preferred embodiment,

 is 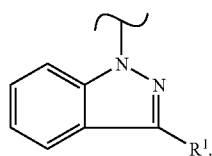.

In another preferred embodiment, $R^1$ is aryl optionally substituted with halo, alkyl, alkoxy, cyano, amino, alkylamino or dialkylamino. More preferably, $R^1$ is phenyl.

In another preferred embodiment, $R^1$ is cycloalkyl optionally substituted with one or two substituents independently selected from the group consisting of alkyl, halo, oxo, hydroxy alkoxy, amino, alkylamino and dialkylamino. More preferably, $R^1$ is cyclopentyl.

In another preferred embodiment, $R^1$ is heterocyclyl selected from the group consisting of:

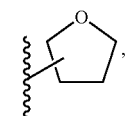, 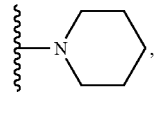, 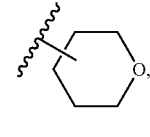,

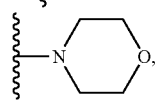, 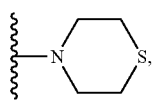, 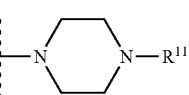,

-continued

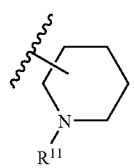 and 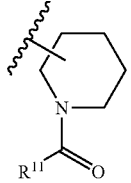

More preferably, $R^1$ is tetrahydropyran-4-yl.

In another preferred embodiment, $R^3$ is heterocyclylalkyl selected from the group consisting of:

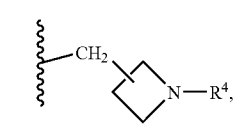 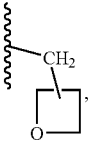 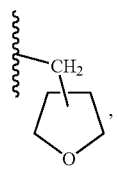

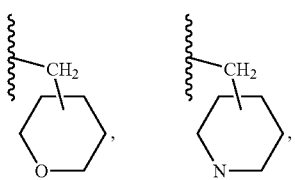 and

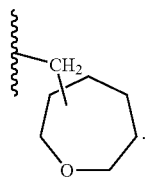

More preferably, $R^3$ is

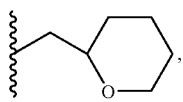, 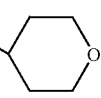 or

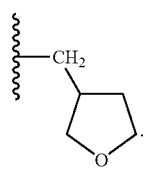

In another preferred embodiment, $R^3$ is heterocyclyl selected from the group consisting of:

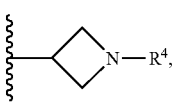 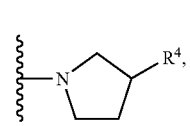

-continued

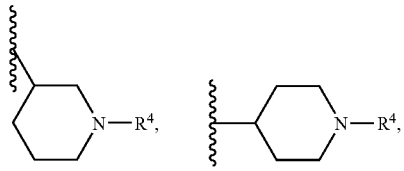

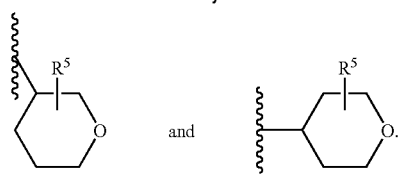

More preferably, $R^3$ is

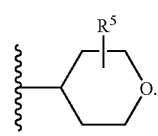

In another preferred embodiment, $R^3$ is cycloalkylalkyl selected from the group consisting of:

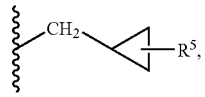 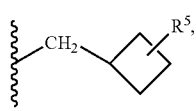

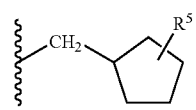 and 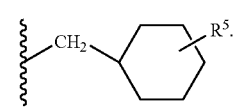

More preferably, $R^3$ is

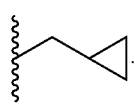

In another preferred embodiment, $R^3$ is alkyl optionally substituted with one or two substituents independently selected from the group consisting of hydroxy, alkoxy, halogen, amino, alkylamino, and dialkylamino. More preferably, $R^3$ is

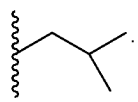

In another preferred embodiment, $R^3$ is arylalkyl selected from the group consisting of:

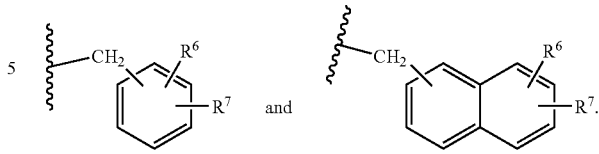

More preferably, $R^3$ is

In another preferred embodiment, $R^3$ is heteroarylalkyl selected from the group consisting of:

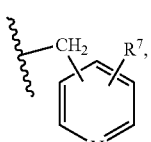 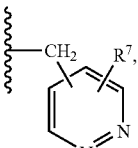

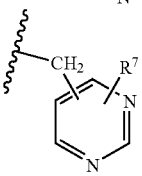 and 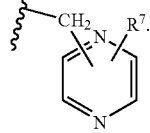

More preferably, $R^3$ is

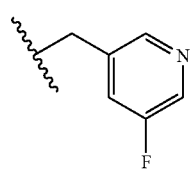 or 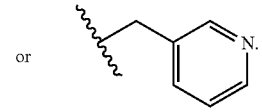

In another preferred embodiment, the present invention provides for a compound of formula I

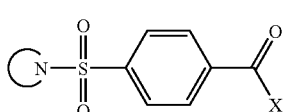

Formula I wherein:

is a 6,5-bicyclic ring selected from the group consisting of:

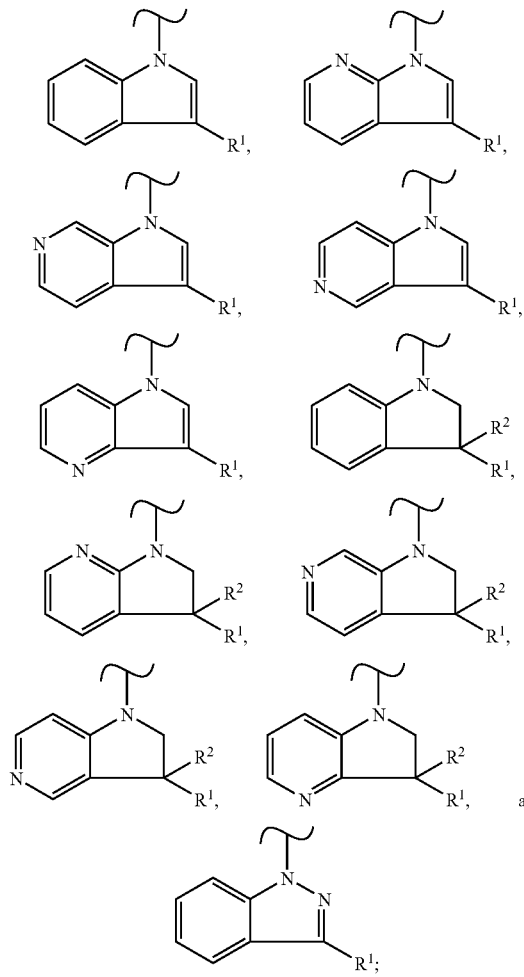

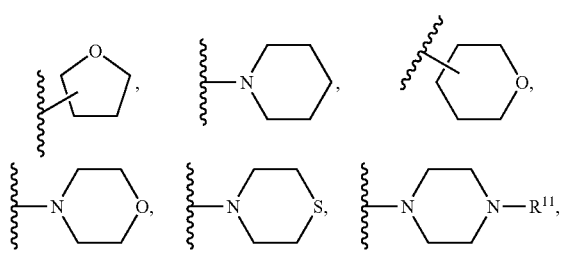

R[1] is selected from the group consisting of:
(a) hydrogen,
(b) alkylcarbonyl optionally substituted with heterocyclyl,
(c) heterocyclylcarbonyl optionally substituted with alkyl or acetyl,
(d) alkyl or haloalkyl,
(e) cycloalkyl optionally substituted with one or two substituents independently selected from the group consisting of alkyl, halo, oxo, hydroxy, alkoxy, amino, alkylamino and dialkylamino,
(f) heterocyclyl selected from the group consisting of:

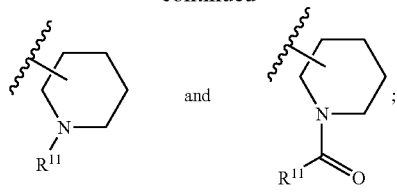

(g) aryl optionally substituted with halo, alkyl, alkoxy, cyano, amino, alkylamino or dialkylamino, and
(h) heteroaryl selected from the group consisting of:

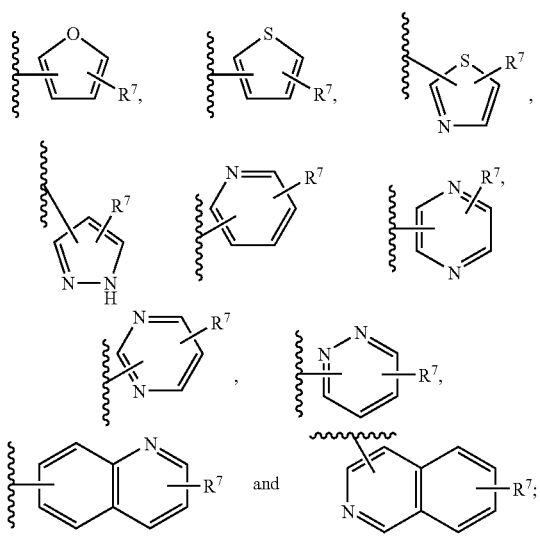

R[2] is hydrogen, alkyl, heterocyclyl or, together with R[1] and the carbon to which they are attached, forms a saturated ring substituent selected from the group consisting of:
(a) cycloalkyl, and
(b) heterocyclyl selected from the group consisting of: tetrahydrofuranyl, tetrahydropyranyl and piperidinyl optionally N-substituted with alkyl, acetyl or aryl, X is —NR[13]R[3] or

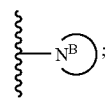

R[3] is selected from the group consisting of:
(a) hydrogen,
(b) alkyl optionally substituted with one or two substituents independently selected from the group consisting of hydroxy, alkoxy, halogen, amino, alkylamino and dialkylamino,
(c) cycloalkyl optionally substituted with one or two substituents independently selected from the group consisting of hydroxy, alkoxy, halo, amino, alkylamino and dialkylamino,
(d) heterocyclyl selected from the group consisting of:

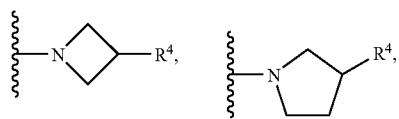

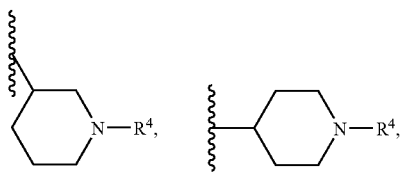

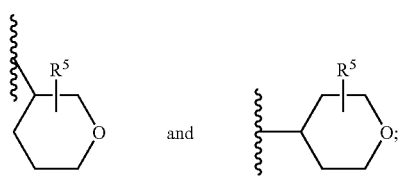

(e) cycloalkylalkyl selected from the group consisting of:

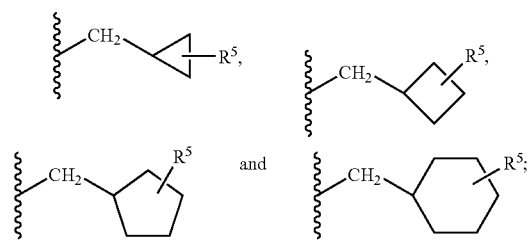

(f) heterocyclylalkyl selected from the group consisting of:

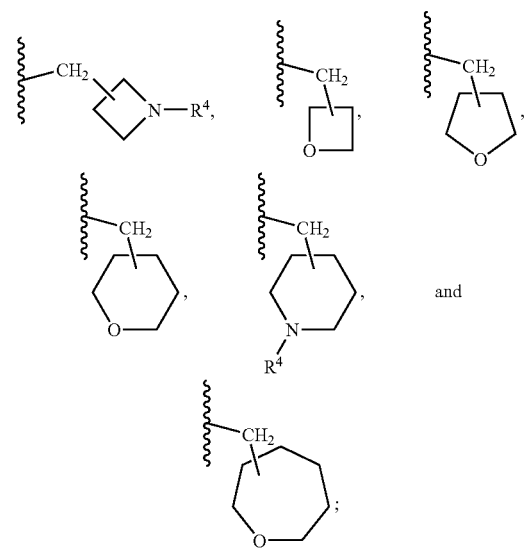

(g) arylalkyl selected from the group consisting of

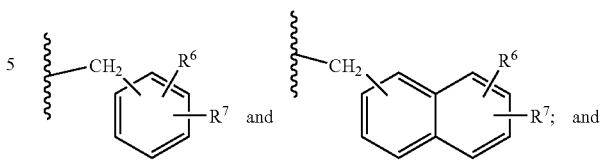

(h) heteroarylalkyl selected from the group consisting of:

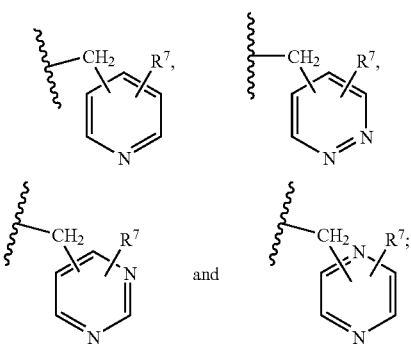

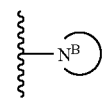

is a heterocyclic ring selected from the group consisting of:

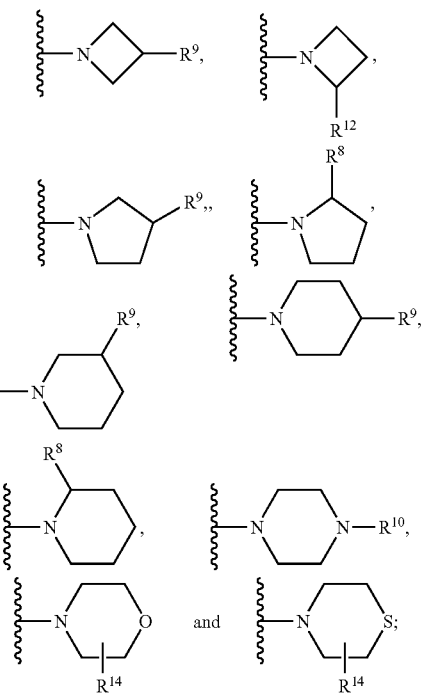

$R^4$ is hydrogen, phenyl, halophenyl, acyl or alkoxycarbonyl;

$R^5$ is hydrogen, hydroxy or alkoxy;

each of $R^6$ and $R^7$ is independently selected from hydrogen, halo, cyano, alkyl, alkoxy, haloalkyl, haloalkoxy, amino, alkylamino, dialkylamino, alkoxycarbonyl, dialkylaminocarbonyl, aryl and aryloxy;

$R^8$ is hydrogen, hydroxyalkyl, acyl, oxo, aryl, pyridinyl, alkyl-$SO_2$—O—, $R^b$—NH—$CH_2$—, arylalkyl, or $R^c{}_2$N—CO—O—;

$R^9$ is hydrogen, hydroxy, hydroxyalkyl, acyl, halo, dihalo, oxo, aryl, haloaryl-$CH_2$—, pyridinyl, alkyl-$SO_2$—O—, $R^a$—NH—, $R^b$—NH—$CH_2$—, arylalkyl,

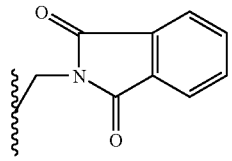

or $R^c{}_2$N—CO—O—;

$R^{10}$ is hydrogen, alkyl, alkoxycarbonyl, aryl or haloaryl;

$R^{11}$ is hydrogen, alkyl or aryl;

$R^{12}$ is hydrogen or aryl;

$R^{13}$ is hydrogen or allyl;

$R^{14}$ is hydrogen, alkyl, aryl or acyl;

$R^a$ is hydrogen, alkoxycarbonyl or halophenyl;

$R^b$ is hydrogen, alkoxy, phenyl, halophenyl, halophenylalkyl, halopyridinyl, pyrimidinyl, alkoxycarbonyl, dialkylaminocarbonyl, or dialkylaminothiocarbonyl; and $R^c$ is hydrogen or alkyl;

and all optical and geometric isomers, and crystalline forms thereof and with the proviso that the compound of formula (I) is other than [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, and [4-(2,3-dihydro-indole-1-sulfonyl)-phenyl]-piperidin-1-yl-methanone.

In another aspect, the present invention provides pharmaceutical compositions comprising a compound of Formula I in an amount effective to antagonize CB-1 receptor stimulation, and a pharmaceutically acceptable carrier, diluent or excipient.

In another aspect, the present invention provides pharmaceutical compositions comprising a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, or [4-(2,3-dihydro-indole-1-sulfonyl)-phenyl]-piperidin-1-yl-methanone in an amount effective to antagonize CB-1 receptor stimulation, and a pharmaceutically acceptable carrier, diluent or excipient.

In another aspect, the present invention provides pharmaceutical compositions comprising a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, or [4-(3-Fluoro-phenyl)-piperidin-1-yl]-[4-(3-phenyl-indole-1-sulfonyl)-phenyl]-methanone in an amount effective to reduce endocannabinoid neurotransmission through CB-1 receptors, and a pharmaceutically acceptable carrier, diluent or excipient.

In another aspect, the present invention provides pharmaceutical compositions comprising a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, or [4-(3-Fluoro-phenyl)-piperidin-1-yl]-[4-(3-phenyl-indole-1-sulfonyl)-phenyl]-methanone and a pharmaceutically acceptable carrier, diluent or excipient.

In another aspect, the present invention provides a method for treating a condition which is treatable by reducing CB-1 receptor stimulation, comprising administering to a mammal in need thereof a compound of Formula I or a pharmaceutical composition comprising a compound of Formula I in an amount effective to antagonize CB-1 receptor stimulation, or to reduce endocannabinoid neurotransmission and a pharmaceutically acceptable carrier, diluent or excipient.

In another aspect, the present invention provides a method for treating a condition which is treatable by reducing CB-1 receptor stimulation, comprising administering to a mammal in need thereof a compound selected from the group consisting of a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, and [4-(3-Fluoro-phenyl)-piperidin-1-yl]-[4-(3-phenyl-indole-1-sulfonyl)-phenyl]-methanone In another aspect, the present invention provides a method for treating a condition which is treatable by reducing CB-1 receptor stimulation, comprising administering to a mammal in need thereof a pharmaceutical composition comprising a compound selected from the group consisting of a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, and [4-(3-Fluoro-phenyl)-piperidin-1-yl]-[4-(3-phenyl-indole-1-sulfonyl)-phenyl]-methanone in an amount effective to antagonize CB-1 receptor stimulation, or to reduce endocannabinoid neurotransmission and a pharmaceutically acceptable carrier, diluent or excipient.

In another aspect, the present invention provides for a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, or [4-(3-Fluoro-phenyl)-piperidin-1-yl]-[4-(3-phenyl-indole-1-sulfonyl)-phenyl]-methanone for use in therapy.

In another aspect, the present invention provides use of a compound of Formula I for the manufacture of a medicament for treating a condition which is treatable by reducing CB-1 receptor stimulation.

In another aspect, the present invention provides use of a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, or [4-(3-Fluoro-phenyl)-piperidin-1-yl]-[4-(3-phenyl-indole-1-sulfonyl)-phenyl]-methanone for the manufacture of a medicament for treating a condition which is treatable by reducing CB-1 receptor stimulation.

In another aspect, the present invention provides a method for treating a condition selected from the group consisting of psychosis, memory deficit, cognitive disorder, migraine, neuropathy, neuroinflammatory disorder, cerebral vascular accident, head trauma, anxiety disorder, stress, depression, epilepsy, Parkinson's disease, schizophrenia, substance abuse disorder, obesity, and an eating disorder associated with excessive food intake comprising administering to the mammal in need thereof a compound of Formula I, [4-(2,3-dihydro-indole-1-sulfonyl)-phenyl]-(4-phenyl-piperazin-1-yl)-methanone, [4-(2,3-dihydro-indole-1-sulfonyl)-phenyl]-morpholin-4-yl-methanone, [4-(2,3-dihydro-indole-1-sulfonyl)-phenyl]-piperidin-1-yl-methanone, or [4-(3-Fluoro-phenyl)-piperidin-1-yl]-[4-(3-phenyl-indole-1-sulfonyl)-phenyl]-methanone. More preferably, the condition is obesity.

In a preferred embodiment, the condition which is treatable by reducing CB-1 receptor stimulation is psychosis, memory deficit, cognitive disorder, migraine, neuropathy, neuroinflammatory disorder, cerebral vascular accident, head trauma, anxiety disorder, stress, depression, epilepsy, Parkinson's disease, schizophrenia, substance abuse disorder, obesity, or eating disorder associated with excessive food intake. More preferably, the condition is obesity.

In another preferred embodiment, the mammal being treated is a human. In another aspect, the invention provides for compounds of formula (IIa)

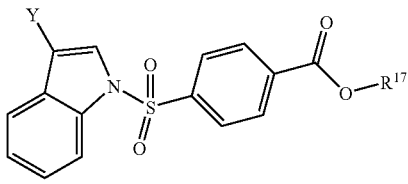

(IIa)

wherein:
Y is halogen, cyclopent-1-enyl, or cyclopentyl and $R^{17}$ is alkyl.

It will be appreciated the all combinations of the aspects and embodiments discussed above and the examples discussed below are contemplated as being encompassed by the present invention. In addition, all examples described herein are for illustrative purposes, and are not intended to narrow the scope of the invention in any way.

DETAILED DESCRIPTION

As used above, and throughout the description of the invention, the following terms, unless otherwise indicated, shall be understood to have the following meanings:

"Acyl" means an alkylcarbonyl (i.e., alkyl-CO—, wherein the alkyl group is as herein described) or heterocyclylcarbonyl (i.e., heterocycyl-CO—, wherein heterocyclyl is as herein described). Preferred acyls contain a lower alkyl (e.g., acetyl).

"Alkoxy" means an alkyl-O— group, wherein the alkyl group is as herein described. Exemplary alkoxy groups include methoxy, ethoxy, n-propoxy, I-propoxy, and n-butoxy.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means a saturated aliphatic hydrocarbon group, which may be straight or branched, having 1 to 6 carbon atoms in the chain. Preferred alkyl groups have 1 to 4 carbon atoms in the chain. For example, methyl, ethyl, propyl, isopropyl, butyl, sec-butyl, and tert-butyl.

"Alkylamino" means an alkyl-NH— group wherein the alkyl group is as herein described.

"Alkylcarbonyl" means alkyl-CO— group wherein the alkyl group is as herein described.

"Alkylthio" means an alkyl-S— group wherein the alkyl group is as herein described. Exemplary alkylthio groups include methylthio, ethylthio, I-propylthio and n-butylthio.

"Aryl" means an aromatic mono- or bi-cyclic ring system of 6 to about 10 carbon atoms. Exemplary aryl groups include phenyl and 1- and 2-naphthyl.

"Arylalkyl" means an aryl-alkyl- group wherein the aryl and alkyl groups are as defined herein.

"Aryloxy" means an aryl-O— group wherein the aryl group is as defined herein. Exemplary groups include phenoxy and naphthyloxy.

"Aryloxycarbonyl" means an aryl-O—C(O)— group wherein the aryl group is as defined herein. Exemplary aryloxycarbonyl groups include phenoxycarbonyl and naphthoxycarbonyl.

"Arylthio" means an aryl-S— group wherein the aryl group is as herein described. Exemplary arylthio groups include phenylthio and naphthylthio.

"Carboxy" means a HO(O)C— (i.e., carboxylic acid) group.

"Cycloalkyl" means a fully saturated, mono-carbocyclic ring system of about 3 to about 6 carbon atoms. Exemplary cycloalkyl groups include cyclopropyl, cyclobutyl, cyclopentyl, and cyclohexyl.

"Cycloalkylalkyl" means cycloalkyl-alkyl- group wherein the cycloalkyl group and the alkyl group are as defined herein.

"Dialkylamino" means an $(alkyl)_2$-N— group wherein the alkyl group is as defined herein. It is understood that the two alkyl groups can be the same or different.

"Dialkylaminocarbonyl" means a $(alkyl)_2$-N—C(O)— group wherein the alkyl group is as defined herein. It is understood that the two alkyl groups can be the same or different.

"Dialkylaminothiocarbonyl" means a dialkylamino-C(S)— group wherein the dialkylamino group is as defined herein. It is understood that the two alkyl groups can be the same or different.

"Effective amount" is means an amount of a compound/composition according to the present invention effective in producing the desired therapeutic effect.

"Halo" means fluoro, chloro, bromo, or iodo. A preferred halo is fluoro.

"Haloalkyl" refers to an alkyl group, as described herein, which is substituted with one to six halo groups, as described herein. Preferred haloalkyls include fluoroalkyls, such as fluoromethyl, difluoromethyl, trifluoromethyl, 2-fluoroethyl, 2,2,2-trifluoroethyl, 1,1,2,2,2-pentafluoroethyl, 3-fluoropropyl, 3,3,3-trifluoropropyl, and 1,1,1,3,3,3-hexafluoroprop-2-yl.

"Haloalkoxy" refers to an alkoxy group, as described herein, which is substituted with one to six halo groups, as described herein. Preferred haloalkoxy groups include fluoroalkoyls, such as fluoromethoxy, difluoromethoxy, trifluoromethoxy.

"Haloaryl" refers to an aryl group, as described herein, which is substituted by halogen, as described herein.

"Haloarylalkyl" refers to an allyl group, as described herein, which is substituted by a haloaryl group, as described herein.

"Halophenyl" refers to a phenyl group which is substituted by halogen, as described herein.

"Halophenylalkyl" refers to an alkyl group, as described herein, which is substituted by a halophenyl group, as described herein.

"Halopyridinyl" refers to a pyridinyl group which is substituted by a halogen group, as described herein.

"Heteroaroyl" means a heteroaryl-CO— group, wherein the heteroaryl group is as herein described. Exemplary groups include thiophenoyl, nicotinoyl, pyrrol-2-ylcarbonyl, 1- and 2-naphthoyl, and pyridinoyl.

"Heteroaryl" means a monocyclic or bicyclic fully unsaturated ring system of about 5 to 10 ring atoms in which one or two of the ring atoms is a hetero element(s) other than carbon (e.g., nitrogen, oxygen or sulfur) and the remainder of the ring atoms are carbon. Preferred ring sizes include 5 to 6 ring atoms. Exemplary heteroaryl groups include pyrrolyl, furanyl, thienyl, pyrazolyl, imidazolyl, thiazolyl, pyridinyl, pyridazinyl, pyrimidinyl, pyrazinyl, quinolinyl, and isoquinolinyl.

"Heteroarylalkyl" means heteroaryl-alkyl- wherein the heteroaryl group is as described herein.

"Heterocyclyl" means a monocyclic, fully-saturated ring system of about 3 to about 7 ring atoms, in which one or two of the ring atoms is a hetero element(s) other than carbon (e.g., nitrogen, oxygen or sulfur) and the remainder of the ring atoms are carbon. Heterocyclyl groups may be optionally substituted, for example with alkyl, hydroxy, alkoxy, aryl, acyl, in particular, methyl, phenyl, halophenyl, alkoxycarbonyl. Exemplary heterocyclyl rings, for example include pyrrolidinyl, tetrahydrofuranyl, tetrahydrothiophenyl, piperidyl, tetrahydropyranyl, tetrahydrothiopyranyl, piperazinyl, morpholinyl, and thiomorpholinyl.

"Heterocyclyalkyl" means heterocycly-alkyl- wherein the heterocyclyl group is as herein described.

"Hydrate" means a solvate, as defined herein, wherein the solvent molecule(s) is/are $H_2O$.

"Hydroxyalkyl" means HO-alkyl- group, wherein the alkyl group is as herein described.

"Obesity" refers to a condition whereby a mammal has a Body Mass Index (BMI), which is calculated as weight per height squared ($kg/m^2$), of at least 25.9. Conventionally, those persons with normal weight have a BMI of 19.9 to less than 25.9.

"Phenylalkyl" refers to an alkyl group, as described herein, which is substituted by a phenyl group.

The term "salt(s)" refers to pharmaceutically acceptable salts, as defined herein.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinateslaurylsulphonate salts, and the like. See, for example S. M. Berge, et al., "Pharmaceutical Salts," *J. Pharm. Sci.*, 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use for example, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

"Substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of all of the above. In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation. Other "substance abuse disorders" include substance-induced anxiety disorder with onset during withdrawal; substance-induced mood disorder with onset during withdrawal; and substance-induced sleep disorder with onset during withdrawal.

"Therapeutically effective amount" means the amount the compound of structural formula I that will elicit the biological or medical response of a tissue, system, animal or human that is being sought by the researcher, veterinarian, medical doctor or other clinician.

"Treatment" or "treating" (of obesity) refers to reducing the BMI of the mammal and in certain cases where it is desirable for weight loss. The treatment or treating suitably results in a reduction in food or calorie intake by the mammal.

The symbol "⌇" or "~" in a molecular structure indicates the position of attachment for that particular substituent.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity.

Under standard nomenclature used throughout this disclosure, the terminal portion of the designated side chain is described first, followed by the adjacent functionality toward the point of attachment. For example, an arylcarbonylaminoalkyl substituent is equivalent to aryl-C(O)—NH-alkyl-.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The present invention also provides novel crystalline forms of the compounds of formula (I). Novel crystalline forms may be prepared by crystallization under controlled conditions. Crystallization from a solution and slurrying techniques are contemplated to be within the scope of the present process. In practice, a number of factors can influence the form obtained, including temperature, solvent composition and also optional seeding. Seed crystals can be obtained from previous synthesis of the compound in which crystals were isolated.

A number of methods are available to characterize crystalline forms of organic compounds. For example, methods include differential scanning calorimetry, solid state NMR spectrometry, infra-red spectroscopy, and X-ray powder diffraction. Among these X-ray powder diffraction and solid state NMR spectroscopy are very useful for identifying and distinguishing between crystalline forms.

It will be understood that, as used herein, references to the compounds of Formula I are meant to also include the pharmaceutically acceptable salts.

Compounds of this invention are modulators of the CB1 receptor and as such are useful for the prevention and treatment of disorders or diseases associated with the CB1 receptor. Accordingly, another aspect of the present invention provides a method for the treatment (including prevention, alleviation, amelioration or suppression) of diseases or disorders or symptoms mediated by CB1 receptor binding and subsequent cell activation, which comprises administering to a mammal an effective amount of a compound of Formula I. Such diseases, disorders, conditions or symptoms are, for example, but not limited to, psychosis, memory deficits, cognitive disorders, migraine, neuropathy, anxiety disorders, depression, stress, epilepsy, Parkinson's disease, schizophrenia, substance use disorders, particularly to opiates, alcohol, and nicotine, obesity, and eating disorders associated with excessive food intake. See DSM-IV-TR, *Diagnostic and Statistical Manual of Mental Disorders. Revised,* $4^{th}$ Ed., Text Revision (2000). See also DSM-IV, *Diagnostic and Statistical Manual of Mental Disorders* $4^{th}$ Ed., (1994). The DSM-IV and DSM-IV-TR were prepared by the Task Force on Nomenclature and Statistics of the American Psychiatric Association, and provides descriptions of diagnostic categories. The skilled artisan will recognize that there are alternative nomenclatures, nosologies, and classification systems for pathologic psychological conditions and that these systems evolve with medical scientific progress.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. In addition, the compound of formula (I) can be used to ameliorate weight gain, whether or not the associated weight gain can be classified as clinically obese.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

"Neutral antagonists" are ligands without intrinsic activity, i.e. they do not influence the receptor's own activity (constitutive receptor activity) and prevent competitively the binding of an agonist (often endogenous) to the receptor.

"Inverse agonists" are ligands with negative intrinsic activity, they inhibit the receptor's own activity (constitutive receptor activity) shifting the equilibrium of the receptor conformation to its inactive state.

There is evidence suggesting that CB1 receptor ligands act as either neutral antagonists or inverse agonists; these ligands will reduce endocannabinoid neurotransmission through CB1 receptors either by competitive receptor antagonism or by receptor inactivation, respectively.

Compounds of formula Ia (i.e., compounds of Formula I wherein
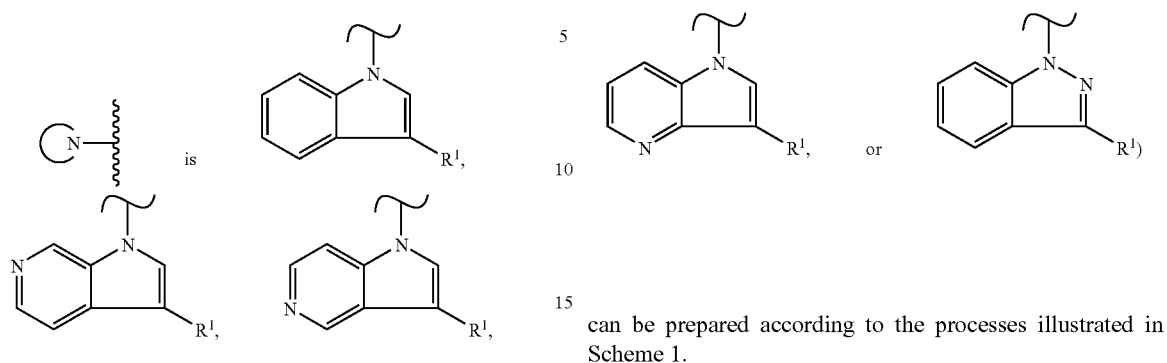
can be prepared according to the processes illustrated in Scheme 1.
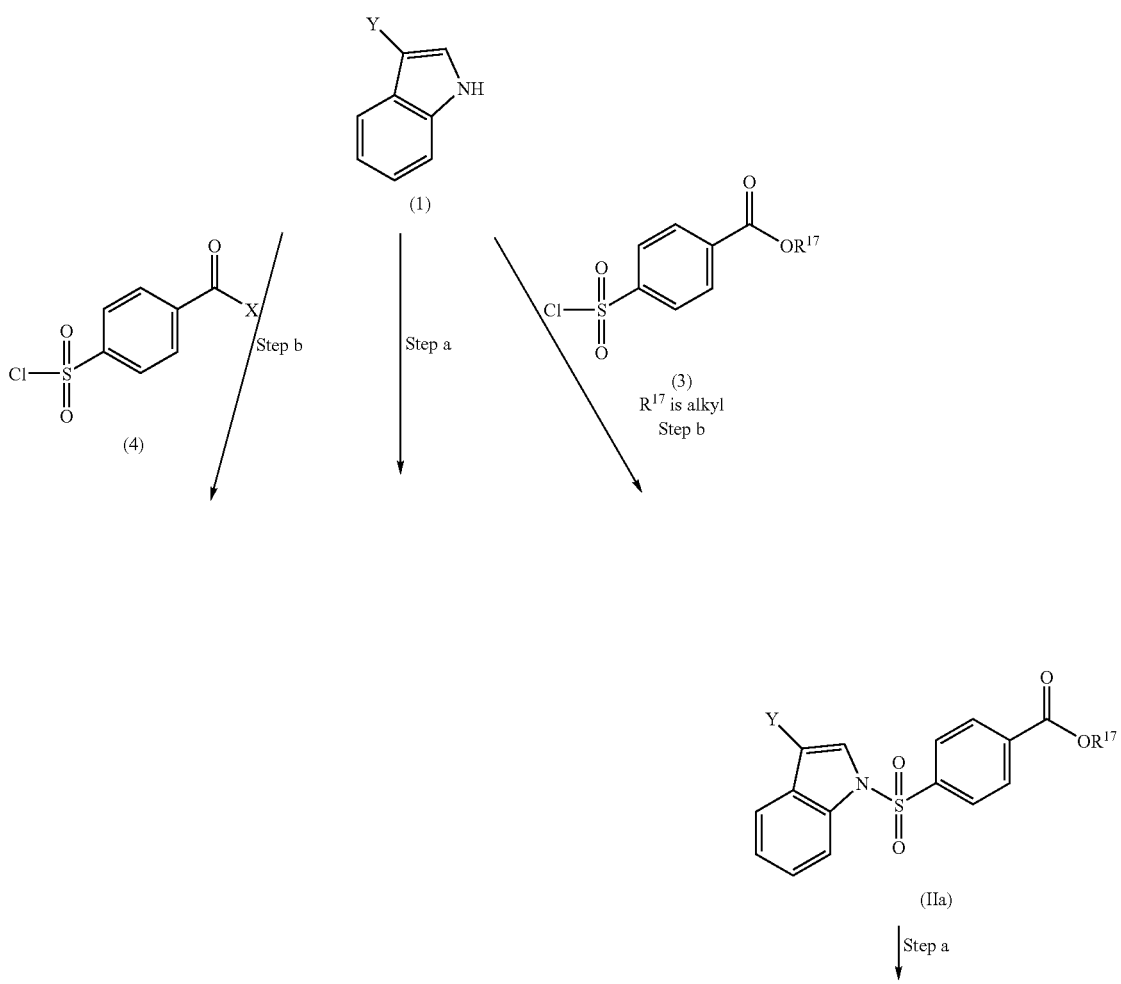

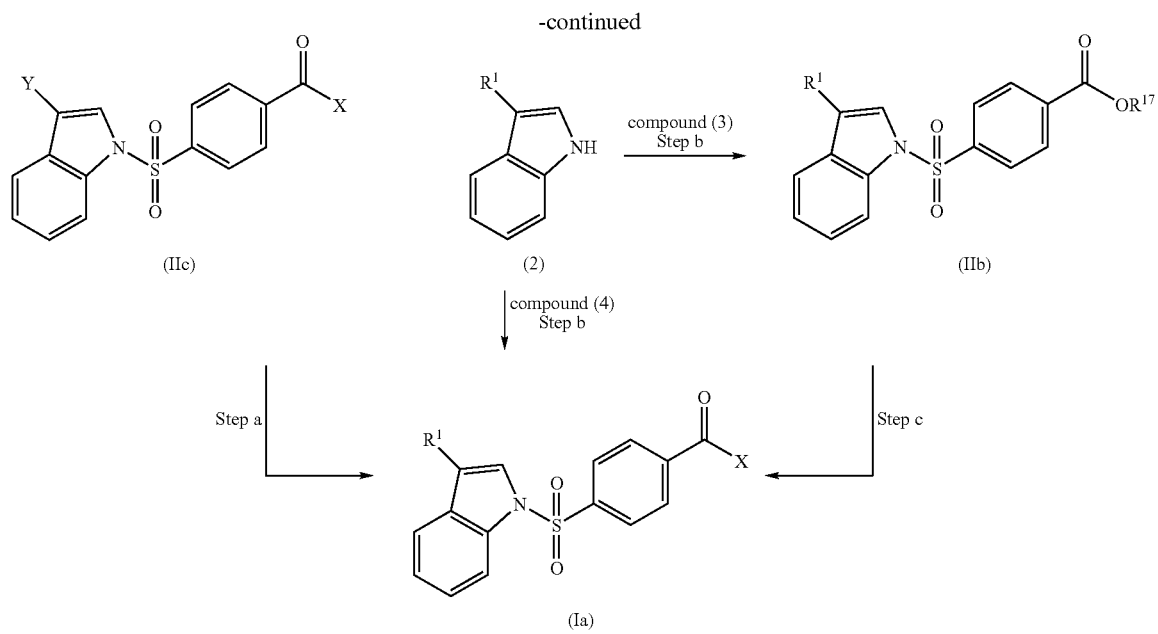

In Scheme 1, Step a involves the introduction of $R^1$-substitution at the 3-position on the indole moiety of compound (1), (IIa) or (IIc) (wherein Y is I, Br, $B(OH)_2$,

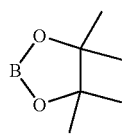

or $SnMe_3$) under standard conditions employed for palladium mediated cross-coupling reactions. For example, a 3-haloindole of formula (1), (IIa), or (IIc) is reacted with a suitable aryl boronic acid (Suzuki-type) or with a suitable aryl stannane (Stille-type), as generally described in Handbook of Palladium Catalyzed Organic Reactions, Malleron. J.-L.; Fiaud, J.-C.; Legros, J.-Y.; Academic Press, USA, 1997, p. 23-47. It is understood by one of ordinary skill in the art that, in general, an aryl boronic ester can be used in place of the aryl boronic acid in the palladium cross-coupling reactions described herein. By way of illustration, the aryl boronic acids include, but are not limited to, the following:

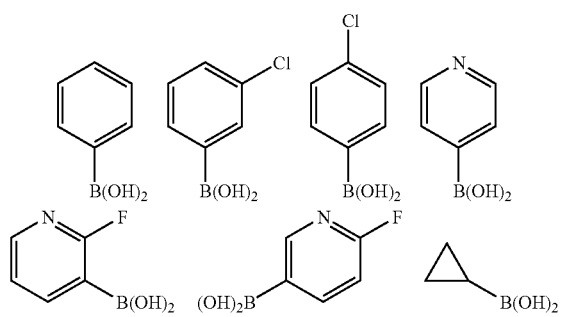

More specifically, compound (1), (IIa) or (IIc) (Y is I or Br) and the suitable aryl boronic acid or the suitable aryl boronic ester, along with a base (e.g., aqueous sodium carbonate) and a catalyst (e.g., [1,1'-bis(diphenylphosphino)ferrocene] dichloropalladium(II) complex) are dissolved in a suitable solvent such as dichloromethane, and the mixture is heated. Aqueous work-up and chromatographic purification affords the desired compound (2), (IIb) or (Ia). More specifically, in the Stille-type reaction, a 3-iodoindole compound (1), (IIa) or (IIc) is combined with an aryl stannane (e.g., 2-tributylstannyl pyrazine, 3-tributylstannylpyridine, 2-tributylstannylpyridine) and a catalyst (e.g., tetrakis(triphenylphosphine)Pd(0)) in an appropriate solvent (e.g., DMF) and heated. After an aqueous work-up, compound (2), (Ia) or (IIb) is isolated by chromatographic purification.

Alternatively, a 3-haloindole compound (1), (IIa) or (IIc) is subjected to a palladium-mediated coupling with an olefin (e.g., cyclopentene) or an α,β-unsaturated ketone or ester (Heck-type), then the resulting intermediate is hydrogenated to provide the desired compound (2), (IIb) or (Ia). (see generally Handbook of Palladium Catalyzed Organic Reactions, Malleron, J.-L.; Fiaud, J.-C.; Legros, J.-Y.; Academic Press, USA 1997 p. 61-71.) More specifically, a 3-iodoindole compound (1), (IIa) or (IIc) is combined with an olefin and a catalyst (e.g., palladium (II) acetate) along with tetrabutylammonium chloride and a base (e.g., potassium acetate) and the resulting mixture heated. After an aqueous work-up, the intermediate product is isolated by chromatographic purification, then subjected to hydrogenation to remove the resulting olefin, thereby providing the desired compound (2), (Ia), or (IIb).

Alternatively, a 3-haloindole compound (1), (IIa) or (IIc) is subjected to a metal halogen exchange with a reagent such as cyclopentyl magnesium bromide and then treated with a ketone such as tetrahydro-4H-pyran-4-one. The resulting alcohol is isolated and treated with a reducing agent (e.g., triethylsilane and TFA) to provide the desired compound (2), (Ia) or (IIb).

Alternatively, a compound (1), (IIa), or (IIc) when Y is $B(OH)_2$,

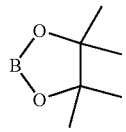

or $SnMe_3$ is reacted via a palladium-mediated coupling employing a suitable aryl halide in a manner analogous procedure set forth above. By way of illustration, suitable aryl halides include, but are not limited to, 5-bromo-2-methoxy pyridine, 5-bromo-2-fluoro-pyridine, 2-bromo-5-chloro-thiophene, 4-bromo-isoquinoline, 2-bromo-5-chloro-thiophene, 3-bromo-toluene, 4-bromo-toluene, 1-bromo-3-methoxy-phenyl, 6-bromo-quinoline, 1-bromo-4-dimethylamino-phenyl, 1-bromo-3-fluoro-pyridine, 2-bromo-pyrimidine and 5-bromo-pyrimidine.

In scheme 1 step b, a sulfonamide of formula (Ia), (IIa), (IIb) or (IIc) is prepared via treatment of the appropriate indole of formula (1) or (2) with the requisite sulfonyl chloride of formula (3) or (4) in the presence of a base under standard conditions. More specifically, the indole of formula (1) or (2) and the sulfonyl chloride of formula (3) or (4) are combined with a base (e.g., diisopropylethylamine, potassium tertbutoxide or sodium hydride) in an appropriate solvent (e.g., N,N-dimethylformamide, dioxane or tetrahydrofuran). Alternatively, the indole of formula (1) or (2) and sulfonyl chloride of formula (3) or (4) are combined with a catalyst (e.g., DMAP or 4-pyrrolidin-1-yl-pyridine) with or without a base in an appropriate solvent (e.g., N,N-dimethylformamide, dioxane or acetonitrile). An aqueous work-up and chromatographic purification affords compound (Ia), (IIa), (IIb) or (IIc).

In Scheme 1, step c, the conversion of an ester of formula (IIb) to an amide of formula (Ia) is achieved under standard conditions via the carboxylic acid or acid chloride, as referenced in Comprehensive Organic Transformations, R. C. Larock VCH Publishers Inc, New York, N.Y. 1989. p. 972-976. More Specifically, the ester of formula (IIb) is hydrolyzed to the acid in the presence of a base (e.g., sodium hydroxide), converted to the acid chloride with reagents such as oxalyl chloride, and then treated with the requisite amine in the presence of a base (e.g., triethylamine) to form the compound (Ia). Alternatively the acid is coupled with the amine using a coupling reagent (e.g., EDC, BOP or PyBOP) with or without a catalyst (e.g., NHS). After an aqueous work-up, the products are isolated by chromatographic purification to yield the compound (Ia).

Compounds of formula (Ia) can also be prepared according to the processes illustrated in Scheme 2.

Scheme 2

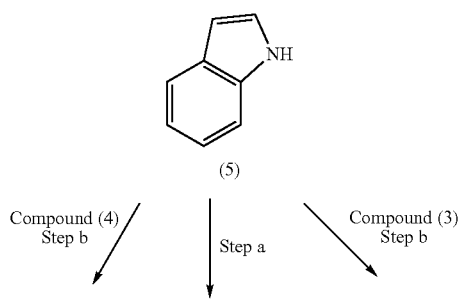

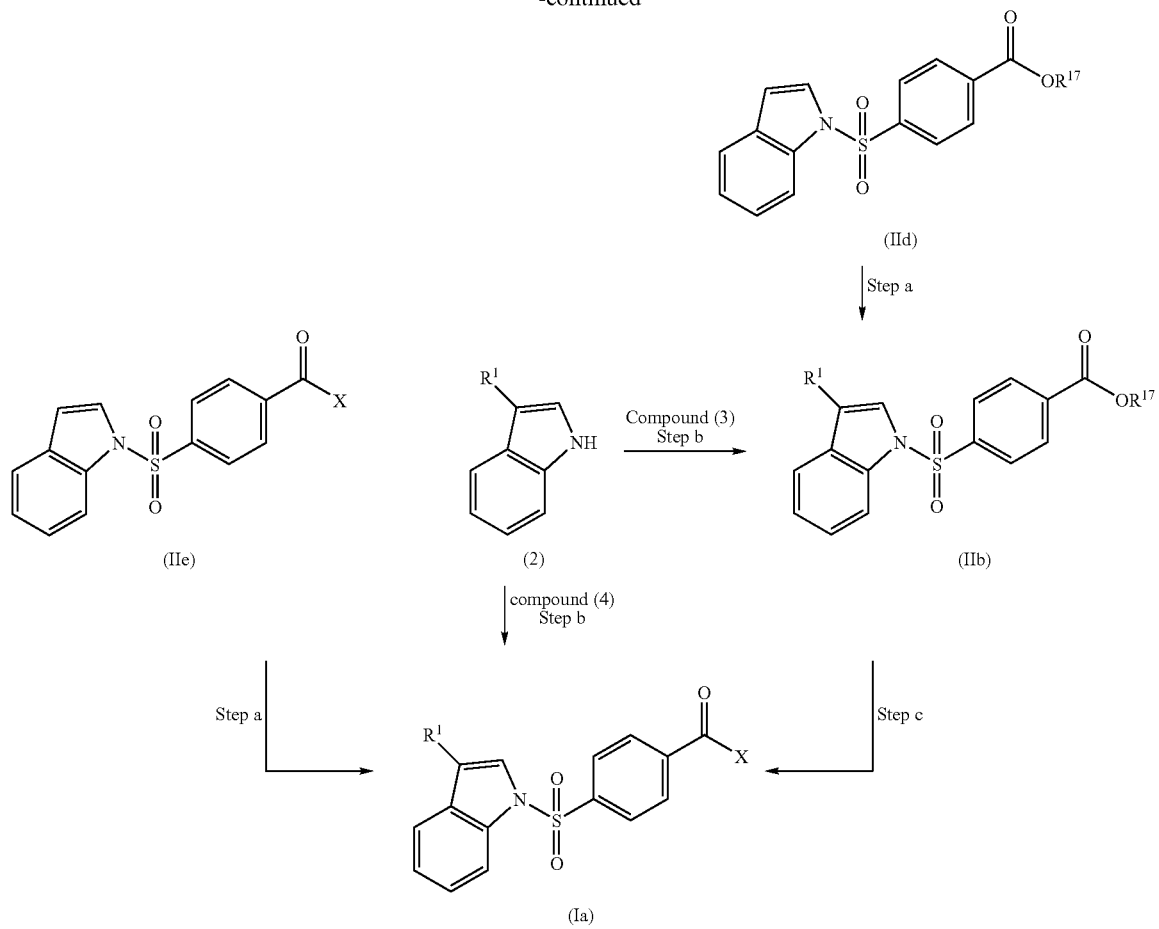

In Scheme 2, step a, direct alkylation of a compound (5), (IId) or (IIe) is achieved via heating with a ketone (e.g., cyclohexanone or 2-methoxycyclohexanone) and a base (e.g., potassium hydroxide). The resulting olefin is hydrogenated to form a compound of formula (2), (IIb), or (Ia) (see, e.g., *J. Med. Chem.* (1997), 40, 250). Alternatively, direct alkylation of a compound of formula (5), (IId), (IIe) is achieved under protic or lewis acid conditions with an alcohol (e.g., tert-butyl alcohol) or alkyl bromide (e.g., as described in *J. Org. Chem.* (2002), 67, 2705). Alternatively, conjugate addition to an α,β-unsaturated ketone is achieved in the presence of indium tribromide and isopropylamine in solvents such as dichloromethane, as described in *J. Org. Chem* (2002), 67, 3700 to form compound (2), (IIb), or (Ia). Steps b and c in Scheme 2 are carried out as described in steps b and c of Scheme 1, respectively.

It should be noted that when $R^1$ is

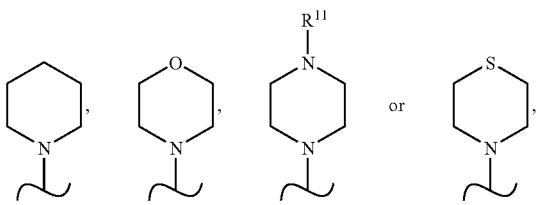

step a of Schemes 1 and 2 must be modified as shown in Scheme 3.

Scheme 3

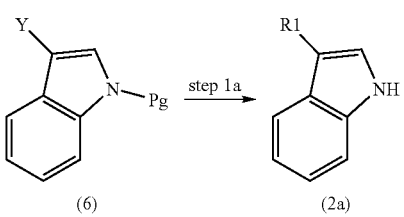

In Scheme 3, step a1, a 3-amino □eaction□ed indole compound (2a) is prepared via a palladium-mediated coupling of an amine with a 3-haloindole of formula (6) bearing a protecting group on nitrogen (as described for example in *Organic Lett.* (2002), 4, 2885) followed by removal of the N-protecting group. More specifically, 3-bromoindole N-protected with a triisopropylsilanyl group is combined with an amine (e.g., piperidine, morphline, or 1-methyl piperazine), a catalyst (e.g., tris(dibenzylideneacetone)dipalladium(0) chloroform adduct and 2-dicyclohexylphosphino-2'-(N,N-dimethylamino)biphenyl), and a base (e.g., lithium bis(trimethylsilyl)amide), and the mixture heated in an appropriate solvent (e.g., THF). The resulting intermediate is deprotected with tetrabutyl ammonium fluoride, after which an aqueous work-up and chromatographic purification yields isolated compound (2a).
Compounds of formula Ib (i.e. where
is
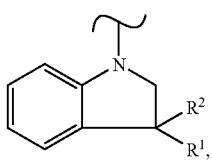 , 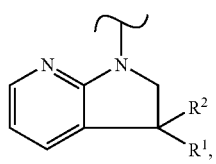 ,
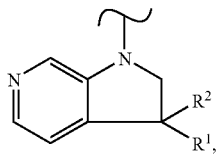 , 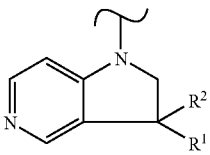 or
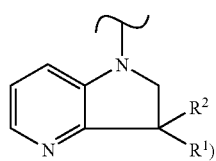 )
can be synthesized by methods known in the art, as illustrated in Scheme 4.
Scheme 4
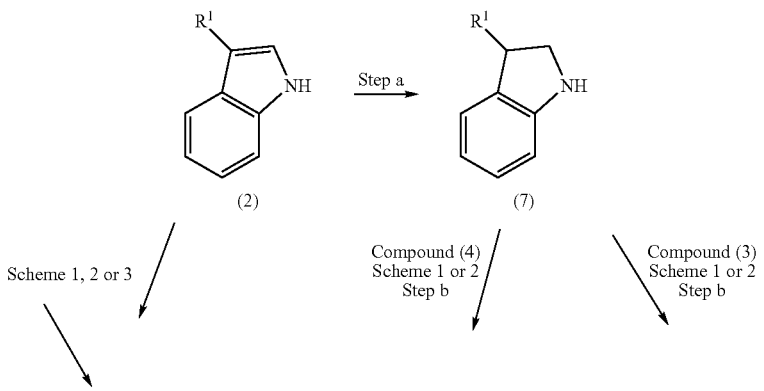
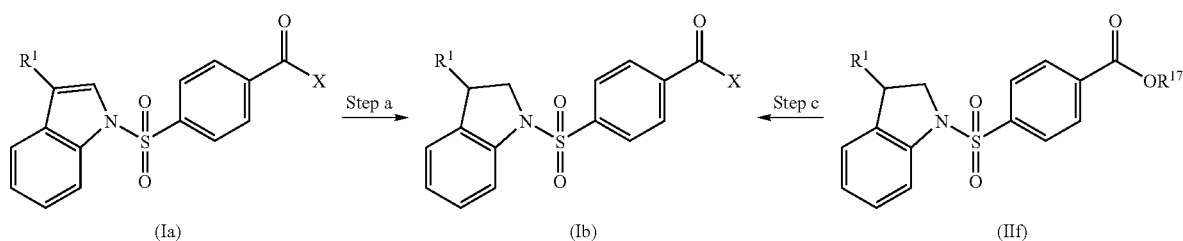

In Scheme 4, step a involves reduction of the indole compound (2) to the corresponding indoline compound (7) utilizing standard conditions such as sodium borohydride or sodium cyanoborohydride, and as described in Yamamoto, Y et al. Bull Chem. Soc. Jpn 44, 1971, 541-545. Step b involves reaction of the indoline compound (7) with the appropriate sulfonyl chloride compound (4) or (3) under standard conditions described above in Scheme 1 or 2. Alternatively, the indole compound (2) is coupled to the sulfonyl chloride according to Schemes 1, 2, or 3, followed by reduction according to step a to give (Ib). Alternatively, compound (Ia) can be prepared by one of the general methods found in Schemes 1, 2 or 3. In general, when $R^1$ is aryl, step a is accomplished as the first step. When $R^1$ is alkyl or cycloalkyl, step b is accomplished as the first step. Compounds, wherein $R^1$ and $R^2$ are taken together to form a ring as synthesized by methods known in the art.

The examples set forth herein represent typical syntheses of the compounds of the present invention. The reagents and starting materials are readily available to one of ordinary skill in the art.

Preparation 1

3-(6-Methoxy-cyclohex-1-enyl)-1H-indole

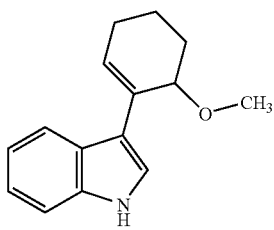

Add 5 ml dry MeOH to a flask under $N_2$ containing indole (1 g, 8.5 mmol, 8.5 eq) and potassium hydroxide (202 mg, 3.59 mmol, 1 eq). Add to this solution 2-Methoxy-cyclohexanone (834 mg, 6.5 mmol, 6.5 eq). Heat reaction to 63° C. for 18 hours. Cool reaction and purify crude material by silica gel chromatography to give 442 mg (30% yield) of 3-(6-Methoxy-cyclohex-1-enyl)-1H-indole as a waxy yellow solid. Mass Spectrum (m/e): 228.02 (MH+).

Preparation 2

3-(2-Methoxy-cyclohexyl)-1H-indole

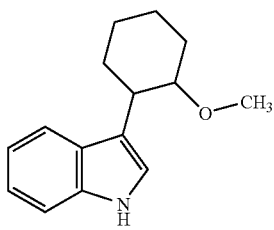

Treat 3-(6-methoxy-cyclohex-1-enyl)-1H-indole (200 mg, 0.879 mmol) with 10% Pd/C (40 mg) in EtOAc under atmospheric hydrogenation conditions for 1.5 hours. Filter resulting solution over Celite to remove catalyst. Concentrate crude on rotovap and purify on silica gel chromatography to give 3-(2-Methoxy-cyclohexyl)-1H-indole (127 mg, 63% yield). Mass Spectrum (m/e): 230.03 (MH+), 228.14 (M−).

Preparation 3

3-(1H-Indol-3-yl)-cyclopentanone

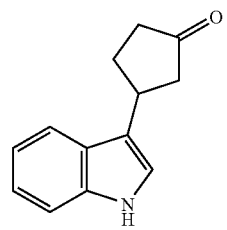

Conduct reaction according to literature procedure (JOC, vol 67, 2002, pg 3700-3704) to give final 3-(1H-Indol-3-yl)-cyclopentanone (1.38 g, 81% yield) as a light pink solid. Mass Spectrum (m/e): 199.99 (MH+).

Preparation 10

N-[2-Phenyl-eth-(Z)-ylidene]-N'-pyridin-4-yl-hydrazine

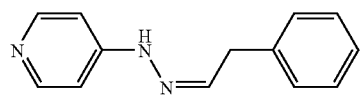

React 4-hydrazinopyridine HCl with phenylacetaldehyde under literature conditions (J Chem Soc, 1959, pg 3830). Instead of $NH_3$, neutralize with 1N NaOH and extract with $CHCl_3$. Dry organics over $MgSO_4$ and concentrate on rotovap to give N-[2-Phenyl-eth-(Z)-ylidene]-N'-pyridin-4-yl-hydrazine (7.3 g, approx quantitative) as a crude thick oil that can be used without further purification. Mass Spectrum (m/e): 212.02 (MH+).

Preparation 11

3-Phenyl-1H-pyrrolo[3,2-c]pyridine

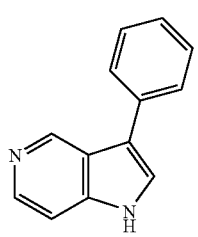

React crude N-[2-Phenyl-eth-(Z)-ylidene]-N'-pyridin-4-yl-hydrazine (7.25 g, 34.22 mmol) under literature conditions (Can J Chem, vol 44, 1966, pg 2455) to give 3-Phenyl-1H- pyrrolo[3,2-c]pyridine (2.28 g, 34% yield) after silica gel chromatography: Mass Spectrum (m/e): 194.96 (MH+).

Preparation 12

4-(4-Fluoro-benzylcarbamoyl)-benzenesulfonyl chloride

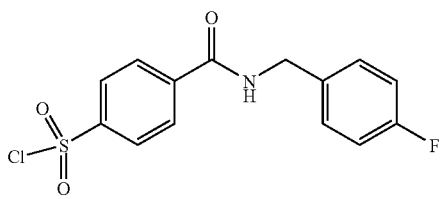

Add 4-chlorosulfonyl-benzoyl chloride (103 g (0.433 mol) and anhydrous THF (1.2 L) to a 5-L 3-neck round bottom equipped with overhead stirrer, dropping funnel, $N_2$ line, and temperature probe and cool to −78° C. Add to the stirring solution dropwise over 4 h a solution of 4-fluorobenzylamine (52 g, 0.416 mol), triethylamine (42 g, 0.415 mol), and 4-DMAP (5.3 g, 0.043 mol) in dry THF (1.2 L). Slowly bring to room temperature the resulting mixture and stir overnight. Filter the solids, back-wash with THF, and concentrate the filtrate to a solid. Partion the solid between 1N HCl (1 L) and ethyl acetate (2×1 L). Combine the organics, dry over magnesium sulfate, filter, and concentrate to a solid. Suspend the solid in methyl t-butyl ether (1 L), stir at room temperature for 2 h, filter, and back-wash with ethyl ether (500 mL). Dry the resulting white powder (20 mm Hg, 40° C.) to give 4-(4-fluoro-benzylcarbamoyl)-benzenesulfonyl chloride as a white solid (108.5 g, 80%): $^1$HNMR (DMSO-$d_6$) δ 9.07 (t, J=5.9 Hz, 1H), 7.82 (d, J=8.3 Hz, 2H), 7.65 (d, J=7.8 Hz, 2H), 7.35 (m, 2H), 7.14 (t, J=8.8 Hz, 2H), 4.44 (d, J=5.9 Hz, 2H); MS (ESI) m/z 326 (m−H); HPLC, 93.6%.

Preparation 14

3-(3,3-Difluoro-cyclopentyl)-1H-indole

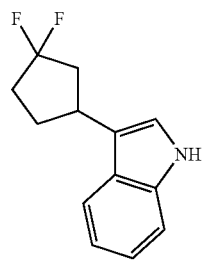

Following a literature procedure (Tet, Vol 46, No 13-14, pg 4925, 1990) previously reported to convert 3-(1H-Indol-3-yl)-cyclopentanone to 3-(3,3-difluoro-cyclopentyl)-1H-indole (246 mg, 22% yield): Mass Spectrum (m/e): 220.11 (MH−).

Preparation 15

3-Morpholin-4-yl-1-triisopropylsilanyl-1H-indole

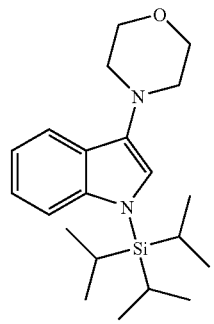

Combine 3-bromo-1-triisopropylsilanyl-1H-indole (0.33 g, 0.94 mmol), morpholine (0.10 mL, 1.15 mmol), 2-dicyclohexylphosphino-2'-(N,N-dimethylamino)biphenyl (0.012 g, 0.03 mmol), and tris(dibenzylideneacetone)dipalladium(0) chloroform adduct (0.012 g, 0.01 mmol) in a pressure tube. Add 1N solution of lithium bis(trimethylsilyl)amide in THF (2.00 mL, 2.00 mmol), flush tube with nitrogen gas, and close the tube. Stir at 65° C. for 18 h, cool to room temperature, dilute with water, and extract with EtOAc. Wash EtOAc layer with water, brine, dry ($Na_2SO_4$), and concentrate under vacuum. Purify the residue by flash chromatography using 0 to 50% of EtOAc in hexanes to give the title compound (0.20 g 60%): MS (ES) 359.1 (M+1)+.

Preparation 16

3-(4-Methyl-piperazin-1-yl)-1-triisopropylsilanyl-1H-indole

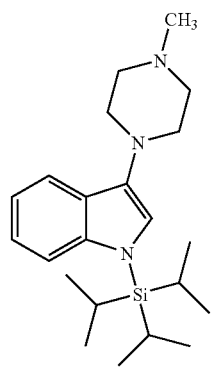

Following a method similar to 3-morpholin-4-yl-1-triisopropylsilanyl-1H-indole using 3-bromo-1-triisopropylsilanyl-1H-indole (0.70 g, 1.99 mmol), 1-methyl-piperazine (0.30 g, 3.00 mmol), 2-dicyclohexylphosphino-2'-(N,N-dimethylamino)biphenyl (0.02 g, 0.05 mmol), tris(dibenzylideneacetone)dipalladium(0) chloroform adduct (0.05 g, 0.05 mmol) and 1N solution of lithium bis(trimethylsilyl)amide in THF (2.40 mL). Purify by flash chromatography using 0 to 12% of MeOH in dichloromethane to give the title compound (0.23 g, 32%). MS (ES) 372.1 (M+1)+.

Preparation 17

3-Piperidin-1-yl-1-triisopropylsilanyl-1H-indole

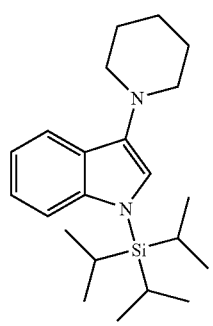

Following a method similar to 3-morpholin-4-yl-1-triisopropylsilanyl-1H-indole using 3-bromo-1-triisopropylsilanyl-1H-indole (0.70 g, 1.99 mmol), piperidine (0.26 g, 3.04 mmol), 2-dicyclohexylphosphino-2'-(N,N-dimethylamino)biphenyl (0.02 g, 0.05 mmol), tris(dibenzylideneacetone)dipalladium(0) chloroform adduct (0.05 g, 0.05 mmol) and 1N solution of lithium bis(trimethylsilyl)amide in THF (2.40 mL) to prepare the title compound. Purify by flash chromatography using 0 to 40% of EtOAc in hexanes to give the title compound (0.20 g, 29%): MS (ES) 357.1 (M+1)+.

Preparation 18

3-Morpholin-4-yl-1H-indole

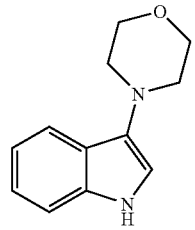

Add 1N solution of tetrabutylammonium fluoride (0.70 mL, 0.70 mmol) to a solution of 3-Morpholin-4-yl-1-triisopropylsilanyl-1H-indole (0.20 g, 0.56 mmol) in THF (2.0 mL). Stir at room temperature for 2 h, dilute with water, and extract with EtOAc. Wash EtOAc with saturated NaHCO$_3$, water, dry (Na$_2$SO$_4$), and concentrate under vacuum. Purify the residue by flash chromatography using 20 to 80% of EtOAc in hexanes to give the title compound (0.10 g 89%). MS (ES) 203.1 (M+1)+.

Preparation 19

3-(4-Methyl-piperazin-1-yl)-1H-indole

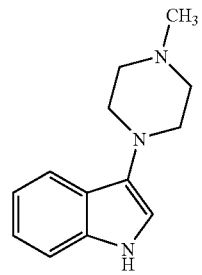

Following a method similar to 3-morpholin-4-yl-1H-indole using 3-(4-Methyl-piperazin-1-yl)-1-triisopropylsilanyl-1H-indole (0.35 g, 0.94 mmol) and 1N solution of tetrabutylammonium fluoride (1.40 mL) to prepare the title compound. Purify by flash chromatography using 2 to 12% methanol in dichloromethane to give the title compound (0.12 g 60%). MS (ES) 216.1 (M+1)+.

Preparation 20

3-Piperidin-1-yl-1H-indole

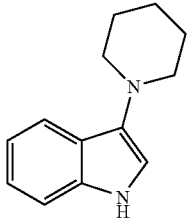

Following a method similar to 3-morpholin-4-yl-1H-indole using 3-Piperidin-1-yl-1-triisopropylsilanyl-1H-indole (0.30 g, 0.84 mmol) and 1N solution of tetrabutylammonium fluoride (1.30 mL). Purify by flash chromatography using 20 to 50% of EtOAc in hexanes to give the title compound (0.12 g 71%). MS (ES) 201.1 (M+1)+.

Preparation 21

1-(2-Fluoro-phenyl)-cyclobutanecarbonitrile

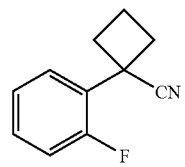

Slowly add NaH (922 mg, 23.0 mmol) to a solution of (2-fluorophenyl)-acetonitrile (1.27 mL, 9.95 mmol) in DMSO (40.0 mL). Stir the mixture at RT for 30 mins then add via cannula a solution of 1,3-dichloropropane (0.95 mL, 10.0 mmol) in DMSO (20 mL). After addition is complete stir at 75° C. for 5 h. Pour mixture over ice (60 g) and extract with Et₂O (3×50 mL). Combine the organic solutions and wash with brine (50 mL), dry filter and concentrate. Purify the material by flash chromatography (using a linear gradient of 100% hexanes to 35% EtOAc/hexanes) to give the title compound (1.4 g, 80%) as a yellow oil. ¹H NMR (400 MHz, CDCl₃): δ 7.32 (m, 1H), 7.25 (dt, 1H, J=1.9, 8.0), 7.16 (dt, 1H, J=0.9, 7.5), 7.09 (ddd, 1H, J=1.2, 8.1, 10.7), 2.86 (m, 2H), 2.69 (m, 2H), 2.50 (m, 1H), 2.05 (m, 1H).

Preparation 22

4-(2-Fluoro-phenyl)-tetrahydro-pyran-4-carbonitrile

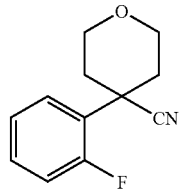

Slowly add NaH (920 mg, 23.0 mmol) to a solution of (2-fluorophenyl)-acetonitrile (1.27 mL, 9.95 mmol) in DMSO (40.0 mL). Stir the mixture at RT for 30 mins then add via cannula a solution of 1,3-dichloropropane (1.0 mL, 8.53 mmol) in DMSO (20 mL). After addition is complete stir at 75° C. for 5 h. Pour mixture over ice (60 g) and extract with Et₂O (3×50 mL). Combine the organic solutions and wash with brine (50 mL), then dry filter and concentrate. Purify the material by flash chromatography (using a linear gradient of 100% hexanes to 35% EtOAc/hexanes) to give the title compound (1.4 g, 80%) as a yellow oil. ¹HNMR (400 MHz, CDCl₃): δ 7.43 (dt, 1H, J=1.7, 7.9), 7.36 (m, 1H), 7.19 (dt, 1H, J=1.4, 7.7), 7.13 (ddd, 1H, J=1.4, 6.6, 14.5), 4.08 (m, 2H), 3.94 (dt, 2H, J=1.7, 7.9), 2.26 (dt, 2H, J=4.4, 13.7), 2.19 (m, 2H).

Preparation 23

Spiro[indoline-3,4'-tetrahydro-pyran]

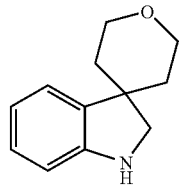

Add LiAlH₄ (398 mg, 10.5 mmol) to a solution of 4-(2-fluoro-phenyl)-tetrahydro-pyran-4-carbonitrile (1.39 g, 6.77 mmol) in dimethoxyethane (25 mL). Stir the solution at reflux overnight then add aq. Satd Rochelle's salt solution (30 mL) and stir for an additional 1 h at RT. Extract the mixture with CH₂Cl₂ (3×30 mL). Combine the organic extracts and wash with additional aq satd Rochelle's salt solution (30 mL) and brine (30 mL). Dry, filter and concentrate the organic solution then purify the crude material by flash chromatography, using a linear gradient of 100% hexanes and 50% EtOAc/hexanes, to give the title compound (581 mg, 45%) as a white solid. ¹H NMR (400 MHz CDCl3): δ 7.09 (d, 1H, J=7.3), 7.06 (t, 1H, J=7.6), 6.77 (m, 1H), 6.67 (m, 1H), 3.97 (m, 2H), 3.94 (dt, 2H, J=1.7, 7.9), 3.56 (dt, 2H, J=2.1, 11.8), 3.55 (s, 2H), 1.99 (m, 2H), 1.67 (m, 2H).

Preparation 24

C-[1-(2-Fluoro-phenyl)-cyclobutyl]-methylamine

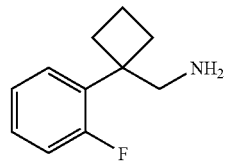

Add LiAlH₄ (461 mg, 12.1 mmol) to a solution of 1-(2-fluoro-phenyl)-cyclobutanecarbonitrile (1.38 g, 7.88 mmol) in dimethoxyethane (30 mL). Stir the solution at reflux overnight then add aq. Satd Rochelle's salt solution (30 mL) and stir for an additional 1 h at RT. Extract the mixture with CH₂Cl₂ (3×30 mL). Combine the organic extracts and wash with additional aq satd Rochelle's salt solution (30 mL) and brine (30 mL). Dry, filter and concentrate the organic solution then purify the crude material by flash chromatography, using 20% MeOH/CH₂Cl₂, to give the title compound (1 g, 71%) as a white solid. MS (ES) 180.1 (M+1)+.

Preparation 25

Spiro[cyclobutane-1,3'-indoline]

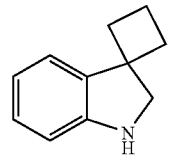

Add LiAlH₄ (266 mg, 7.01 mmol) to a solution of 4-(2-fluoro-phenyl)-tetrahydro-pyran-4-carbonitrile (488 mg, 2.72 mmol) in dimethoxyethane (30 mL). Stir the solution at reflux for 4d, then add aq. Satd Rochelle's salt solution (30 mL) and stir for an additional 1 h at RT. Extract the mixture with Et₂O (3×30 mL). Combine the organic extracts and wash with brine (30 mL). Dry, filter and concentrate the organic solution then purify the crude material by flash chromatography, using a linear gradient of 100% hexanes to 30% EtOAc/hexanes, to give the title compound (44 mg, 10%) as a white solid. ¹H NMR (400 MHz, CDCl₃): δ 7.31 (m, 1H), 7.03 (dt, 1H, J=1.4, 7.5), 6.79 (dt, 1H, J=0.9, 7.5), 6.64 (d, 1H, J=7.9), 2.36 (m, 2H), 2.21 (m, 2H), 2.02 (m, 2H).

Preparation 26

3-Cyclopropyl-1-triisopropylsilanyl-1H-indole

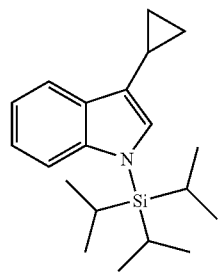

Dissolve 3-bromo-1-triisopropylsilanyl-1H-indole (1.02 g, 2.89 mmol), cyclopropylboronic acid (259 mg, 3.01 mmol) and $K_3PO_4$ (1.8 g, 8.5 mmol) in a mixture of toluene (20 mL) and water (0.8 mL). Add tricyclohexyl-phosphane (86 mg, 0.31 mmol) and palladium(II) acetate (50 mg, 0.22 mmol) and stir the mixture at 70° C. for 3 h. Filter the mixture through celite and wash the solids with EtOAc (30 mL). Collect and concentrate the filtrate and purify the residue by flash chromatography, using a linear gradient of 100% hexanes to 10% EtOAc/hexanes, to give the title compound as a clear oil 765 mg (84%): MS (ES) 314.1 (M+1)+.

Preparation 27

3-tert-Butyl-1H-indole

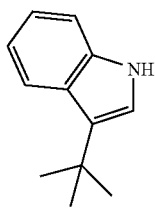

Add trifluoroacetic acid (TFA; 1.0 mL, 1.5 g, 13 mmol, 1.6 equiv) to a solution of indole (1.00 g, 8.54 mmol, 1 equiv) and tert-butyl alcohol (1.0 mL, 0.78 g, 10 mmol, 1.2 equiv) in anhydr 1,2-dichloroethane (40 mL). The colorless solution slowly turns to brown while heating to reflux. After 1 h reflux, add more TFA (2 mL) and tert-butyl alcohol (2 mL). After 16 h reflux, rotary evaporate the reaction solution (80° C.) giving a dark-brown solid. Transfer this material to a column of silica gel (235 mm×35 mm dia.) and elute (0-10% EtOAc/hex) the desired 3-tert-butyl-1H-indole which co-elutes with a trifluoroacetate derivative of itself (3:1) yielding 284 mg of a brown oil. Elute this material with (10% EtOAc/hex) again through a column of silica gel (125 mm×25 mm dia.) yielding 124 mg (8.4%) of pure 3-tert-butyl-1H-indole as a light-orange crystalline solid. MS (m/z): 173.

Preparation 28

1-Bromo-1-methyl-cyclopentane

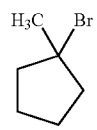

Stir 1-methylcyclopentanol (1.12 g, 11.2 mmol, 1 equiv) vigorously with aq HBr (48%; 5.0 mL, 7.4 g [0.48]=3.6 g HBr, 44 mmol, 4.0 equiv) for 30 min. Separate the organic layer and extract the aqueous layer with hexanes (5 mL). Combine the organic layers, dry (anhydr $MgSO_4$) and rotary evaporate (35° C.; some of the product distills) yielding 657 mg (36.0%) of 1-bromo-1-methyl-cyclopentane as a light-green liquid.

Preparation 29

3-(1-Methyl-cyclopentyl)-1H-indole

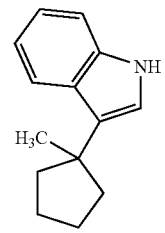

Add N,N-Diisopropylethylamine (890 μL, 660 mg, 5.1 mmol, 2.2 equiv) to a mixture of indole (410 mg, 3.5 mmol, 2.0 equiv), tetrabutylammonium iodide (860 mg, 2.3 mmol, 1.0 equiv), and zinc triflate (1000 mg, 2.8 mmol, 1.2 equiv) in anhydrous toluene (10 mL). After stirring 15 min, add 1-bromo-1-methyl-cyclopentane (380 mg, 2.3 mmol, 1 equiv). After 15 h, quench the reaction mixture with satd aq $NH_4Cl$ (10 mL). Separate the organic layer and extract the aqueous layer with $Et_2O$ (10 mL). Dry the combined organic layers (anhydr $MgSO_4$) and rotary evaporate (40° C.) to give 440 mg of material as a light-yellow oil. Transfer this material to a column of silica gel (125 mm×25 mm dia.) and elute (5-20% $CH_2Cl_2$/hex). Much desired product co-elutes with starting material indole. Transfer this material to a column of silica gel (80 mm×20 mm dia.) and elute (0-15% $CH_2Cl_2$/ hex) to yield 99 mg (21%) of pure 3-(1-methyl-cyclopentyl)-1H-indole as a colorless oil. MS (m/z): 199.

Preparation 30

1-[(Toluene-4-sulfonyl)-1H-indol-3-yl]-ethanone

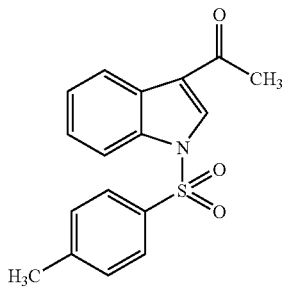

Add 1.0 M t-BuOK (3.0 mL, 0.003 mol) to a stirring solution of 3-acetyl indole (0.478 g, 0.0030 mol) in dry DMF (20 mL) under $N_2$ at ambient temperature and stir for 30 min. Add toluenesulfonyl chloride to this solution and stir the resulting mixture overnight. Pour the reaction into EtOAc—$H_2O$, separate the organic layer and extract several times with $H_2O$ wash with brine, dry ($MgSO_4$), filter, and evaporate on the rotary evaporator. Chromatograph on the ISCO eluting with a gradient hexane-EtOAc (0-100%) over 30 minutes to give 0.73 g (78%) of the title compound as a solid: $^1H$ ($CDCl_3$). δ 7.8 (d, 1H), 8.2 (s, 1H), 7.9 (d, 1H), 7.7 (d, 2H), 7.4 (m, 2H), 7.3 (d, 2H), 2.6 (s, 3H), 2.4 (s, 3H).

Preparation 31

2-[1-(Toluene-4-sulfonyl)-1H-indol-3-yl]-pro-pan-2ol

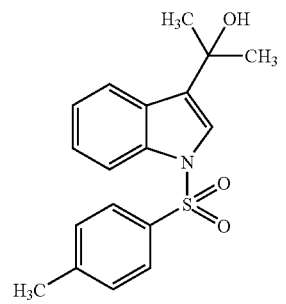

Add methyl magnesium bromide 3.0M (0.40 mL) to a stirring solution of 1-[(toluenesulfonyl)-1H-indol-3-yl]-ethanone 0.31 g, 0.0010 mol) in dry THF under $N_2$ at −30. A solid precipitates immediately. Allow the reaction mixture to warm to 0-10° C. and stir for 1 h. Cool the mixture in an ice bath and quench with a saturated solution of $NH_4Cl$. Dilute with $Et_2O$, and separate the organic layer, wash with brine, dry ($MgSO_4$) filter. Concentrate to give an oil (0.36 g). Chromatograph using a gradient hexane-EtOAc (0-100 over 30 minutes) to give 0.20 g (62%) of the desired as an off white solid: $^1H$ NMR ($CDCl_3$) δ 8.0 (d, 1H) 7.8 (m, 3H), 7.45 (s, 1H), 7.4-7.2 (m, 4H), 2.4 (s, 3H), 1.7 (s, 6H).

Preparation 32

3-Isopropyl-1-(toluene-4-sulfonyl-1H-indole

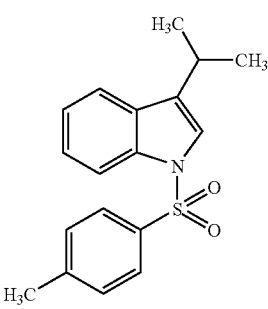

Add TFA (1.35 mL, 0.0174 mol) to a stirring solution of 2-[1-(Toluene-4-sulfonyindol-3-yl]-propan-2ol (0.358 g, 0.001 mol) in $CH_2Cl_2$ (20 mL) at 0° C. Stir the resulting mixture at 0-5° C. for 1 h and allow to warm to ambient temperature and stir for 1½ h. Pour the solution into a mixture of saturated $NaHCO_3$—$CH_2Cl_2$. Separate the organic layer, filter, and evaporate on the rotary evaporator to give 0.103 g of the desired compound: $^1H$ NMR ($CDCl_3$) δ 8.0 (d, 2H), 7.8 (d, 2H), 7.55 (d, 1H), 7.3-7.2 (m, 5H), 3.1 (m, 1H), 2.38 (3H), 1.28 (d, 6H).

Preparation 33

3-Isopropyl indole

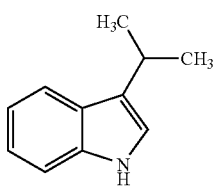

Add five molar NaOH (3.0 mL), 0.015 mol) to a suspension of 3-isopropyl-1-(toluene-4-sulfonyl)-1H-indole 0.100 g, 0.032 mmol) in EtOH (6.0 mL) at ambient temperature and heat the resulting mixture and stir at 90° C. overnight. Dilute the mixture with $H_2O$ (5.0 mL) and concentrate on the rotary evaporatory. Extract the resulting suspension with $Et_2O$. Separate the organic layer, dry ($MgSO_4$) and filter. Evaporate to give the title compound 0.0387 (77%) as a yellow oil: $^1H$ NMR (CDCl₃) δ 7.88-7.82 (bs, 1H), 7.7 (d, 1H), 7.4 (d, 1H), 7.25 (t, 1H), 7.2 (t, 1H), 7.0 (d, 1H), 3.3 (m, 1H), 1.43 (d, 6H).

Preparation 34

4-(3-Phenyl-indole-1-sulfonyl)-benzoic acid

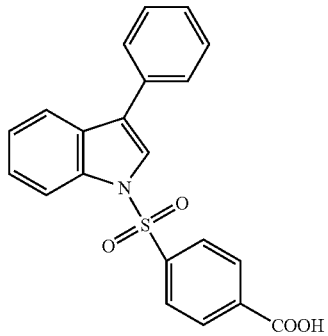

Add to a 2 L 3-neck flask equipped with reflux condenser, thermometer and nitrogen inlet, 4-(3-iodo-indole-1-sulfonyl)-benzoic acid methyl ester (0.1 mol, 44.1 g), phenylboronic acid (0.12 mol, 22.35 g), 1,1-bis(diphenylphosphino)ferrocene dichloropalladium (0.0025 mol, 2.04 g), 2M sodium carbonate (140 ml) and 0.5 L THF. Heat the mixture to reflux under nitrogen for 2 hours. Remove THF under vacuum, and add MTBE (500 ml) and DI water (200 ml) to the residue. Filter the solution through a pad of Celite, and wash with MTBE (500 ml). Separate the organic layer and concentrate under vacuum to give a brown solid. Dissolve the solid in THF (250 ml). Add to this solution 5N NaOH (35 ml) dropwise over a 30 minute period. Stir the reaction at ambient temperature for 3 hours, and quench with DI water (250 ml) and MTBE (250 ml). Separate the water layer and back extract the organic layer with DI water (250 ml). Combine the aqueous layers and wash with MTBE (500 ml). Stir the aqueous layer at ambient temperature and adjust the pH is to 1 with concentrated HCl. Stir the slurry at ambient temperature for 2 hours, filter and wash with DI water (500 ml). Dry the off-white, gray solid in vacuum oven at 65° C. for 16 hours to obtain 25.44 g. ¹H NMR (DMSO) 8.2 (d, 2H), 8.1 (m, 3H), 7.9 (d, 1H), 7.7 (d, 2H), 7.4 (m, 5H). MS (ES-)=376.2 (M-1). Anal. Calcd. For C₂₁H₁₅NO₄S: C, 66.8308; H, 4.0060; N, 3.7112. found C, 66.54; H, 4.07; N, 3.20.

Preparation 35

4-(3-Isopropyl-indole-1-sulfonyl)-benzoic acid methyl ester

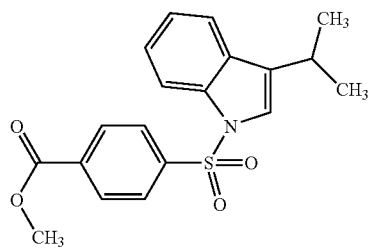

Add potassium tert butoxide 1.0 M (1.6 mL, 0.0016 mol) dropwise to a stirring solution of 3-isopropyl indole (0.217 g, 00136 mol) in dry DMF (20 mL) under N₂ at ambient temperature. Stir the reaction mixture for 30 minutes and add portionwise 4-chlorosulfonyl benzoic acid methyl ester (0.328 g, 0.0014 mol). The light brown reaction mixture decolorizes immediately. Stir the resulting yellow solution overnight. Pour into a EtOAc—H₂O mixture (100 to 300 mL). Separate the EtOAc and sequentially extract with H₂O (3×250 mL), wash with brine, dry (MgSO₄), filter and evaporate giving 0.38 g. Chromatograph on the ISCO using a gradient hexane-EtOAc (0-50%, 30 30 minutes) to give 0.249 g (51%) of the title compound as a waxy solid. Mass spectrum (m/e) (M+H) 358.1113. found (M+H) 358.1129.

Preparation 36

4-(3-Isopropyl-indole-1-sulfonyl)-benzoic acid

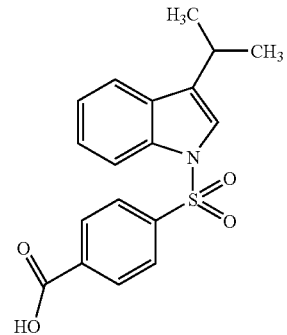

Add five molar NaOH (1.5 mL 0.0075 mol) to a stirring solution of 4-(3-isopropyl-indole-1-sulfonyl)-benzoic acid methyl ester (0.230 g, 0.00061 mol) in THF (10.0 mL) at ambient temperature under N₂. Stir the resulting mixture overnight Dilute with 5% NaHCO₃ (75 mL) and extract with Et₂O. Separate the aqueous layer and acidify with 37% HCl. Extract the resulting precipitate into EtOAc, wash with brine, dry (MgSO₄), filter and evaporate giving 0.187 g of the title compound as an off white solid: Mass spectrum (m/e) (M−H) 342.0800; Found (M−H) 342.0802.

Preparation 37

4-[3-(2-Fluoro-pyridin-3-yl)-indole-1-sulfon)]-benzoic acid

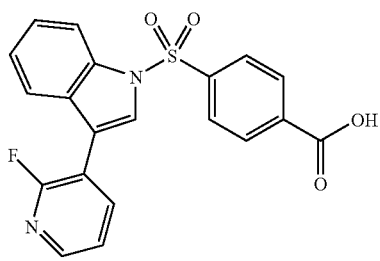

Reflux a mixture of 4-(3-iodo-indole-1-sulfonyl)-benzoic acid methyl (ester (1.33 g, 3.01 mmol, 1 equiv), 2-fluoropyridine-3-boronic acid (Frontier Scientific®; 0.47 g, 3.3 mmol, 1.1 equiv), sodium carbonate (2M in H₂O; 3.0 mL, 6.0 mmol, 2.0 equiv), and [1,1'-bis(diphenylphosphino)ferrocene] dichloropalladium(II) complex with dichloromethane (62 mg, 0.080 mmol, 0.025 equiv) in THF (15 mL) under N₂ for 2 h (reaction mixture turned very dark when heated). Rotary evaporate the reaction mixture. Dissolve the resultant residue in Et₂O (15 mL) and wash with H₂O (5 mL). Back-extract the aqueous layer is with Et₂O (5 mL). Dry the combined organic layers with (anhydr Na₂SO₄), and rotary evaporate (40° C.) giving the crude 4-[3-(2-fluoro-pyridin-3-yl)-indole-1-sulfonyl]-benzoic acid methyl ester as a brown foam. Dissolve this material in THF (10 mL) and add 5M aq NaOH (2 mL). After 18 h, add H₂O (25 mL) and Et₂O (25 mL). Separate the aqueous layer and extract the organic layer with H₂O (25 mL). Combine the aqueous layers and wash with Et₂O (25 mL). Acidify this aqueous layer with 1M aq HCl (8 mL) to pH 5 causing much precipitation. Extract this mixture with CHCl₃ (1×50 mL, 2×25 mL). Dry the combined organic layers (anhydr Na₂SO₄) and rotary evaporate (40° C.) yielding 673 mg (56.3%) of 4-[3-(2-fluoro-pyridin-3-yl)-indole-1-sulfonyl]-benzoic acid as a brown powder. MS (m/e): 396.94 (M+1); 394.99 (M−1).

Preparation 38

4-[3-(6-Fluoro-pyridin-3-yl)-indole-1-sulfonyl]-benzoic acid

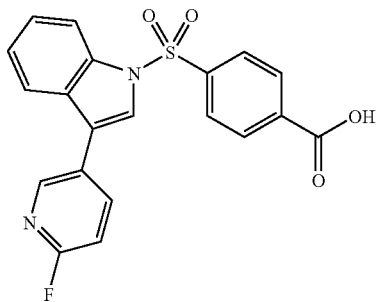

Prepare the title compound by a similar method described for 4-[3-(2-fluoro-pyridin-3-yl)-indole-1-sulfonyl]-benzoic acid using 4-(3-iodo-indole-1-sulfonyl)-benzoic acid methyl ester (1.33 g, 3.01 mmol, 1 equiv), 2-fluoropyridine-5-boronic acid (Frontier Scientific®; 0.47 g, 3.3 mmol, 1.1 equiv) to give 965 mg (80.8%) of brown powder. MS (m/e): 396.94 (M+1); 394.98 (M−1).

Preparation 39

4-(3-Cyclopropyl-indole-1-sulfonyl)-benzoic acid methyl ester

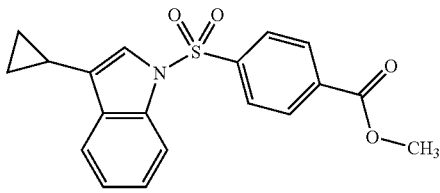

Add a solution of tetrabutylammonium fluoride (3.0 mL, 3.0 mmol; 1.0M in THF) to a solution of 3-cyclopropyl-1-triisopropylsilanyl-1H-indole (0.76 g, 2.4 mmol) in THF (15.0 mL). Stir at RT for 15 min, concentrate to a viscous oil, and re-dissolve in Et₂O (50 mL). Wash the organic solution with water (30 mL) and satd NaHCO₃ (30 mL). Dry, filter and concentrate the organic solution and purify the residue by flash chromatography, using a linear gradient of 100% hexanes to 30% EtOAc/hexanes, to give the title compound as a light yellow oil still containing triisopropylfluoride as an impurity. Use the material directly in the next reaction without further purification.

Add potassium ter-t-butoxide (280 mg, 2.49 mmol) to a solution of the above 3-cyclopropyl-1H-indole in DMF (10.0 mL). Treat the solution with 4-chlorosulfonyl-benzoic acid methyl ester (590 mg, 2.51 mmol) and stir at RT for 2 h. Dilute the solution with EtOAc (30 mL) and wash with water (20 mL) and satd NaHCO₃ (20 mL). Dry, filter and concentrate the organic solution and purify the residue by flash chromatography, using a linear gradient of 100% hexanes to 20% EtOAc/hexanes, to give the title compound as a light yellow oil (505 mg, 59%, 2 steps). MS (ES) 355.9 (M+1)+.

Preparation 40

4-(3-Cyclopropyl-indole-1-sulfonyl)-benzoic acid

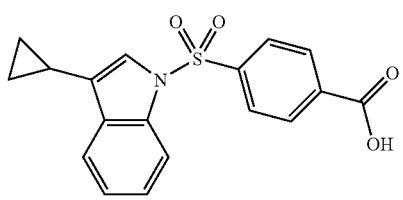

Add lithium hydroxidemonohydrate (181 mg, 4.31 mmol) to a solution of 4-(3-cyclopropyl-indole-1-sulfonyl)-benzoic acid methyl ester (505 mg, 1.42 mmol) in 3:1 dioxane:water (6.0 mL). Stir the mixture at RT for 4 h, dilute with water (80 mL) and add 1N HCl until mixture reaches pH 2. Collect the white solid by filtration and dry overnight under vacuum to give the title compound (450 mg, 93%). MS (ES) 341.9 (M+1)+, 340.1 (M−1)−.

Preparation 41

4-[3-(4-Hydroxy-tetrahydro-pyran-4-yl)-indole-1-sulfonyl]-benzoic acid methyl ester

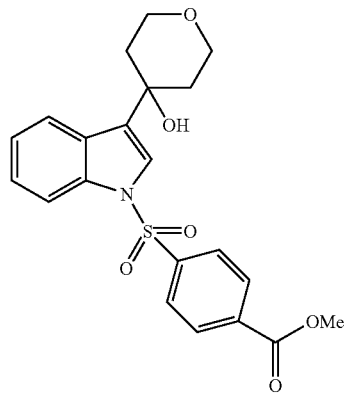

[Note: Dry all glassware in an oven at 120° C. and assemble warm prior to reaction.] Equip a 5-L 3-neck roundbottom flask with an overhead stirrer, temperature probe, $N_2$ line, and septa and charge with 4-(3-iodo-indole-1-sulfonyl)-benzoic acid methyl ester (159.0 g, 0.360 mol). Introduce THF (1 L) via cannula and stir the solution and cool to −75° C. under $N_2$. Dry a dropping funnel as above and assemble on the flask and add 2 M cyclopentylmagnesium bromide in diethyl ether (200 mL, 0.400 mol) to the dropping funnel via cannula. Add dropwise the solution over 0.5 h and stir the resulting mixture for 0.5 h. Warm the mixture to 0° C., stir an additional 0.5 h, cool back down to −10° C., and treat with a solution of tetrahydro-4H-pyran-4-one (43.0 g, 0.429 mol) in THF (100 mL) add via cannula to a new previously dried dropping funnel. Add the ketone over 0.5 h as to maintain the internal temperature below −10° C. Warm the solution to room temperature and stir for 1.5 h in the process. Quench the mixture under $N_2$ by the addition of aqueous saturated ammonium chloride (1 L), separate layers, and dry the organic layer over sodium sulfate. Concentrate to provide a dark oil and dissolve in MTBE (1 L). Addition of 0.5 L of hexanes provides a solid and allows the solid to stand overnight at room temperature. Filter the solid, back-wash with 2:1 MTBE/hexanes (150 mL) to give a tan solid. Reslurry the solid in ethyl acetate (1 L), stir at room temperature for 2 h, filter, dry (20 mm Hg, 50° C.) and found to be highly title compound (49.2 g, 33%); $^1$H NMR (DMSO-$d_6$) δ 8.15 (m, 4H), 7.94 (d, J=8.2 Hz, 1H), 7.88 (d, J=7.7 Hz, 1H), 7.60 (s, 1H), 7.36 (t, J=7.7 Hz, 1H), 7.27 (t, J=7.7 Hz, 1H), 5.27 (s, 1H), 3.85 (s, 3H), 3.81 (m, 2H), 3.69 (m, 2H), 2.06 (m, 2H), 1.78 (m, 2H); MS (ESI) m/z 398 (m+H, m−$H_2O$). [Note: Concentrate the filtrate from the ethyl acetate reslurry and filter the resulting solid from methylene chloride/hexanes/ethyl ether to provide a second crop of alcohol of good quality, 32 g. Thus, the overall yield is 81.2 g, 54%. Concentrate the initial filtrate from the MTBE/hexanes crystallization to an oil and addition of methylene chloride/hexanes/ethyl ether to provide a solid consisting majorly of the corresponding 3-protoindole analog, 28 g.

Preparation 42

4-[3-(Tetrahydro-pyran-4-yl)-indole-1-sulfonyl]-benzoic acid methyl ester

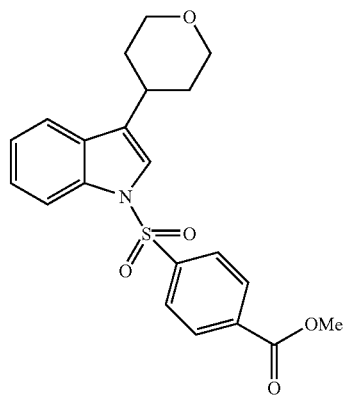

Add to a solution of 4-[3-(4-hydroxy-tetrahydro-pyran-4-yl)-indole-1-sulfonyl]-benzoic acid methyl ester (20.0 g, 48.19 mmol) in anhydrous methylene chloride (500 mL) at room temperature, triethylsilane (20.0 mL, 125.19 mmol) and trifluoroacetic acid (61.5 mL, 798.2 mmol). Stir the resulting solution for 1 h, concentrate, and obtain the oil and partition between ethyl acetate (500 mL) and saturated sodium bicarbonate (500 mL). Dry the organic layer over sodium sulfate, filter through a silica gel pad, and back-wash with ethyl acetate (400 mL). Concentrate the filtrate to low volume, add hexanes, and a separate the solid. Filter the solid and hold aside, 14 g. Concentrate the filtrate to low volume and add MTBE to provide a second crop of crystals, filter and found identical by TLC (3:2 hexanes/ethyl acetate) to the original lot, 2.8 g. Combine the two lots and dry (20 mmg Hg, 40° C.) to provide one lot of highly pure title compound for subsequent hydrolysis (16.8 g, 87%); $^1$H NMR (DMSO-$d_6$) δ 8.10 (m, 4H), 7.93 (d, J=8.2 Hz, 1H), 7.68 (d, J=7.7 Hz, 1H), 7.57 (s, 1H), 7.37 (t, J=7.7 Hz, 1H), 7.28 (t, J=7.1 Hz, 1H), 3.94 (m, 2H), 3.85 (s, 3H), 3.50 (t, J=11.5 Hz, 2H), 3.03 (m, 1H), 1.86 (m, 2H), 1.70 (m, 2H); MS (ESI) m/z 400 (m+H).

Preparation 43

4-[3-(Tetrahydro-pyran-4-yl)-indole-1-sulfonyl]-benzoic acid

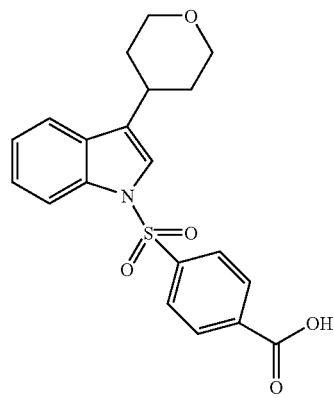

Add to a suspension of 4-[3-(tetrahydro-pyran-4-yl)-indole-1-sulfonyl]-benzoic acid methyl ester (16.7 g, 41.83 mmol) in methanol (200 mL) with stirring THF (600 mL). Treat the solution with 5N NaOH (23.5 ml, 2.8 eq.) and stir for 2 h at room temperature. Concentrate the solution to near dryness and treat with 1N HCl (125 mL), a solid separates. Dilute to 500 mL total volume with water, filter, back-wash with water, and dry (20 mm Hg, 60° C.) to give a resulting solid found to be pure title compound (15.8 g, 98%); $^1$H NMR (DMSO-$d_6$) 13.57 (s, 1H), 8.08 (m, 4H), 7.93 (d, J=8.2 Hz, 1H), 7.68 (d, J=8.2 Hz, 1H), 7.57 (s, 1H), 7.37 (t, J=8.2 Hz, 1H), 7.27 (t, J=7.1 Hz, 1H), 3.95 (m, 2H), 3.47 (t, J=12.0 Hz, 2H), 3.03 (m, 1H), 1.85 (m, 2H), 1.70 (m, 2H); MS (ESI) m/z 384 (m−H).

Preparation 44

4-(3-Cyclopent-1-enyl-indole-1-sulfonyl)-benzoic acid methyl ester

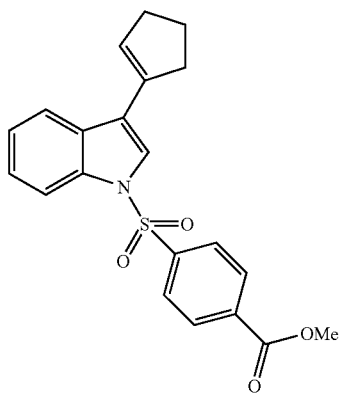

Add to a 2-L 3-neck round bottom flask equipped with overhead stirrer, N$_2$ line, and temperature probe 4-(3-Iodo-indole-1-sulfonyl)-benzoic acid methyl ester (69.0 g, 0.156 mol) and anhydrous DMF (700 mL). Add to the stirring solution at room temperature cyclopentene (138.0 mL, 1.57 mol), palladium II acetate (1.8 g, 0.0 mmol), tetrabutylammonium chloride (43.5 g, 0.156 mol), and potassium acetate (46.0 g, 0.469 mol). Warm the resulting dark mixture at 60-65° C. for 16 h. Cool the reaction mixture filter through celite, and back-wash with ethyl acetate (1 L). Partition the solution with 2×1 L of brine, dry the organic layer over sodium sulfate, and chromatographe over flash silica gel (10% ethyl acetate in hexanes gradually increasing to 20% ethyl acetate in hexanes) to provide pure title compound (48.3 g, 81%); MS (ESI) m/z 382 (m+H); $^1$H NMR (DMSO-d$_6$) reveals the material to actually be a mixture of olefinic 3-substituted cyclopentene indoles (approx. 1:1, with olefinic H's at 5.8, 5.9, and 6.0 ppm integrating to 1H each), suitable as such for subsequent hydrogenation.

Preparation 45

4-(3-Cyclopentyl-indole-1-sulfonyl)-benzoic acid methyl ester

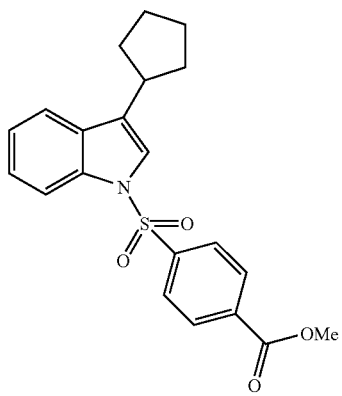

Dissolve 4-(3-cyclopent-1-enyl-indole-1-sulfonyl)-benzoic acid methyl ester (2.2 g, 5.77 mmol) in ethanol (25 mL) and ethyl acetate (25 mL) and hydrogenate with 10% palladium on carbon (300 mg) at 33 psi for 16 h. Filter the catalyst over celite and back-wash with 1:1 ethanol/ethyl acetate (50 mL). Concentrate to give a dark solid and dissolve in 1:1 ethyl acetate/hexanes (50 mL) and pass through a silica gel plug. Back-wash the plug with 1:1 ethyl acetate/hexanes (100 mL) and concentrate the filtrate to an oil, which solidifies upon standing and found to be pure title compound (2.0 g, 90%); $^1$H NMR DMSO-d$_6$) δ8.10 (m, 4H), 7.93 (d, J=8.2 Hz, 1H), 7.55 (d, J=7.7 Hz, 1H), 7.53 (s, 1H), 7.36 (t, J=7.1 Hz, 1H), 7.28 (t, J=7.7 Hz, 1H), 3.84 (s, 3H), 3.16 (m, 1H), 2.08 (m, 2H), 1.62 (m, 6H); MS (ESI) m/z 384 (m+H).

Preparation 46

C-(5-Fluoro-pyridin-3-yl)-methylamine

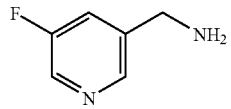

Add to a Parr Bottle 2,6 dichloro-3-cyano-5-fluoropyridine (5 g, 26.18 mmol), ethanol (50 ml), concentrated hydrochloric acid (4.3 ml) and 10% Pd—C (0.5 g). Place on a Parr Shaker Apparatus under 36 psig hydrogen for 6 hours at ambient temperature. Add potassium acetate (10.28 g, 104.72 mmol) and continue under 48 psig hydrogen overnight at ambient temperature. Filter the reaction over Celite and concentrate the filtrate under vacuum to a residue. Add to the residue THF (100 ml). Filter the solid, and concentrate the filtrate under vacuum to give (5-Fluoro-pyridin-3-yl)-methylamine as a clear oil (6 g). $^1$H NMR (DMSO): 8.6 (d, 2H), 8.0 (d, 1H), 4.2 (s, 2H). MS (ES+)=127.5.

Preparation 47

C-(2-Fluoro-pyridin-3-yl)-methylamine hydrochloride

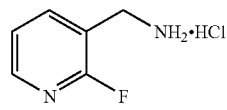

Add concentrated HCl (0.46 mL) to a suspension 2-fluoronicotinonitrile (0.34 g, 2.8 mmol) and 5% Pd/C (0.5 g) in methanol (10 mL) at RT. Stir suspension under an atmosphere of hydrogen at 1 atm. For 6 hours. Filter reaction mixture and concentrate the filtrate. Add ether to the residue, bubble HCl gas through the suspension, filter precipitate, and dry to give the title compound (0.37 g, 82%). MS (ES) 127.1 (M+1)$^+$. $^1$H NMR (400 MHz, DMSO) δ: 8.65 (brs, 3H), 8.24 (m, 1H), 8.16 (m, 1H), 7.41 (m, 1H), 4.06 (m, 2H).

Preparation 48

C-(2-Fluoro-pyridin-4-yl)-methylamine hydrochloride

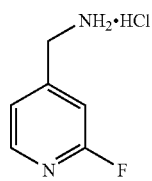

Following a method similar to C-(2-Fluoro-pyridin-3-yl)-methylamine hydrochloride, using 2-fluoro-isonicotinonitrile (0.65 g, 5.3 mmol), concentrated HCl (1.2 mL), and 5% Pd/C (1.2 g) to give the title compound (0.43 g, 50%). MS (ES) 127.1 (M+1)$^+$.

Preparation 49

C-(4-Trifluoromethyl-pyridin-3-yl)-methylamine

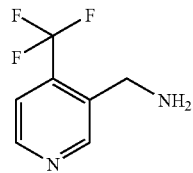

Add Raney nickel (0.5 g) to a solution of 4-trifluoromethyl-nicotinonitrile (1.0 g, 5.8 mmol) in ethanol saturated with ammonia (20.0 mL) and shake under hydrogen at 500 psi for 1 hour. Filter reaction, concentrate the filtrate, and dry the solid obtained to give the title compound (1.0 g, 98%). MS (ES) 177.0 (M+1)$^+$.

Preparation 50

2-Fluoro-isonicotinonitrile

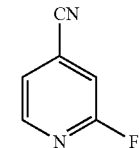

Treat a solution of 2-chloro-4-cyanopyridine (6.0 g, 43.5 mmol) and potassium fluoride (7.56 g, 130.3 mmol) in 1-methyl-2-pyrrolidinone (20 mL) with tetrabutylphosphonium bromide (14.8 g, 43.7 mmol) and heat to 100° C. for 18 hours. Dilute with water and extract with EtOAc. Wash EtOAc with water, brine, dry with Na$_2$SO$_4$, and concentrate to give the title compound (2.3 g, 43%). MS (ES) 123.1 (M+1)$^+$. $^1$H NMR (400 MHz, CHCl$_3$) δ 8.43 (d, 1H, J=5.2 Hz), 7.45 (m, 1H), 7.22 (m, 1H).

Preparation 51

2-Fluoro-nicotinonitrile

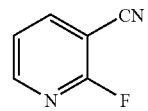

Add resin bound triphenylphosphine (4.0 g, 12.0 mmol) to a solution of 2-fluoro-nicotinamide (0.6 g, 4.3 mmol) in dichloroethane (20.0 mL) and carbon tetrachloride (20.0 mL). Reflux for 18 hours, cool to RT, filter, and concentrate the filtrate under vacuum. Purify by flash column on silica gel eluting with 10-60% EtOAc in hexanes to give the title compound (0.34 g, 64%). MS (ES) 123.1 (M+1)$^+$. $^1$H NMR (400 MHz, CHCl$_3$) δ 8.46 (m, 1H), 8.09 (m, 1H), 7.37 (m, 1H).

Preparation 52

2-Fluoro-nicotinamide

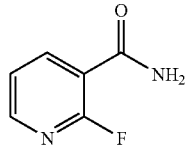

Add thionyl chloride (40 mL) to 2-fluoro-nicotinic acid (2.0 g, 14.3 mmol), reflux for 18 hours, cool to RT, and concentrate under vacuum. Add benzene (100 mL) to the residue and bubble ammonia gas into suspension for 3 hours. Stopper flask, stir for another 18 hours, and concentrate. Add water to residue and extract with EtOAc. Wash EtOAc with water, brine, then dry with Na$_2$SO$_4$, and concentrate under vacuum to give the title compound (0.6 g, 30%). MS (ES) 141.1 (M+1)$^+$. $^1$H NMR (400 MHz, CHCl$_3$) δ 8.32 (d, 1H, J=4.5), 8.17 (m, 1H), 7.92 (brs, 1H), 7.79 (brs, 1H), 7.44 (m, 1H).

Preparation 53

C-Pyrazin-2-yl-methylamine

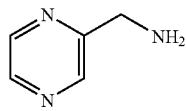

In a Parr bottle, charge pyrazine-2-carbonitrile (1 g) in absolute ethanol (10 ml). Add 10% Pd—C (w/w, 0.4 g) and place on a Parr Hydrogenation Apparatus under 50 psig hydrogen at ambient temperature for sixteen hours. Filter the

Preparation 54

C-Pyridazin-3-yl-methylamine

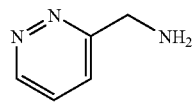

Hydrogenate pyridazine-3-carbonitrile using H₂, NH₃, MeOH, Raney Nickel at 40° C. and 60 psi. Filter crude material to remove catalyst. Dissolve in MeOH and purify on an SCX column to give basic material. Use material crude in the amide coupling without further purification.

Preparation 55

2-Methoxy-cyclohexylamine

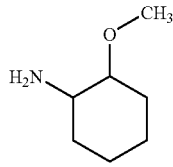

Shake a mixture of o-anisidine (5.0 g, 41 mmol) and rhodium on carbon (5% Rh; 5.0 g) in AcOH (65 mL) under H₂ (60 psig) at 60° C. for 6 h. Filter the reaction mixture and rotary, evaporate the filtrate (75° C.). Dissolve this material in CHCl₃ (100 mL) and basifiy with satd aq NaHCO₃ (50 mL). Dry the organic layer (Na₂SO₄) and rotary evaporate (40° C.) to yield 1.20 g of 2-methoxy-cyclohexylamine as a yellow oil.

Preparation 56

1-(4-Fluoro-phenyl)-piperidin-4-ylamine

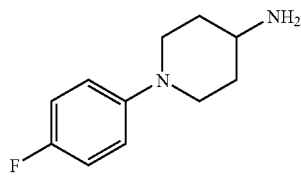

Stir 4-Bromo-fluorobenzene (0.300 g, 1.714 mmole), 4-Boc-amino-piperidine (0.411 g, 2.057 mmoles), sodium tert-butoxide (0.230 g, 2.4 mmole), Tris(Dibenzylideneaceton)Dipalladium (0.249 g, 0.257 mmole), 2-(Di-t-butylphosphineol-biphenol (0.1278 g, 0.4285 mmole) in toluene until reaction is complete. Dilute solution with EtOAc and filter. Concentrate the residue and purify via column chromatography with a mixture of EtOAc and hexane. Stir the isolated material in TFA and remove solvent. Dilute the residue with methanol in the presence of hydroxy resin until pH is basic. Decant solvent and concentrate to yield 0.115 g of product (yield=34.5%). Mass Spectrum (m/e) 195.03 (M⁺).

Preparation 57

(R)-1-(4-Fluoro-phenyl)-pyrrolidin-3-ylamine

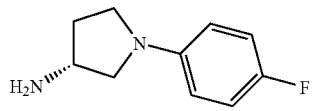

Prepare the title compound by a similar method described for 1-(4-Fluoro-phenyl)-piperidin-4-ylamine above using (R)-2-ditertbutylphosphinobiphenyl (0.108 g, 0.362 mmole) to isolate 0.136 g of solid material (Yield=52%) Mass Spectrum (m/e): 181.0 (M⁻).

Preparation 58

(S)-1-(4-Fluoro-phenyl)-pyrrolidin-3-ylamine

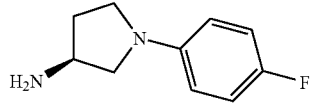

Prepared the title compound by a similar method described for 1-(4-Fluoro-phenyl)-piperidin-4-ylamine above using (S)-2-ditertbutylphosphinobiphenyl (0.108 g, 0.362 mmole) to isolate 0.090 g of solid material (Yield=34%) Mass Spectrum (m/e): 180.99 (M⁺).

Preparation 59

1-(4-Fluoro-phenyl)-azetidin-3-yl-amine

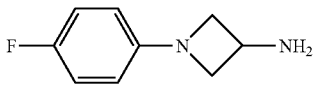

Prepare the title compound by a similar method described for 1-(4-Fluoro-phenyl)-piperidin-4-ylamine above using Azetidin-3-yl-carbamic acid tert-butyl ester (0.270 g, 0.186 mmole) to isolate 0.115 g of solid material (Yield=47%) Mass Spectrum (m/e): 168 (M⁺).

Preparation 60

C-(1-Phenyl-piperidin-4-yl)-methylamine

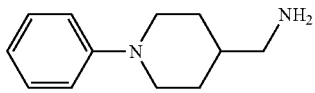

Prepare as in methods described in J. of Med. Chem. 1999 vol. 42 (no 17) p 3342-3355.

Preparation 61

[1-(4-Fluoro-phenyl)-azetidin-3-ylmethyl]-carbamic acid tert-butyl ester

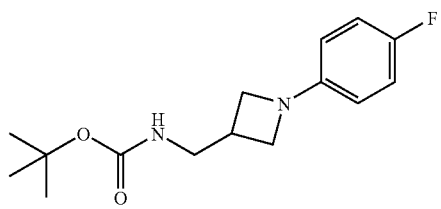

Prepare the title compound by a similar method described for [3-[(4-Fluoro-phenylamino)-methyl]-azetidin-1-yl]-[4-(3-phenyl-indole-1-sulfonyl)-phenyl]-methanone using azetidin-3-ylmethyl-carbamic acid tert-butyl ester (215 mg, 1.15 mmol) to isolate 137 mg (42.3%) of light-yellow foam. MS (m/e): 225.00 (M+1−C$_4$H$_8$).

Preparation 62

3-(tert-Butoxycarbonylamino-methyl)-azetidine-1-carboxylic acid methyl ester

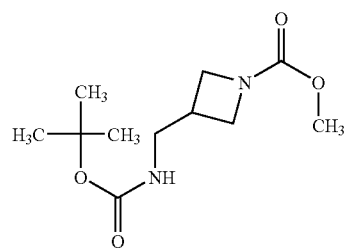

Prepare the title compound by a similar method described for 3-[4-(3-phenyl-indole-1-sulfonyl)-benzoylamino]-azetidine-1-carboxylic acid methyl ester using azetidin-3-ylmethyl-carbamic acid tert-butyl ester (Beta Pharma; 559 mg, 3.00 mmol, 1 equiv) to isolate 686 mg (93.6%) of colorless oil.

Preparation 63

3-Aminomethyl-azetidine-1-carboxylic acid methyl ester

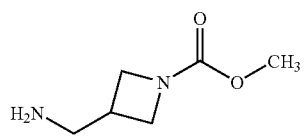

Prepare the title compound by a similar method described for (3-aminomethyl-azetidin-1-yl)-[4-(3-phenyl-indole-1-sulfonyl)-phenyl]-methanone using 3-(tert-butoxycarbony-lamino-methyl)-azetidine-1-carboxylic acid methyl ester (675 mg, 2.76 mmol) to isolate 399 mg (100%) of light-yellow oil. MS (m/e): 144.98 (M+1).

Preparation 64

[1-(4-Fluoro-phenyl)-pyrrolidin-3-yl]-carbamic acid tert-butyl ester

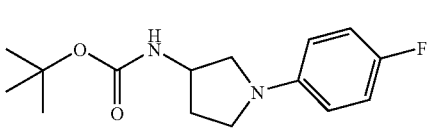

Prepare the title compound by a similar method described for N-[1-(4-fluoro-phenyl)-azetidin-3-yl]-4-(3-phenyl-indole-1-sulfonyl)-benzamide using 3-(tert-butoxycarbonylamino) pyrrolidine to isolate 341 mg (60.7%) of light-yellow crystalline solid. MS (m/e): 281.00 (M+1).

Preparation 65

1-(4-Fluoro-phenyl)-pyrrolidin-3-ylamine

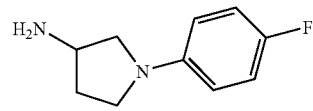

Prepare the title compound by a similar method described for (3-aminomethyl-azetidin-1-yl)-[4-(3-phenyl-indole-1-sulfonyl)-phenyl]-methanone using [1-(4-fluoro-phenyl)-pyrrolidin-3-yl]-carbamic acid tert-butyl ester (330 mg, 1.18 mmol) to isolate 204 mg (95.1%) of yellow oil. MS (m/e): 181.04 (M+1).

Preparation 66

5-Cyano-nicotinic acid methyl ester

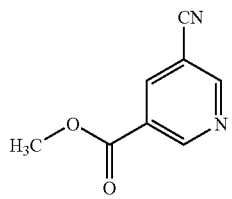

Reflux a solution of methyl 5-bromonicotinate (2.16 g, 10.0 mmol, 1 equiv) and copper(I) cyanide (1.79 g, 20.0 mmol, 2.0 equiv) in anhydr DMF (10 mL) for 15 h. After allowing to cool, filter the reaction mixture through Celite®, rinse with EtOAc (100 mL). A black precipitate forms in the filtrate. Wash the filtrate with salted H$_2$O (3×100 mL). Dry the organic layer (anhydr Na$_2$SO$_4$) and rotary evaporate (40° C.) giving 546 mg (33.7%) of product as a light-yellow solid. Transfer this material to a column of silica gel (80 mm×20 mm dia.) and elute (20-35% EtOAc/hex) to yield 501 mg (30.9%) of 5-cyano-nicotinic acid methyl ester as an off-white solid. MS (m/e): 163.07 (M+1).

Preparation 67

5-Hydroxymethyl-nicotinonitrile

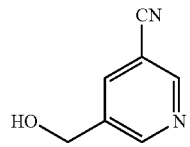

Add lithium aluminum hydride (1.0M in THF; 1.5 mL, 1.5 mmol, 0.5 equiv) over a period of 3 min to a solution of 5-cyano-nicotinic acid methyl ester (479 mg, 2.95 mmol, 1 equiv) in anhydr THF (15 mL) and cool to −78° C. After 1 h while still at −78° C., quench the reaction with $H_2O$ (60 μL), 5M aq NaOH (60 μL), and more $H_2O$ (180 μL). Filter the reaction mixture through paper. Rotary evaporate the filtrate (40° C.) to give 369 mg of material as a yellow solid. Transfer this material to a column of silica gel (130 mm×25 mmdia.) and elute (2% MeOH/$CH_2Cl_2$) to yield 180 mg of a mixture of ester, hemiacetal, and aldehyde as a yellow solid and 45 mg (11%) of 5-hydroxymethyl-nicotinonitrile as a yellow solid. MS (m/e): 163.07 (M+1).

Preparation 68

5-Chloromethyl-nicotinonitrile

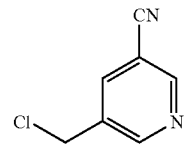

Add thionyl chloride (1 mL) to a solution of 5-hydroxymethyl-nicotinonitrile (45 mg, 0.34 mmol, 1 equiv) in anhydr $CH_2Cl_2$ (1 mL). After 20 min, basify the reaction with satd aq $NaHCO_3$ (12 mL). Extract this mixture with $Et_2O$ (2×5 mL). Dry the combined organic layers (anhydr $MgSO_4$) and rotary evaporate (40° C.) to yield 4.9 mg (9.6%) of 5-chloromethyl-nicotinonitrile as a yellow film. MS (m/z): 152.

Preparation 69

5-Aminomethyl-nicotinonitrile

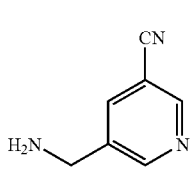

Dissolve 5-chloromethyl-nicotinonitrile (4.9 mg, 0.032 mmol) in 2.0M $NH_3$ in MeOH (1 mL). Transfer this solution to a pressure tube. Heat the reaction solution at 80° C. for 2 h.

Rotary evaporate the reaction solution (40° C.) to yield 5.1 mg of crude 5-aminomethyl-nicotinonitrile as a yellow oil. MS (m/e): 134.00 (M+1).

Preparation 70

Methanesulfonic acid tetrahydro-furan-3-ylmethyl ester

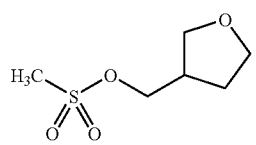

Add triethylamine (6.0 mL, 4.4 g, 43 mmol, 2.1 equiv) to a solution of tetrahydro-3-furanmethanol (2.0 mL, 2.1 g, 21 mmol, 1 equiv) and methanesulfonic anhydride (3.7 g, 21 mmol, 1.0 equiv) in anhydr $CH_2Cl_2$ (100 mL). After stirring 20 h, wash the reaction solution with 1 M aq HCl (100 mL). Dry the organic layer (anhydr $MgSO_4$) and rotary evaporate (40° C.) to yield 2.77 g (74.0%) of methanesulfonic acid tetrahydro-furan-3-ylmethyl ester as a light-yellow liquid.

Preparation 71

3-Azidomethyl-tetrahydro-furan

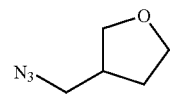

Add sodium azide (1.5 g, 23 mmol, 1.5 equiv) to a solution of methanesulfonic acid tetrahydro-furan-3-ylmethyl ester (2.76 g, 15.3 mmol, 1 equiv) in anhydr DMF (10 mL). Heat the reaction mixture at 50° C. for 16 h. Dilute the reaction mixture with $H_2O$ (100 mL) and extract with $Et_2O$ (2×50 mL). Wash the combined organic layers with $H_2O$ (2×50 mL), dry (anhydr $Na_2SO_4$), and rotary evaporate (40° C.) to yield 1.20 g (61.6%) of 3-azidomethyl-tetrahydro-furan as a nearly-colorless liquid.

Preparation 72

(Tetrahydro-furan-3-yl)-methylamine

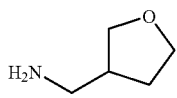

Stir a mixture of 3-azidomethyl-tetrahydro-furan (1.19 g, 9.36 mmol, 1 equiv) and palladium on carbon (10% Pd; 120 mg) in EtOH (20 mL) under $H_2$ (1 atm) for 18 h. Filter the reaction mixture through Celite® and rotary evaporate the filtrate (40° C.) to yield 777 mg (82.1%) of crude (tetrahydro-furan-3-yl)-methylamine as a nearly-colorless liquid.

Preparation 73

4-Aminomethyl-benzonitrile

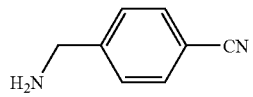

Stir 4-bromomethyl-benzonitrile (2.0 g, 0.010 mmoles) in sealed vessel in a solution of 2N ammonia in methanol at 80° C. until completion. Reduce solvent in volume. Dissolve residue in ethyl acetate and wash with 1N HCl. Basify aqueous layer with 5N NaOH. Extract aqueous layer into dichloromethane. Dry organic layer over $MgSO_4$ and reduce in volume to isolate 0.223 g. Yield=16.8%. Mass Spectrum (m/e): (M−).

Preparation 74

C-(Tetrahydro-pyran-2-yl)-methylamine

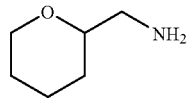

Heat 2-(bromomethyl)tetrahydropyran (2.0 g, 11.16 mmoles), sodium azide (1.088 g, 65.01 mmoles), and DMF to 50° C. with stirring and until reaction is complete. Dilute the reaction mixture with $Et_2O$ and wash with water once. Extract water layer with ether. Combine organic portions and dry over $MgSO_4$ and reduce in volume. Dilute residue ethanol and introduce to 10% Palladium (0.500 g) on carbon in the presence of hydrogen until reaction is complete. Remove palladium on carbon via filtration and concentrated to isolate 0.723 g. Yield=56%.

Preparation 75

3-Amino-pyrrolidine-1-carboxylic acid methyl ester

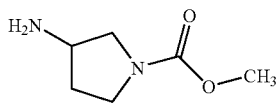

Add methyl chloroformate (460 µL, 560 mg, 6.0 mmol, 3.0 equiv) to a solution of 3-(tert-butoxycarbonylamino)pyrrolidine (TCI; 373 mg, 2.00 mmol, 1 equiv) and triethylamine (1.1 mL, 800 mg, 7.9 mmol, 3.9 equiv) in anhydr $CH_2Cl_2$ (4 mL). Vigorous gas evolution, a slight exotherm, and precipitation can occur. After stirring 30 min, rotary evaporate the reaction mixture (60° C.). Dissolve the resultant material in MeOH to quench any residual chloroformate and rotary evaporate the solution (60° C.). Add trifluoroacetic acid (5 mL) to this material causing gas evolution. Rotary evaporate the reaction solution (40° C.; azeotroping 2× with MeOH). Resultanting in a yellow oil then dissolve in MeOH (30 mL) and add hydroxide resin (Bio-Rad AG® 1-X8, 20-50 mesh; 9.3 g) to free-base the amine. Filter the mixture and evaporate the filtrate by rotary (40° C.; azeotroped 2× with $CH_2Cl_2$) to yield 914 mg (300%) of crude product as a light-brown oil.

Mass spec indicates desired product is present. Absorb this oil to an SCX column (20 g) activated with 10% AcOH/MeOH. Push MeOH through the column to elute any non-amine material. Elute the product with 2.0 M $NH_3$ in MeOH to yield 269 mg (93.2%) of 3-amino-pyrrolidine-1-carboxylic acid methyl ester as a yellow oil.

Preparation 77

N-(4-Fluoro-benzyl)-4-(3-iodo-indole-1-sulfonyl)-benzamide

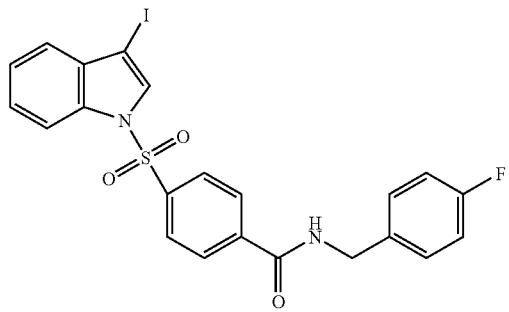

Dissolve indole (2.93 g 0.025 mole) in 10 ml DMF. Cool the solution in an ice-water bath. Add potassium-t-butoxide (3.08 g, 0.0275 mole) and 10 ml DMF. Stir in an ice-bath for 22 minutes. Add iodine (7.61 g, 0.03 mole) and stir in an ice-bath for 12 minutes. Add the second shot of potassium-t-butoxide (3.08 g, 0.0275 mole) and 10 ml DMF. Add the appropriate sulfonyl chloride, 4-(4-fluoro-benzylcarbamoyl)-benzenesulfonyl chloride, (9.01 g, 0.0275 mole) and 10 ml DMF. Stir at ambient temperature for 16 hours. Quench the reaction with 100 ml water, and extract with ethyl acetate (3×150 ml). Wash the organics with sodium metabisulfate (10 g in 100 ml water), water (3×200 ml) and saturated brine (1×200 ml). Concentrate the organics and purify over silica gel using 20% ethyl acetate in heptane to obtain 6.96 g (yield=52.2%) of the desired product as an off-white solid: $^1$H NMR (DMSO): 9.2 (t, 1H), 8.1 (m, 3H), 8.0 (m, 3H), 7.4 (m, 5H), 7.1 (m, 2H), 4.4 (d, 4H). MS (ES−)=532.91 (M−1).

Preparation 78

N-(4-Fluoro-benzyl)-4-[3-(4,4,5,5-tetramethyl-[1,3,2]dioxaborolan-2-yl)-indole-1-sulfonyl]-benzamide

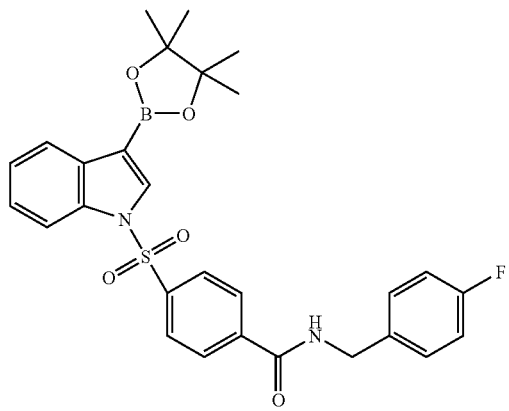

Combine N-(4-fluoro-benzyl)-4-(3-iodo-indole-1-sulfonyl)-benzamide (19 g, 35.65 mmol), bis pinnacolborane (10.86 g, 42.78 mmol), potassium acetate (10.49 g, 106.95 mmol), PdCl$_2$(dppf)$_2$ (2.92 g, 3.57 mmol) in DMF (125 ml). Heat the mixture to 100° C. under nitrogen for 5 hours. Cool the mixture to ambient temperature and quench with ethyl acetate (200 ml) and water (200 ml). Filter the mixture through Celite. Separate the layers and wash the organics with water (3×200 ml) and a saturated brine solution (200 ml). Dry the organics over magnesium sulfate, filter and concentrate to an oil which was crystallized with ether (200 ml). Filter the white solid and dry in a vacuum oven at 50° C. overnight to provide (5.6 g) as a white solid. Mp 158-160° C.; $^1$H NMR (DMSO): 9.2 (t, 1H), 8.1 (m, 3H), 8.0 (m, 3H), 7.4 (m, 5H), 7.1 (m, 2H), 4.4 (d, 4H), 1.3 (s, 12H). MS (ES)=533.4 (M−1).

Preparation 79

4-(3-Cyclopentyl-indole-1-sulfonyl)-benzoic acid

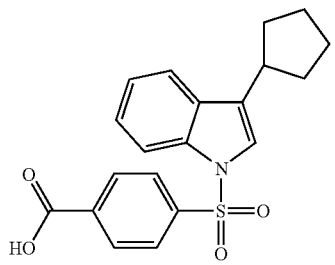

Add to a stirring solution of 4-(3-Cyclopentyl-indole-1-sulfonyl)-benzoic acid methyl ester (2.0 g, 5.22 mmol) in THF (50 mL) and MeOH (25 mL), 5N NaOH (3 mL, 2.9 eq.). Stir the solution for 2 h at room temperature and the remove solvents to give a paste. Treat the paste with 1N HCl (25 mL) and a solid results. Dilute further with water (50 mL). Filter the solid, back-wash with water, and dry (20 mm Hg, 60° C.) to provide the pure title compound (1.63 g, 84%); $^1$H NMR (DMSO-d$_6$) δ 8.06 (m, 4H), 7.93 (d, J=8.2 Hz, 1H), 7.63 (d, J=7.7 Hz, 1H), 7.53 (s, 1H), 7.37 (t, J=7.7 Hz, 1H), 7.28 (t, J=7.7 Hz, 1H), 3.17 (m, 1H), 2.08 (m, 2H), 1.69 (m, 6H); MS (ESI) m/z 368 (m−H).

Preparation 80

4-(3-Chloro-indazole-1-sulfonyl)-N-(4-fluoro-benzyl)-benzamide

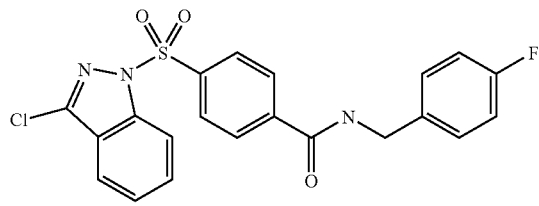

Dissolve 3-chloro-1H-indazole (120 mg, 0.79 mmol) and 4-(4-fluoro-benzylcarbamoyl)-benzenesulfonyl chloride (114 mg, 0.35 mmol) in CH$_2$Cl$_2$ (2.0 mL) and treat with Et$_3$N (50 L, 0.36 mmol). Stir the solution for 1 h at RT, then dilute with additional CH$_2$Cl$_2$ (20.0 mL) and wash with satd aq. NaHCO$_3$ (15 mL). Dry, filter, and concentrate the organic phase and purify the crude material by flash chromatography (100% hexanes to 50% EtOAc/hexanes linear gradient) to give the title compound (129 mg, 83%) as a white foam. MS (ES+) 443.9 (M+1)$^+$, (ES−) 442.0 (M−1)$^−$. $^1$H NMR (400 MHz, CDCl$_3$): δ 8.17 (d, 1H, J=8.3), 8.03 (d, 2H, J=8.2), 7.83 (d, 2H, J=8.9), 7.64 (m, 2H), 7.41 (t, 1H, J=7.4), 7.27 (m, 2H), 7.01 (t, 2H, J=8.9), 6.31 (br s, 1H), 4.57 (d, 2H, J=5.9).

Preparation 81

2-Phenyl-azetidine

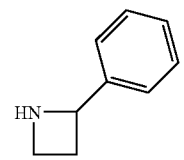

Dissolve 4-phenyl-azetidin-2-one (1.0 g, 4.28 mmol) in anhydrous THF (20 mL) and treat with 1.0 M solution of lithium aluminum hydride (8.57 mL, 2.0 equiv.) at room temperature. Stir for 15 h, cool to 0° C. in an ice bath and quench with 8.5 mL 1.0 M NaOH then 8.5 mL H$_2$O. Filter resulting solution through celite with additional EtOAc, dry with MgSO$_4$, filter and evaporate to yield a milky white oil that solidifies upon standing. Use 2-Phenyl-azetidine without further purification.

Preparation 82

4-(3-Iodo-indole-1-sulfonyl)-benzoic acid methyl ester

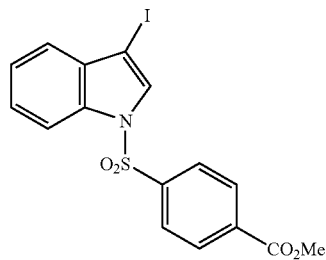

Slurry 250 g of 4-sulfobenzoic acid in 750 ml thionyl chloride. Add 0.5 ml DMF, and heat the mixture to reflux for 6 hours. Add 2 L of toluene and azeotropically remove the thionyl chloride. Cool the mixture to ambient temperature and filter. Concentrate the filtrate under vacuum to give an oil which crystallizes upon standing. To obtain 222 g of 4-Chlorosulfonyl-benzoyl chloride as a low melting solid.

In a 22 L RBF, charge 4-Chlorosulfonyl-benzoyl chloride (990 g, 4.159 mole) in 8.3 L THF and cool to −78° C. In an addition funnel charge triethylamine (588 ml, 4.159 mole), methanol (168 ml, 4.159 mole), DMAP (5 g, 0.041 mole) and 4 L THF; add this solution dropwise to the reaction keeping the exotherm <−70° C. over 5 hours. After the addition is complete, stir the reaction in a cold bath overnight. Filter the reaction and rinse with 3×500 ml THF. Concentrate under vacuum the filtrate to give a yellow solid. Dissolve the solid in 7 L EtOAc and 7 L 1N HCl. Separate the organic layer and wash with 5 L brine. Dry the organics over Na₂SO₄, filter and concentrate under vacuum to give a white solid, 4-Chlorosulfonyl-benzoic acid methyl ester. Yield=93.1% (906 g).

In a 22 L RBF, charge indole (181 g, 1.545 mole) and 800 ml DMF. Cool to <10° C. in an ice-water bath. Add the first shot of potassium-t-butoxide (190.4 g, 1.70 mole). Exotherm to 18.5° C. Rinse with 400 ml DMF. Stir 30 minutes while cooling back to <10° C. Dissolve Iodine (470.6 g) in 400 ml DMF and charge to the addition funnel. Add this solution dropwise to the reaction over 30 minutes. Keeping the temperature <10° C. Stir at <10° C. for 2.5 hours. Add the second shot of potassium-t-butoxide (190.4 g, 1.70 mole) and rinse with 400 ml DMF. Stir 30 minutes while cooling to 10° C. (and add 4-Chlorosulfonyl-benzoic acid methyl ester all at once. Exotherm to 28° C. Rinse with 400 ml DMF. Cool to <10° C. and then stir to ambient temperature overnight. Add 6 L DI water at ambient temperature. Exotherm to 31° C. and reaction is thick with solids. Add 5 L EtOAc and stir 15 min. Filter the solids (which is the product). Obtain 315.1 g white solid as the first crop. Separate the filtrate from the first crop, and extract the aqueous layer 2×3 L EtOAc. Combine all the organics and wash 2×625 g of sodium hydrogensulfite in 4 L DI water and 2×3 L DI water and 1×3 L Brine. Dry organics over Na₂SO₄, filter and rinse with EtOAc. Remove the organics under vacuum to give an orange-yellow solid slurry solid in 4 L ether overnight to give a second crop of product 240 g. Total yield=81.4% (555.1 g). MS (EI) m/z 440.9 (M+H).

Preparation 83

5-Chloro-2-cyanopyridine

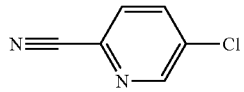

Add in a 22-L 3-neck round bottom equipped with overhead stirrer, reflux condenser, and thermometer, N,N-dimethylacetamide (DMAC, 6 L), 2,5-dichloropyridine (347.0 g, 2.34 mol), zinc cyanide (138.0 g, 1.17 mol), bis(diphenylphosphino)dipalladium II CH₂Cl₂ complex (DPPF, 20.8 g, 0.02 mol), and zinc dust (1.6 g, 0.02 mol). Slowly warm the reaction mixture to 160° C. As the temperature reaches 160° C., an exotherm (controllable) may result and the internal temperature may rise to 180-185° C. Remove the heat from the dark solution and cool the mixture slowly cool to room temperature. Extract the bulk reaction mixture by taking 2 L of the dark solution, diluting with brine (2 L), filtering over celite, and addition of ethyl acetate (4 L). Repeat the process 3 times to extract all material, and dry the combined organics over magnesium sulfate. Cautious concentration at 25-30° C. might give a dark liquid. (Note: Product volatility maybe observed at higher temperatures so the temperature upon concentration is kept low in all steps.) Stir the liquid and add water (5 L), resulting in a solid After 1 h, filter, and back-wash with water (2 L). Dry the filter cake to give 215 g of crude product. Extract the aqueous filtrate with ethyl ether (8 L). Dry the organics over magnesium sulfate and concentrate to provide 51 g of crude product. Combine with the 215 g lot and purify by chromatography over silica gel (biotage 150; eluting with 5% ethyl acetate in hexanes increasing to 10% ethyl acetate in hexanes) to provide a white solid of pure title compound (193 g, 59%); ¹H NMR (CDCl₃) δ 8.68 (d, J=2.0 Hz, 1H), 7.84 (dd, J=2.7, 8.6 Hz, 1H), 7.66 (d, J=8.3 Hz, 1H).

Preparation 84

2-Cyano-5-fluoropyridine

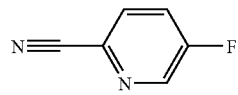

Add in a 5-L 3-neck roundbottom equipped with overhead stirrer, reflux condenser, thermometer, and N₂ line, 5-chloro-2-cyanopyridine (193.0 g, 1.39 mol) and 1-methyl-2-pyrrolidinone (NMP, 2 L). Heat the mixture and stir at 210-220° C. for 4 h. Cool the reaction mixture to room temperature, stir overnight, and filter. Wash the filter cake with ethyl ether (1 L). Extract the filtrate with water (6 L) and ethyl ether (3×5 L). Combine the organics and back-extract with water (8 L) and dry over magnesium sulfate. Concentrate at 25-30° C. to give an oily semi-solid, 193 g. Chromatograph over flash silica gel (5% ethyl acetate in hexanes gradually increasing to 10% ethyl acetate in hexanes) to provide the title compound as a white solid. Dissolve the solid in ethyl ether, filter, and add hexanes. Concentrate to low volume to provide a primary crop of pure title compound, 60 g. Repeat the process of crystallization on the filtrate to provide a second crop of highly pure title compound, 24.0 g. (Concentrate the final filtrate to a white solid of product of good quality, and re-chromatograph, conditions as above, to provide an additional 38.6 g of material.) Obtain a total yield of title compound of 122.4 g, 72%; ¹H NMR (CDCl₃) δ 8.59 (d, J=3.0 Hz, 1H), 7.75 (m, 1H), 7.55 (m, 1H).

Preparation 85

2-Aminomethyl-5-fluoropyridine (dihydrochloride)

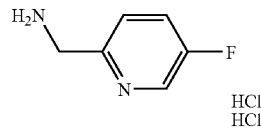

Combine a mixture of 2-cyano-5-fluoropyridine (63.2 g, 0.52 mol), 22.5 g of Raney nickel, and ethanol (1.5 L) saturated with ammonia and hydrogenate at 500 p.s.i. and 70° C. for 16 h. Chromatograph the dark purple liquid over flash silica gel (methylene chloride/methanol/ammonia hydroxide—95:4.5:0.5) to give, after concentration at 25-30° C., a yellow liquid of the pure desired free base, 25.0 g (44%); ¹H NMR (DMSO-d₆) δ 8.43 (d, J=2.9 Hz, 1H), 7.66 (m, 1H), 7.50 (m, 1H), 3.77 (s, 2H), 2.10 (br, 2H); MS (ESI) m/z 127 (m+H). Add to a solution of the free base (20.0 g, 159.0 mmol) in 150 ml of 1,4-dioxane, 4N HCl in dioxane (150 mL, 3.8 eq.) and a white solid separates immediately. Dilute the solid with ethyl ether (300 mL) and filter. Dry the product at 20 mm Hg, 60° C., to give the pure dihydrochloride title compound, 30.0 g (95%); ¹H NMR (DMSO-d₆) δ 8.61 (d, J=2.9 Hz, 1H), 8.50 (brs, 3H), 7.82 (m, 1H), 7.62 (m, 1H), 7.50 (br, 1H), 4.18 (m, 2H); MS (ESI) m/z 127 (m+H, free base).

Preparation 87

N-Pyridin-2-yl-N'-styryl-hydrazine

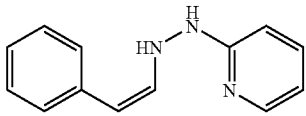

React Pyridin-2-yl-hydrazine and Phenyl-acetaldehyde under literature conditions (Azaindoles. I. Preparation of 7-azaindoles by thermal indolization of 2-pyridylhydrazones. Canadian Journal of Chemistry (1966), 44(21), 2455-9) to give N-Pyridin-2-yl-N'-styryl-hydrazine (10 g, 100% yield crude material) Mass Spectrum (m/e): 211.96 (MH+).

Preparation 88

3-Phenyl-1H-pyrrolo[2,3-b]pyridine

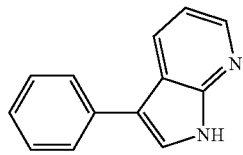

React N-pyridin-2-yl-N'-styryl-hydrazine according to published literature conditions (Azaindoles. I. Preparation of 7-azaindoles by thermal indolization of 2-pyridylhydrazones. Canadian Journal of Chemistry (1966), 44(21), 2455-9) to give 3-Phenyl-1H-pyrrolo[2,3-b]pyridine (2.5 g, 45% yield) as a dark solid. Mass Spectrum (m/e): 194.96 (MH+).

Preparation 91

4-[3-(1-Hydroxy-cyclohexyl)-indole-1-sulfonyl]-benzoic acid methyl ester

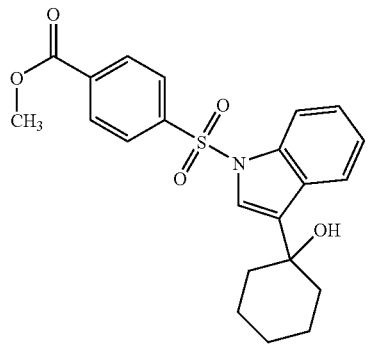

Via addition funnel slowly add over 0.5 hours the 2M EtOEt solution of cyclopropyl magnesium bromide (2.16 g, 6.23 ml, 12.46 mmol, 1.1 eq) to the −78° C. THF solution (30 ml) of 4-(3-Iodo-indole-1-sulfonyl)-benzoic acid methyl ester (5 g, 11.33 mmol, 1.00 eq). Stir for 2 hours and then warm to 0° C. Stir for 0.5 hours. Recool to −10° C. and then slowly add a THF solution (3 ml) of cyclohexanone (1.298 g, 13.03 mmol, 1.15 eq). Stir for 15 min and warm to room temperature. Stir for 1.5 days. Quench reaction with saturated aqueous ammonium chloride, remove organics on rotovap, and add EtOAc to crude mix. Extract product into organics, separate organics, dry over MgSO$_4$, and concentrate on rotovap to give crude product as an oil. Purify by silica gel chromatography to give 4-[3-(1-Hydroxy-cyclohexyl)-indole-1-sulfonyl]-benzoic acid methyl ester (948 mg, 20% yield).

Preparation 92

4-(3-Cyclohexyl-indole-1-sulfonyl)-benzoic acid methyl ester

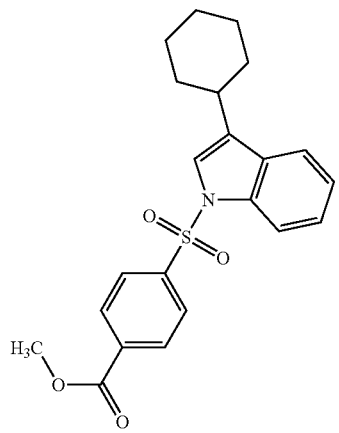

Under N$_2$, add triethylsilane (676 mg, 0.929 ml, 5.82 mmol, 2.6 eq) followed by trifluoroacetic acid (4.08 g, 2.7 ml, 35.79 mmol, 16.0 eq) to a CH$_2$Cl$_2$ solution (20 ml) of 4-[3-(1-Hydroxy-cyclohexyl)-indole-1-sulfonyl]-benzoic acid methyl ester (9.25 mg, 2.24 mmol, 1 eq). Stir for 1.5 hours and then remove volatiles on rotovap. Add EtOAc to crude mix and workup with sat aqueous sodium bicarbonate. Extract product into organics, separate organics, dry over MgSO$_4$, and concentrate on rotovap to give crude product as a pink oil. Purify by silica gel chromatography to give 4-(3-Cyclohexylindole-1-sulfonyl)-benzoic acid methyl ester (775 mg, 87% yield) as a white solid. Mass Spectrum (m/e): 397.99 (MH+).

Preparation 93

4-(3-Cyclohexyl-indole-1-sulfonyl)-benzoic acid

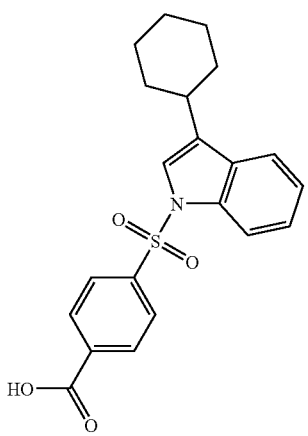

Add 5N sodium hydroxide (1.17 ml, 3 eq) to a solution of 4-(3-Cyclohexyl-indole-1-sulfonyl)-benzoic acid methyl ester (775 mg, 1.95 mmol, 1 eq) dissolve in a mixture of 10 ml THF and 5 ml MeOH. Stir for 1.5 hours. Remove solvent on rotovap and add 1 N HCl. Dissolve the solid that crashes out of solution in EtOAc. Extract product into organics, separate organics, dry over MgSO$_4$, and concentrate on rotovap to give 4-(3-Cyclohexyl-indole-1-sulfonyl)-benzoic acid (646 mg, 86% yield) as a white solid.

Preparation 94

4-[3-(3,3-Difluoro-cyclopentyl)-indole-1-sulfonyl]-benzoic acid methyl ester

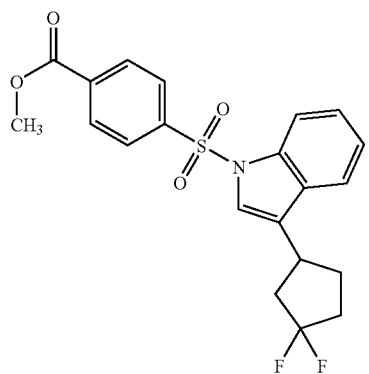

Add potassium tertbutoxide (368 mg, 3.28 mmol, 1.1 eq) to a 3 ml dioxane solution of 3-(3,3-difluoro-cyclopentyl)-1H-indole (660 mg, 2.98 mmol, 1.0 eq) under N$_2$. Stir solution for 5 minutes. Add 4-Chlorosulfonyl-benzoic acid methyl ester 117 mg, 0.497 mmol, 1.1 eq). Stir reaction for 4 hours at room temperature. Strip reaction of solvent and purify by silica gel chromatography to give 4-[3-(3,3-Difluoro-cyclopentyl)-indole-1-sulfonyl]-benzoic acid methyl ester (466 mg, 37% yield).

Preparation 95

4-[3-(3,3-Difluoro-cyclopentyl)-indole-1-sulfonyl]-benzoic acid

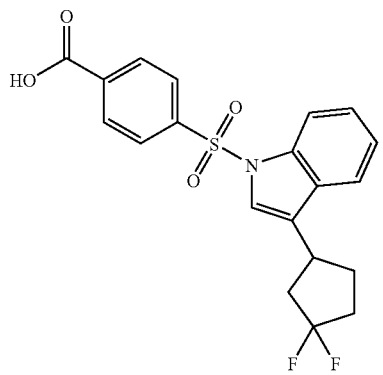

Add aqueous sodium hydroxide (5N, 0.72 ml, 3 eq) to a solution of 4-[3-(3,3-Difluoro-cyclopentyl)-indole-1-sulfonyl]-benzoic acid methyl ester (500 mg, 1.20 mml, 1 eq) in 5 ml THF, 2.5 ml MeOH. Stir reaction at room temperature for 2 hours. Remove solvent on rotovap and add 1N HCl and EtOAc. Extract products into organics, separate organics, and then dry organics with MgSO4. Filter off drying agent, and remove organics on rotovap to give 4-[3-(3,3-Difluoro-cyclopentyl)-indole-1-sulfonyl]-benzoic acid (450 mg, 92% yield) which was used without further purification.

Preparation 96

3-Piperidin-1-yl-1-triisopropylsilanyl-1H-indole

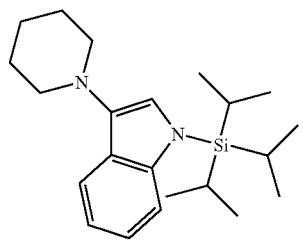

Dissolve piperidine (1.28 mL, 12.9 mmol) in THF (10 mL) and treat with lithium bis(trimethylsilyl)-amide (1.0M in THF, 11.2 mL, 11.2 mmol). To the above solution add 3-bromo-1-triisopropylsilanyl-1H-indole (TCI-US, 3.04 g, 8.62 mmol), (2'-dicyclohexyl-phosphanyl-biphenyl-2-yl)-dimethyl-amine (88 mg, 0.22 mmol), and Pd$_2$ dba$_3$.CHCl$_3$ (225 mg, 0.22 mmol). Heat the red solution to 70° C. for 4 h then cool to RT and concentrate. Purify the crude material by flash chromatography, using a linear gradient of 100% hexanes to 40% EtOAc/hexanes, to give the title compound (837 mg, 27%). MS (ES$^+$) 357.2 (M+1)$^+$. $^1$H NMR (400 MHz, CDCl$_3$): δ 7.61 (d, 1H, J=8.4), 7.41 (d, 1H, J=8.4), 7.07 (m, 2H), 6.68 (s, 1H), 3.03 (m, 4H), 1.79 (m, 4H), 1.65 (septet, 3H, J=7.7), 1.58 (m, 2H), 1.12 (d, 18H, J=7.1).

Preparation 97

3-Piperidin-1-yl-1H-indole

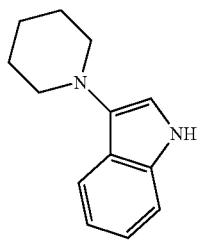

Add nBu₄NF (1.0M in THF, 3.2 mL, 3.2 mmol) to a solution of 3-piperidin-1-yl-1-triisopropylsilanyl-1H-indole (835 mg, 2.34 mmol) in THF (10 mL). Stir the red solution at RT for 1 h, then dilute with EtOAc (40 mL) and wash with satd NaHCO₃ (20 mL). Dry, filter, and concentrate the organic solution then purify the crude material by flash chromatography, using a linear gradient of 100% hexanes to 40% EtOAc/hexanes. Obtain the title compound (347 mg, 74%) as a grey solid. MS (ES⁺) 201.1 (M+1)⁺. ¹H NMR (400 MHz, CDCl₃): δ 7.65 (d, 1H, J=8.1), 7.59 (br s, 1H), 7.29 (d, 1H, J=8.4), 7.16 (t, 1H, J=7.5), 7.06 (t, 1H, J=7.9), 6.70 (s, 1H), 3.03 (m, 4H), 1.80 (m, 4H), 1.59 (m, 2H).

Preparation 98

4-Fluoro-3-methoxy-benzylamine

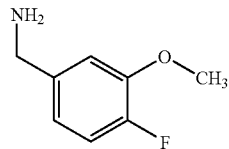

Add 4-fluoro-3-methoxy-benzonitrile (2 g, 0.01 mol), 10% palladium on carbon (0.400 g) and glacial acetic acid (120 ml) to a pressure vessel. Purge the reaction vessel with nitrogen, purge the reaction vessel with hydrogen, pressurize the reaction mixture with hydrogen (415 Kpa), seal the vessel, and agitate the reaction. After 8 hours stop the agitation, vent the excess hydrogen from the vessel and purge the vessel with nitrogen. Filter the reaction mixture to remove the 5% palladium on carbon and return the filtrate for product isolation. Concentrate the crude solution, re-dissolve in CH₂Cl₂ (80 mL) and washe with 5N NaOH (35 mL). Separate the organic and aqueous phases and extract the aqueous with additional CH₂Cl₂ (20 mL). Combine the organic solutions, dry, filter and concentrate to give the crude material 2.08 g (100%). The title compound as the major product (Rf=0.12, 10% MeOH/CH₂Cl₂) is used without further purification. MS (ES⁺) 156.1 (M+1)⁺. ¹H NMR (400 MHz, CDCl₃): δ 7.01 (dd, 1H, J=8.2, 11.4), 6.95 (dd, 1H, J=2.1, 8.4), 6.80 (m, 1H), 3.89 (s, 3H), 3.82 (s, 2H), 1.54 (br s, 2H).

Preparation 99

4-(4-Fluoro-3-methoxy-benzylcarbamoyl)-benzene-sulfonyl chloride

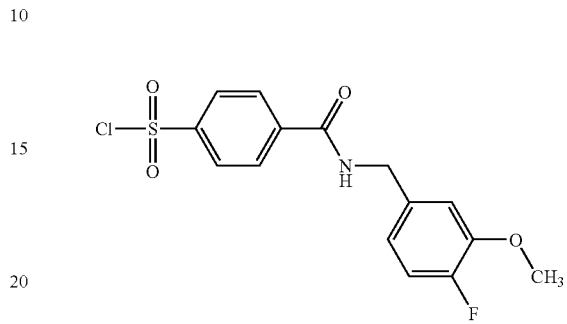

Dissolve 4-chlorosulfonyl-benzoyl chloride (3.18 g, 13.3 mmol) in THF (25 mL) and cool to −78° C. Slowly add a pre-mixed solution of 4-fluoro-3-methoxybenzyl-amine (1.91 g, 12.3 mmol), Et₃N (1.64 mL, 11.8 mmol), and DMAP (150 mg, 1.23 mmol) in THF (25 mL) to the above cooled solution over 1 h. Stir the resulting mixture at −78° C. for 1 h, then warm to RT and stir for 4 h. Remove all solids by filtration and wash with THF (5 mL). Concentrate the filtrate and re-dissolve the crude material in EtOAc (30 mL) and wash with 1N HCl (30 mL). Separate the organic and aqueous layers and extract the aqueous phase with additional EtOAc (30 mL). Combine the organic solutions dry, filter, and concentrate. Purify the crude material by flash chromatography, using a linear gradient of 100% hexanes to 40% EtOAc/hexanes) to give the title compound as a white solid (1.36 g, 28%). MS (ES⁻) 356.1 (M−1)⁻. ¹H NMR (400 MHz, CDCl₃): δ 8.11 (d, 2H, J=8.3), 8.00 (d, 2H, J=8.8), 7.05 (dd, 1H, J=8.2, 11.1), 6.96 (dd, 1H, J=1.9, 8.0), 6.86 (m, 1H), 6.44 (br s, 1H), 4.61 (d, 2H, J=5.7), 3.88 (s, 3H).

Preparation 100

Cyclopentyl-(2-fluoro-phenyl)-methanone

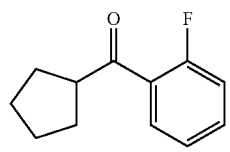

Stir 2-Fluorobenzonitrile (5.0 g, 41.01 mmole) in 80 ml of THF with a 2 molar cyclopentyl magnesium bromide THF solution (20.51 ml, 41.01 mmole) and CuBr (0.100 g, 0.697 mmole) for 15 hrs at 60° C. under argon gas. Add a 15% solution of sulfuric acid to the reaction at 0° C. and stir for 15 hrs. Extract the reaction mixture three times with diethyl ether. Combine organic layers and dry over MgSO₄ and concentrate. Purify residue via column chromatography using mixture of Ethyl Acetate and hexanes; to give 3.085 grams. Yield 40% MS (ES)=192.15 (M+1)+.

Preparation 101

3-Cyclopentyl-1H-indazole

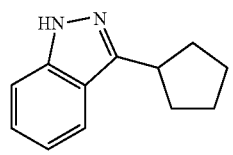

Dissolve Cyclopentyl-(2-fluoro-phenyl)-methanone (2.5 g 13.005 mmoles) in hydrazine (20 ml) heat to 130° C. for 72 hrs. Cool mixture to 0° C. Filter the precipitate and wash with cold water to give the title compound: 2.171 g (yield=89%) MS ES+ 187.12:MSES– 185.22.

Preparation 102

4-(3-Cyclopentyl-indazole-1-sulfonyl)-benzoic acid methyl ester

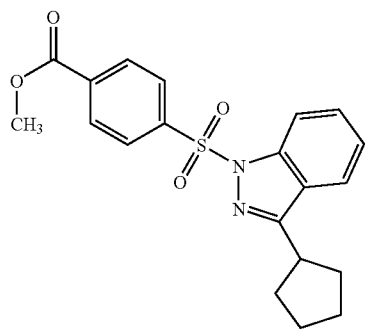

Combine 3-Cyclopentyl-1H-indazole (2.168 g 11.640 mmole) with triethylamine (3.526 g, 34.92 mmoles) in 50 mls of dichloromethane. Dissolve 4-Chlorosulfonyl-benzoic acid methyl ester (4.085 g, 17.460 mmole) in dichloromethane 50 ml and add drop wise to solution at 0° C. Stir the reaction is for 12 hrs. Dilute the reaction and wash with NaHCO$_3$. Dry organic layer over MgSO$_4$ and concentrate. Purify the residue via column chromatography with a mixture of ethyl acetate and hexanes to isolate 2.046 g (Yield=48.5%) of the title compound: MS ES+ 385.3.

Preparation 103

4-(3-Cyclopentyl-indazole-1-sulfonyl)-benzoic acid

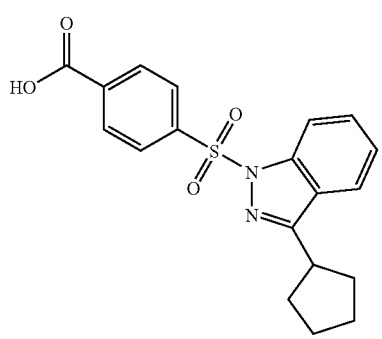

Combine 4-(3-Cyclopentyl-indazole-1-sulfonyl)-benzoic acid methyl ester (2.045 g, 5.325 mmoles) in 50 ml of THF. Add 3 ml of 5 N NaOH and allow to stir for 15 hrs. Make the reaction acidic with HCl and extract into diethyl ether. Dry organic layer over MgSO$_4$ and concentrate to isolate 1.243 g (Yield=63%) of the title compound: MS ES+ 369.47; MS ES– 369.46.

Preparation 104

(S)-1-(4-Fluoro-phenyl)-pyrrolidin-3-ylamine

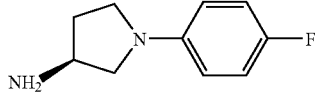

Combine (S)-pyrrolidin-3-yl-carbamic acid tert-butyl ester (1.741 mmole) 1-bromo-4-Fluorobenzene (1.45 mmole), Pd$_2$dba (0.217 mmole), NaOtBu (2.03 mmole), 2-di-t-butylphospineolbiphenyl (0.362 mmole) in 30 ml of toluene and stir at 80° C. Dilute solution with ethyl acetate and filter. Concentrate the solution. Purify the residue via column chromatography with a mixture of ethyl acetate and hexanes and add a mixture of methanol and Trifluoro acetic acid and stir for 1 hr at 0° C. Concentrate the reaction and dissolve in methanol in presence of hydroxy resin until pH is 10. Filter the solution and concentrate to isolate 0.136 of title compound yield=52 MS ES−=182.0.

Preparation 105

Azetidin-3-yl-(4-fluoro-phenyl)-amine

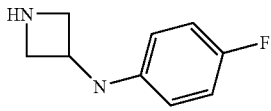

Using a procedure similar to 1-(4-Fluoro-phenyl)-pyrrolidin-3-ylamine to give 0.053 g (yield=21%) of the title compound. MS ES not observed.

Preparation 106

C-(Tetrahydro-pyran-2-yl)-methylamine

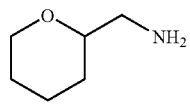

Combine C-(Tetrahydro-pyran-2-yl)-methylamine with Sodium azide and heat to 50° C. for 15 hrs in 30 ml of DMF. Dilute the reaction with dichloromethane and wash with NaHCO$_3$. Treat organic layer with MgSO$_4$ and concentrate. Dissolve the residue in 30 ml of ethanol with Palladium on carbon in the presence of hydrogen gas until reaction is complete. Filter the reaction mixture. Concentrate solvent to produce 1.32 g of the title compound (yield=54.9%) MS ES+ 115.95.

Preparation 107

4-(3-Cyclopent-1-enyl-indole-1-sulfonyl)-benzoic acid methyl ester

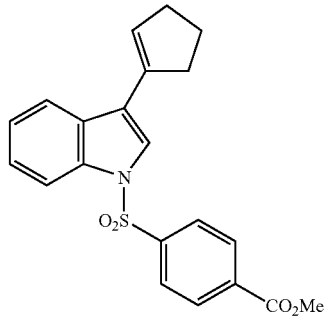

In a 12 L RBF, charge 4-(3-iodo-indole-1-sulfonyl)-benzoic acid methyl ester (620 g, 1.406 mol), cyclopentene (958 g, 14.06 mol), potassium acetate (414 g, 4.218 mol), tetrabutylammonium chloride (391 g, 1.406 mol), palladium acetate (15.8 g, 0.0703 mol) and DMF (6.2 L). Heat the mixture to 60° C. for sixteen hours, cool and filter through Hyflo. Wash the filter cake with ethyl acetate (5 L). Add additional ethyl acetate (4 L) and DI water (12 L). Stir for 30 minutes, separate the layers and wash the organic layer with brine (6 L). Dry the organic layer over sodium sulfate, filter and rinse the cake with ethyl acetate (2 L). Remove the solvents under vacuum to give 609 g of a dark oil. Dissolve the oil in methylene chloride (1 L) and filter through silica gel (6 kg). Wash the silica plug with MTBE (20 L) to eluent the product. Concentrate the MTBE layer under vacuum to give 535 g of an oil (yield=99.8%) of the title compound.

Preparation 108

4-(3-Cyclopentyl-indole-1-sulfonyl)-benzoic acid methyl ester

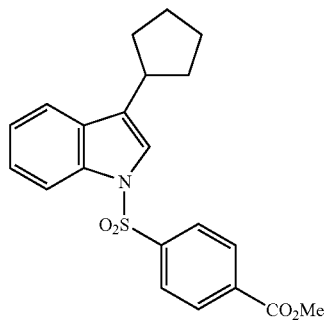

In a 3 gallon autoclave, charge 4-(3-Cyclopent-1-enyl-indole-1-sulfonyl)-benzoic acid methyl ester (475 g), ethyl acetate (2.5 L), absolute ethanol (2.5 L) and 10% Pd—C (45 g, w/w) under 35 psi hydrogen at ambient temperature for 5 hours. Filter the crude reaction over Hyflo. Concentrate the filtrate under vacuum to give a light yellow solid (465 g) of the title compound.

Preparation 109

4-(3-Cyclo-pentyl-indole-1-sulfonyl)-benzoic acid

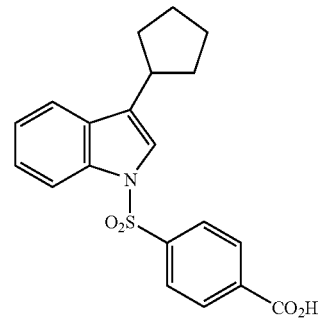

In a 12 L RBF, charge 4-(3-cyclopentyl-indole-1-sulfonyl)-benzoic acid methyl ester (465 g 1.213 mol) and THF (4.7 L). Add 5N NaOH (485 ml) dropwise at ambient temperature. Stir the solution at room temperature overnight. Bring the pH of the reaction to 1 with c.HCl. Separate the layers and extract the aqueous layer with ethyl acetate (4 L). Dry the combined organic layers over sodium sulfate, filter and rinse with ethyl acetate. Concentrate the organics under vacuum to give an off-white solid (401 g, yield=89.5%) of the title compound.

Preparation 110

Tetrahydro-pyran-4-carboxylic acid amide

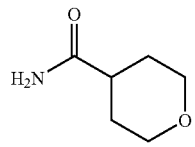

In a 5 L flask, charge methyltetrahydropyran-4-carboxylate (500 ml, 3.75 mol) and concentrated ammonium hydroxide (1.3 L) and stir the reaction at room temperature for 48 hours. Filter the reaction and dry the white solid in a vacuum oven at 60° C. overnight. to obtained 36.33 g white solid of the title compound.

Preparation 111

C-(Tetrahydro-pyran-4-yl)-methylamine

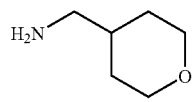

In a 2 L flask, charge tetrahydro-pyran-4-carboxylic acid amide (51 g, 0.395 mol) and THF (1.3 L) and cool the reaction in an ice-bath. Add LAH (30 g, 0.791) portion-wise. Stir the reaction at 10° C. for 16 hours and quench by the drop-wise addition of DI water (30 ml), 15% NaOH (30 ml), and DI water (90 ml). Stir the reaction at ambient temperature for 16 hours. Filter the salts and concentrate the filtrate under vacuum to give 36.79 g clear oil of the title compound.

Preparation 112

4-{[4-(3-Phenyl-indole-1-sulfonyl)-benzoylamino]-methyl}-benzoic acid

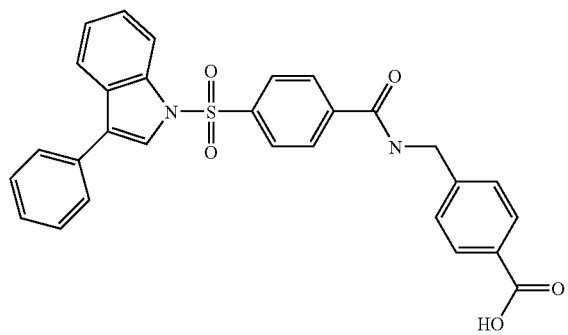

Combine 4-(3-Phenyl-indole-1-sulfonyl)-benzoic acid (1.324 mmole) with N-hydroxy-succinamide (NHS– 1.457 mmoles), and EDC (1.324 mmoles) and stir in 20 ml dichloromethane for 15 hr. Condense the reaction to produce a solid. Isolate 0.613 g (yield=97.6%). React 1.05 mmole of residue with 4-aminomethyl-benzoic acid (1.05 mmole) in 3 ml dichloromethane for 15 hrs. Dilute reaction mixture and wash with 1 N HCl. Treat dichloromethane with MgSO$_4$ and concentrate. Isolate a mixture of 4-(3-Phenyl-indole-1-sulfonyl)-benzoic acid and the title compound 0.258 g (48%): MS ES+ 5.10-77 MS ES– 509.21.

Example 1

N-(4-Fluoro-benzyl)-4-(3-phenyl-pyrrolo[3,2-c]pyridine-1-sulfonyl)-benzamide

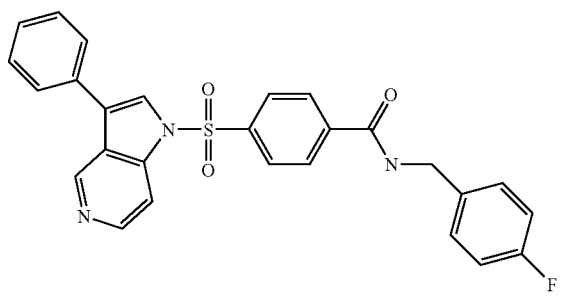

Add a 5 ml THF solution of 3-Phenyl-1H-pyrrolo[3,2-c]pyridine (500 mg, 2.57 mmol, 1 eq) to a 4 ml THF solution of KotBu (303 mg, 2.70 mmol, 1.05 eq) under N$_2$ atmosphere. Stir reaction for 10 minutes and then add a 5 ml THF solution of 4-(4-Fluoro-benzylcarbamoyl)-benzenesulfonyl chloride (844 mg, 2.57 mmol, 1 eq). Stir reaction for 16 hours, remove solvent on rotovap, and purify by silica gel chromatography to give N-(4-Fluoro-benzyl)-4-(3-phenyl-pyrrolo[3,2-c]pyridine-1-sulfonyl)-benzamide (982 mg, 79% yield). Mass Spectrum (m/e): 485.96 (MH+).

Example 2

N-(4-Fluoro-benzyl)-4-[3-(3-oxo-cyclopentyl)-indole-1-sulfonyl]-benzamide

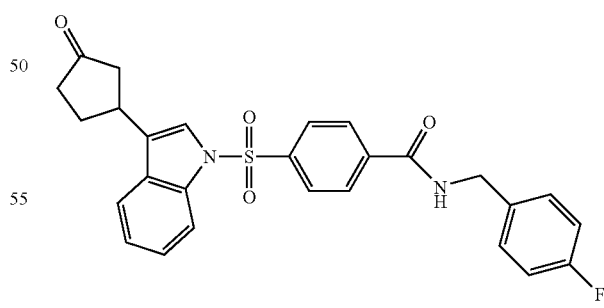

Add a 3 nm DMF solution of 3-(1H-Indol-3-yl)-cyclopentanone (500 mg, 2.57 mmol, 1 eq) to a 3 ml DMF solution of NaH (155 mg, 60% by weight, 3.86 mmol, 1.1 eq) under N$_2$ atmosphere. Stir reaction for 15 minutes and then add a 5 ml DMF solution of 4-(4-Fluoro-benzylcarbamoyl)-benzenesulfonyl chloride (1.27 g, 3.86 mmol, 1.1 eq). Stir reaction for 48 hours, remove solvent on rotovap, and purify by silica gel chromatography to give N-(4-Fluoro-benzyl)-4-[3-(3-oxo-cyclopentyl)-indole-1-sulfonyl]-benzamide (375 mg, 22% yield). Mass Spectrum (m/e): 490.53 (MH+).

Example 3

N-(4-Fluoro-benzyl)-4-(3-propyl-indole-1-sulfonyl)-benzamide

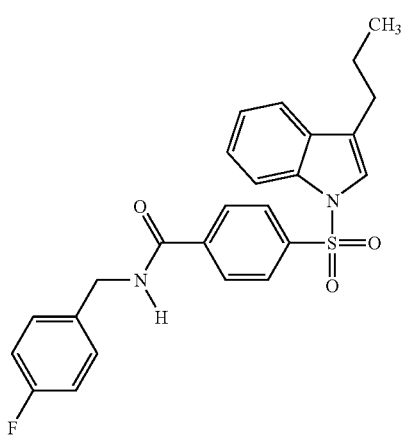

Add NaH 60% in mineral oil (0.080 g, 2.0 mmol) to a stirred solution of 3-propyl-indole (0.266 g, 1.67 mmol) in dr THF (25 mL) under N2. Stir the reaction mixture at ambient temperature for 45 min. Add 4-(4-fluoro-benzylcarbamoyl)-benzenesulfonyl chloride (0.547 g, 1.67 mmol) portion wise at ambient temperature. Stir the reaction mixture overnight at ambient temperature. Pour the reaction mixture into a two-phase mixture of EtOAc (150 mL) and saturated solution of NaHCO₃ (50 mL). Separate the organic layer, wash with brine, separate and dry (MgSO₄). Filter and evaporate the filtrate. Purify the residue on the chromatron using a 4 mm plate and eluting with a gradient hexane-EtOAC system to give 0.262 g (34%) of N-(4-fluoro-benzyl)-4-([3-propyl-indole-1-sulfonyl]-benzamide. Mass spectrum (m/e) ⊛M+1) 451.1.

Example 5

N-(4-Fluoro-benzyl)-4-(pyrrolo[2,3-b]pyridine-1-sulfonyl)-benzamide

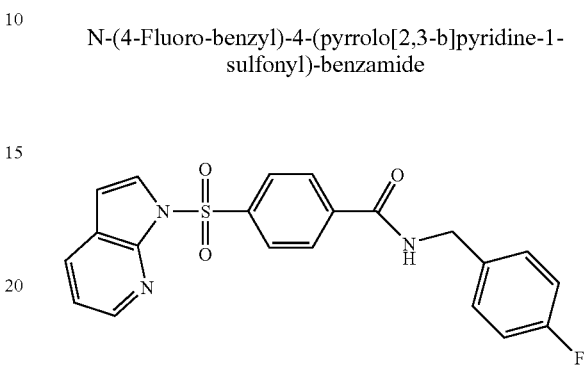

Add MeCN (2 ml) to a flask under N₂ containing 4-(4-Fluoro-benzylcarbamoyl)-benzenesulfonyl chloride (50 mg, 0.152 mmol), 1H-pyrrolo[2,3-b]pyridine (18 mg, 0.152 mmol), 4-Pyrrolidin-1-yl-pyridine (2 mg, 0.167 mmol), and triethylamine (17 mg, 0.167 mmol). Heat reaction to 80° C. for 16 hours. Cool the solution to room temperature, remove MeCN on rotovap. Purify crude material on silica gel to give 45 mg (73% yield) of N-(4-Fluoro-benzyl)-4-(pyrrolo[2,3-b]pyridine-1-sulfonyl)-benzamide. Mass Spectrum (m/e): 410.1 (M+).

Prepare the following sulfonamides in Table 1 using methods similar to the noted reference examples.

TABLE 1

| Ex. No. | Name | Structure | Mass Spec (M + H) except where noted | Reference Examples |
|---|---|---|---|---|
| 9 | N-(4-Fluoro-benzyl)-4-(indole-1-sulfonyl)-benzamide | 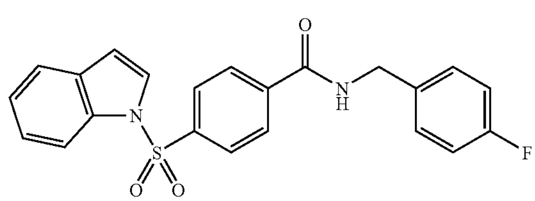 | 409.0 | 2 |
| 10 | N-(4-Fluoro-benzyl)-4-[3-spiro N-methylpiperidin-4-yl)(indole-1-sulfonyl]-benzamide | 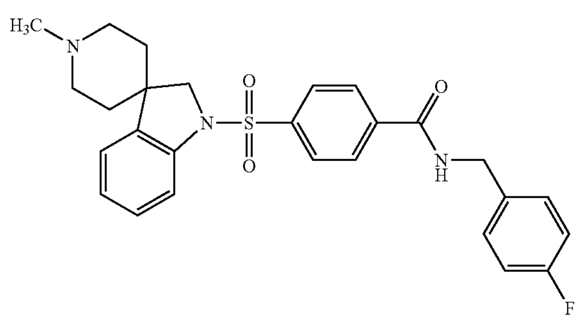 | 494.0 | 2 |

TABLE 1-continued

| Ex. No. | Name | Structure | Mass Spec (M + H) except where noted | Reference Examples |
|---|---|---|---|---|
| 14 | N-(4-Fluoro-benzyl)-4-[3-(2-methoxy-cyclohexyl)-indole-1-sulfonyl]-benzamide | 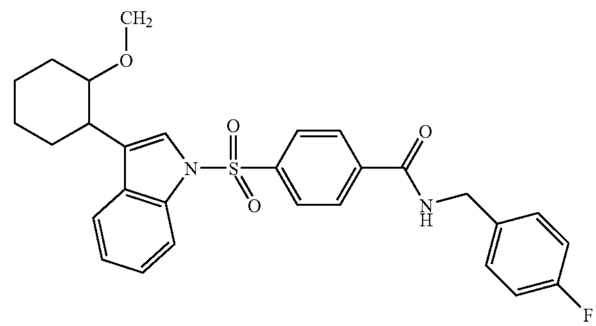 | 521.05 | 2 |
| 22 | N-(4-Fluoro-benzyl)-4-[3-(1-methyl-piperidin-4-yl)-indazole-1-sulfonyl]-benzamide | 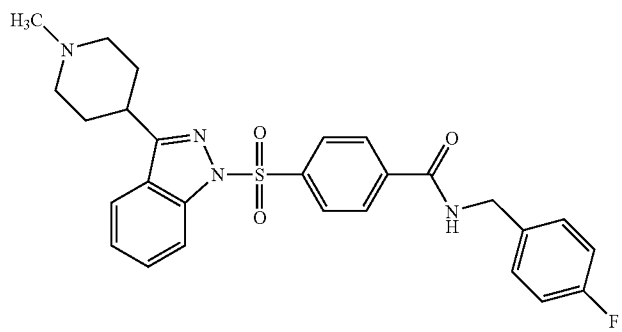 | 507.02 | 1 |
| 23 | N-(4-Fluoro-benzyl)-4-(3-phenyl-indazole-1-sulfonyl)-benzamide | 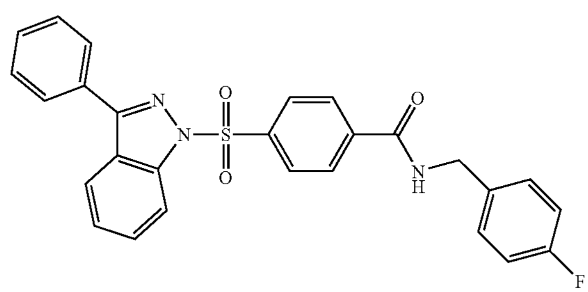 | 485.96 | 1 |
| 25 | 4-(2,3-Dihydro-indole-1-sulfonyl)-N-(4-fluoro-benzyl)-benzamide | 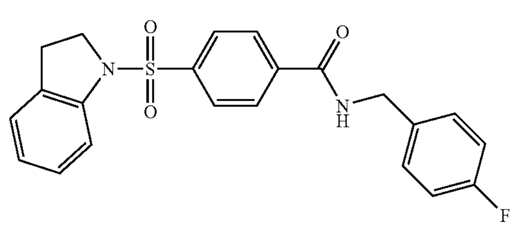 | 411.1 | 5 |

TABLE 1-continued

| Ex. No. | Name | Structure | Mass Spec (M + H) except where noted | Reference Examples |
|---|---|---|---|---|
| 26 | N-(4-Fluoro-benzyl)-4-(3-methyl-indole-1-sulfonyl)-benzamide | 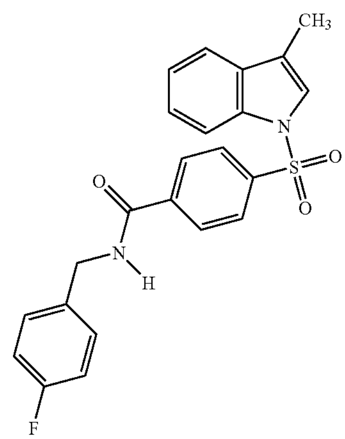 | 423.12 | 3 |
| 30 | 4-(3-Acetyl-indole-1-sulfonyl)-N-(4-fluoro-benzyl)-benzamide | 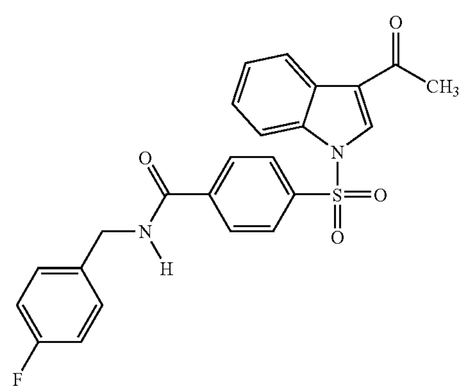 | 451.1 | 3 |
| 33 | N-(4-Fluoro-benzyl)-4-(3-trifluoromethyl-indazole-1-sulfonyl)-benzamide | 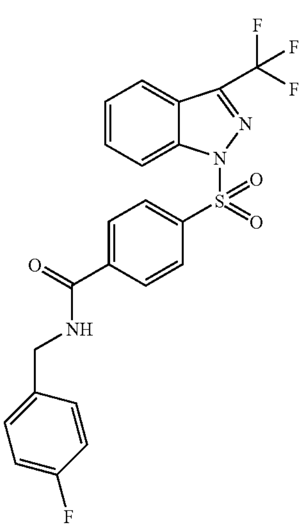 | 476.07 (M − H) | 1 |

TABLE 1-continued

| Ex. No. | Name | Structure | Mass Spec (M + H) except where noted | Reference Examples |
|---|---|---|---|---|
| 34 | 4-[3-(1-Acetyl-piperidin-4-yl)-indole-1-sulfonyl]-N-(4-fluoro-benzyl)-benzamide | 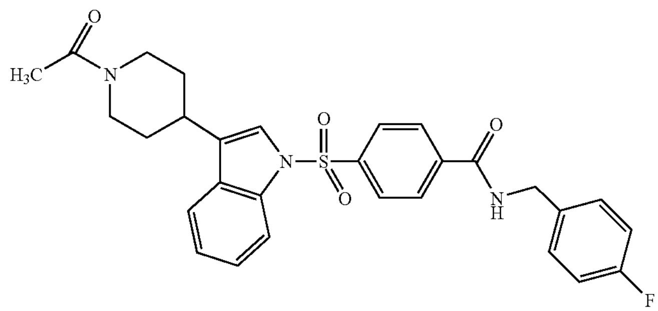 | 534.03 | 2 |
| 35 | N-(4-Fluoro-benzyl)-4-[3-(4-methyl-piperazine-1-carbonyl)-indole-1-sulfonyl]-benzamide | 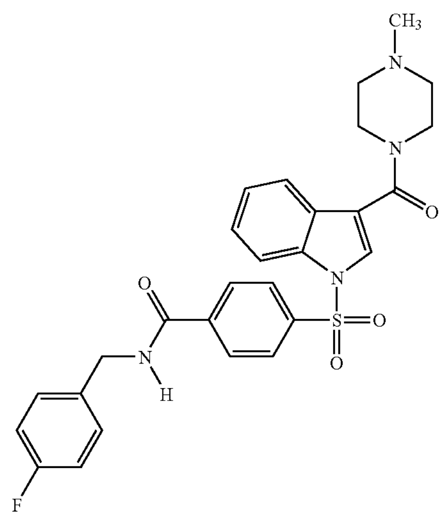 | 534.94 | 2 |
| 36 | N-(4-Fluoro-benzyl)-4-[3-(1-methyl-piperidin-2-yl)-indole-1-sulfonyl]-benzamide | 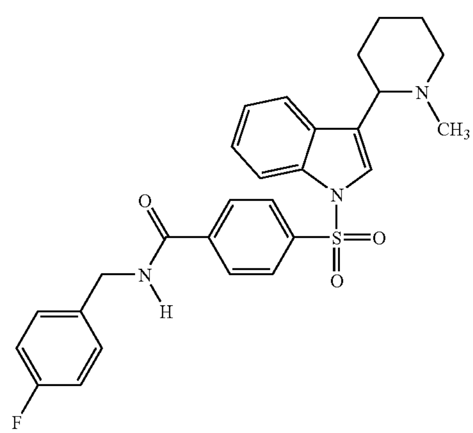 | 505.97 | 2 |

TABLE 1-continued

| Ex. No. | Name | Structure | Mass Spec (M + H) except where noted | Reference Examples |
|---|---|---|---|---|
| 37 | N-(4-Fluoro-benzyl)-4-[3-(2-morpholin-4-yl-acetyl)-indole-1-sulfonyl]-benzamide | 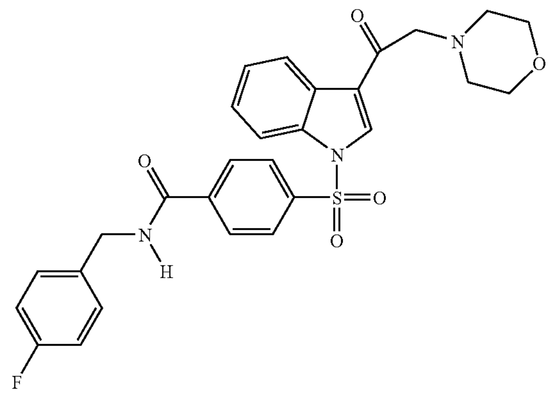 | 535.94 | 2 |
| 38 | N-(4-Fluoro-benzyl)-4-[3-(2-tetrahydropyran-1-acetyl)-indole-1-sulfonyl]-benzamide | 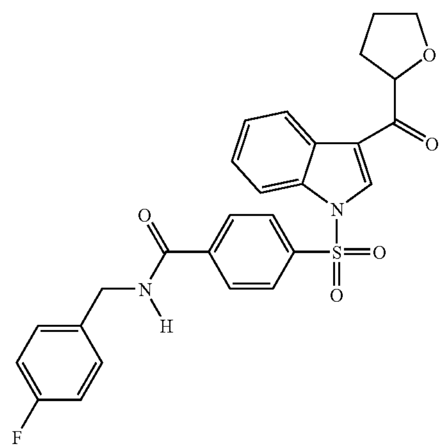 | 506.9 | 2 |
| 39 | N-(4-Fluoro-benzyl)-4-[3-(1-methyl-piperidin-4-yl)-indole-1-sulfonyl]-benzamide | 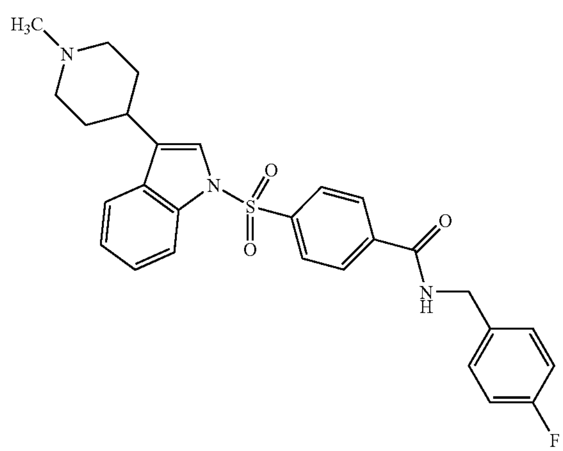 | 505.98 | 2 |

TABLE 1-continued

| Ex. No. | Name | Structure | Mass Spec (M + H) except where noted | Reference Examples |
|---|---|---|---|---|
| 40 | N-(4-Fluoro-benzyl)-4-[3-(3,3-difluorocyclopentyl)-indole-1-sulfonyl]-benzamide | 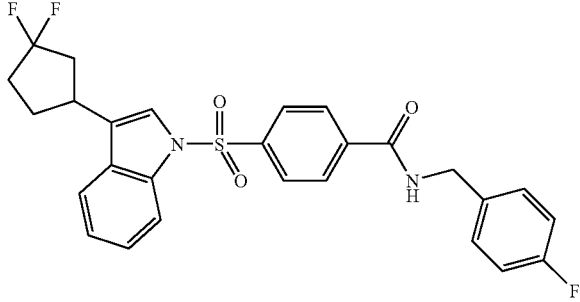 | 512.93 | 2 |
| 41 | 4-(3-Ethyl-3-methyl-2,3-dihydro-indole-1-sulfonyl)-N-(4-fluoro-benzyl)-benzamide | 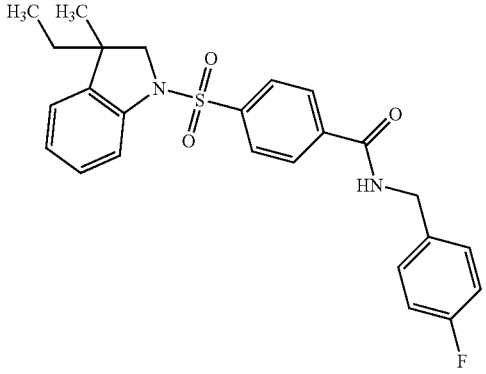 | 453.2 | 2 dioxane as solvent Amine ref: Takayama et al. Tetrahedron Lett.; 1973, 365, 366 |
| 42 | N-(4-Fluoro-benzyl)-4-(spiro[cyclopentane-1,3'-indoline])-benzamide | 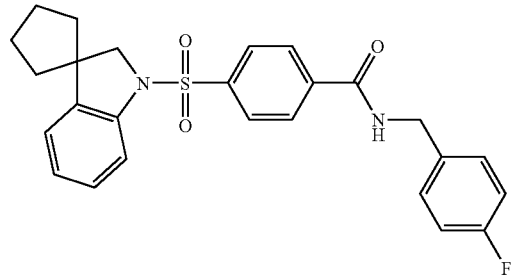 | 464.9 | 2 dioxane as solvent Joiner, K. A.; King, F. D European Patent 0287, 196, 1988. |
| 43 | N-(4-Fluoro-benzyl)-4-(spiro[indoline-3,4'-tetrahydro-pyran])-benzamide | 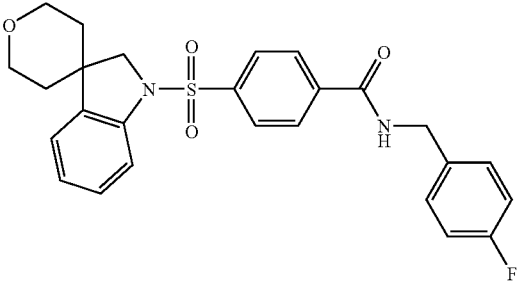 | 481.4 | 2 dioxane as solvent |

TABLE 1-continued

| Ex. No. | Name | Structure | Mass Spec (M + H) except where noted | Reference Examples |
|---|---|---|---|---|
| 44 | N-(4-Fluoro-benzyl)-4-(spiro[cyclopropane-1,3'-indoline])-benzamide | 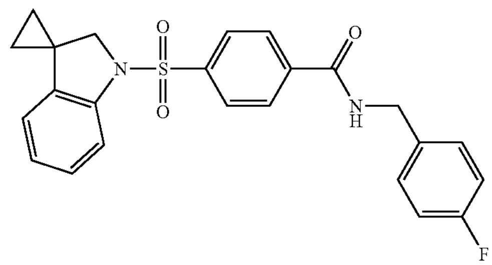 | 436.9 | 2 dioxane as solvent Joiner, K. A.; King, F. D European Patent 0287, 196, 1988. |
| 45 | N-(4-Fluoro-benzyl)-4-(spiro[cyclohexane-1,3'-indoline])-benzamide | 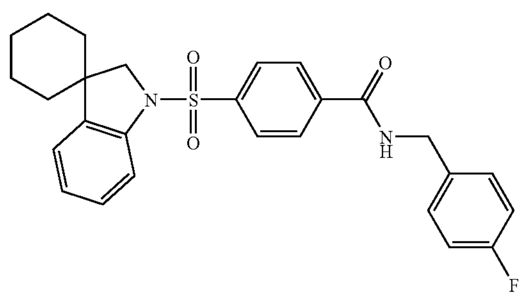 | 478.9 | 2 dioxane as solvent Joiner, K. A.; King, F. D European Patent 0287, 196, 1988. |
| 46 | N-(4-Fluoro-benzyl)-4-(spiro[cyclobutane-1,3'-indoline])-benzamide | 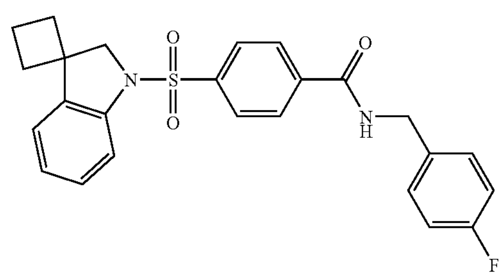 | 450.9 | 2 dioxane as solvent |
| 47 | N-(4-Fluoro-benzyl)-4-(3-morpholin-4-yl-indole-1-sulfonyl)-benzamide | 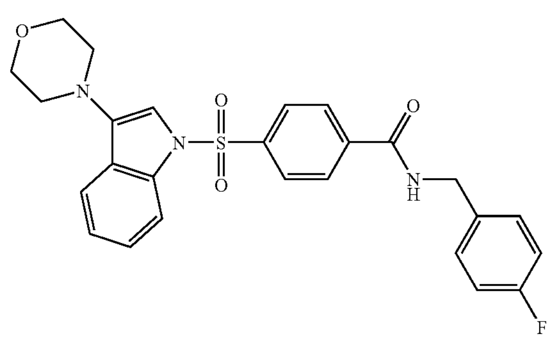 | 494 | 2 dioxane as solvent |

TABLE 1-continued

| Ex. No. | Name | Structure | Mass Spec (M + H) except where noted | Reference Examples |
|---|---|---|---|---|
| 48 | N-(4-Fluoro-benzyl)-4-[3-(4-methyl-piperazin-1-yl)-indole-1-sulfonyl]-benzamide | 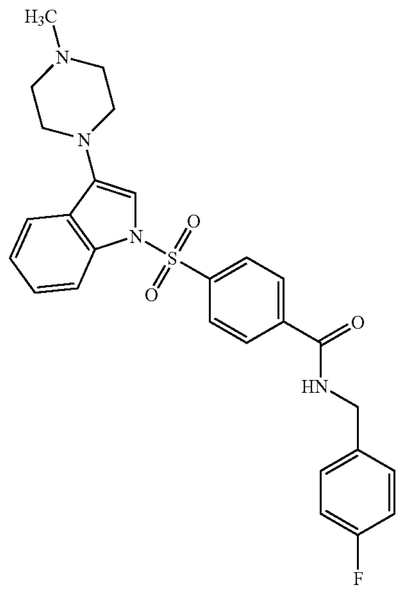 | 507 | 2 dioxane as solvent |
| 49 | N-(4-Fluoro-benzyl)-4-(3-piperidin-1-yl-indole-1-sulfonyl)-benzamide | 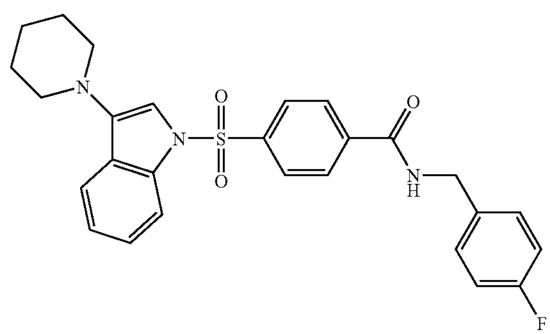 | 492 | 2 dioxane as solvent |
| 50 | 4-(3-tert-Butyl-indole-1-sulfonyl)-N-(4-fluoro-benzyl)-benzamide | 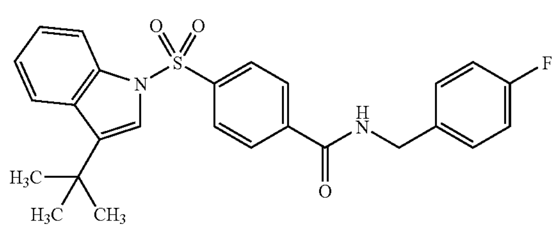 | 464.97 | 1 |
| 51 | N-(4-Fluoro-benzyl)-4-[3-(1-methyl-cyclopentyl)-indole-1-sulfonyl]-benzamide | 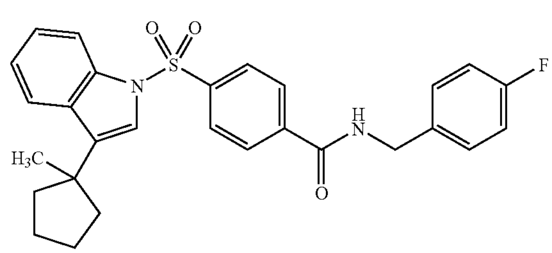 | 490.93 | 1 |

Example 53

N-(4-Fluoro-benzyl)-4-(3-piperidin-1-yl-indazole-1-sulfonyl)-benzamide

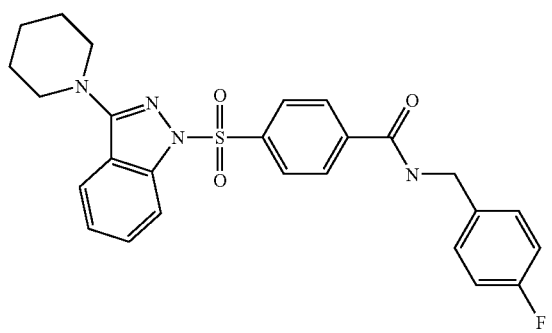

Dissolve 4-(3-chloro-indazole-1-sulfonyl)-N-(4-fluoro-benzyl)-benzamide (91 mg, 0.20 mmol) in piperidine (11.0 mL) and stir at 90° C. overnight. Dilute the solution with EtOAc (30 mL) and wash with 1N HCl (15 mL) and satd NaHCO$_3$ (15 mL). Dry, filter and concentrate the organic solution and purify the residue by flash chromatography, using a linear gradient of 100% hexanes to 50% EtOAc/hexanes, to give the title compound as a light yellow foam (7 mg, 7%). MS (ES) 493.0 (M+1)+, 491.2 (M−1)−.

Example 54

N-(4-Fluoro-benzyl)-4-(3-morpholin-4-yl-indazole-1-sulfonyl)-benzamide

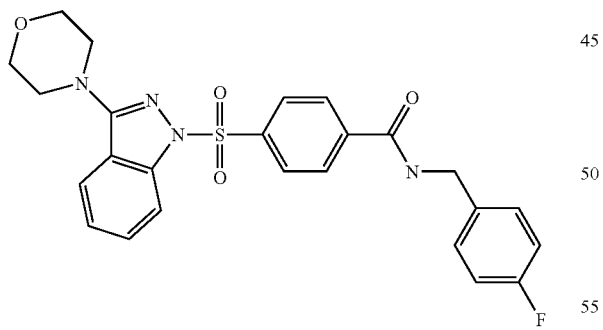

Dissolve 4-(3-chloro-indazole-1-sulfonyl)-N-(4-fluoro-benzyl)-benzamide (91 mg, 0.20 mmol) in morpholine (1.0 mL) and stir at 100° C. overnight. Dilute the solution with EtOAc (30 mL) and wash with 1N HCl (11 mL), water (10 mL), and satd NaHCO$_3$ (10 mL). Dry, filter and concentrate the organic solution and purify the residue by flash chromatography, using a linear gradient of 20% to 80% EtOAc/hexanes, to give the title compound as a white foam (17 mg, 34%). MS (ES) 495.0 (M+1)+, 493.1 (M−1)−.

Example 55

N-(4-Fluoro-benzyl)-4-[3-(3-hydroxy-cyclopentyl)-indole-1-sulfonyl]-benzamide

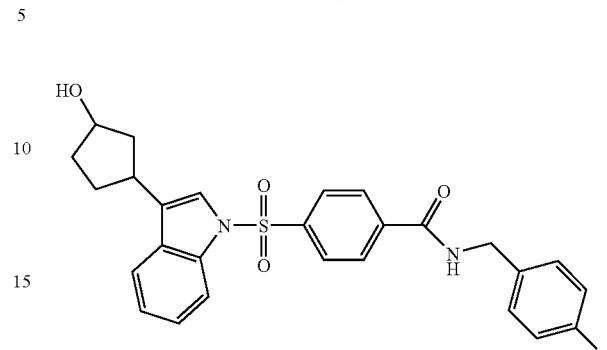

Add sodium borohydride (23 mg, 0.601 mmol) to a 0° C. solution of N-(4-fluoro-benzyl)-4-[3-(3-oxo-cyclopentyl)-indole-1-sulfonyl]-benzamide (295 mg, 0.601 mmol) in MeOH (7 ml) under N$_2$. Stir for 30 min and them warm to room temperature. Stir for 18 hours. Add a small amount of water to quench reaction and then remove MeOH on rotovap. Add EtOAc and water and extract the product into organics. Separate, and dry organics over MgSO$_4$. Condense organics on rotovap and then purify by silica gel chromatography to give N-(4-fluoro-benzyl)-4-[3-(3-hydroxy-cyclopentyl)-indole-1-sulfonyl]-benzamide (205 mg, 69% yield) as a light orange solid. Mass Spectrum (m/e): 493.01 (MH+).

Example 56

4-[3-(2,3-Dihydro-furan-3-yl)-indole-1-sulfonyl]-N-(4-fluoro-benzyl)-benzamide

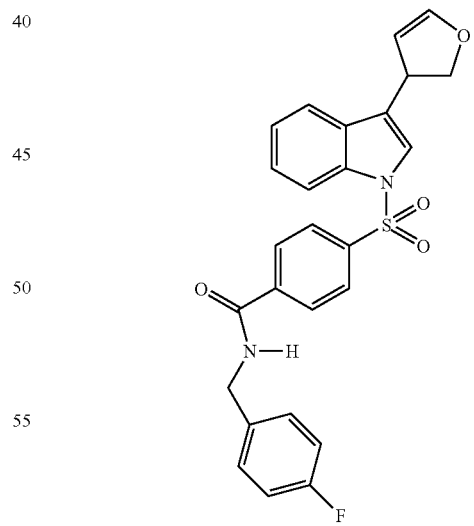

Add 3,4dihydrofuran (0.70 g, 0.76 mL, 0.01 mol) to N-(fluoro-benzyl)-4-(3-iodo-indole-1-sulfonyl)-benzamide (0.534 g, 0.001 mol) followed sequentially by Pd(Oac)$_2$ (0.024 g, 0.075 mmol), tetra butyl ammonium chloride (0.283 g, 0013 mol), and DMF (16.0 mL). Add sodium acetate (0.246 g, 003 mol) and stir and heat the resulting mixture at 50° C. for 8 h. Pour the reaction mixture into a DMF-H$_2$O mixture Separate the EtOAc layer and extract it several times with H₂O. Wash with brine, dry, filter and chromatograph on the chromatron eluting with EtOAc-hexane (3:7) to give 0.040 g of the title compound as a viscous gum. Mass spectrum (m/e) (M+1) 477; (M−1) 475.

Example 57

N-(4-Fluoro-benzyl)-4-[(3-tetrahydro-furan-3-yl)-indole-1-sulfonyl]-benzamide

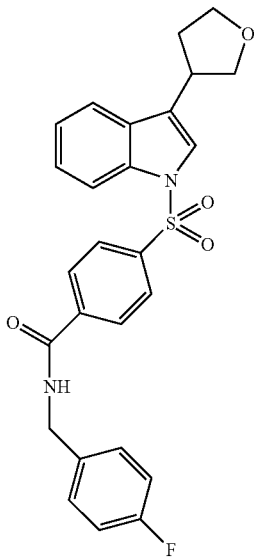

Add 4-[3-(2,3-dihydro-furan-3-yl)-indole-1-sulfonyl]-N-(4-fluoro-benzyl)-benzamide (0.095 g, 0.10 mmol) to absolute EtOH (25 mL) and 5% P/C 0.0029 g and hydrogenate in a PARR shaker overnight at 60 lbs per square inch. Filter the catalyst and evaporate the solvent giving 0.071 g of oil. Chromatograph on the ISCO using a gradient EtOAc-hexane system (0-100%) to give a viscous oil which solidifies to a glass 0.050 g. Mass spectrum (m/e) (M+1) 479.1441; Found (M+1) 479.1457.

Example 60

N-(4-Fluoro-benzyl)-4-(3-phenyl-2,3-dihydro-indole-1-sulfonyl)-benzamide

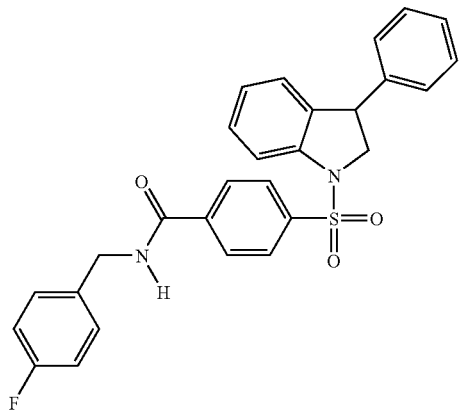

Add 3-phenyl-2,3-dihydro-1H-indole (Yamamoto, Y et al. Bull Chem. Soc. Jpn 44, 1971, 541-545) (0.158, 0.81 mmol), 4-(4-fluoro-benzylcarbamoyl)-benzenesulfonyl chloride (0.266 g, 0.81 mmol), Et₃N (0.161 g, 0.23 mL, 1.5 mmol) and DMAP (0.011 g, 0.09 mmol) to CH₂Cl₂ (25 mL) and stir at ambient temperature under N₂ overnight. Dilute the reaction to 150 mL with CH₂Cl₂ and pour into saturated NaHCO₃ (50 mL). Separate the organic layer and extract with 1M HCl (2×75 mL). Wash with brine, separate dry (MgSO₄) filter and evaporate the filtrate. Chromatograph the residue on the ISCO using a gradient EtOAc-hexane system (0-100%) to give 0.167 g of the title compound. Mass spectrum (m/e) (M+1) 487.1492; Found: 487.1479.

Example 60a

Isomer 1

Separate on a chiracel column OD (0.46×255 cm) at a flow rate of 1.0 mL./min, 255 nM eluting with ⅔ EtOH/heptane and 20 μL injection to give 0.060 g of the desired enantiomer. RT=5.45 min.

Example 60b

Isomer 2

Separate on a Chiracel column OD (0.46×255 cm) at a flow rate of 1.0 mL./min, 255 nM, eluting with ⅔ EtOH/heptane and 20 μL injection to give 0.061 g of the desired enantiomer. RT=7.20 min.

Example 61

N-(4-Fluoro-benzyl)-4-[3-(tetrahydro-pyran-4-yl)-indole-1-sulfonyl]-benzamide

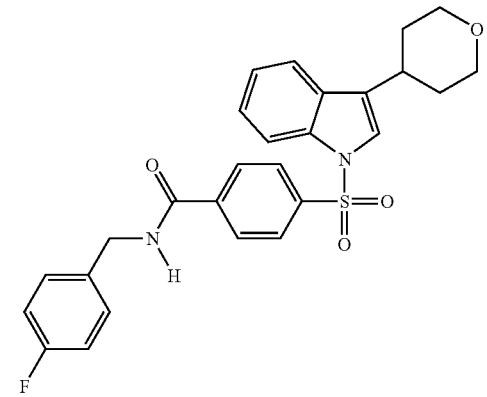

Add to a 1 L 3-neck roundbottom flask previously dried overnight at 120° C. is assembled warm with an overhead stirrer, N₂ line, temperature probe, and dropping funnel 4-(3-tetrahydro-pyran-4-yl)-indole-1-sulfonyl)-benzoic acid (15.0 g, 38.94 mmol) and anhydrous THF (200 mL), stir the solution and cool to 0° C. under N₂. Add N-methylmorpholine (4.3 mL, 39.09 mmol) at once via syringe, following by 2-chloro-4,6-dimethoxy-1,3,5-triazine (CDMT, 6.8 g, 38.80 mmol) in portions as a solid. Stir the mixture for 1 h at 0° C. and treat with a solution of 4-fluorobenzylamine (4.9 mL, 42.89 mmol) in anhydrous THF (50 mL) via dropping funnel over 10 min. Warm the resulting mixture to room temperature, stir for 3 h, cool back down to 0° C., and quench with 1N HCl (150 mL). Add ethyl acetate (150 mL) and separate the layers (add a small amount of brine to more efficiently separate the layers). Wash the organic layer with brine (150 mL), dry over sodium sulfate, and concentrate to an oil. Dissolve the oil in methylene chloride and add to a flash 65M biotage cartridge. Elute with 3:1 hexanes/ethyl acetate followed by 3:2 hexanes/ethyl acetate to provide isolation of the major product as a foam. Treat the foam with MTBE and re-concentrate to a paste. After standing awhile at room temperature, crystallization of the material occurs. Recrystallize from ethyl acetate/hexanes to provide a solid. Reslurry in MTBE (400 mL) and stir at room temperature for 3 h. longer. Filter the solid, back-wash with MTBE, dry (20 mm Hg, 55° C., to give homogeneous title compound (14.5 g, 76%); $^1$H NMR (DMSO-$d_6$) δ 9.24 (t, J=6.0 Hz, 1H), 8.10 (m, 2H), 7.98 (m, 3H), 7.67 (d, J=7.7 Hz, 1H), 7.58 (s, 1H), 7.32 (m, 5H), 7.12 (t, J=8.8 Hz, 1H), 4.42 (d, J=5.5 Hz, 2H), 3.96 (m, 2H), 3.50 (t, J=11.5 Hz, 2H), 3.02 (m, 1H), 1.85 (m, 2H), 1.71 (m, 2H); MS (ESI) m/z 493 (m+H); LC/MS, 100% DAD.

Example 63

(3-Aminomethyl-azetidin-1-yl)-[4-(3-phenyl-indole-1-sulfonyl)-phenyl]-methanone

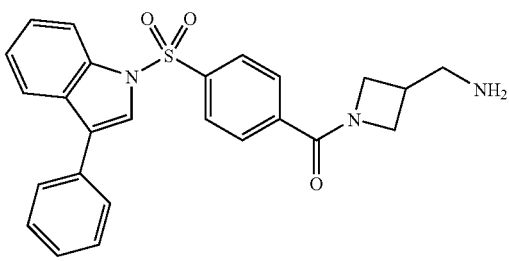

Add trifluoroacetic acid (5 mL) to [1-[4-(3-phenyl-indole-1-sulfonyl)-benzoyl]-azetidin-3-ylmethyl]-carbamic acid tert-butyl ester (853 mg, 1.56 mmol) causing much gas evolution. Rotary evaporate the reaction solution (40° C.; azeotroping 2× with MeOH). Dissolve the resultant yellow oil in MeOH (10 mL) and add hydroxide resin (Bio-Rad AG® 1-X8, 20-50 mesh; 5 g) to free-base the amine. Filter the mixture and rotary evaporate the filtrate (40° C.; azeotroped 3× with CH$_2$Cl$_2$) to yield 664 mg (95.3%) of (3-aminomethyl-azetidin-1-yl)-[4-(3-phenyl-indole-1-sulfonyl)-phenyl]-methanone as an off-white foam. MS (m/e): 446.02 (M+1).

Example 64

N-Azetidin-3-yl-4-(3-phenyl-indole-1-sulfonyl)-benzamide

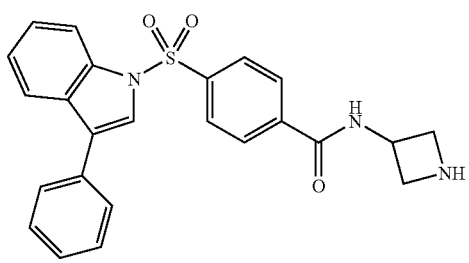

Prepare the title compound by a similar method described for (3-aminomethyl-azetidin-1-yl)-[4-(3-phenyl-indole-1-sulfonyl)-phenyl]-methanone using 3-[4-(3-phenyl-indole-1-sulfonyl)-benzoylamino]-azetidine-1-carboxylic acid tert-butyl ester (792 mg, 1.49 mmol) to give 568 mg (88.4%) of off-white foam. MS (m/e): 431.92 (M+1); 430.03 (M−1).

Example 65

(R)-3-Amino-pyrrolidin-1-yl)-[4-(3-phenyl-indole-1-sulfonyl)-phenyl]-methanone

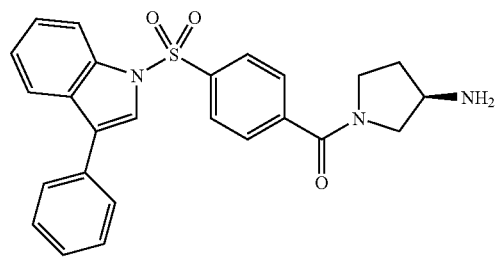

Prepare the title compound by a similar method described for (3-aminomethyl-azetidin-1-yl)-[4-(3-phenyl-indole-1-sulfonyl)-phenyl]-methanone using [(R)-1-[4-(3-phenyl-indole-1-sulfonyl)-benzoyl]-pyrrolidin-3-yl]-carbamic acid tert-butyl ester (655 mg, 1.20 mmol) to give 474 mg (88.6%) of white foam. MS (m/e): 445.95 (M+1).

Example 66

((S)-3-Amino-pyrrolidin-1-yl)-[4-(3-phenyl-indole-1-sulfonyl)-phenyl]-methanone

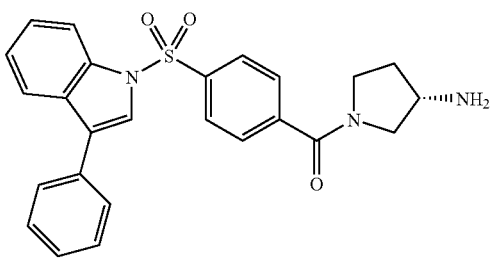

Prepare the title compound by a similar method described for (3-aminomethyl-azetidin-1-yl)-[4-(3-phenyl-indole-1-sulfonyl)-phenyl]-methanone using [(S)-1-[4-(3-phenyl-indole-1-sulfonyl)-benzoyl]-pyrrolidin-3-yl]-carbamic acid tert-butyl ester (903 mg, 1.65 mmol) to give 674 mg (91.4%) of white foam. MS (m/e): 445.95 (M+1).

Example 67

(3-Amino-azetidin-1-yl)-[4-(3-phenyl-indole-1-sulfonyl)-phenyl]-methanone

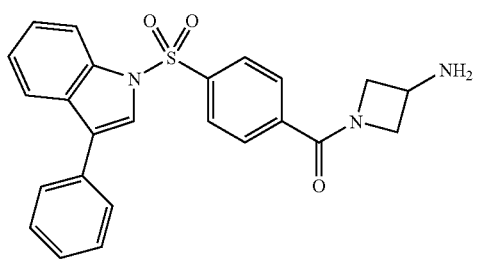

Prepare the title compound by a similar method described for (3-aminomethyl-azetidin-1-yl)-[4-(3-phenyl-indole-1-sulfonyl)-phenyl]-methanone using [1-[4-(3-phenyl-indole-1-sulfonyl)-benzoyl]-azetidin-3-yl]-carbamic acid tert-butyl ester (325 mg, 0.611 mmol) to give 239 mg (90.6%) of white foam. MS (m/e): 431.97 (M+1).

Example 70

4-(3-Phenyl-indole-1-sulfon)-N-pyrazin-2-ylmethyl-benzamide

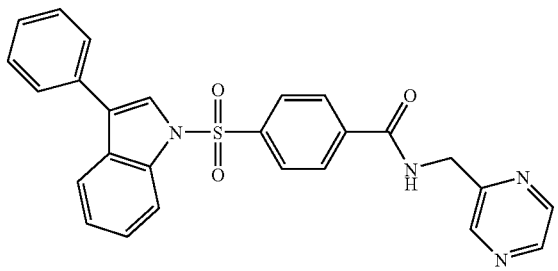

Add 10 ml dry DMF to a flask under N2 containing 4-(3-Phenyl-indole-1-sulfonyl)-benzoic acid (500 mg, 1.33 mmol, 1.0 eq), 1-(3-dimethylaminopropyl)-3-ethylcarbodiimide hydrochloride (279 mg, 1.46 mmol, 1.1 eq), Dimethyl-pyridin-4-yl-amine (16 mg, 0.132 mmol, 0.1 eq), and C-Pyrazin-2-yl-methylamine (217 mg, 1.99 mmol, 1.5 eq). Stir for 18 hours at room temperature. Remove solvent on rotovap and purify by silica gel chromatography to give 4-(3-Phenyl-indole-1-sulfonyl)-N-pyrazin-2-ylmethyl-benzamide (127 mg, 20% yield). Mass Spectrum (m/e): 468.95 (MH+).

Example 71

N-(4-Cyano-benzyl)-4-[(3-tetrahydro-pyran-4-yl)-indole-1-sulfonyl]-benzamide

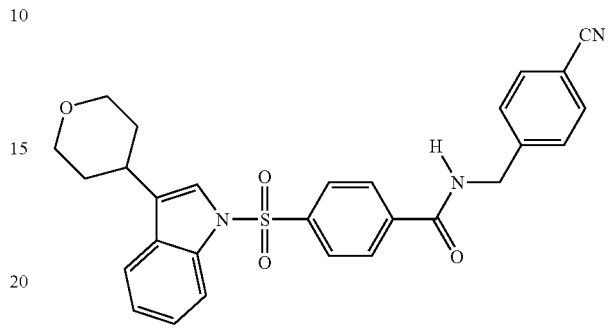

Stir 4-(3-tetrahydro-pyran-4-yl)-indole-1-sulfonyl)-benzoic acid (0.200 g, 0.518 mmole) with EDC [1892-57-5] (0.118 g, 0.662 mmoles) 4-aminomethyl-benzonitrile (0.082 g, 0.662 mmoles) in dichloromethane until completion. Dilute reaction and wash with 1 N HCl. Dry organic layer over MgSO$_4$ and concentrate. Purify the residue via flash column chromatography with a mixture of methanol and dichloromethane or EtOAc and dichloromethane to isolate 0.102 g of solid material (Yield=41%). Mass Spectrum (m/e): 498.04 (M−).

Example 72

(2-Phenyl-azetidin-1-yl)-[4-(3-phenyl-indole-1-sulfonyl)-phenyl]-methanone

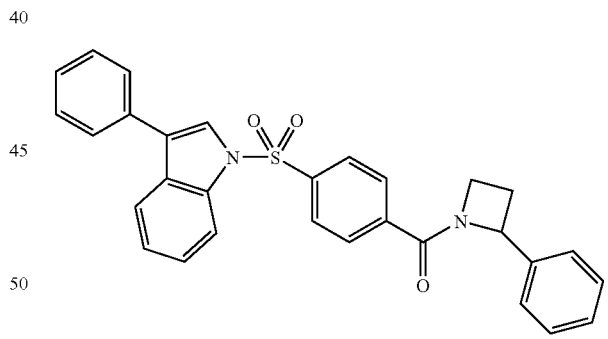

Combine 4-(3-phenyl-indole-1-sulfonyl)-benzoic acid (125 mg, 0.33 mmol) and 2-phenyl-azetidine (100 mg, 0.75 mmol, excess) in dichloromethane (1.0 mL) and triethylamine (0.300 mL, 2.15 mmol, excess) and add benzotriazol-1-yloxytris(dimethylamino)phosphonium hexfluorophosphate (BOP Reagent) (0.150 mg, 0.33 mmol) at room temperature. Stir for 30 minutes, load entire reaction directly onto pre-packed silica gel column and purify by flash column chromatography (EtOAc/Hexanes) to yield 149 mg of (2-Phenyl-azetidin-1-yl)-[4-(3-phenyl-indole-1-sulfonyl)-phenyl]-methanone as a glassy solid (92%). LRMS: MH+ 493.08.

Prepare the following sulfonamides in Table 2 using methods similar to the noted reference examples.

TABLE 2

| Ex. No. | Name | Structure | Amine | Mass spec (M + H) except where designated | Reference Examples |
|---|---|---|---|---|---|
| 73 | 4-(3-Phenyl-indole-1-sulfonyl)-N-pyrimidin-2-ylmethyl-benzamide | 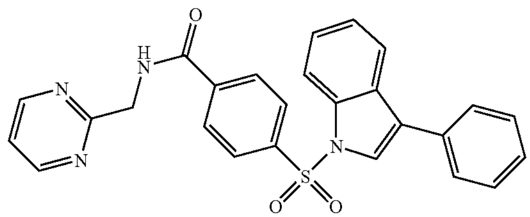 | C-Pyrimidin-2-yl-methylamine | 468.9 | 70 |
| 74 | [4-(3-Phenyl-indole-1-sulfonyl)-phenyl]-(3,4,5,6-tetrahydro-2H-[4,4']bipyridinyl-1-yl)-methanone | 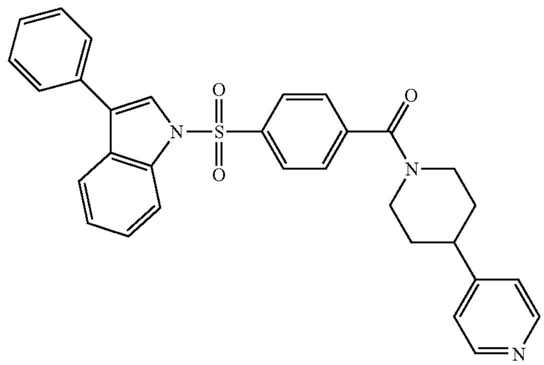 | 1,2,3,4,5,6-Hexahydro-[4,4']bipyridinyl | 522.1 | 70 |
| 75 | 4-(3-Phenyl-indole-1-sulfonyl)-N-pyridin-3-ylmethyl-benzamide hydrochloride* | 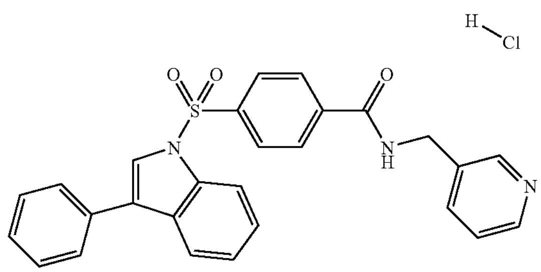 | Pyridin-3-yl-methylamine | 467.93 | 72 |
| 76 | N-(5-Fluoro-pyridin-3-ylmethyl)-4-(3-phenyl-indole-1-sulfonyl)-benzamide Hydrochloride* | 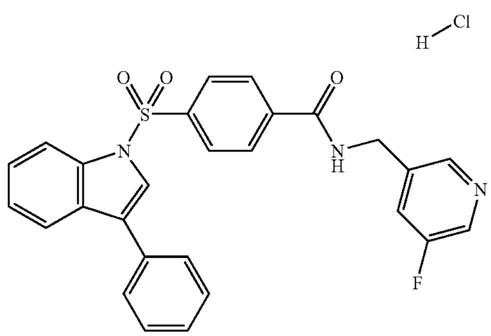 | 5-Fluoro-pyridin-3-yl-methylamine | 485.82 | 72 |
| 77 | N-(5-Fluoro-pyridin-2-ylmethyl)-4-(3-phenyl-indole-1-sulfonyl)-benzamide Hydrochloride* | 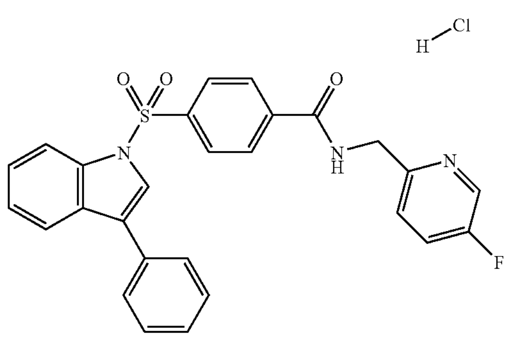 | 5-Fluoro-pyridin-2-yl-methylamine | 485.95 | 72 |

TABLE 2-continued

| Ex. No. | Name | Structure | Amine | Mass spec (M + H) except where designated | Reference Examples |
|---|---|---|---|---|---|
| 78 | Trans-N-(2-Hydroxy-cyclohexylmethyl)-4-(3-phenyl-indole-1-sulfonyl)-benzamide | | Trans-2-Aminomethyl-cyclohexanol | 489.07 | 72 |
| 79 | Cis-N-(2-Hydroxy-cyclohexylmethyl)-4-(3-phenyl-indole-1-sulfonyl)-benzamide | | Cis-2-Aminomethyl-cyclohexanol | 488.98 | 72 |
| 80 | (S)-4-(3-Phenyl-indole-1-sulfonyl)-N-(tetrahydro-furan-2-ylmethyl)-benzamide | 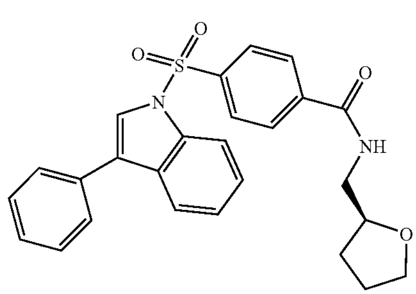 | (S)-(+)-Tetrahydro-furan-2-yl-methylamine | 461.00 | 72 |

TABLE 2-continued

| Ex. No. | Name | Structure | Amine | Mass spec (M + H) except where designated | Reference Examples |
|---|---|---|---|---|---|
| 81 | (R)-4-(3-Phenyl-indole-1-sulfonyl)-N-(tetrahydro-furan-2-ylmethyl-benzamide | 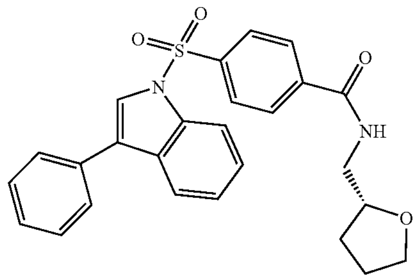 | (R)-(−)-Tetrahydro-furan-2-yl-methylamine | 461.01 | 72 |
| 82 | 4-(3-Phenyl-indole-1-sulfonyl)-N-pyridin-2-ylmethyl-benzamide hydrochloride* | 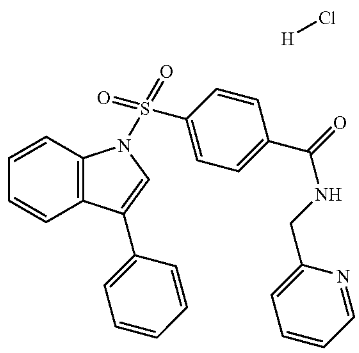 | Pyridin-2-yl-methylamine | 467.94 | 72 |
| 83 | 4-(3-Phenyl-indole-1-sulfonyl)-N-pyridin-4-ylmethyl-benzamide hydrochloride* | 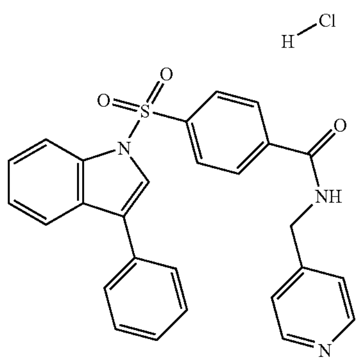 | Pyridin-4-yl-methylamine | 467.99 | 72 |
| 84 | Trans-N-(2-Hydroxy-cyclohexyl)-4-(3-phenyl-indole-1-sulfonyl)-benzamide | | Trans-2-Amino-cyclohexanol | 474.98 | 72 |

TABLE 2-continued

| Ex. No. | Name | Structure | Amine | Mass spec (M + H) except where designated | Reference Examples |
|---|---|---|---|---|---|
| 85 | Cis-N-(2-Hydroxy-cyclohexyl)-4-(3-phenyl-indole-1-sulfonyl)-benzamide | | Cis-2-Amino-cyclohexanol | 474.99 | 72 |
| 86 | Azetidin-1-yl[4-(3-phenyl-indole-1-sulfonyl)-phenyl]-methanone | 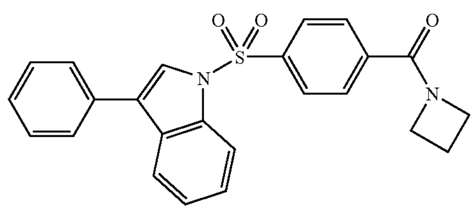 | Azetidine | 416.94 | 72 |
| 87 | (4-Benzyl-piperidin-1-yl)-[4-(3-phenyl-indole-1-sulfonyl)-phenyl]-methanone | 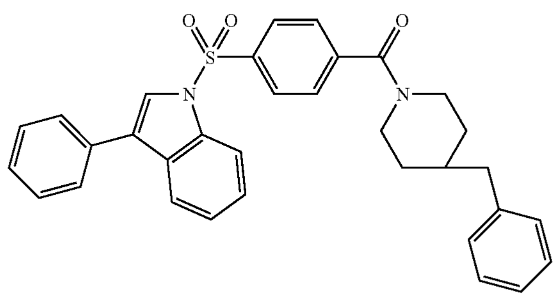 | 4-Benzyl-piperidine | 536.05 | 72 |
| 88 | (4,4-Difluoro-piperidin-1-yl)-[4-(3-phenyl-indole-1-sulfonyl)-phenyl]-methanone | 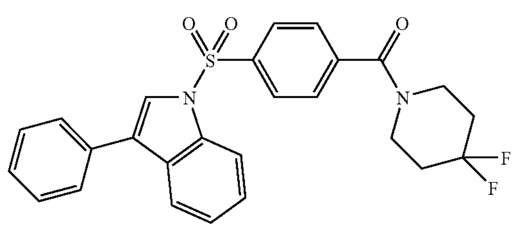 | 4,4-Difluoro-piperidine | 480.97 | 72 |
| 89 | [4-(3-Phenyl-indole-1-sulfonyl)-phenyl]-piperidin-1-yl-methanone | 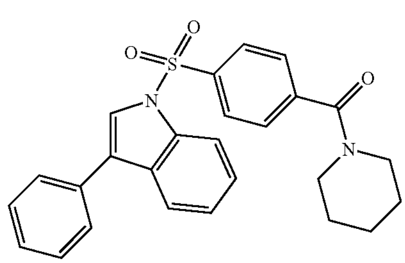 | Piperidine | 444.97 | 72 |

TABLE 2-continued

| Ex. No. | Name | Structure | Amine | Mass spec (M + H) except where designated | Reference Examples |
|---|---|---|---|---|---|
| 90 | [4-(3-Phenyl-indole-1-sulfonyl)-phenyl]-pyrrolidin-1-yl-methanone | 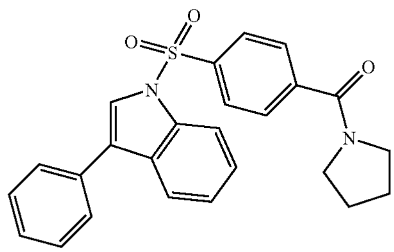 | Pyrrolidine | 430.96 | 72 |
| 91 | 4-(3-Phenyl-indole-1-sulfonyl)-N-(tetrahydro-pyran-4-yl)-benzamide | 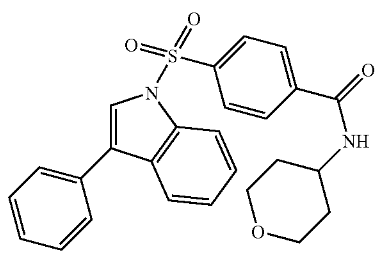 | Tetrahydro-pyran-4-ylamine | 461.20 | 72 |
| 92 | N,N-Dimethyl-4-(3-phenyl-indole-1-sulfonyl)-benzamide | 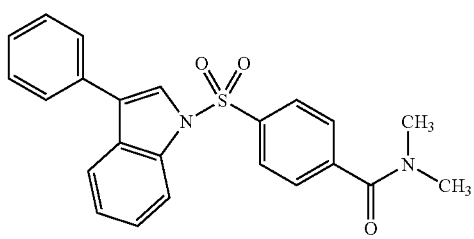 | Dimethylamine | 405.10 | 72 |
| 93 | 1-[4-(3-Phenyl-indole-1-sulfonyl)-benzoyl]-piperidin-4-one | 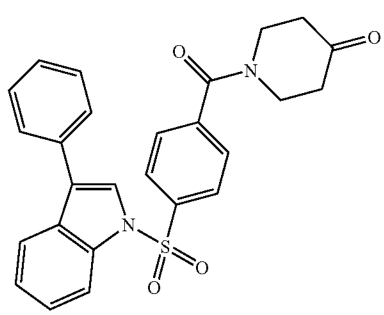 | Piperidin-4-one | 528.90 | 72 |
| 94 | (3-Hydroxy-piperidin-1-yl)-[4-(3-phenyl-indole-1-sulfonyl)-phenyl]-methanone | 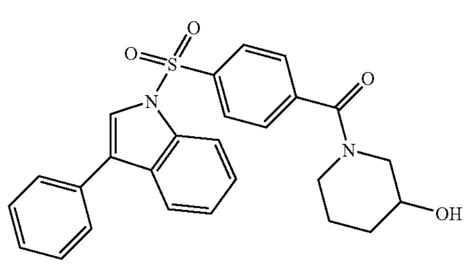 | 3-Hydroxy-piperidine | 460.95 | 72 |

TABLE 2-continued

| Ex. No. | Name | Structure | Amine | Mass spec (M + H) except where designated | Reference Examples |
|---|---|---|---|---|---|
| 95 | Morpholin-4-yl-[4-(3-phenyl-indole-1-sulfonyl)-phenyl]-methanone | 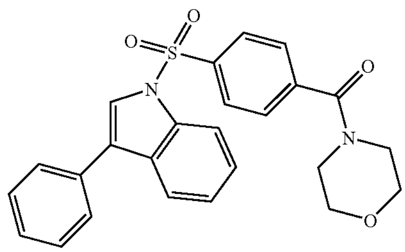 | Morpholine | 446.96 | 72 |
| 96 | (2-Hydroxymethyl-piperidin-1-yl)-[4-(3-phenyl-indole-1-sulfonyl)-phenyl]-methanone | 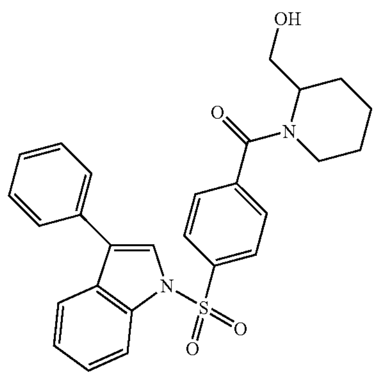 | Piperidin-2-yl-methanol | 474.90 | 72 |
| 97 | (3-Hydroxymethyl-piperidin-1-yl)-[4-(3-phenyl-indole-1-sulfonyl)-phenyl]-methanone | 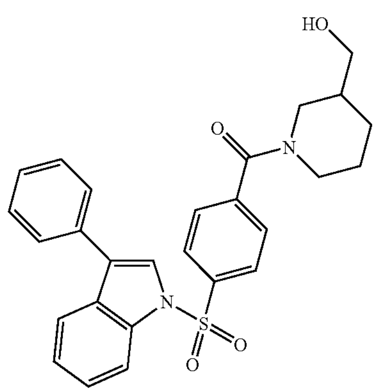 | Piperidin-3-yl-methanol | 475.00 | 72 |
| 98 | Trans-N-(4-Hydroxy-cyclohexyl)-4-(3-phenyl-indole-1-sulfonyl)-benzamide | 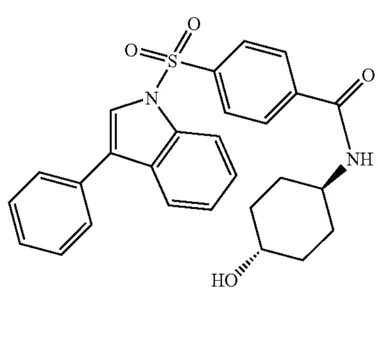 | Trans-4-Amino cyclohexanol | 474.99 | 72 |

TABLE 2-continued

| Ex. No. | Name | Structure | Amine | Mass spec (M + H) except where designated | Reference Examples |
|---|---|---|---|---|---|
| 100 | 4-(3-Phenyl-indole-1-sulfonyl)-N-pyridazin-3-ylmethyl-benzamide | 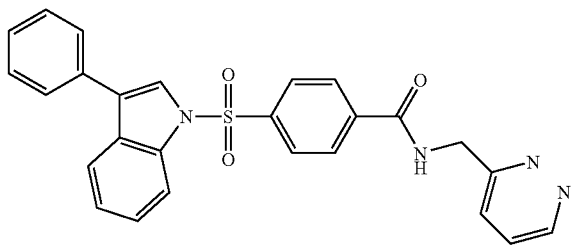 | C-Pyridazin-3-yl-methylamine | 469.01 | 70 |
| 101 | N-[1-(4-Fluoro-phenyl)-piperidin-4-yl]-4-(3-phenyl-indole-1-sulfonyl)-benzamide | 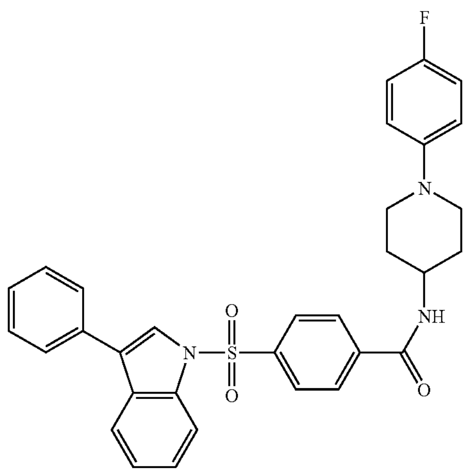 | 1-(4-Fluoro-phenyl)-piperidin-4-ylamine | 552.38 (M−) | 70 |
| 102 | 4-(3-Phenyl-indole-1-sulfonyl)-N-(1-phenyl-piperidin-4-ylmethyl)-benzamide | 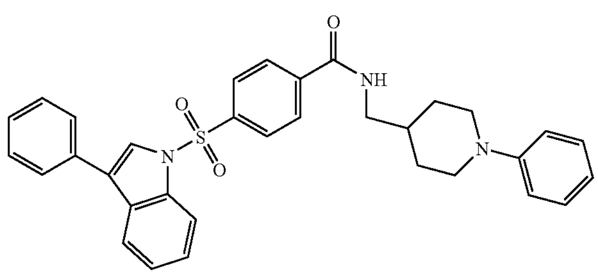 | C-(1-Phenyl-piperidin-4-yl)-methylammine | 550.06 | 70 |
| 103 | (R)-N-[1-(4-Fluoro-phenyl)-pyrrolidin-3-yl]-4-(3-phenyl-indole-1-sulfonyl)-benzamide | 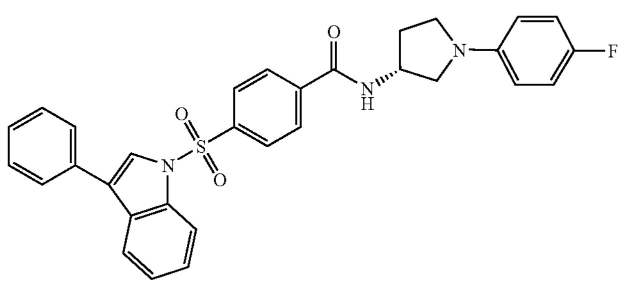 | (R)-1-(4-Fluoro-phenyl)-pyrrolidin-3-ylamine | 539.97 | 70 |

TABLE 2-continued

| Ex. No. | Name | Structure | Amine | Mass spec (M + H) except where designated | Reference Examples |
|---|---|---|---|---|---|
| 104 | (S)-N-[1-(4-Fluoro-phenyl)-pyrrolidin-3-yl]-4-(3-phenyl-indole-1-sulfonyl)-benzamide | 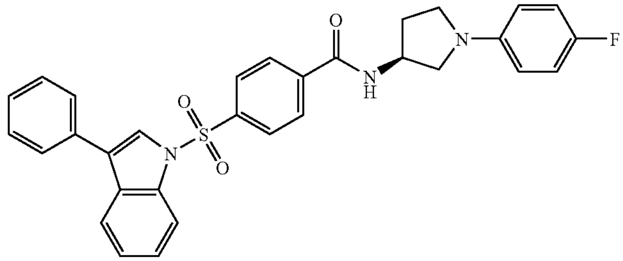 | (S)-1-(4-Fluoro-phenyl)-pyrrolidin-3-ylamine | 540.00 | 70 |
| 105 | N-[1-(4-Fluoro-phenyl)-azetidin-3-yl]-4-(3-phenyl-indole-1-sulfonyl)-benzamide | 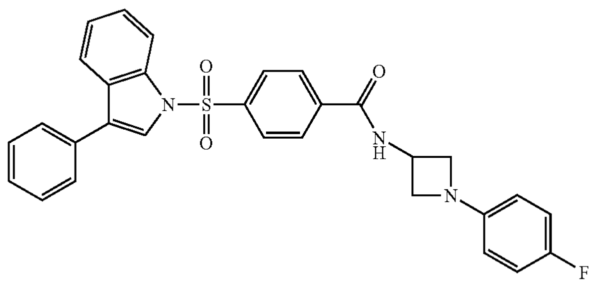 | 1-(4-Fluoro-phenyl)-azetidin-3-ylamine | 525.96 | 72 |
| 106 | 4-(3-Phenyl-indole-1-sulfonyl)-N-(tetrahydro-pyran-4-ylmethyl)-benzamide | 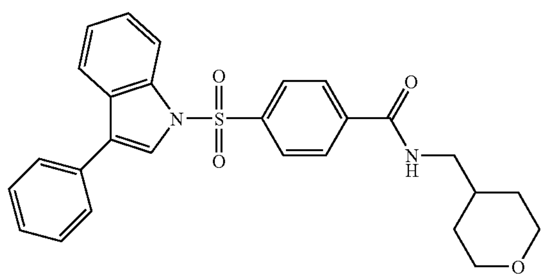 | 4-aminomethyl tetrahydropyran | 475.0 | 72 |
| 107 | N-(2-Methoxy-ethyl)-4-(3-phenyl-indole-1-sulfonyl)-benzamide | 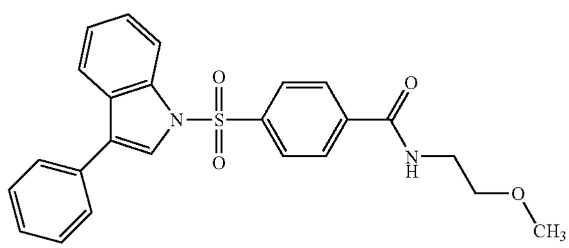 | 2-methoxy ethylamine | 434.96 | 72 |
| 108 | N-(2-Isopropoxy-ethyl)-4-(3-phenyl-indole-1-sulfonyl)-benzamide | 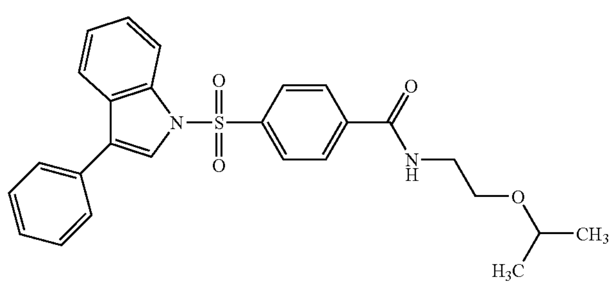 | 2-aminoethyl-propylamine | 462.99 | 72 |

TABLE 2-continued

| Ex. No. | Name | Structure | Amine | Mass spec (M + H) except where designated | Reference Examples |
|---|---|---|---|---|---|
| 109 | N-(2-Ethoxy-ethyl)-4-(3-phenyl-indole-1-sulfonyl)-benzamide | 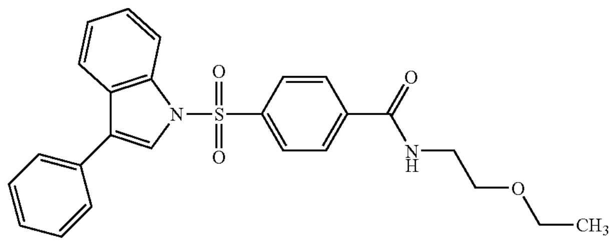 | 2-ethoxyethyl-amine | 434.96 | 72 |
| 110 | 4-[[4-(3-Phenyl-indole-1-sulfonyl)-benzoylamino]-methyl]-benzoic acid methyl ester | 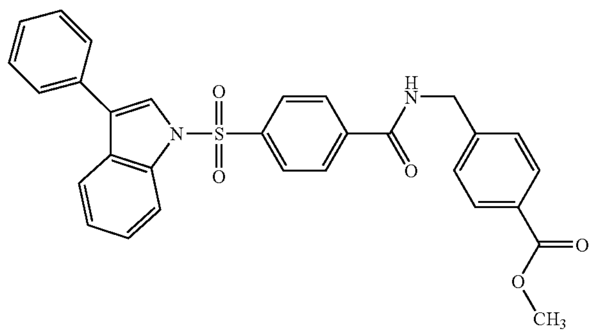 | 4-aminomethyl-benzoic acid methyl ester | 525.07 | 72 |
| 111 | N-(3-Methoxy-benzyl)-4-(3-phenyl-indole-1-sulfonyl)-ethyl-benzamide | 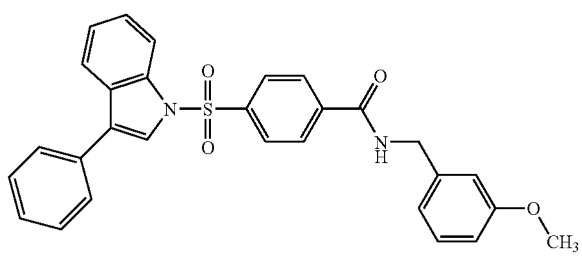 | 3-methoxybenzyl amine | 496.93 | 72 |
| 112 | N-(4-Dimethylamino-benzyl)-4-(3-phenyl-indole-1-sulfonyl)-benzamide | 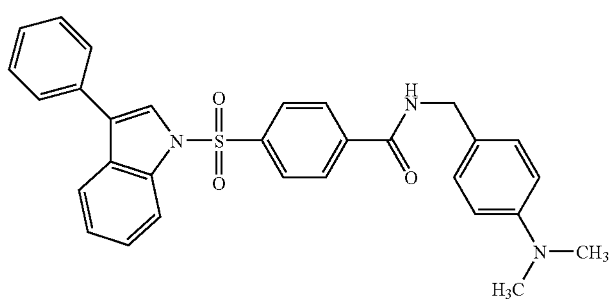 | 4-dimethylamino-benzyl amine | 510.01 | 72 |
| 113 | N-(4-amino-benzyl)-4-(3-phenyl-indole-1-sulfonyl)-benzamide | 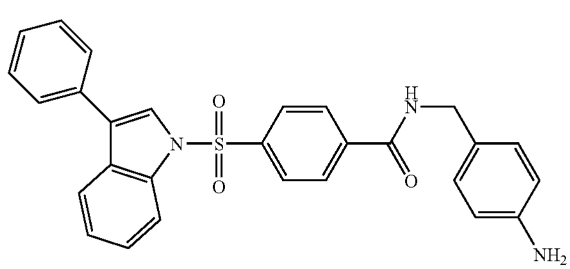 | 4-aminobenzyl amine | 481.94 | 72 |

TABLE 2-continued

| Ex. No. | Name | Structure | Amine | Mass spec (M + H) except where designated | Reference Examples |
|---|---|---|---|---|---|
| 114 | (2-Phenylaminomethyl-pyrrolidin-1-yl)-[4-(3-phenyl-indole-1-sulfonyl)-phenyl]-methanone | 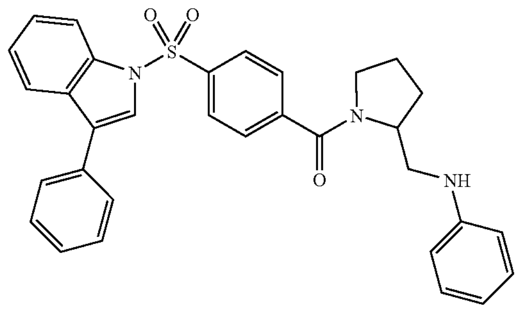 | (4-Fluoro-phenyl)-pyrrolidin-3-ylmethyl-amine | 536.03 | 70 |
| 115 | 2-[1-[4-(3-Phenyl-indole-1-sulfonyl)-benzoyl]-azetidin-3-ylmethyl]-isoindole-1,3-dione | 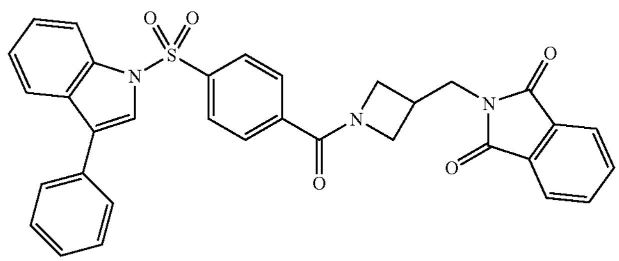 | 2-Azetidin-3-ylmethyl-isoindole-1,3-dione | 576.02 | 70 |
| 116 | 3-[4-(3-Phenyl-indole-1-sulfonyl)-benzoylamino]-azetidine-1-carboxylic acid tert-butyl ester | 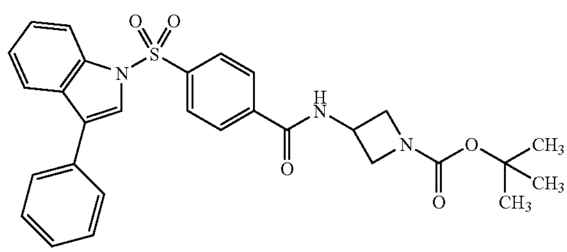 | 3-Amino-azetidine-1-carboxylic acid tert-butyl ester | 531.95 | 70 |
| 117 | (R)-1-[4-(3-Phenyl-indole-1-sulfonyl)-benzoyl]-pyrrolidin-3-yl]-carbamic acid tert-butyl ester | 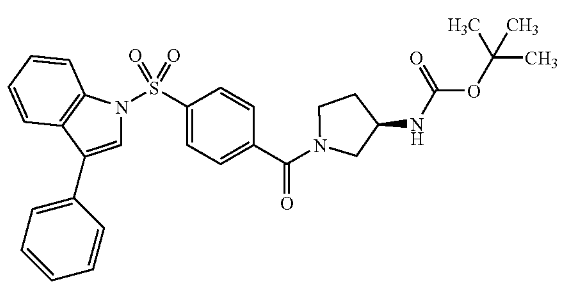 | (R)-Pyrrolidin-3-yl-carbamic acid tert-butyl ester | 546.05 | 70 |
| 118 | [(S)-1-[4-(3-Phenyl-indole-1-sulfonyl)-benzoyl]-pyrrolidin-3-yl]-carbamic acid tert-butyl ester | 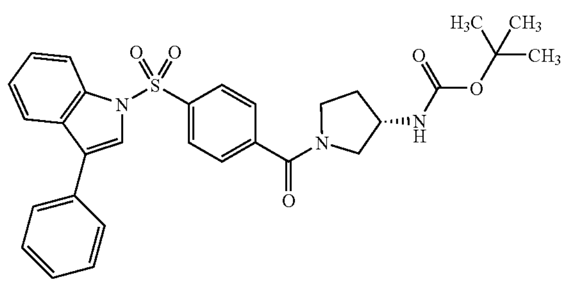 | (S)-Pyrrolidin-3-yl-carbamic acid tert-butyl ester | 546.01 | 70 |

TABLE 2-continued

| Ex. No. | Name | Structure | Amine | Mass spec (M + H) except where designated | Reference Examples |
|---|---|---|---|---|---|
| 119 | [1-[4-(3-Phenyl-indole-1-sulfonyl)-benzoyl]-azetidin-3-ylmethyl]-carbamic acid tert-butyl ester | 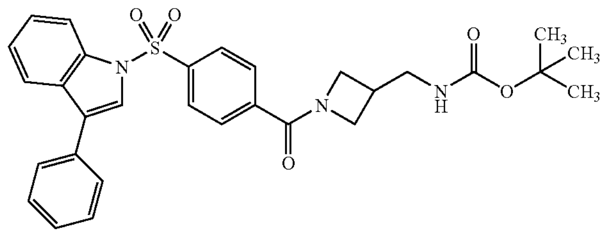 | Azetidin-3-ylmethyl-carbamic acid tert-butyl ester | 546.17 | 70 |
| 120 | [1-[4-(3-Phenyl-indole-1-sulfonyl)-benzoyl]-azetidin-3-yl]-carbamic aacid tert-butyl ester | 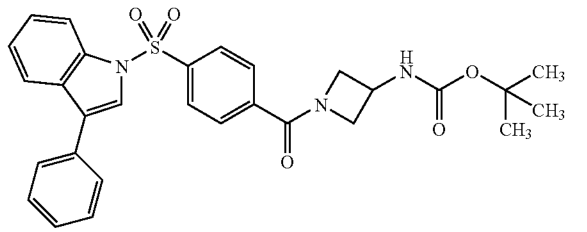 | Azetidin-3-yl-carbamic acid tert-butyl ester | 532.02 | 70 |
| 121 | N-Cyclobutyl-4-(3-phenyl-indole-1-sulfonyl)-benzamide | 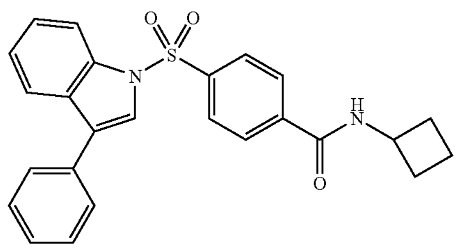 | Cyclobutyl amine | 430.98 | 70 |
| 122 | 3-[[4-(3-Phenyl-indole-1-sulfonyl)-benzoylamino]-methyl]-azetidine-1-carboxylic acid methyl ester | 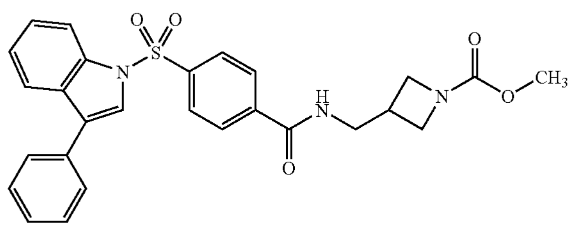 | 3-Aminomethyl-azetidine-1-carboxylic acid methyl ester | 503.98 | 70 |
| 123 | (3-Hydroxymethyl-azetidin-1-yl)-[4-(3-phenyl-indole-1-sulfonyl)-phenyl]-methanone | 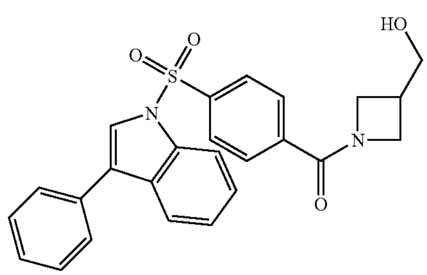 | Azetidin-3-yl-methanol | 447.2 | 72 |
| 124 | N-(Tetrahydro-(R)-furan-2-ylmethyl)-4-[3-(tetrahydro-pyran-4-yl)-indole-1-sulfonyl]-benzamide | 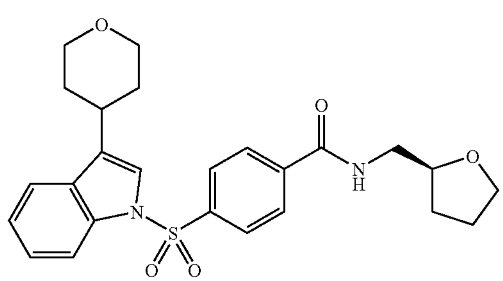 | (R)(−)(Tetrahydro-furan-2-yl)-methanol | 468.9 | 72 |

TABLE 2-continued

| Ex. No. | Name | Structure | Amine | Mass spec (M + H) except where designated | Reference Examples |
|---|---|---|---|---|---|
| 126 | N-(2-Methoxy-cyclohexyl)-4-(3-phenyl-indole-1-sulfonyl)-benzamide | 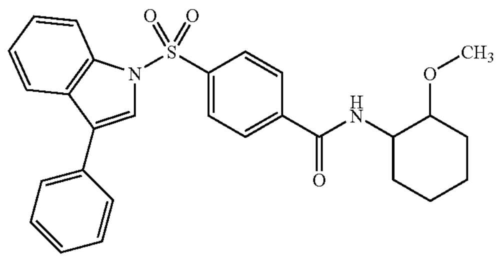 | 2-Methoxy-cyclohexylamine | 489.05 | 70 |
| 127 | N-[1-(4-Fluoro-phenyl)-pyrrolidin-3-yl]-4-(3-phenyl-indole-1-sulfonyl)-benzamide | 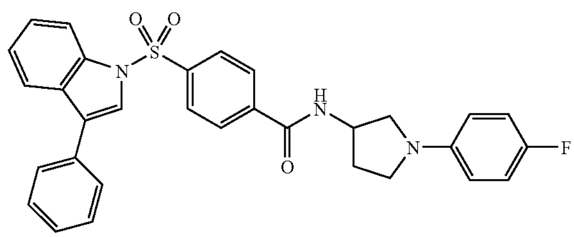 | 1-(4-Fluoro-phenyl)-pyrrolidin-3-ylamine | 540.2 | 70 |
| 128 | 3-[-(3-Phenyl-indole-1-sulfonyl)-benzoylamino]-pyrrolidine-1-carboxylic acid methyl ester | 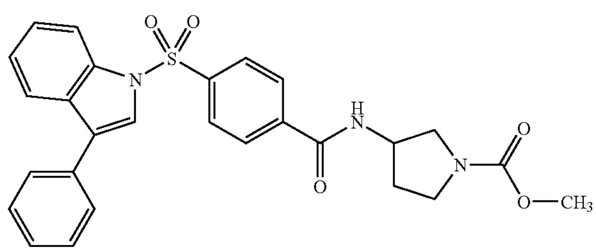 | 3-Amino-pyrrolidin-1-carboxylic acid methyl ester | 504.02 | 70 |
| 129 | [4-(3-Fluoro-phenyl)-piperidin-1-yl]-[4-(3-phenyl-indole-1-sulfonyl)-phenyl]-methanone | 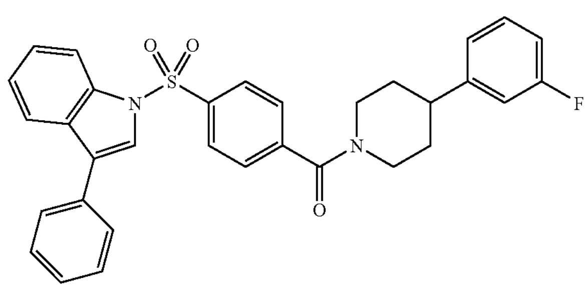 | 4-(3-Fluoro-phenyl) piperidine | 539.09 | 70 |
| 130 | 4-[3-(2-Fluoro-pyridin-3-yl)-indole-1-sulfonyl]-N-(tetrahydro-pyran-4-ylmethyl)-benzamide | 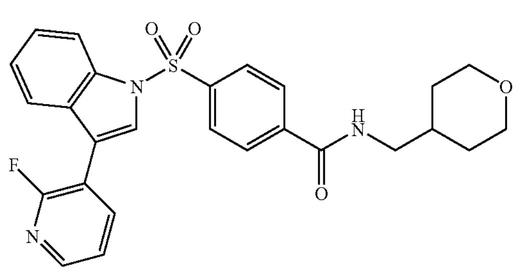 | 4-aminomethyl tetrahydropyran | 494.01 | 70 |

TABLE 2-continued

| Ex. No. | Name | Structure | Amine | Mass spec (M + H) except where designated | Reference Examples |
|---|---|---|---|---|---|
| 131 | N-Cyclobutyl-4-[3-(2-fluoro-pyridin-3-yl)indole-1-sulfonyl]-benzamide | 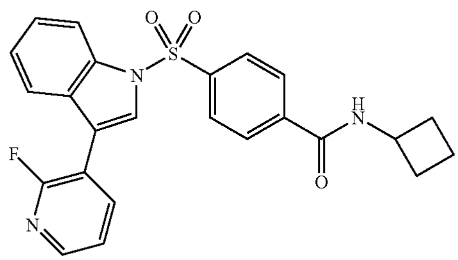 | Cyclobutyl amine | 449.99 | 70 |
| 132 | N-Cyclopropyl-methyl-4-[3-(2-fluoro-pyridin-3-yl)-indole-1-sulfonyl]-benzamide | 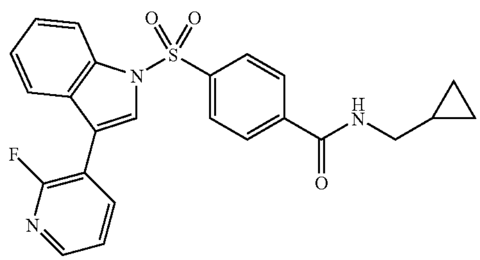 | Cyclopropyl methyl amine | 449.94 | 70 |
| 133 | 4-[3-(6-Fluoro-pyridin-3-yl)-indole-1-sulfonyl]-N-(tetrahydro-pyran-4-ylmethyl)-benzamide | 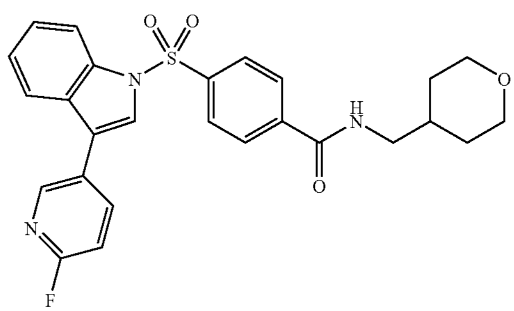 | 4-aminomethyl tetrahydropyran | 493.90 | 70 |
| 134 | N-Cyclopropylmethyl-4-[3-(6-fluoro-pyridin-3-yl)-indole-1-sulfonyl]-benzamide | 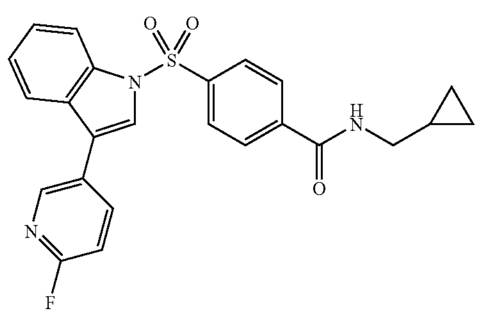 | Cyclopropyl methyl amine | 449.94 | 70 |
| 135 | 4-(3-Cyclopentyl-indole-1-sulfonyl)-N-cyclopropylmethyl-benzamide | 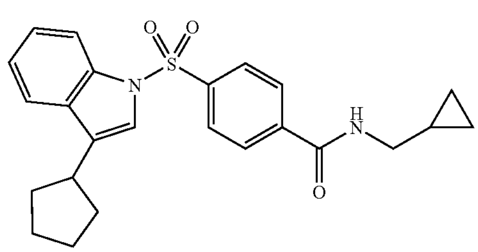 | Cyclopropyl methyl amine | 422.99 | 70 |

TABLE 2-continued

| Ex. No. | Name | Structure | Amine | Mass spec (M + H) except where designated | Reference Examples |
|---|---|---|---|---|---|
| 136 | 4-(3-Cyclopentyl-indole-1-sulfonyl)-N-cyclopropylmethyl-benzamide | 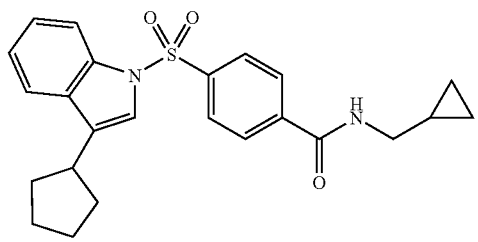 | Cyclopropyl methylamine | 423.00 | 72 |
| 137 | 4-(3-Cyclopentyl-indole-1-sulfonyl)-N-cyclobutyl-benzamide | 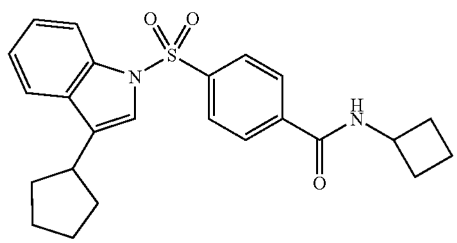 | Cyclopropyl amine | 423.00 | 70 |
| 138 | Azetidin-1-yl-[4-(3-cyclopentyl-indole-1-sulfonyl)-phenyl]-methanone | 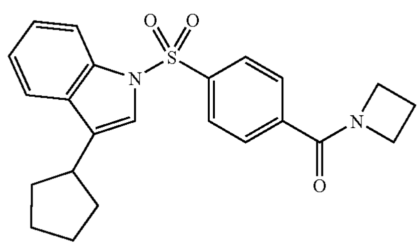 | azetidine | 409.02 | 70 |
| 139 | N-(5-Cyano-pyridin-3-ylmethyl)-4-(3-phenyl-indole-1-sulfonyl)-benzamide | 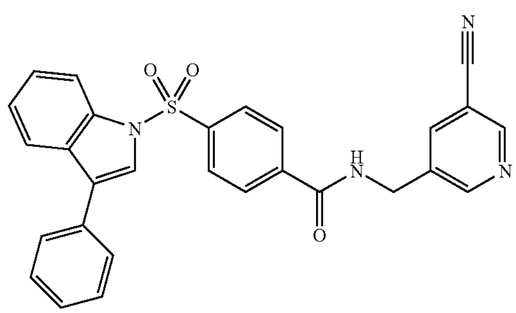 | 5-Aminomethyl-nicotinonitrile | 492.91 | 70 |
| 140 | 4-(3-Cyclopentyl-indole-1-sulfonyl)-N-[(R)-1-(tetrahydro-furan-2-yl)methyl]-benzamide | 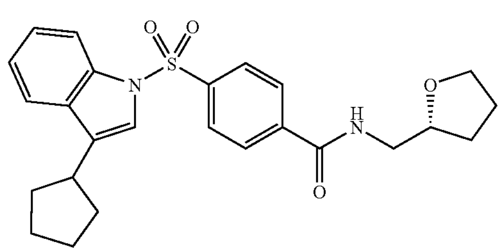 | R-(Tetrahydro-furan-2-yl)-methylamine | 452.96 | 70 |

TABLE 2-continued

| Ex. No. | Name | Structure | Amine | Mass spec (M + H) except where designated | Reference Examples |
|---|---|---|---|---|---|
| 141 | N-Cyclopropylmethyl-4-[3-(tetrahydro-pyran-4-yl)-indole-1-sulfonyl]-benzamide | 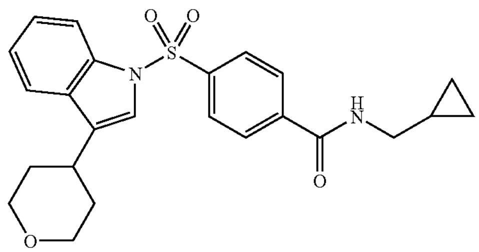 | Cyclopropyl methyl amine | 438.93 | 72 |
| 142 | 4-(3-Phenyl-indole-1-sulfonyl)-N-(tetrahydro-ffuran-3-ylmethyl)-benzamide | 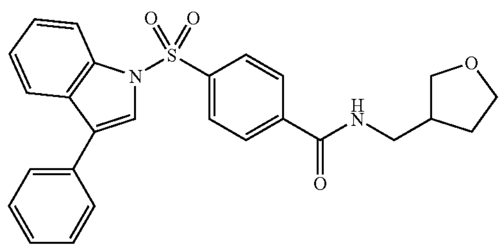 | C-(Tetrahydro-furqan-3-yl)-methylamine | 460.96 | 72 |
| 143 | N-(4-Cyano-benzyl)-4-[3-(cyclopentyl)-indole-1-sulfonyl]-benzamide | 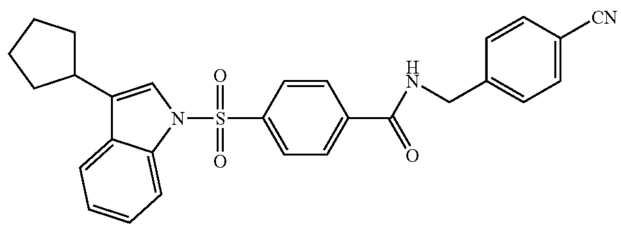 | 4-Aminomethyl-benzonitrile | 498.04 | 72 |
| 144 | N-(4-Cyano-benzyl)-4-(3-cyclopropyl-indole-1-sulfonyl)-benzamide | 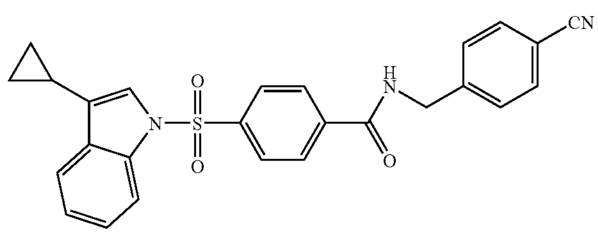 | 4-Aminomethyl-benzonitrile | 455.92 | 70 |
| 145 | 4-(3-Cyclopentyl-indole-1-sulfonyl)-N-(tetrahydro-pyran-2-ylmethyl)-benzamide | 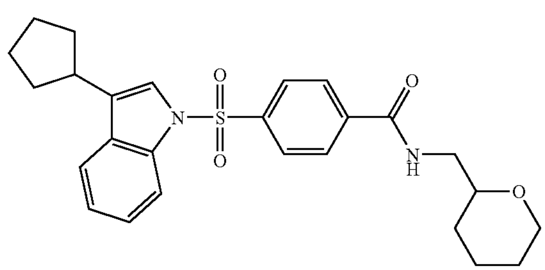 | C-(Tetrahydro-pyran-2-yl)-methylamine | 473.11 (M + 1)− | 72 |

TABLE 2-continued

| Ex. No. | Name | Structure | Amine | Mass spec (M + H) except where designated | Reference Examples |
|---|---|---|---|---|---|
| 146 | N-(4-Amino-benzyl)-4-(3-phenyl-indole-1-sulfonyl)-benzamide | 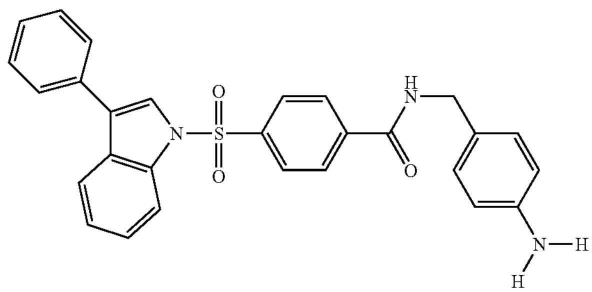 | 4-Aminomethyl-benzonitrile | 482.07 (M + 1)− | 72 |
| 147 | N-Isobutyl-4-(3-phenyl-indole-1-sulfonyl)-benzamide | 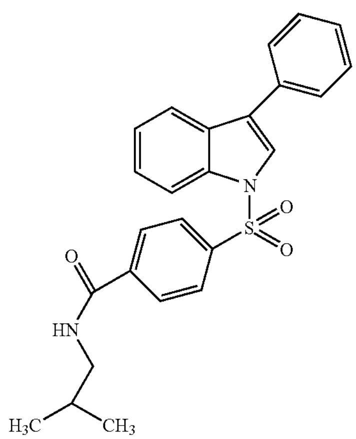 | isobutylamine | 433.1598 | 70 |
| 148 | N-Isoamyl-4-(3-phenyl-indole-1-sulfonyl)-benzamide | 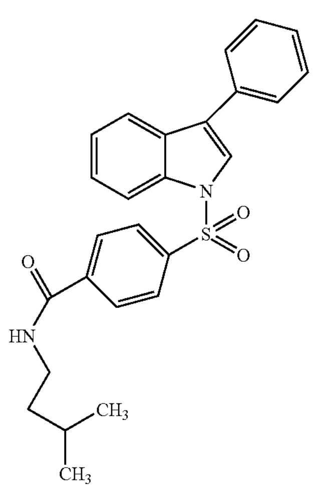 | isoamylamine | 447.1752 | 70 |

TABLE 2-continued

| Ex. No. | Name | Structure | Amine | Mass spec (M + H) except where designated | Reference Examples |
|---|---|---|---|---|---|
| 149 | N-2-methylbutylamine-4-(3-phenyl-indole-1-sulfonyl)-benzamide | 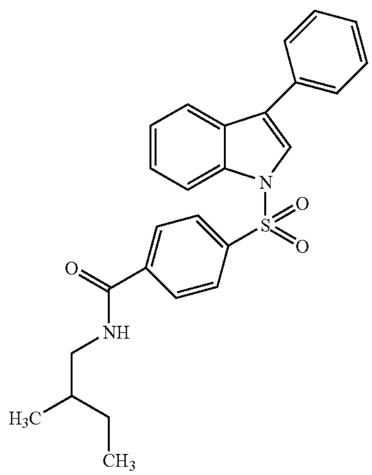 | 2-methylbutyl amine | 447.1738 | 72 |
| 150 | 4-(3-Cyclopropyl-indole-1-sulfonyl)-N-(5-fluoro-pyridin-2-ylmethyl)-benzamide | 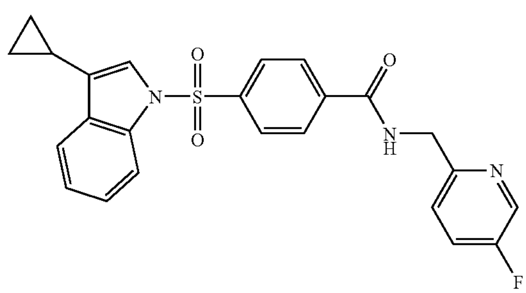 | C-(5-Fluoro-pyridin-2-yl)-methylamine | 450 | 70 |
| 151 | 4-(3-Cyclopropyl-indole-1-sulfonyl)-N-(tetrahydro-pyran-4-ylmethyl)-benzamide | 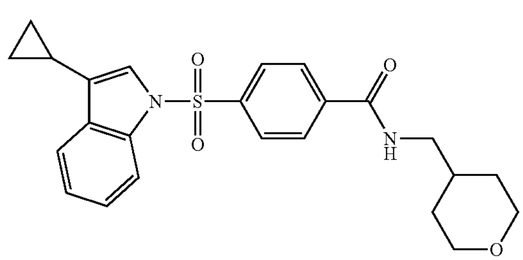 | 4-aminomethyl tetrahydropyran | 439.1 | 70 |
| 152 | 4-(3-Cyclopropyl-indole-1-sulfonyl)-N-(2-ispropoxy-ethyl)-benzamide | 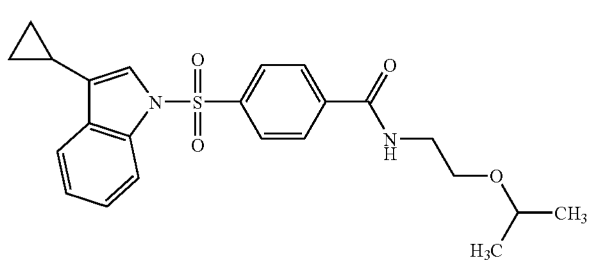 | 2-Isopropoxy-ethylamine | 427 | 70 |

TABLE 2-continued

| Ex. No. | Name | Structure | Amine | Mass spec (M + H) except where designated | Reference Examples |
|---|---|---|---|---|---|
| 153 | N-(4-Cyano-benzyl)-4-(3-phenyl-indole-1-sulfonyl)-benzamide | 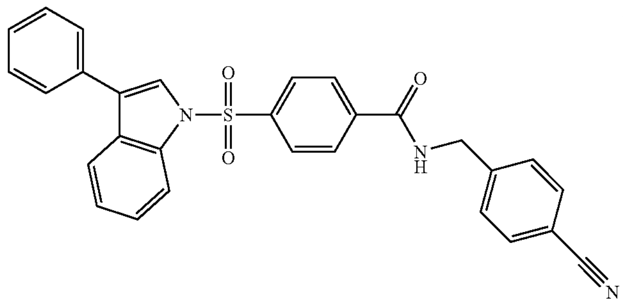 | 4-Aminomethyl-benzonitrile | 491.94 | 72 |
| 154 | N-(5-Fluoro-pyridin-2-ylmethyl)-4-[3-(tetrahydro-pyran-4-yl)-indole-1-sulfonyl]-benzamide | 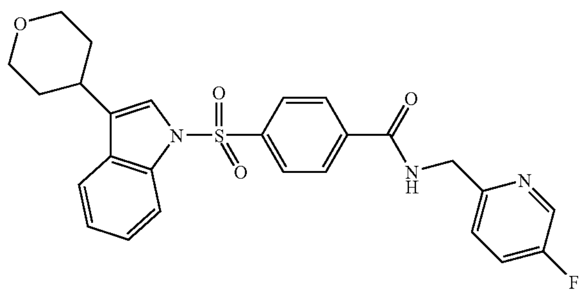 | C-(5-Fluoro-pyridin-2-yl)-methylamine | 493.89 | 72 |
| 155 | 4-[3-(Tetrahydro-pyran-4-yl)-indole-1-sulfonyl]-N-(tetrahydro-pyran-4-ylmethyl)-benzamide | 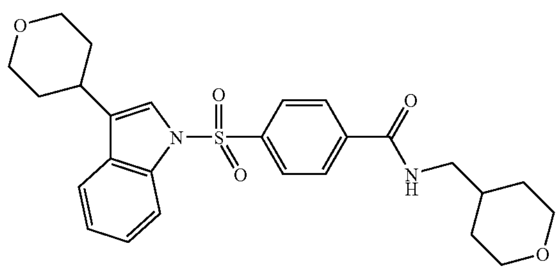 | 4-aminimethyl tetrahydropyran | 482.93 | 72 |
| 156 | N-Cyclobutyl-4-[3-(tetrahydro-pyran-4-yl)-indole-1-sulfonyl]-benzamide | 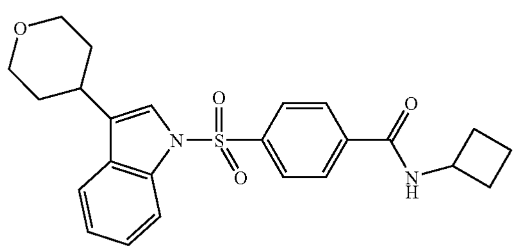 | Cyclobutyl amine | 438.98 | 72 |
| 157 | N-(5-Fluoro-pyridin-3-ylmethyl)-4-[3-(tetrahydro-pyran-4-yl)-indole-1-sulfonyl]-benzamide | 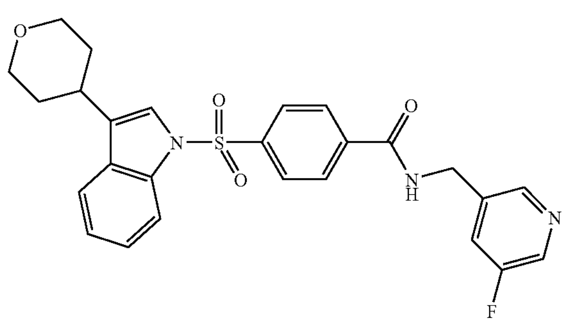 | C-(5-Fluoro-pyridin-3-yl)-methylamine | 493.95 | 72 |

TABLE 2-continued

| Ex. No. | Name | Structure | Amine | Mass spec (M + H) except where designated | Reference Examples |
|---|---|---|---|---|---|
| 157a | N-Cyclopropylmethyl-4-(3-phenyl-indole-1-sulfonyl)-benzamide | 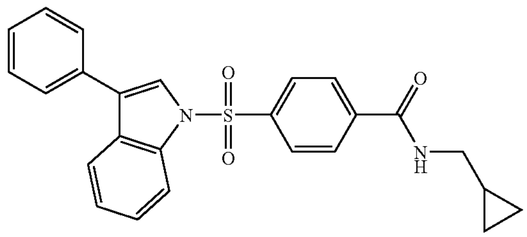 | cyclopropyl methyl amine | 431.2 | 72 |
| 157b | 4-(3-Cyclopentyl-indole-1-sulfonyl)-N-pyridin-3-ylmethyl-benzamide | 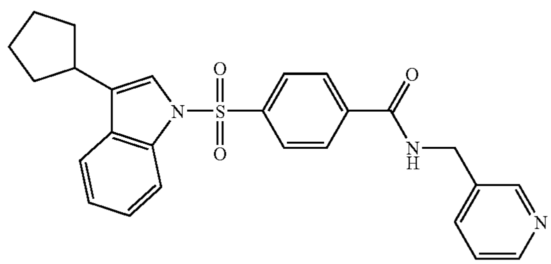 | Pyridin-3-yl-methylamine | M − 1 458 | 72 |
| 157c | 4-(3-Cyclopentyl-indole-1-sulfonyl)-N-piperidin-1-yl-benzamide | 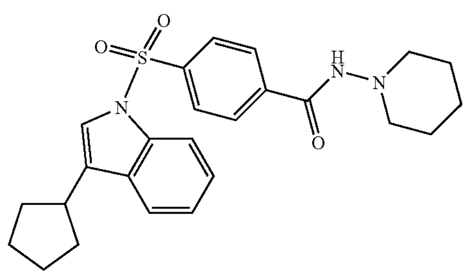 | N-aminopiperidine | 452.1 | 72 |
| 157d | 4-(3-Phenyl-indole-1-sulfonyl)-N-piperidin-1-yl-benzamide | 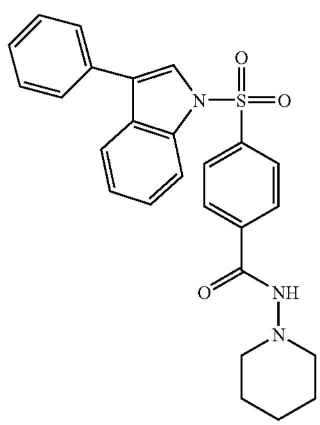 | N-aminopiperidine | 460.1 | 72 |

*Dissolve the purified compound in a minimum amount of tetrahydrofuran, cool to 0° C. and treat wwith 1-2 equivalents of anhydrous HCl in THF and evaporate the solvents to give the final HCl salt.

Example 158

Resolution of Cis-N-(2-Hydroxy-cyclohexyl)-4-(3-phenyl-indole-1-sulfonyl)-benzamide

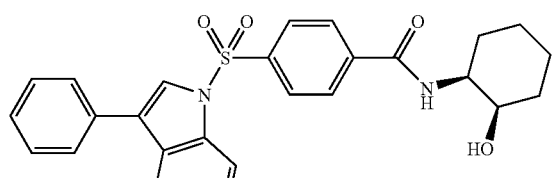

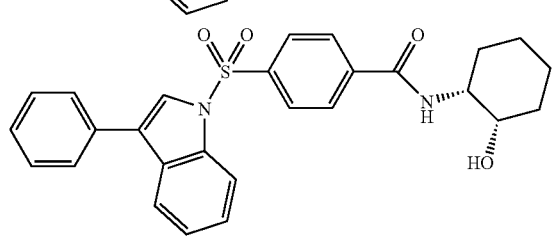

Separate the title compound by chiral chromatography (prep ChiralPak AD, 100% EtOH, 14 mL/min, analytical ChiralPak AD, 100% EtOH, 1.0 mL/min. Isomer 1 retention time (analytical) 8.35 min LRMS: 475.06. Isomer 2 retention time (analytical) 11.85 min LRMS: 475.05.

Example 159

Resolution of Trans-N-(2-Hydroxy-cyclohexylmethyl)-4-(3-phenyl-indole-1-sulfonyl)-benzamide

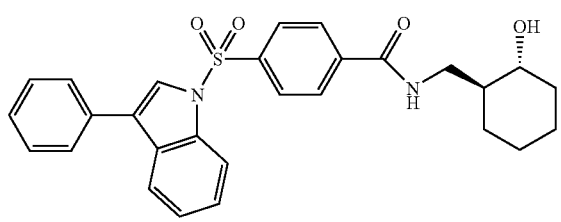

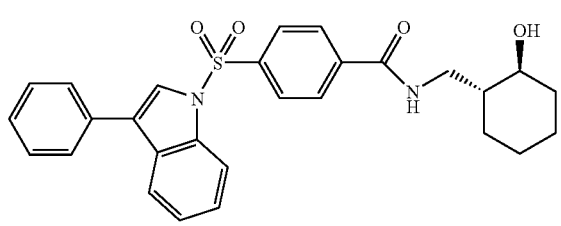

Separate the title compounds by chiral chromatography (prep ChiralPak AD, 100% EtOH, 14 mL/min, analytical ChiralPak AD, 100% EtOH, 1.0 mL/min. Isomer 1 retention time (analytical) 6.75 min LRMS: 489.10. Isomer 2 retention time (analytical) 9.55 min LRMS: 489.11.

Example 161

(3-Hydroxy-azetidin-1-yl)-[4-(3-phenyl-indole-1-sulfonyl)-phenyl]-methanone

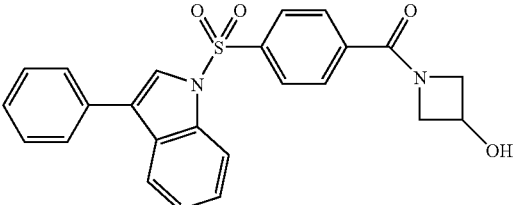

Dissolve 1-Benzhydryl-azetidin-3-ol (250 mg, 1.04 mmoL) in methanol (3.0 mL) and add to Pd(OH)$_2$ (50 mg) under nitrogen. Degas reaction vessel and purge with 60 psi H2 (g). Repeat degass/H$_2$ purge cycle again. Allow to stir under 60 psi H$_2$ for 15 h. Release reaction and filter through celite with additional methanol. Evaporate methanol to yield azetidin-3-ol as a liquid which is used without further purification. Combine 4-(3-Phenyl-indole-1-sulfonyl)-benzoic acid (200 mg, 0.53 mmol) and azetidin-3-ol (50 mg, 0.68 mmol, excess) in dichloromethane (1.0 mL) and triethylamine (0.500 mL, 3.58 mmol, excess) and add benzotriazol-1-yloxytris(dimethylamino)phosphonium hexfluorophosphate (BOP Reagent) (300 mg, 0.66 mmol, excess) at room temperature. Stir for 30 minutes, load entire reaction directly onto pre-packed silica gel column and purify by flash column chromatography (EtOAc/Hexanes) to yield 167 mg of (3-Hydroxy-azetidin-1-yl)-[4-(3-phenyl-indole-1-sulfonyl)-phenyl]-methanone as a white foam (73%). LRMS: MH+ 432.97.

Example 162

Methanesulfonic acid 1-[4-(3-phenyl-indole-1-sulfonyl)-benzoyl]-azetidin-3-yl ester

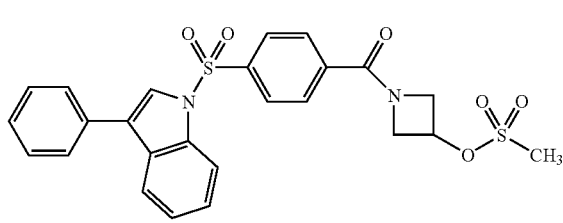

Prepare the title compound utilizing Methanesulfonic acid 1-benzhydryl-azetidin-3-yl ester in the same procedure as above.

Example 163

Dimethyl-carbamic acid 1-[4-(3-phenyl-indole-1-sulfonyl)-benzoyl]-azetidin-3-yl ester

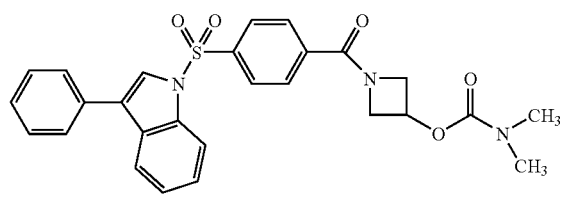

Combine (3-Hydroxy-azetidin-1-yl)-[4-(3-phenyl-indole-1-sulfonyl)-phenyl]-methanone (95 mg, 0.219 mmol), triethylamine (0.200 mL, 1.43 mmol, excess) and 4-dimethylaminopyridine (5 mg, 0.04 mmol) in dichloromethane (1.0 mL) and treat with N,N-dimethylcarbamoyl chloride (0.050 mL) at room temperature. Stir for 15 h, load directly onto pre-packed silica gel column and purify by flash column chromatography (EtOAc/Hexanes) to yield 82 mg of Dimethyl-carbamic acid 1-[4-(3-phenyl-indole-1-sulfonyl)-benzoyl]-azetidin-3-yl ester as a white foam (74%). LRMS: MH+ 503.97.

Example 164

N-[1-(4-Fluoro-phenyl)-azetidin-3-ylmethyl]-4-(3-phenyl-indole-1-sulfonyl)-benzamide

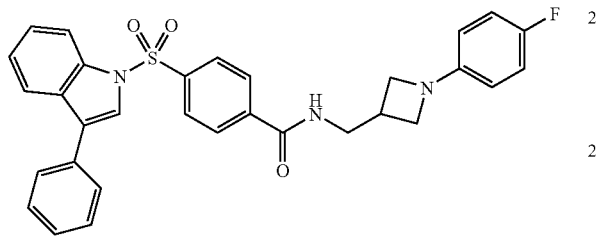

Add trifluoroacetic acid (2 mL) to [1-(4-fluoro-phenyl)-azetidin-3-ylmethyl]-carbamic acid tert-butyl ester (135 mg, 0.482 mmol) causing much gas evolution. Rotary evaporate the reaction solution (40° C.; azeotroping 3× with $CH_2Cl_2$). Dissolve this material in anhydr $CH_2Cl_2$ (3 mL). Add 4-(3-Phenyl-indole-1-sulfonyl)-benzoic acid (200 mg, 0.53 mmol, 1.1 equiv), 1-(3-dimethylaminopropyl)-3-ethylcarbodiimide hydrochloride (EDC; 140 mg, 0.73 mmol, 1.5 equiv), and 4-(dimethylamino)pyridine (DMAP; 270 mg, 2.3 mmol, 4.7 equiv). After stirring 16 h, transfer the reaction solution to a column of silica gel (80 mm×20 mm dia.) and elute (10-45% EtOAc/hex) to yield 31 mg (12%) of N-[1-(4-fluoro-phenyl)-azetidin-3-ylmethyl]-4-(3-phenyl-indole-1-sulfonyl)-benzamide as a light-yellow foam. MS (m/e): 539.99 (M+1); 538.16 (M−1).

Example 165

[3-[(4-Fluoro-phenylamino)-methyl]-azetidin-1-yl]-[4-(3-phenyl-indole-1-sulfonyl)-phenyl]-methanone

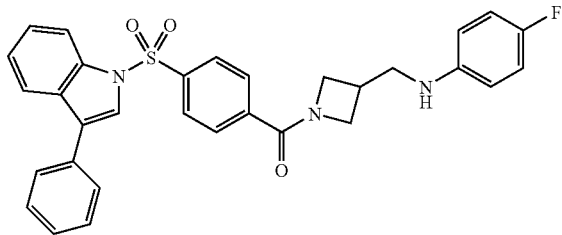

Add 1-bromo-4-fluorobenzene (220 μL, 350 mg, 2.0 mmol, 2.0 equiv) to a mixture of (3-aminomethyl-azetidin-1-yl)-[4-(3-phenyl-indole-1-sulfonyl)-phenyl]-methanone (446 mg, 1.00 mmol, 1 equiv), tris(dibenzylideneacetone) dipalladium(0) (23 mg, 0.025 mmol, 0.025 equiv), 2-(di-tert-butylphosphino)biphenyl (15 mg, 0.057 mmol, 0.050 equiv), and sodium tert-butoxide (120 mg, 1.2 mmol, 1.2 equiv) in anhydr toluene (4 mL) and heat at 100° C. for 19 h. After cooling, transfer the reaction mixture through a 0.45-μm filter disc to a column of silica gel (125 mm×25 mm dia.) and elute (10-100% EtOAc/hex) to yield 98 mg (18%) of [3-[(4-fluoro-phenylamino)-methyl]-azetidin-1-yl]-[4-(3-phenyl-indole-1-sulfonyl)-phenyl]-methanone as a light-yellow foam. $^1$H NMR indicated pure desired product. MS (m/e): 540.07 (M+1); 538.19 (M−1).

Example 166

[(R)-3-(4-Fluoro-phenylamino)-pyrrolidin-1-yl]-[4-(3-phenyl-indole-1-sulfonyl)-phenyl]-methanone

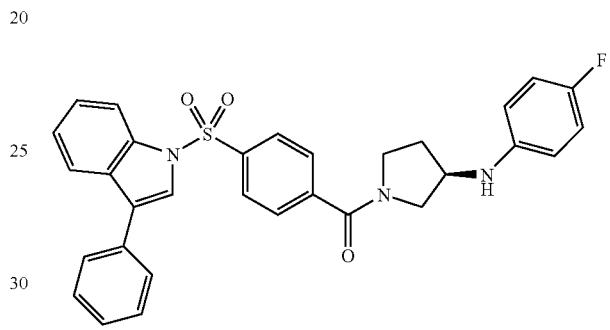

Prepare the title compound by a similar method described for [3-[(4-Fluoro-phenylamino)-methyl]-azetidin-1-yl]-[4-(3-phenyl-indole-1-sulfonyl)-phenyl]-methanone using ((R)-3-Amino-pyrrolidin-1-yl)-[4-(3-phenyl-indole-1-sulfonyl)-phenyl]-methanone (334 mg, 0.750 mmol) to isolate 35 mg (8.7%) of light-yellow foam. MS (m/e): 540.01

Example 167

[(S)-3-(4-Fluoro-phenylamino)-pyrrolidin-1-yl]-[4-(3-phenyl-indole-1-sulfonyl)-phenyl]-methanone

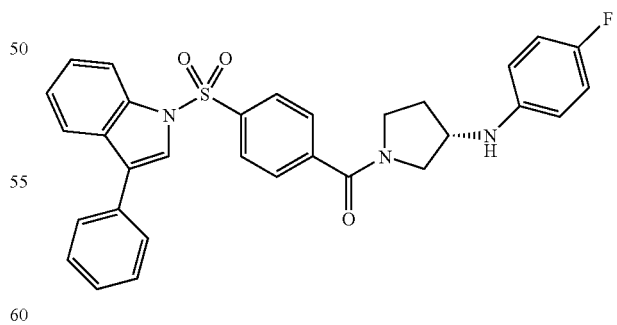

Prepare the title compound by a similar method described for [3-[(4-Fluoro-phenylamino)-methyl]-azetidin-1-yl]-[4-(3-phenyl-indole-1 sulfonyl)-phenyl]-methanone using ((S)-3-Amino-pyrrolidin-1-yl)-[4-(3-phenyl-indole-1-sulfonyl)-phenyl]-methanone (334 mg, 0.750 mmol) to isolate 59 mg (15%) of light-yellow foam. MS (m/e): 540.02 (M+1).

Example 170

[3-[(6-Fluoro-pyridin-2-ylamino)-methyl]-azetidin-1-yl]-[4-(3-phenyl-indole-1-sulfonyl)-phenyl]-methanone

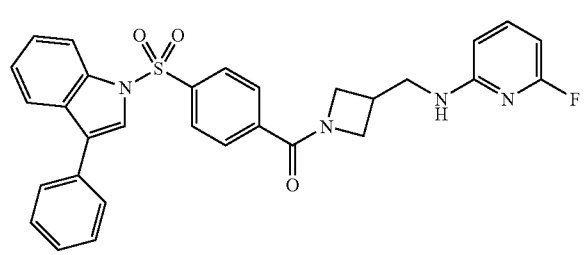

Add 2,6-difluoropyridine (55 µL, 70 mg, 0.61 mmol, 2.0 equiv) to a solution of (3-aminomethyl-azetidin-1-yl)-[4-(3-phenyl-indole-1-sulfonyl)-phenyl]-methanone (134 mg, 0.301 mmol, 1 equiv) and triethylamine (120 µL, 87 mg, 0.86 mmol, 2.9 equiv) in 1,4-dioxane (3 mL) and heat at 80° C. for 16 h. Mass spec shows no desired product. Add more triethylamine (120 µL) and 2,6-difluoropyridine (110 µL). After 32 h at 80° C., LC/MS shows a small amount of desired product. Add more triethylamine (200 µL) and 2,6-difluoropyridine (110 µL). After 38 h, add more triethylamine (200 µL) and 2,6-difluoropyridine (110 µL). After 100 h, transfer the reaction solution to a column of silica gel (80 mm×20 mm dia.) and elute (50-65% EtOAc/hex) to yield 65 mg (40%) of [3-[(6-fluoro-pyridin-2-ylamino)-methyl]-azetidin-1-yl]-[4-(3-phenyl-indole-1-sulfonyl)-phenyl]-methanone as a white foam. MS (m/e): 541.02 (M+1); 539.17 (M−1).

Example 171

[4-(3-Phenyl-indole-1-sulfonyl)-phenyl]-[3-(pyrimidin-2-ylaminomethyl)-azetidin-1-yl]-methanone

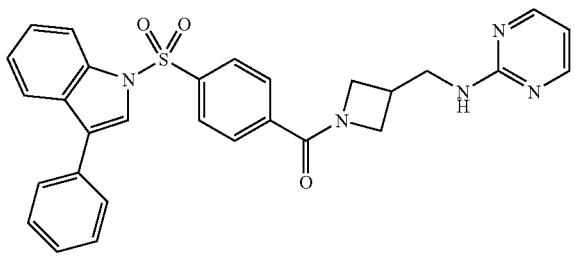

Prepared the title compound by a similar method as described for [3-[(6-Fluoro-pyridin-2-ylamino)-methyl]-azetidin-1-yl]-[4-(3-phenyl-indole-1-sulfonyl)-phenyl]-methanone using (3-aminomethyl-azetidin-1-yl)-[4-(3-phenyl-indole-1-sulfonyl)-phenyl]-methanone (134 mg, 0.301 mmol) to isolate 56 mg (36%) of off-white foam. MS (m/e): 524.01 (M+1).

Example 172

1,1-Dimethyl-3-[1-[4-(3-phenyl-indole-1-sulfonyl)-benzoyl]-azetidin-3-ylmethyl]-urea

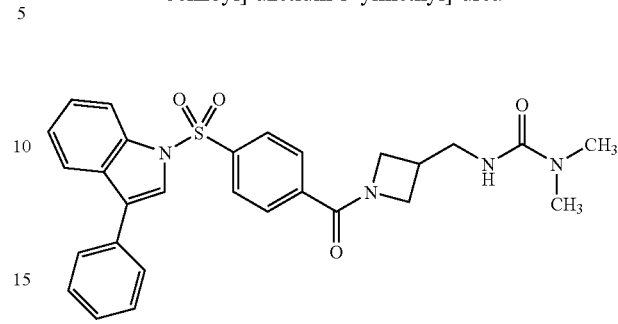

and

Example 173

1,1-Dimethyl-3-[1-[4-(3-phenyl-indole-1-sulfonyl)-benzoyl]-azetidin-3-ylmethyl]-thiourea

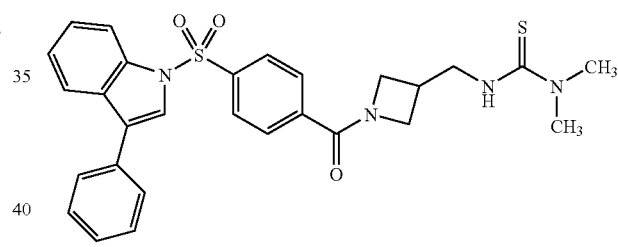

Add dimethylthiocarbamoyl chloride (350 mg, 2.8 mmol, 12 equiv) to a suspension of (3-aminomethyl-azetidin-1-yl)-[4-(3-phenyl-indole-1-sulfonyl)-phenyl]-methanone (101 mg, 0.227 mmol, 1 equiv) and triethylamine (130 µL, 94 mg, 0.93 mmol, 4.1 equiv) in anhydr CH$_2$Cl$_2$ (3 mL). After stirring 17 h, transfer the reaction to a column of silica gel (80 mm×20 mm dia.) and elute (20-100% EtOAc/hex; 2% MeOH/CH$_2$Cl$_2$) to yield 15 mg (12%) of 1,1-dimethyl-3-[1-[4-(3-phenyl-indole-1-sulfonyl)-benzoyl]-azetidin-3-ylmethyl]-urea as a white foam. The starting dimethylthiocarbamoyl chloride contains some dimethylcarbamoyl chloride.

Elute the column of silica gel with more polar solvent (20% MeOH/CH$_2$Cl$_2$) to give the thiourea along with triethylamine hydrochloride. Dissolve this material in CH$_2$Cl$_2$ and wash with satd aq NaHCO$_3$. Dry the organic layer (anhydr MgSO$_4$) and rotary evaporate (40° C.) to yield 30 mg (25%) of 1,1-dimethyl-3-[1-[4-(3-phenyl-indole-1-sulfonyl)-benzoyl]-azetidin-3-ylmethyl]-thiourea as a tan foam.

Example 174

3-[(4-Fluoro-benzylamino)-methyl]-azetidin-1-yl]-[4-(3-phenyl-indole-1-sulfonyl)-phenyl]-methanone

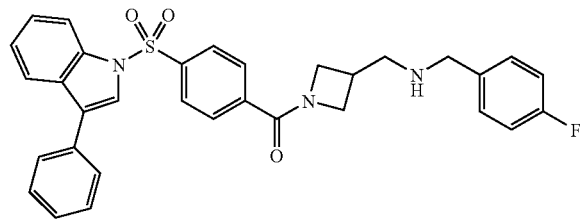

Add 4-fluorobenzaldehyde (26 μL, 31 mg, 0.25 mmol, 1.0 equiv) to a solution of (3-aminomethyl-azetidin-1-yl)-[4-(3-phenyl-indole-1-sulfonyl)-phenyl]-methanone (112 mg, 0.251 mmol, 1 equiv) in MeOH (1 mL). After a few minutes, observe white precipitate. After 1 h, add H$_2$O and extract the reaction mixture with CHCl$_3$ (3×). Combine the organic layers, dry and rotary evaporate (40° C.) to give 120 mg of imine as a colorless film. Dissolve the imine anhydr THF (2 mL) and add sodium triacetoxyborohydride (80 mg, 0.38 mmol, 1.5 equiv). After 19 h, quench the reaction mixture with satd aq NaHCO$_3$ (5 mL) and extract with EtOAc (5 mL). Dry the organic layer (anhydr MgSO$_4$) and rotary evaporate (40° C.). Transfer the resultant colorless oil to a column of silica gel (60 mm×12 mm dia.) and elute (2% MeOH/CH$_2$Cl$_2$) to yield 54 mg (39%) of [3-[(4-fluoro-benzylamino)-methyl]-azetidin-1-yl]-[4-(3-phenyl-indole-1-sulfonyl)-phenyl]-methanone as a white foam. MS (m/e): 553.96 (M+1).

Example 175

N-[1-(4-Fluoro-phenyl)-azetidin-3-yl]-4-(3-phenyl-indole-1-sulfonyl)-benzamide

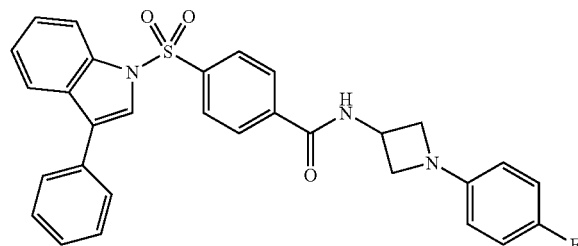

Add 1-bromo-4-fluorobenzene (110 μL, 180 mg, 1.0 mmol, 2.0 equiv) to a mixture of N-azetidin-3-yl-4-(3-phenyl-indole-1-sulfonyl)-benzamide (216 mg, 0.501 mmol, 1 equiv), tris(dibenzylideneacetone)dipalladium(0) (12 mg, 0.012 mmol, 0.025 equiv), 2-(di-tert-butylphosphino)biphenyl (8 mg, 0.03 mmol, 0.05 equiv), and sodium tert-butoxide (58 mg, 0.60 mmol, 1.2 equiv) in anhydr toluene (2 mL). Heat the reaction mixture at 100° C. for 14 h. After cooling, dilute the reaction mixture with CH$_2$Cl$_2$ and transfer through a 0.45-μm filter disc to a column of silica gel (80 mm×20 mm dia.) and elute (10-35% EtOAc/hex) to yield 63 mg (24%) of N-[1-(4-fluoro-phenyl)-azetidin-3-yl]-4-(3-phenyl-indole-1-sulfonyl)-benzamide as a white solid.

Example 176

3-[4-(3-Phenyl-indole-1-sulfonyl)-benzoylamino]-azetidine-1-carboxylic acid methyl ester

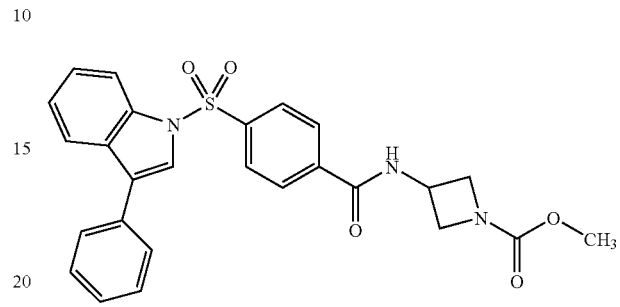

Add methyl chloroformate (60 μL, 73 mg, 0.78 mmol, 3.1 equiv) to a suspension of N-azetidin-3-yl-4-(3-phenyl-indole-1-sulfonyl)-benzamide (108 mg, 0.250 mmol, 1 equiv) and triethylamine (140 μL, 100 mg, 1.0 mmol, 4.0 equiv) in anhydr (CH$_2$Cl$_2$ (3 mL). Observe a vigorous gas evolution. After stirring 4 h, rotary evaporate the reaction solution. Transfer the resultant material to a column of silica gel (80 mm×20 mm dia.) and elute (20-60% EtOAc/hex) to yield 84 mg (69%) of 3-[4-(3-phenyl-indole-1-sulfonyl)-benzoylamino]-azetidine-1-carboxylic acid methyl ester as an off-white foam. MS (m/e): 489.96 (M+1); 488.09 (M−1).

Example 177

[(R)-1-[4-(3-Phenyl-indole-1-sulfonyl)-benzoyl]-pyrrolidin-3-yl]-carbamic acid methyl ester

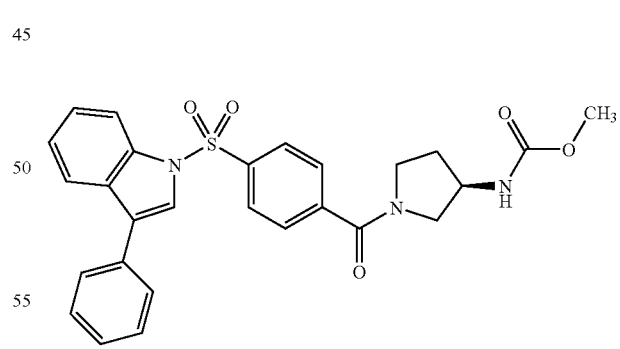

Prepare the title compound by a similar method described for 3-[4-(3-phenyl-indole-1-sulfonyl)-benzoylamino]-azetidine-1-carboxylic acid methyl ester using ((R)-3-amino-pyrrolidin-1-yl)-[4-(3-phenyl-indole-1-sulfonyl)-phenyl]-methanone (111 mg, 0.249 mmol) to isolate 98 mg (78%) of white foam. MS (m/e): 503.98 (M+1); 502.09 (M−1).

Example 178

[(S)-1-[4-(3-Phenyl-indole-1-sulfonyl)-benzoyl]-pyrrolidin-3-yl]-carbamic acid methyl ester

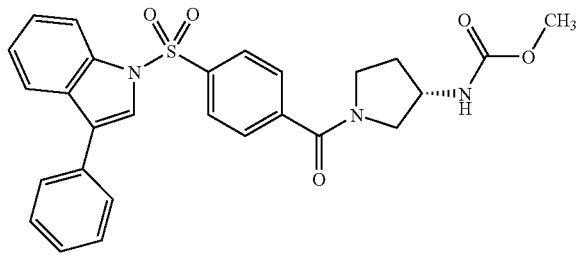

Prepare the title compound by a similar method described for 3-[4-(3-phenyl-indole-1-sulfonyl)-benzoylamino]-azetidine-1-carboxylic acid methyl ester using ((S)-3-amino-pyrrolidin-1-yl)-[4-(3-phenyl-indole-1-sulfonyl)-phenyl]-methanone (111 mg, 0.249 mmol) to isolate 97 mg (77%) of white foam. MS (m/e): 504.00 (M+1); 502.09 (M−1).

Example 179

[1-[4-(3-Phenyl-indole-1-sulfonyl)-benzoyl]-azetidin-3-yl-methyl]-carbamic acid methyl ester

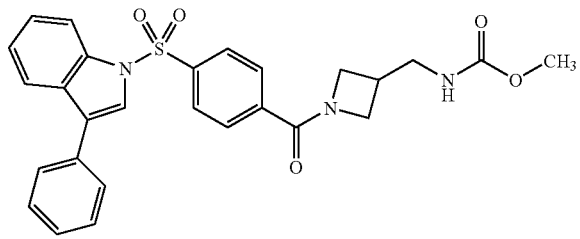

Prepare the title compound by a similar method described for 3-[4-(3-phenyl-indole-1-sulfonyl)-benzoylamino]-azetidine-1-carboxylic acid methyl ester using (3-aminomethyl-azetidin-1-yl)-[4-(3-phenyl-indole-1-sulfonyl)-phenyl]-methanone (111 mg, 0.249 mmol) to isolate 99 mg (79%) of white foam. MS (m/e): 504.02 (M+1); 502.15 (M−1).

Example 180

[1-[4-(3-Phenyl-indole-1-sulfonyl)-benzoyl]-azetidin-3-yl]-carbamic acid methyl ester

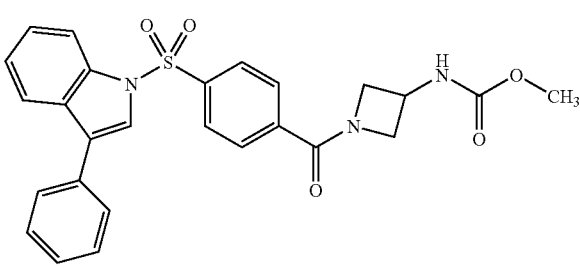

Prepare the title compound by a similar method described for 3-[4-(3-phenyl-indole-1-sulfonyl)-benzoylamino]-azetidine-1-carboxylic acid methyl ester using (3-amino-azetidin-1-yl)-[4-(3-phenyl-indole-1-sulfonyl)-phenyl]-methanone (111 mg, 0.249 mmol) to isolate 99 mg (79%) of white foam. MS (m/e): 489.99 (M+1): 488.04 (M−1).

Example 183

N-(4-Fluoro-benzyl)-4-(3-pyridin-3-yl-indole-1-sulfonyl)-benzamide hydrochloride

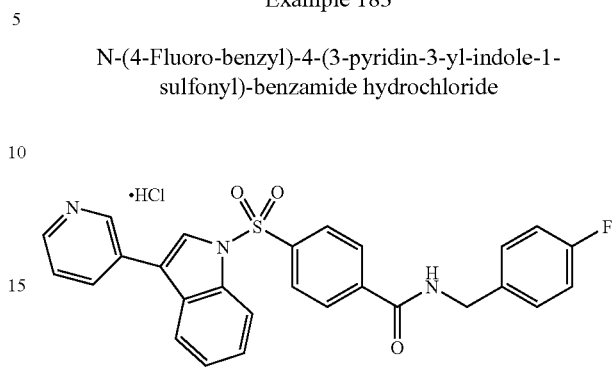

Combine N-(4-fluoro-benzyl)-4-(3-iodo-indole-1-sulfonyl)-benzamide 300 mg, 0.56 mmol, 1 equiv), 3-tributylstannylpyridine (Frontier Scientific®; 90%; 230 mg (0.90)=210 mg, 0.56 mmol, 1.0 equiv), and tetrakis(triphenylphosphine)palladium(0) (100 mg, 0.087 mmol, 0.15 equiv) in deoxygenated toluene (3 mL) and heat at 100° C. for 18 h. Transfer the reaction solution to a column of silica gel (125 mm×25 mm dia.) and elute (0-70% EtOAc/hex) to yield 73 mg (27%) of free amine as an orange oil. Dissolve this material in MeOH (5 mL) and add 12 M aq HCl (2 drops). Rotary evaporate this solution (40° C.) to yield 78 mg (27%) of N-(4-fluoro-benzyl)-4-(3-pyridin-3-yl-indole-1-sulfonyl)-benzamide hydrochloride as a brown glass. MS (m/e): 485.95 (M+1); 484.10 (M−1).

Example 184

N-(4-Fluoro-benzyl)-4-(3-pyridin-2-yl-indole-1-sulfonyl)-benzamide hydrochloride

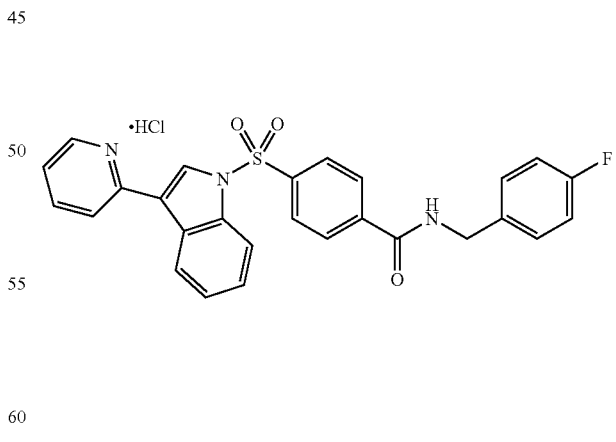

Prepare the title compound by a method similar to Example 183 using 2-tributylstannylpyridine (Frontier Scientific®; 85%; 250 mg [0.85]=210 mg, 0.58 mmol, 1.0 equiv) to isolate 109 mg (37%) of yellow glass. MS (m/e): 485.96 (M+1); 484.10 (M−1).

Example 185

N-(4-Fluoro-benzyl)-4-[3-(6-methoxy-pyridin-3-yl)-indole-1-sulfonyl]-benzamide

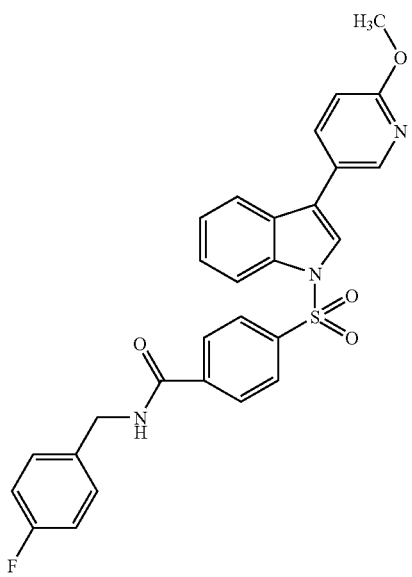

Combine N-(4-Fluoro-benzyl)-4-[3-(4,4,5,5-tetramethyl-[1,3,2]-dioxaboralan-2-yl)-indole-1-sulfonyl]-benzamide (0.534 g, 1.0 mmol), 5-Bromo-2-methoxy pyridine (0.155 mL, 1.2 mmol) and PdCl$_2$(dppf).CH$_2$Cl$_2$ (0.088 g, 0.07 mmol) in dry DMF (40 mL). Add 2M Na$_2$CO$_3$ (1.40 mL, 2.8 mmol) and heat under N$_2$ at 100° C. for 4 h. Stir overnight at ambient temperature. Pour the reaction mixture into EtOAc—H$_2$O, separate, extract several times with H$_2$O and wash with brine. Dry the EtOAc (MgSO$_4$) and filter through Celite®. Evaporate and chromatograph using a hexane-EtOAc gradient 0-100% EtOAc to give 0.347 g (67%) of the desired compound. MS (M+1) 516; (M−1) 514.

Example 186

N-(4-Fluoro-benzyl)-4-[3-(6-fluoro-pyridin-3-yl)-indole-1-sulfonyl]-benzamide

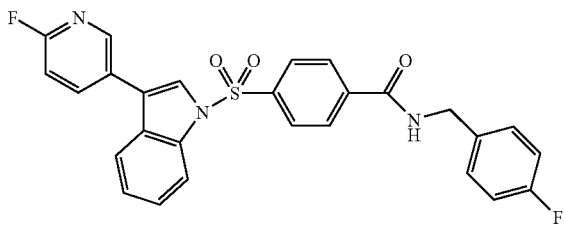

Combine N-(4-Fluoro-benzyl)-4-[3-(4,4,5,5-tetramethyl-[1,3,2]dioxaborolan-2-yl)-indole-1-sulfonyl]-benzamide (150 mg, 0.28 mmol), 5-Bromo-2-fluoro-pyridine (0.05 mL, 0.56 mmol), CsF (212 mg, 1.4 mmol) and Pd(Ph$_3$P)$_4$ (32 mg, 0.028 mmol) in 1.0 mL DMF and 0.100 mL of water. Evacuate the reaction vessel and place under an atmosphere of nitrogen. Heat the resulting reaction at 90 degrees 12 h. Load the reaction directly onto silica gel and purify by flash column chromatography (EtOAc/Hexanes) to yield 98 mg of white foam (70%) LRMS: MH+ 504.02.

Example 187

4-[3-(5-Chloro-thiophen-2-yl)-indole-1-sulfonyl]-N-(4-fluoro-benzyl)-benzamide

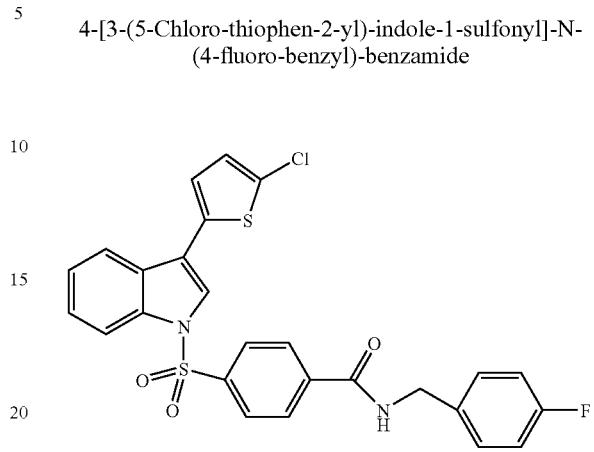

Combine N-(4-Fluoro-benzyl)-4-[3-(4,4,5,5-tetramethyl-[1,3,2]-dioxaboralan-2-yl)-indole-1-sulfonyl]-benzamide (0.534 g, 1.0 mmol), 2-bromo-5-chloro-thiophene (0.012 mL, 1.1 mmol), PdCl$_2$(dppf), CH$_2$Cl$_2$ (0.051 g, 0.069 mmol) and KOAc (0.294 g, 3.0 mmol) in dry DMF (22.0 mL) under N$_2$ heat and stir at 100° C. for 16 h. Cool to ambient temperature and pour into a mixture of EtOAc—H$_2$O. Separate and extract the EtOAc several times with H$_2$O, wash with brine and dry (MgSO$_4$). Filter and evaporate to an oily residue. Purify the product by chromatography using a hexane-EtOAc gradient 0-100% EtOAc to give 0.209 g (40%) of a viscous oil. TOF MS (M−1) 523.0332.

Example 188

4-(3-Cyclopropropyl-indole-1-sulfonyl)-N-(4-fluoro-benzyl)-benzamide

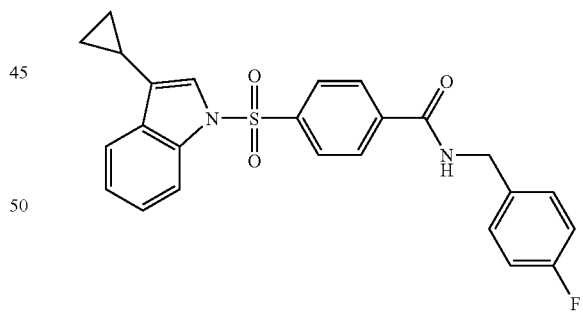

Combine N-(4-fluoro-benzyl)-4-(3-iodo-indole-1-sulfonyl)-benzamide (0.50 g, 0.94 mmol), cyclopropylboronic acid (0.24 g, 2.8 mmol), tricyclohexylphosphine (0.05 g, 0.18 mmol), potassium phosphate (0.70 g, 3.30 mmol), and palladium acetate (0.02 g, 0.09 mmol) in a mixture of toluene (15 mL) and water (0.4 mL). Heat to 100° C. under nitrogen for 18 hours, filter through celite, and wash solids with EtOAc. Wash EtOAc with saturated NaHCO$_3$ (30 mL), then dry with Na$_2$SO$_4$, and concentrate under vacuum. Purify by flash column on silica gel eluting with 0-50% EtOAc in hexanes to give the title compound (0.25 g, 60%). MS (ES) 449.2 (M+1)+, 447.4 (M−1)−.

Example 189

N-(4-Fluoro-benzyl)-4-(3-thiophen-3-yl-indole-1-sulfonyl)-benzamide

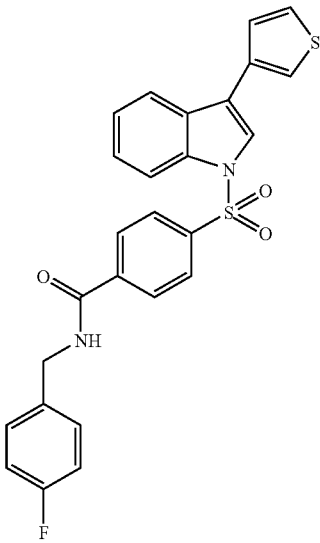

Combine N-(Fluoro-benzyl)-4-(3-iodo-indole-1-sulfonyl)-benzamide (0.534 g, 1.1 mmol), thiophene-3-boronic acid (0.154 g, 1.25 mmol), PdCl₂(dppf).CH₂Cl₂ (0.10 mmol) and 2 M Na₂CO₃ (1.32 mL)l, 2.64 mmol) respectively in dry DMF (40 mL) under N₂. Stir and heat at 81° C. under N₂ for one and a half hours. Cool to ambient temperature and stir overnight. Pour the reaction into EtOAc (150 mL) and extract with H₂O (3×150 mL). Wash with brine, separate and dry the organic layer (MgSO₄). Filter through celite and evaporate the filtrate on the rotary evaporator. Chromatograph using a hexane-EtOAc gradient from 0-100% EtOAc to give 0.352 g (71%) of the desired compound as and off white solid MS (ES+) (M+1) 491.0; (M−1) 490.10.

Example 190

4-[3-(2-Chloro-phenyl)-indole-1-sulfonyl]-N-(4-fluoro-benzyl)-benzamide

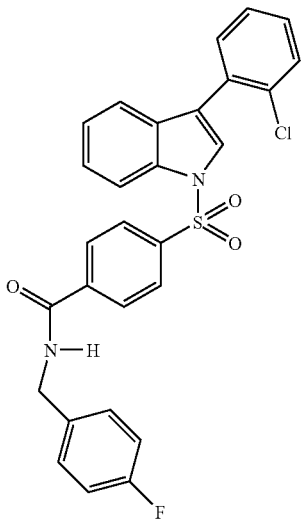

Add N-(4-Fluoro-benzyl)-4-(3-iodo-indole-1-sulfonyl)-benzamide (268 mg, 0.0.50 mmol), 2-chlorophenylboronic acid (78.2 mg, 0.50 mmol), PdCl₂(dppf).CH₂Cl₂ (41 mg, 0.05 mmol) and 2M Na₂CO₃ (0.55 mL, 1.1 mmol) respectively to DMF (15.0 mL) at ambient temperature under N₂. Heat the reaction to 100° C. for 16 h. Cool the reaction to ambient temperature and pour into a H₂O-EtOAc mixture (200 mL/100 mL). Separate the EtOAc, extract several times with H₂O and wash with brine. Dry (MgSO₄), filter and evaporate the filtrate. Purify the crude material on silica gel using a gradient hexane-EtOAc system to give 0.155 g (60% yield) of 4-[3-(2-chloro-phenyl)-indole-1-sulfonyl]-N-(4-fluoro-benzyl)-benzamide: Mass spectrum (m/e) ⊛M−1) 517.0787.

Example 191

N-(4-Fluoro-benzyl)-4-[3-(2-fluoro-pyridin-3-yl)-indole-1-sulfonyl]-benzamide

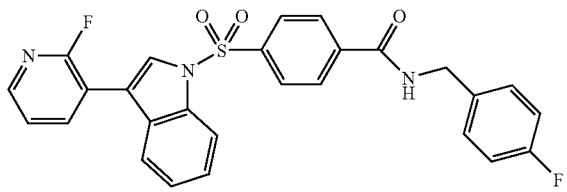

Combine N-(4-Fluoro-benzyl)-4-(3-iodo-indole-1-sulfonyl)-benzamide (300 mg, 0.56 mmol), 2-Fluoro-3-boronic acid-pyridine (140 mg, 1.12 mmol), CsF (170 mg, 1.12 mmol) and Dichlorobis(triphenylphosphine)palladium (100 mg, 0.14 mmol) in dioxane (2.0 mL) and water (0.200 mL). Evacuate the reaction and place under a nitrogen atmosphere. Heat the resulting reaction in an 80 degree oil bath for 15 h. Cool the reaction and filter through a short pad of silica gel with additional ethyl acetate. Evaporate and purify by flash column chromatography (EtOAc/Hexanes) to yield 141 mg of an off white foam (50%) LRMS: MH+ 503.92.

Prepare the following sulfonamides in Table 3 using methods similar to the noted reference examples.

TABLE 3

| Ex. No. | Final Structure | Name | MS data (m/e) (M + H) | Reference Examples |
|---|---|---|---|---|
| 194 | | N-(4-Fluoro-benzyl)-4-(3-pyridin-4-yl-indole-1-sulfonyl)-benzamide | 486.13 | 189 |
| 195 | | N-(4-Fluoro-benzyl)-4-(3-thiophen-2-yl-indole-1-sulfonyl)-benzamide | 512.73 | 189 |
| 196 | | N-(4-Fluoro-benzyl)-4-[3-(2-fluoro-phenyl)-indole-1-sulfonyl]-benzamide | 503.12 | 189 |
| 197 | | N-(4-Fluoro-benzyl)-4-[3-(3-fluoro-phenyl)-indole-1-sulfonyl]-benzamide | 501.2 | 190 |
| 198 | | N-(4-Fluoro-benzyl)-4-[3-(4-fluoro-phenyl)-indole-1-sulfonyl]-benzamide | 503.1 | 189 |
| 199 | | N-(4-Fluoro-benzyl)-4-(3-furan-3-yl-indole-1-sulfonyl)-benzamide | 475.11 | 189 |

TABLE 3-continued

| Ex. No. | Final Structure | Name | MS data (m/e) (M + H) | Reference Examples |
|---|---|---|---|---|
| 200 | | N-(4-Fluoro-benzyl)-4-(3-o-tolyl-indole-1-sulfonyl)-benzamide | 499.1 | 189 |
| 201 | | 4-[3-(4-Chloro-phenyl)-indole-1-sulfonyl]-N-(4-fluoro-benzyl)-benzamide | 517.08 | 189 |
| 202 | | 4-[3-(3-Chloro-phenyl)-indole-1-sulfonyl]-N-(4-fluoro-benzyl)-benzamide | 437.13 | 189 |
| 203 | | N-(4-Fluoro-benzyl)-4-(3-isoquinolin-4-yl-indole-1-sulfonyl)-benzamide | 534.13 | 185 |
| 205 | | N-(4-Fluoro-benzyl)-4-(3-m-tolyl-indole-1-sulfonyl)-benzamide | 499.15 | 187 |

TABLE 3-continued

| Ex. No. | Final Structure | Name | MS data (m/e) (M + H) | Reference Examples |
|---|---|---|---|---|
| 206 | | N-(4-Fluoro-benzyl)-4-[3-(3-methoxy-phenyl)-indole-1-sulfonyl]-benzamide | 515.14 | 187 |
| 208 | | N-(4-Fluoro-benzyl)-4-(3-furan-2-yl-indole-1-sulfonyl)-benzamide | 475.11 | 189 |
| 209 | | N-(4-fluoro-benzyl)-4-[3-(5-methyl-thiophene-2-yl)-indole-1-sulfonyl]-benzamide | 505.1 | 189 |
| 210 | | N-(4-fluorobenzyl)-4-(3-p-tolyl-indole-1-sulfonyl)-benzamide | 499.15 | 185 |
| 211 | | N-(4-Fluoro-benzyl)-4-(3-quinolin-6-yl-indole-1-sulfonyl)-benzamide | 536.14 | 185 |
| 212 | | 4-[3-(4-Dimethylamino-phenyl)-indole-1-sulfonyl]-N-(4-fluoro-benzyl)-benzamide hydrochloride* | 550 | 185 |

TABLE 3-continued

| Ex. No. | Final Structure | Name | MS data (m/e) (M + H) | Reference Examples |
|---|---|---|---|---|
| 213 | | N-(4-Fluoro-benzyl)-4-[3-(3-fluoro-pyridin-4-yl)-indol-1-sulfonyl]-benzamide | MH+ 503.96 | 186 |

*Dissolve the purified compound in minimum amount of tetrahydrofuran, cool to 0° C. and treat with 1-2 equivalents of anhydrous HCl in THF, evaporate the solvents to give the final HCl salt.

Example 214

N-(4-Fluoro-benzyl)-4-(3-pyrimidin-2-yl-indole-1-sulfonyl)-benzamide

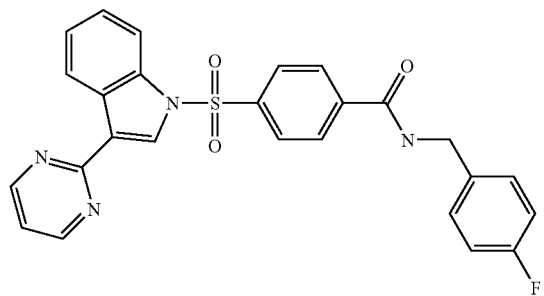

Stir a mixture of N-(4-fluoro-benzyl)-4-[3-(4,4,5,5-tetramethyl-[1,3,2]-dioxaboralan-2-yl)-indole-1-sulfonyl]-benzamide (0.200 g, 0.374 mmoles), 2-bromo-pyrimidine (0.282 g, 1.872 mmole), Tetrakis(triphenylphosphine)palladium(0) (0.043 g, 0.0374 mmoles), Cesium Fluoride (0.282 g, 1.872 mmole) in dioxane until reaction goes to completion at 90° C. Concentrate the reaction and purify via column chromatography using a mixture of EtOAc and Hexanes to give 0.049 g of solid material (yield=27%): Mass Spectrum (m/e): 485.09 (M⁻).

Example 215

N-(4-Fluoro-benzyl)-4-(3-pyrimidin-5-yl-indole-1-sulfonyl)-benzamide

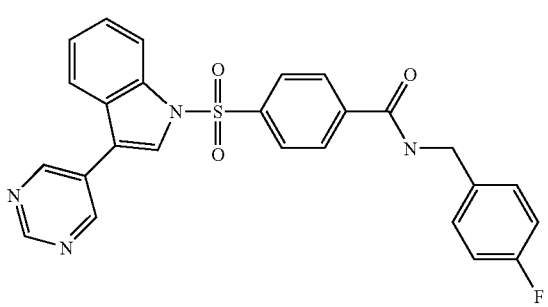

Prepare the title compound by a similar method of N-(4-Fluoro-benzyl)-4-(3-pyrimidin-2-yl-indole-1-sulfonyl)-benzamide using 5-bromo-pyrimidine (0.118 g, 0.748 mmoles) to isolate 0.070 g of solid (yield=95%). Mass Spectrum (m/e): 486.1 (M⁺).

Example 216

N-(4-Fluoro-benzyl)-4-(3-pyrimidin-5-yl-indole-1-sulfonyl)-benzamide:chloride

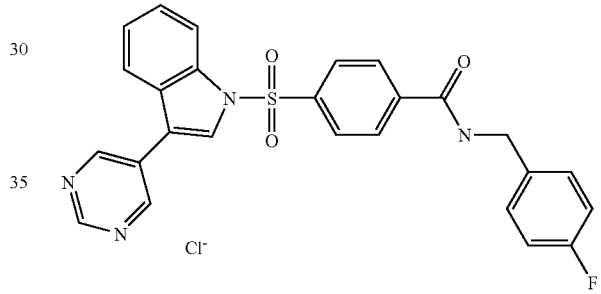

Stir N-(4-Fluoro-benzyl)-4-(3-pyrimidin-5-yl-indole-1-sulfonyl)-benzamide (0.041 g, 0.084 mmole) in dioxane with 1 N HCl until completion and remove solvent to isolate 0.026 g (Yield=61%).

Example 217

N-(4-Fluoro-benzyl)-4-(3-pyrazin-2-yl-indole-1-sulfonyl)-benzamide

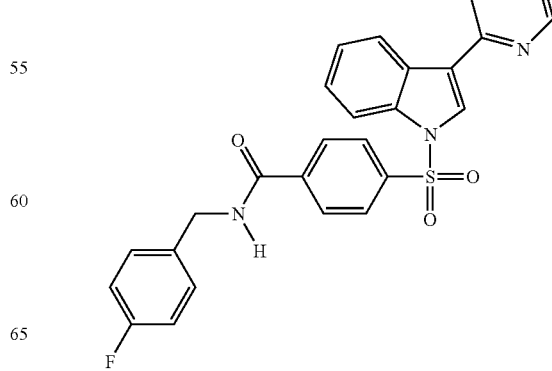

Degas DMF with N₂ for 30 minutes. Add 2-tributylstannyl pyrazine (0.214 g, 0.58 mmol), N-(4-fluoro-benzyl)-4-(3-iodo-indole-1-sulfonyl)-benzamide 0.300 g, 0.56 mmol) and tetrakis(triphenylphosphine)Pd(0) (0.100 g, 0.086 mmol) to DMF (5.0 ml). Heat and stir at 100° under N₂ for 16 h. Pour the reaction mixture into H₂O-EtOAc. Separate the EtOAc layer and extract several times with H₂O, wash with brine, dry (MgSO₄) and filter through celite. Remove the solvent on the rotary evaporator to give an oil. Chromatograph on the chromatron using a 1 mm plate and elute with 1% CH₃OH—CH₂Cl₂ to give the title compound. Mass spectrum (m/e) (M+H) 487.1240; found: 487.1220.

Example 218

N-(4-Fluoro-benzyl)-4-(3-phenyl-indole-1-sulfonyl)-benzamide

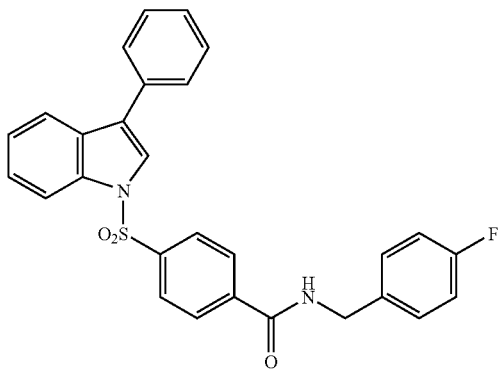

In a 100 ml RBF combine 4-(3-phenyl-indole-1-sulfonyl)-benzoic acid (2.5 g, 6.62 mmol) and THF (25 ml). Cool the solution in an ice water bath and add 4-methylmorpholine (0.73 ml, 7.29 mmol) follow by the portion wise addition of CDMT (1.16 g, 7.29 mmol). Stir the solution in an ice water bath for one hour. Add dropwise, a solution of 4-fluorobenzylamine (0.83 ml, 7.29 mmol) in THF (8 µl) to the reaction at 0° C. Stir the solution at 0° C. for five hours, and quench with 1N HCl (50 ml). Extract the reaction MTBE (2×50 ml), filter and wash with saturated aqueous sodium chloride (50 ml). Dry the organics over magnesium sulfate, filter and concentrate to give N-(4-fluoro-benzyl)-4-(3-phenyl-indole-1-sulfonyl)-benzamide (2.43 g) as a white solid. HPLC=95.5%, MS (ESI) m/z observed 485.1334 calculated 485.1335 (M+H).

Dissolve 4 g of N-(4-fluoro-benzyl)-4-(3-phenyl-indole-1-sulfonyl)-benzamide in 15 mL of absolute ethanol. As the sample wetted, sonicate and observe crystallization. Collect a powder diffraction pattern on these crystals. Characterize the crystals as having a melt onset beginning at 140° C.

Example 219

4-(3-Cyclopentyl-indole-1-sulfonyl)-N-(tetrahydro-pyran-4-yl)-benzamide

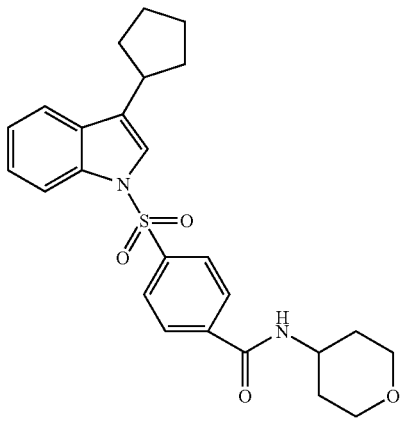

Stir a solution of 4-(3-cyclopentyl-indole-1-sulfonyl)-benzoic acid (19.0 g, 51.43 mmol) in anhydrous THF (250 mL), cool to 5° C., add N-methylmorpholine (5.8 mL, 52.72 mmol) and 2-chloro-4,6-dimethoxy-1,3,5-triazine (CDMT) (9.0 g, 51.34 mmol). Stir the mixture at 0-5° C. for 1 h, add a solution of 4-aminotetrahydro-pyran (5.8 g, 57.36 mmol) in dry THF (75 mL) via dropping funnel. Bring the mixture to room temperature, stir for 3 h, and cool back down to 5° C. Stir the mixture and add 1N HCl (250 mL), add the resulting solution to a separatory funnel, and extract with ethyl acetate (250 mL). Separate the layers, wash the organic layer with brine (250 mL), and combine the aqueous layers and extract with ethyl acetate (250 mL). Combine the organics and wash with saturated aqueous sodium bicarbonate (400 mL) and dry the organic layer over sodium sulfate. Concentrate to give a foam, dissolve in minimum methylene chloride, and add to a biotage flash 65M cartridge. Elute with 3:2 hexanes/ethyl acetate to provide the major product as a foam, and dry (20 mm Hg, 40° C.) to give a white powder of pure product (20.3 g, 87%); MS (ESI) m/z 453 (m+H).

Example 220

4-(3-Cyclopentyl-indole-1-sulfonyl)-N-(tetrahydro-pyran-4-ylmethyl)-benzamide

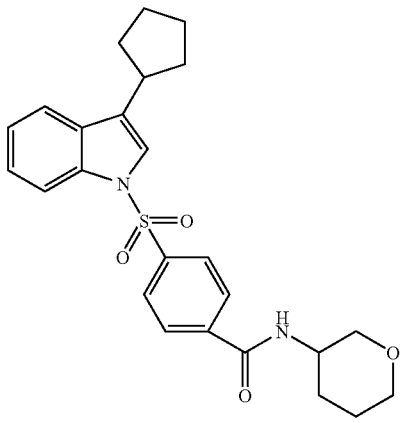

Stir a stir solution of 4-(3-cyclopentyl-indole-1-sulfonyl)-benzoic acid (19.0 g, 51.43 mmol) in anhydrous THF (250 mL) cool to 5° C. under $N_2$ add N-methylmorpholine (5.8 mL, 52.72 mmol) and 2-chloro-4,6-dimethoxy-1,3,5-triazine (CDMT) (9.0 g, 51.34 mmol). Stir the mixture for 1 h and add a solution of 4-aminomethyltetrahydropyran (6.6 g, 57.34 mmol) in dry THF (75 mL) by dropping funnel. Warm the mixture to room temperature and stir for 3 h. Cool the mixture to 5° C., add 1N HCl (250 mL) and partition the resulting solution with ethyl acetate (250 mL). Extract the organic layer with aqueous saturated sodium bicarbonate (250 mL), brine (250 mL), and dry over sodium sulfate. Concentrate to give a foam, dissolve in minimum methylene chloride and add to a flash 65 M cartridge. Elute with 3:2 hexanes/ethyl acetate to give the major product as a solid, filter from hexanes, and dry (20 mm Hg, 40° C.) to give the homogeneous white solid (20.5 g, 85%); MS (ESI) m/z 467 (m+H).

Example 221

4-(3-Cyclopentyl-indole-1-sulfonyl)-N-(4-fluoro-benzyl)-benzamide

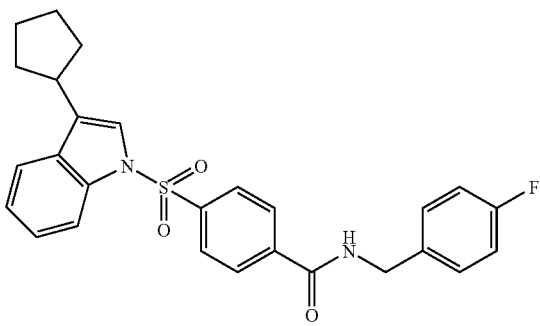

Charge a 500 mL 3-neck roundbottom flask equipped with overhead stirrer, temperature probe, dropping funnel, and $N_2$ line with 4-(3-cyclopentyl-indole-1-sulfonyl)-benzoic acid (7.8 g, 21.1 mmol) in anhydrous THF (100 mL). Cool the solution and stir at 0° C. and add N-methylmorpholine (NMM, 2.4 mL, 21.8 mmol) and 2-chloro-4,6-dimethoxy-1,3,5-triazine (CDMT, 3.7 g, 21.1 mmol). Stir the mixture for 1 h at 0° C. and add a solution of 4-fluorobenzylamine (2.7 mL, 23.6 mmol) in anhydrous THF (30 mL) over 10 minutes via dropping funnel. Bring the resulting suspension to room temperature and stir for 3 h. Cool the mixture to 0° C. and treat with 1N HCl (100 mL). Add ethyl acetate (100 mL) and separate the layers. Dry the organic layer over sodium sulfate and concentrate to a residue which was held aside at this point.

Repeat the reaction exactly as outlined above using 4-(3-cyclopentyl-indole-1-sulfonyl)-benzoic acid (8.8 g, 23.82 mmol), NMM (2.7 mL, 24.5 mmol), CDMT (4.2 g, 23.9 mmol), 4-fluorobenzylamine (3.1 mL, 27.1 mmol) and anhydrous THF (160 mL). Following reaction and work-up as previously described, obtain the crude organic residue (similar, albeit less pure) TLC profile (3:2 hexanes/ethyl acetate) to that from the initial reaction. Independently chromatograph the two organic extracts (biotage 65M, 5% ethyl acetate in toluene) to provide in both cases separation of the major component. Pool the appropriate fractions at this point and concentrate to a white foam. Dry the foam (20 mm Hg, 40° C.) to provide a white powder (14.6 g, 68%); MS (ESI) m/z 477 (m+H). Dissolve 20 mg 4-(3-cyclopentyl-indole-1-sulfonyl)-N-(4-fluoro-benzyl)-benzamide in isopropyl ether, though a small amount of oil remained at the bottom. Vigorously stir the sample until evaporation occurs and a white powder forms: onset of melting is 113° C.

Example 222

N-(5-Fluoro-pyridin-3-ylmethyl)-4-(3-phenyl-indole-1-sulfonyl)-benzamide

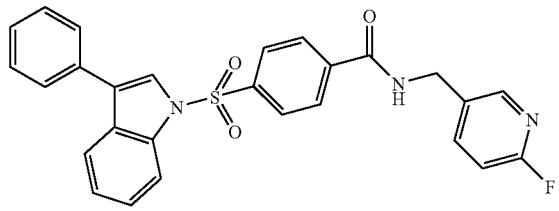

Make a 242.7 mg/mL solution of N-(5-fluoro-pyridin-3-ylmethyl)-4-(3-phenyl-indole-1-sulfonyl)-benzamide in methanol. Allow the solution to evaporate to dryness: onset of melting at 131° C.

Example 223

(N-(5-Fluoro-pyridin-2-ylmethyl)-4-(3-phenyl-indole-1-sulfonyl)-benzamide

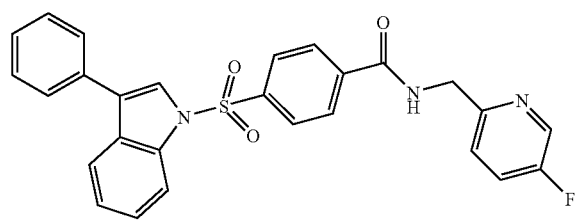

Add to a stirring mixture of 4-(3-phenyl-indole-1-sulfonyl)-benzoic acid (5.0 g, 13.25 mmol) and 2-aminomethyl-5-fluoropyridine (dihydrochloride) (2.9 g, 14.57 mmol) in anhydrous methylene chloride (60 mL), EDCI (3.8 g, 19.82 mmol) and 4-DMAP (6.0 g, 49.10 mmol). Stir the resulting solution overnight at room temperature, concentrate to a paste, and partition between ethyl acetate (100 mL), water (100 mL), and brine (100 mL). Dry the organic layer over sodium sulfate and concentrate to an oil. Dissolve the oil in methylene chloride and add to a biotage 65 cartridge. Elute with 1:1 ethyl acetate/hexanes to provide isolation of the pure 3 (N-(5-Fluoro-pyridin-2-ylmethyl)-4-(3-phenyl-indole-1-sulfonyl)-benzamide as a solid, 5.7 g (89%): $^1$H NMR (DMSO-$d_6$) δ 9.32 (t, J=5.9 Hz, 1H), 8.46 (d, J=2.9 Hz, 1H), 8.20 (d, J=8.3 Hz, 2H), 8.12 (s, 1H), 8.03 (m, 3H), 7.82 (d, J=7.8 Hz, 1H), 7.72 (d, J=6.8 Hz, 2H), 7.62 (dt, J=2.9, 8.8 Hz, 1H), 7.50 (t, J=7.3 Hz, 2H), 7.39 (m, 4H), 4.50 (d, J=5.9 Hz, 2H); MS (ESI) m/z 486 (m+H).

Example 224

(N-(5-Fluoro-pyridin-3-ylmethyl)-4-(3-phenyl-indole-1-sulfonyl)-benzamide

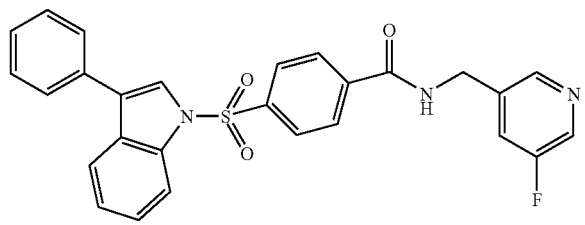

Add to a stirring mixture of 4-(3-phenyl-indole-1-sulfonyl)-benzoic acid (5.0 g, 13.25 mmol), and 2-aminomethyl-4-fluoropyridine (2.9 g, 14.57 mmol) in anhydrous methylene chloride (60 mL) EDCI (3.8 g, 19.82 mmol) and 4-DMAP (6.0 g, 49.10 mmol). Stir the resulting solution overnight at room temperature and concentrate to an oil. Partition the oil between ethyl acetate (100 mL), water (100 mL), and brine (100 mL). Combine the aqueous layers and back-extract with methylene chloride (100 mL) and dry the organics over sodium sulfate. Concentrate to give an oil and dissolve in methylene chloride and add to a biotage 65 cartridge. Elute with 3:2 ethyl acetate/hexanes gradually increasing to 4:1 ethyl acetate/hexanes to give the major product as a foam which is found to be homogeneous 3 (N-(5-Fluoro-pyridin-3-ylmethyl)-4-(3-phenyl-indole-1-sulfonyl)-benzamide 5.6 g (87%); $^1$H NMR (DMSO-$d_6$) δ 9.28 (t, J=5.9 Hz, 1H), 8.44 (d, J=2.9 Hz, 1H), 8.39 (s, 1H), 8.19 (d, J=8.8 Hz, 2H), 8.12 (s, 1H), 8.04 (d, J=8.3 Hz, 1H), 8.00 (d, J=8.3 Hz, 2H), 7.82 (d, J=7.8 Hz, 1H), 7.72 (d, J=7.3 Hz, 2H), 7.60 (m, 1H), 7.49 (t, J=7.3 Hz, 2H), 7.39 (m, 3H), 4.48 (d, J=5.9 Hz, 2H); MS (ESI) m/z 486 (m+H).

Example 226

N-(4-Fluoro-benzyl)-4-(3-phenyl-pyrrolo[2,3-b]pyridine-1-sulfonyl)-benzamide

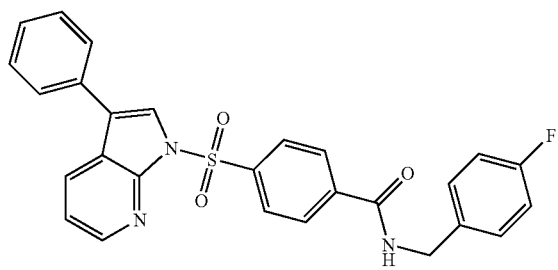

Slowly add 3-phenyl-1H-pyrrolo[2,3-b]pyridine (178 mg, 0.915 mmol, 1.0 eq) as a 2 ml DMF solution to a flask under N$_2$ containing potassium tertbutoxide (108 mg, 0.961 mmol, 1.05 eq) in 1 ml DMF solution. Stir solution for 5 minutes. Slowly add 4-(4-Fluoro-benzylcarbamoyl)-benzenesulfonyl chloride (300 mg, 0.915 mmol, 1.0 eq) as a 3 ml DMF solution. Stir reaction for 18 hours at room temperature. Strip reaction of solvent and purify on silica gel chromatography to give N-(4-Fluoro-benzyl)-4-(3-phenyl-pyrrolo[2,3-b]pyridine-1-sulfonyl)-benzamide (82 mg, 18% yield). Mass Spectrum (m/e): 485.94 (MH+).

Example 228

N-(4-Fluoro-benzyl)-4-[3-(2-piperidin-1-yl-acetyl)-indole-1-sulfonyl]-benzamide

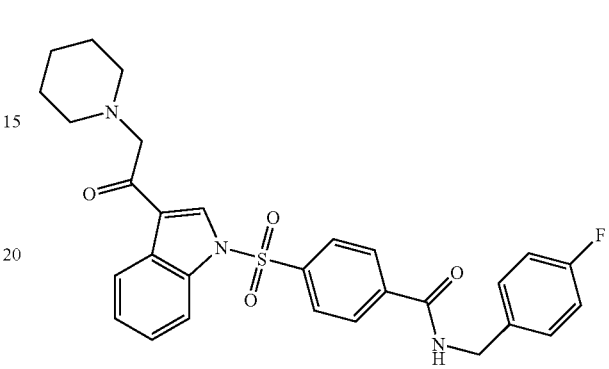

Slowly add 1-(1H-Indol-3-yl)-2-piperidin-1-yl-ethanone (199 mg, 0.821 mmol, 1.0 eq) as a 2 ml DMF solution to a flask under N$_2$ containing sodium hydride (36 mg, 60 wt % on oil, 0.903 mmol, 1.1 eq) in 2 ml DMF solution. Stir solution for 5 minutes. Slowly add 4-(4-Fluoro-benzylcarbamoyl)-benzenesulfonyl chloride (296 mg, 0.903 mmol, 1.1 eq) as a 3 ml DMF solution. Stir reaction for 18 hours at room temperature. Strip reaction of solvent and purify on silica gel chromatography to give N-(4-Fluoro-benzyl)-4-[3-(2-piperidin-1-yl-acetyl)-indole-1-sulfonyl]-benzamide (249 mg, 57% yield). Mass Spectrum (m/e): 534 (MH+).

Example 229

4-(3-Cyclohexyl-indole-1-sulfonyl)-N-(4-fluoro-benzyl)-benzamide

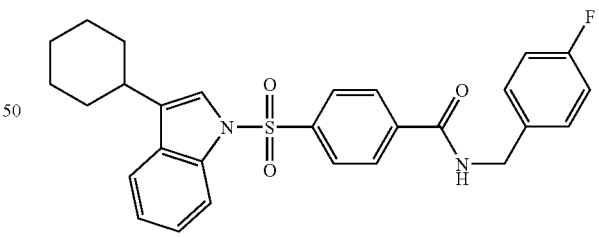

Add 4-Fluoro-benzylamine (72 mg, 0.574 mmol, 1.1 eq) followed by triethylamine (343 mg, 0.472 ml, 3.39 mmol, 6.5 eq) to a CH$_2$CL$_2$ solution (8 ml) of 4-(3-Cyclohexyl-indole-1-sulfonyl)-benzoic acid (200 mg, 0.521 mmol, 1 eq). Add benzotriazol-1-yloxytris(dimethylamino)phosphonium hexafluorophosphate (231 mg, 0.521 mmol, 1 eq) and stir at room temperature for 16 hours. Remove solvent on rotovap and purify crude by silica gel chromatography to give 4-(3-Cyclohexyl-indole-1-sulfonyl)-N-(4-fluoro-benzyl)-benzamide (232 mg, 99% yield). Mass Spectrum (m/e): 490.92 (MH+).

Example 230

4-(3-Cyclohexyl-indole-1-sulfonyl)-N-(tetrahydro-pyran-4-ylmethyl)-benzamide

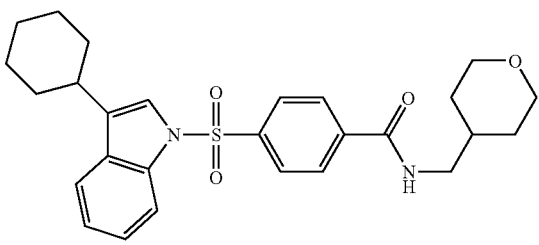

Using a similar procedure as for 4-(3-Cyclohexyl-indole-1-sulfonyl)-N-(4-fluoro-benzyl)-benzamide to give 275 mg (100% yield) of the title compound Mass Spectrum (m/e): 480.97 (MH+).

Example 231

4-(3-Cyclohexyl-indole-1-sulfonyl)-N-(tetrahydro-pyran-4-yl)-benzamide

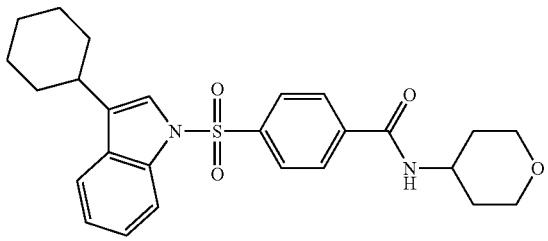

Using a similar procedure as for 4-(3-Cyclohexyl-indole-1-sulfonyl)-N-(4-fluoro-benzyl)-benzamide to give 198 mg (71% yield) of the title compound: Mass Spectrum (m/e): 466.94 (MH+).

Example 232

4-[3-(3,3-Difluoro-cyclopentyl)-indole-1-sulfonyl]-N-(tetrahydro-pyran-4-yl)-benzamide

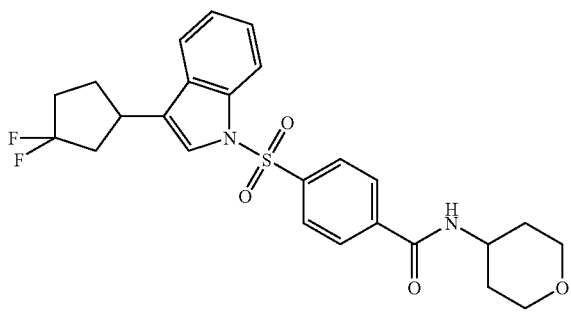

Add a 2 ml CH$_2$Cl$_2$ solution of Tetrahydro-pyran-4-ylamine (62 mg, 0.0610 mmol, 1.1 eq) and triethylamine (365 mg, 3.6 mmol, 6.5 eq) to a 2 ml CH$_2$Cl$_2$ solution of 4-[3-(3,3-Difluoro-cyclopentyl)-indole-1-sulfonyl]-benzoic acid. Add benzotriazol-1-yloxytris(dimethylamino)phosphonium hexafluorophosphate (245 mg, 0.555 mmol, 1.0 eq) and stir reaction at room temperature for 18 hours. Remove volatiles on rotovap and purify by silica gel chromatography, followed by SCX ionic chromatography to give 4-[3-(3,3-Difluoro-cyclopentyl)-indole-1-sulfonyl]-N-(tetrahydro-pyran-4-yl)-benzamide (240 mg, 89% yield). Mass Spectrum (m/e): 489.71 (MH+).

Example 233

4-[3-(3,3-Difluoro-cyclopentyl)-indole-1-sulfonyl]-N-(tetrahydro-pyran-4-ylmethyl)-benzamide

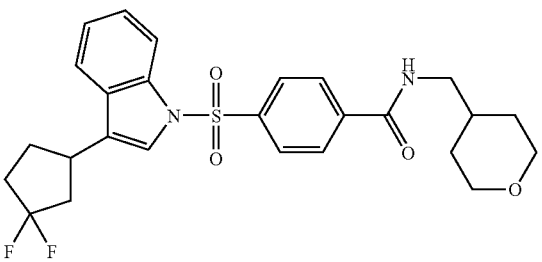

Using a similar procedure as for 4-[3-(3,3-Difluoro-cyclopentyl)-indole-1-sulfonyl]-N-(tetrahydro-pyran-4-yl)-benzamide using C-(Tetrahydro-pyran-4-yl)-methylamine in place of Tetrahydro-pyran-4-ylamine to give 4-[3-(3,3-Difluoro-cyclopentyl)-indole-1-sulfonyl]-N-(tetrahydro-pyran-4-ylmethyl)-benzamide (280 mg, 100% yield). Mass Spectrum (m/e): 503.98 (MH+).

Example 234

N-(4-Fluoro-3-methoxy-benzyl)-4-(3-piperidin-1-yl-indole-1-sulfonyl)-benzamide Hydrochloride

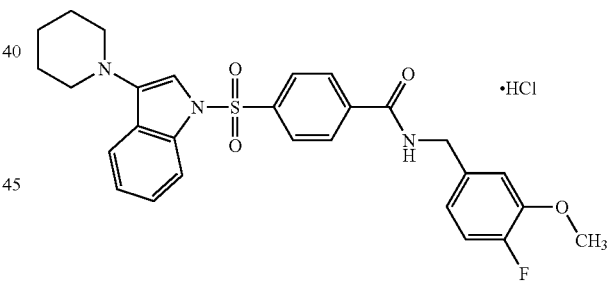

Add KOtBu (211 mg, 1.88 mmol) to a solution of 3-piperidin-1-yl-1H-indole (299 mg, 1.49 mmol) in dioxane (15 mL). Stir the yellow solution at RT for 30 min then treat with 4-(4-fluoro-3-methoxy-benzylcarbamoyl)-benzenesulfonyl chloride (560 mg, 1.56 mmol). Stir the solution at RT for an additional 2 h, then dilute with EtOAc (50 mL) and wash with satd NaHCO$_3$ (25 mL). Remove the organic phase and extract the aqueous layer with additional EtOAc (50 mL). Combine the organic solutions, dry over Na$_2$SO$_4$, filter, and concentrate. Purify the crude material by flash chromatography (3×) using an oversized silica column and a gradient of 100% hexanes to 40% EtOAc/hexanes. Concentrate fractions containing pure material then redissolve in CH$_2$Cl$_2$ (10 mL) and treat with 4M HCl/dioxane (0.5 mL). Filter the off-white precipitate and dry under vacuum to give the title compound as a white powder (417 mg). MS (ES$^+$) 522.1 (M+1)$^+$, (ES$^-$) 520.2 (M−1)$^-$. $^1$H NMR (400 MHz, DMSO-d$_6$): δ 9.19 (m, 1H), 8.03 (d, 2H, J=8.4), 7.97 (m, 1H), 7.95 (d, 2H, J=8.4), 7.61 (d, 1H, J=7.5), 7.37 (t, 1H, J=7.6), 7.26 (t, 2H, J=7.5), 7.06-7.13 (m, 2H), 6.81 (m, 1H), 6.12 (br s, 1H), 4.39 (d, 2H, J=5.7), 3.78 (s, 3H), 3.06 (s, 4H), 1.72 (s, 4H), 1.56 (s, 2H).

Example 240

4-{[4-(3-Phenyl-indole-1-sulfonyl)-benzoylamino]-methyl}-N,N-dimethyl-benzamide

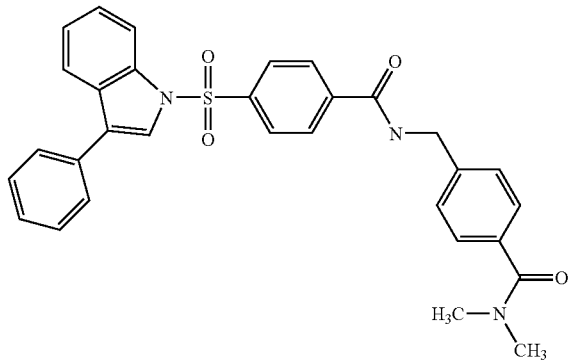

Combine 4-{[4-(3-Phenyl-indole-1-sulfonyl)-benzoylamino]-methyl}-benzoic acid (0.489 mmole) with dimethylamine (0.587 mmole), and EDC (0.733 mmole) in 5 ml of dichloromethane and stir for 15 hrs. Dilute reaction and wash with 1 N HCl. Dry organic layer over MgSO₄ and concentrate. Purify the residue via column chromatography with a mixture of ethyl acetate and dichloromethane to isolate 0.040 g (15.2%) of the title compound: MSES+ 537.95; MSES− 536.08.

General Example 241

EDC Coupling

Combine the amine (0.809 mmole), benzoic acid, for example, 4-(3-Cyclopentyl-indazole-1-sulfonyl)-benzoic acid (0.539 mmole), EDC (0.809 mmole) in 5 ml of dichloromethane and stir for 15 hrs. Dilute the reaction mixture and wash with 1 N HCl. Dry organic material over MgSO₄ and concentrate. Purify the residue via column chromatography using a mixture of ethyl acetate and dichloromethane.

Prepare the following compounds by essentially following General Example 241.

| Ex No | Structure and name of final cmpd | Name of the amine starting material | MS ES+/ MS ES− | % yield |
|---|---|---|---|---|
| 242 | 4-(3-Cyclopentyl-indazole-1-sulfonyl)-N-(4-fluoro-benzyl)-benzamide | 4-Fluoro-benzylamine | 478.30/ 476.50 | 60 |
| 243 | 4-(3-Cyclopentyl-indazole-1-sulfonyl)-N-(tetrahydro-pyran-4-yl)-benzamide | Tetrahydro-pyran-4-ylamine | 454.00/ 452.20 | 46 |
| 244 | 4-(3-Cyclopentyl-indazole-1-sulfonyl)-N-(tetrahydro-pyran-4-ylmethyl)-benzamide | C-(Tetrahydro-pyran-4-yl)-methylamine | 468.00/ 466.20 | 38 |

| Ex No | Structure and name of final cmpd | Name of the amine starting material | MS ES+/ MS ES− | % yield |
|---|---|---|---|---|
| 245 | 4-(3-Cyclopentyl-indazole-1-sulfonyl)-N-isobutyl-benzamide | Isobutylamine | 426.00/ 424.20 | 47 |
| 246 | 4-(3-Cyclopentyl-indazole-1-sulfonyl)-N-cyclopropylmethyl-benzamide | C-Cyclopropyl-methylamine | 424.00/ 422.20 | 47 |
| 247 | 4-{[4-(3-Phenyl-indole-1-sulfonyl)-benzoylamino]-methyl}-N,N,-dimethyl-benzamide | Dimethylamine | 537.95/ 536.08 | 15.2 |

General Example 248

Bop Couplings

Combine the amine (0.525 mmole), BOP (0.421 mmole), Triethylamine (1.05 mmole), and the appropriate benzoic acid (0.350 mmole) and stir in 5 ml of dichloromethane for 4 hrs. Concentrate the reaction and purify vial column chromatography using a mixture of ethyl acetate and dichloromethane.

Prepare the following compounds by essentially following General Example 248.

| Ex No | Structure and name of final cmpd | Name of the amine starting material | MS ES+/ MS ES− | % yield |
|---|---|---|---|---|
| 249 | 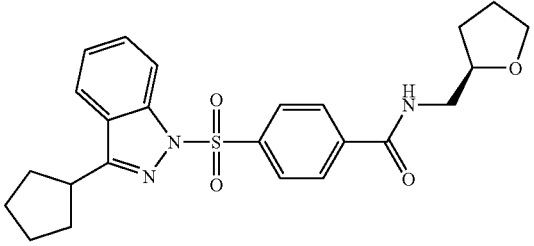<br>(R)-4-(3-Cyclopentyl-indazole-1-sulfonyl)-N-(tetrahydro-furan-2-ylmethyl)-benzamide | (R)-C-(Tetrahydro-furan-2-yl)-methylamine | 454.00/ 452.20 | 80 |
| 250 | 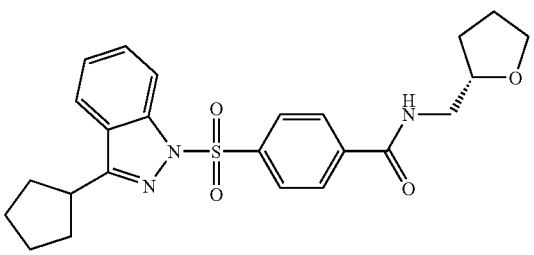<br>(s)-4-(3-Cyclopentyl-indazole-1-sulfonyl)-N-(tetrahydro-furan-2-ylmethyl)-benzamide | (S)-C-(Tetrahydro-furan-2-yl)-methylamine | 454.00/ 452.10 | 75 |
| 252 | 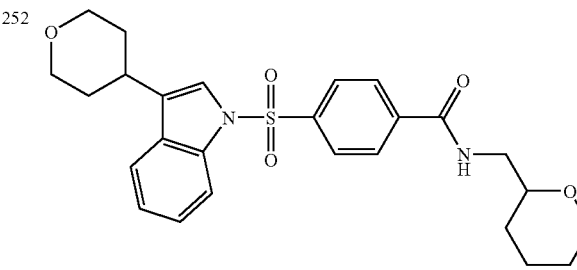<br>4-[3-(tetrahydro-pyran-4-yl)-indole-1-sulfonyl]-N-(tetrahydro-pyran-2-ylmethyl)-benzamide | C-(Tetrahydro-pyran-2-yl)-methylamine | 483.00/ 481.10 | 10.9 |

General Example 253

EDC-DMAP

Combine the amine (0.300 mmole), the appropriate benzoic acid (0.300 mmole), DMAP (0.300 mmole), and EDC (0.450 mmole) in 5 ml of dichloromethane and stir until reaction is complete. Dilute the reaction and wash with 1 N HCl. Dry organic layer over $MgSO_4$ and concentrate. Purify the residue via column chromatography with a mixture of ethyl acetate and dichloromethane.

Prepare the following compounds by essentially following General Example 253.

| Ex No | Structure and name of final cmpd | Name of the amine starting material | MS ES+/ MS ES− | % yield |
|---|---|---|---|---|
| 254 | (R)-N-[1-(4-Fluoro-phenyl)-pyrrolidin-3-yl]-4-(3-phenyl-indole-1-sulfonyl)-benzamide | (R)-1-(4-Fluoro-phenyl)-pyrrolidin-3-ylamine | 539.97/ 538.23 | 52 |
| 254a | (S)-N-[1-(4-Fluoro-phenyl)-pyrrolidin-3-yl]-4-(3-phenyl-indole-1-sulfonyl)-benzamide | (S)-1-(4-Fluoro-phenyl)-pyrrolidin-3-ylamine | | 52 |
| 255 | [3-(4-Fluoro-phenylamino)-azetidin-1-yl]-[4-(3-phenyl-indole-1-sulfonyl)-phenyl]-methanone | Azetidin-3-yl-(4-fluoro-phenyl)-amine | 525.96 | 12.4 |
| 256 | 4-(3-Phenyl-indole-1-sulfonyl)-N-(tetrahydro-pyran-2-ylmethyl)-benzamide | C-(Tetrahydro-pyran-2-yl)-methylamine | 474.99 | 19 |

-continued

| Ex No | Structure and name of final cmpd | Name of the amine starting material | MS ES+/ MS ES− | % yield |
|---|---|---|---|---|
| 257 | 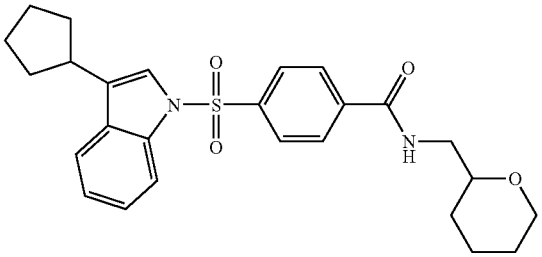<br>4-(3-Cyclopentyl-indole-1-sulfonyl)-N-(tetrahydro-pyran-2-ylmethyl)-benzamide | C-(Tetrahydro-pyran-2-yl)-methylamine | 466.94/ 465.10 | 81.2 |

Example 257a 4-(3-Cyclopentyl-indole-1-sulfonyl)-N-(tetrahydro-pyran-2-ylmethyl)-benzamide Isomer 1

Example 257b 4-(3-Cyclopentyl-indole-1-sulfonyl)-N-(tetrahydro-pyran-2-ylmethyl)-benzamide Isomer 2

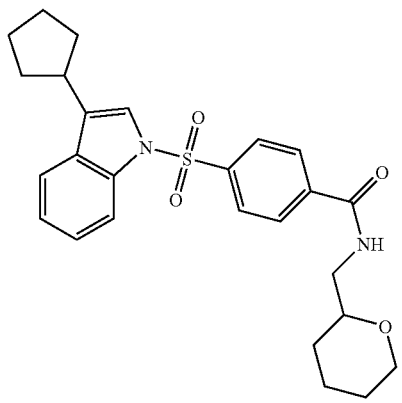

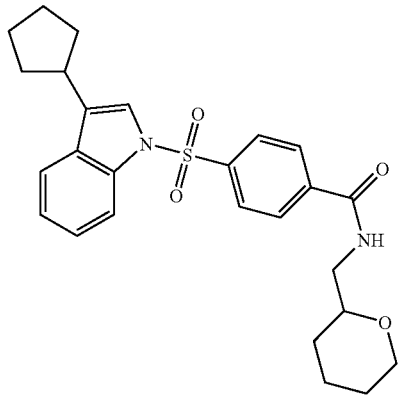

Separate the racemate of 4-(3-Cyclopentyl-indole-1-sulfonyl)-N-(tetrahydro-pyran-2-ylmethyl)-benzamide on a 8×29 cm Chiralpak AD column with 100% 3 A (anhydrous ethanol) using as the mobile phase, 300 ml/min flow rate, and UV detection at 220 nm. Analyze on a 4.6×150 mm Chiralpak AD-H column with 100% 3 A as the mobile phase, 0.6 ml/min flow rate, and UV detection at 219 nm to give the isolation of isomer 1 which elutes at 12.6 min MS ES+ 466.98 MS ES− 465.07.

Separate the racemate of 4-(3-Cyclopentyl-indole-1-sulfonyl)-N-(tetrahydro-pyran-2-ylmethyl)-benzamide on a 8×29 cm Chiralpak AD column with 100% 3 A (anhydrous ethanol) as the mobile phase, 300 ml/min flow rate, and UV detection at 220 nm. Analyze on a 4.6×150 mm Chiralpak AD-H column with 100% 3 A as the mobile phase, 0.6 ml/min flow rate, and UV detection at 219 nm to give the isolation of isomer 2 MS ES+ 467.0 MS ES− 465.1 elutes at 18.8 min.

Example 259

4-(3-Cyclopentyl-indole-1-sulfonyl)-N-pyridin-3yl-methyl-benzamide

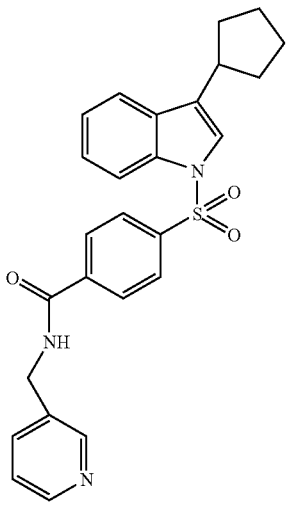

Add to a stirring mixture of 4-(3-cyclopentyl-indole-1-sulfonyl)-benzoic acid (0.188 g, 0.50 m mol), PyBOP (0.0.288 g, 0.50 m mol), and 3-amino-pyridine (0.063 g, 0.59 mmol) in dry $CH_2Cl_2$ (10 mL) under $N_2$, Hunigs base (0.148 g, 0.200 mL, 1.11 m mol.). Stir the reaction is overnight at ambient temperature and evaporate on the rotary evaporator. Chromatograph the residue on the ISCO system using a 40 g column and a hexane-EtOAc gradient system (0-100%) to give 0.048 g of the title compound as white foam: Mass spectrum (m/e) (M+H) 460.1697; found 460.1681.

Example 260

4-(3-Cyclopentylindole-1-sulfonyl)-N—[(R)-1-(tetrahydrofuran-2-yl)methyl]benzamide

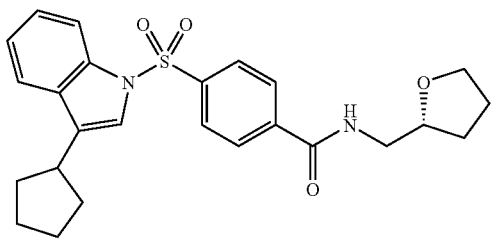

Add 1-(3-dimethylaminopropyl)-3-ethylcarbodiimide hydrochloride (EDC; 98 mg, 0.51 mmol, 1.5 equiv) and 4-(dimethylamino)pyridine (DMAP; 70 mg, 0.57 mmol, 1.7 equiv) to a solution of 4-(3-cyclopentylindole-1-sulfonyl) benzoic acid (126 mg, 0.341 mmol, 1 equiv) and (R)-(−)-tetrahydrofurfurylamine (Aldrich; 140 μL, 140 mg, 1.4 mmol, 4.0 equiv) in anhydr $CH_2Cl_2$ (1 mL). After stirring 16 h, transfer the reaction solution to a column of silica gel (80 mm×20 mm dia.) and elute (10-45% EtOAc/hex) to give 24 mg (16%) of 4-(3-cyclopentylindole-1-sulfonyl)-N—[(R)-1-(tetrahydrofuran-2-yl)methyl]benzamide as a white foam. MS (m/e): 452.96 (M+1); 451.14 (M−1).

Example 261

4-(3-Phenylindole-1-sulfonyl)-N-(tetrahydrofuran-3-ylmethyl)benzamide

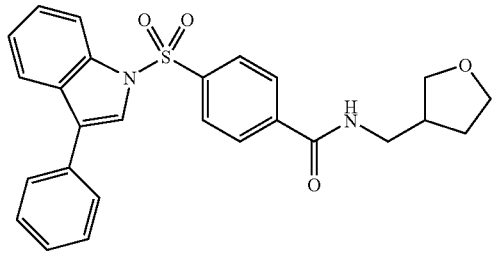

Add benzotriazol-1-yloxytris(dimethylamino)phosphonium hexafluorophosphate (2.2 g, 5.0 mmol, 1.5 equiv) to a solution of 4-(3-phenyl-indole-1-sulfonyl)-benzoic acid (1.23 g, 3.26 mmol, 1 equiv), (tetrahydro-furan-3-yl)-methylamine (331 mg, 3.27 mmol, 1.0 equiv), and triethylamine (2.3 mL, 1.7 g, 17 mmol, 5.0 equiv) in anhydr $CH_2Cl_2$ (12 mL). After 1 h, rotary evaporate the reaction solution and transfer the resultant residue to a column of silica gel (235 mm×35 mm dia.) and elute (50-90% EtOAc/hex). This yields 486 mg (32.4%) of rac-4-(3-phenyl-indole-1-sulfonyl)-N-(tetrahydro-furan-3-ylmethyl)-benzamide as a yellow foam. MS (m/e): 460.96 (M+1); 459.04 (M−1).

Example 261a

4-(3-Phenylindole-1-sulfonyl)-N-(tetrahydrofuran-3-ylmethyl)benzamide isomer 1

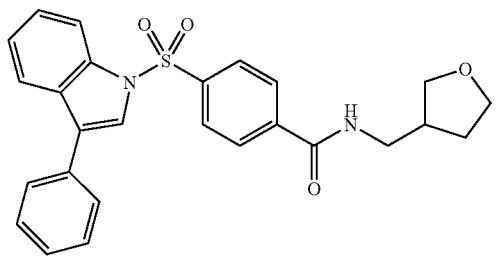

Separate the enantiomers of rac-4-(3-phenyl-indole-1-sulfonyl)-N-(tetrahydro-furan-3-ylmethyl)-benzamide (470 mg) using a Chiralpak AD-H column (4.6×150 mm) with 95% EtOH/MeOH at 0.6 mL/min. Collect peak at 9.8 min followed by rotary evaporation to give 154 mg (32.8%) of 4-(3-phenylindole-1-sulfonyl)-N-(tetrahydrofuran-3-ylmethyl)benzamide isomer 1. MS (m/e): 460.96 (M+1); 459.03 (M−1).

Example 261b

4-(3-Phenylindole-1-sulfonyl)-N-(tetrahydrofuran-3-ylmethyl)benzamide isomer 2

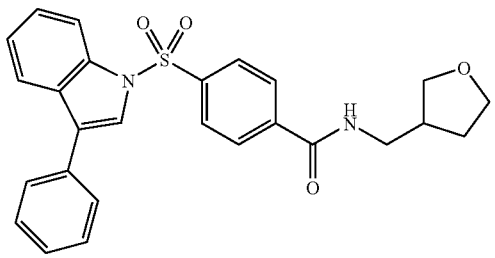

Separate the enantiomers of rac-4-(3-phenyl-indole-1-sulfonyl)-N-(tetrahydro-furan-3-ylmethyl)-benzamide (470 mg) using a Chiralpak AD-H column (4.6×150 mm) with 95% EtOH/MeOH at 0.6 mL/min. Collect peak at 12.6 min followed by rotary evaporation to give 156 mg (33.2%) of 4-(3-phenylindole-1-sulfonyl)-N-(tetrahydrofuran-3-ylmethyl)benzamide isomer 2. MS (m/e): 460.96 (M+1); 459.04 (M−1).

Example 265

(3-Hydroxymethyl-azetidin-1-yl)-[4-(3-phenyl-indole-1-sulfonyl)-phenyl]methanone

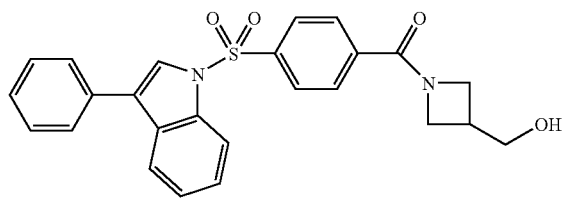

Dissolve azetidine-1,3-dicarboxylic acid mono-tert-butyl ester (300 mg, 1.50 mmol.) in THF (5.0 mL) and treat with lithium aluminum hydride (1.0M in ether, 3.0 mL, 3.0 mmol). Stir for 18 hours, quench with 3.0 mL of 1.0M NaOH, dilute with ether, filter through celite and evaporate. Treat the resulting 3-hydroxymethyl-azetidine-1-carboxylic acid tert-butyl ester with 10 mL of trifluoroacetic acid for 20 minutes an evaporate. Use this material without further purification. Combine 4-(3-Phenyl-indole-1-sulfonyl)-benzoic acid (100 mg, 0.26 mmol) and the resulting azetidin-3-yl-methanol in dichloromethane (1.0 mL) and triethylamine (0.100 mL, 0.717 mmol, excess) and add benzotriazol-1-yloxytris(dimethylamino)phosphonium hexfluorophosphate (BOP Reagent) (150 mg, 0.33 mmol, excess) at room temperature. Stir for 30 minutes, evaporate and load entire reaction directly onto pre-packed silica gel column and purify by flash column chromatography (EtOAc/Hexanes) to give 41 mg of (3-Hydroxymethyl-azetidin-1-yl)-[4-(3-phenyl-indole-1-sulfonyl)-phenyl]-methanone as a white solid (35%). LRMS: MH+ 447.2.

Example 266

4-(3-Cyclopentyl-indole-1-sulfonyl)-N-(tetrahydro-pyran-4-ylmethyl)-benzamide

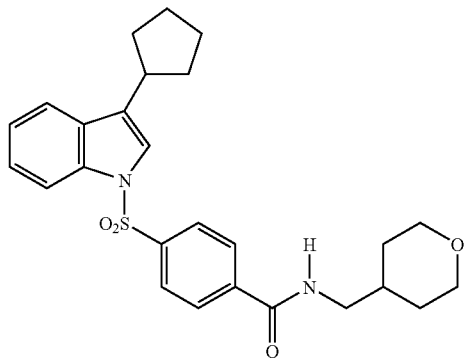

In a 12 L RBF, charge 4-(3-Cyclopentyl-indole-1-sulfonyl)-benzoic acid (400 g, 1.084 mol) and THF (3.6 L) and cool the solution to 5° C., and add 4-methylmorpholine (121 g, 1.192 mol). Add CDMT (209 g, 1.192 mol) over a 5 minute period and stir for 1 hour at 5° C. Add a solution of 4-aminomethyltetrahydropyran (150 g, 1.300 mol) and THF (500 ml) drop-wise over a 1 hour period at 5° C. Remove the cooling bath and stir the reaction for 75 minutes. Cool the solution to 10° C. and quench with 1N HCl (4 L). Add ethyl acetate (2.5 L), DI water (2 L) and back extract the aqueous layer with ethyl acetate (2 L). Wash the organic layers with saturated sodium bicarbonate (3 L), brine (3 L), dry over sodium sulfate, filter and concentrate under vacuum to give 575 g of an oil/foam. Purify the crude material by silica plug filtration and slurry in methanol (2 L) for 2 hours. Cool the slurry to 5° C., stir for 2 hours, filter, rinse with methanol (0.5 L) and dry at 45° C. in a vacuum oven to provide 485 g of a white solid (yield=96%) of the title compound demonstrating two melts one at 136-138° C. and a second at 153-155° C.

Example 267

4-(3-Cyclopentyl-indole-1-sulfonyl)-N-(4-fluorobenzyl)-benzamide

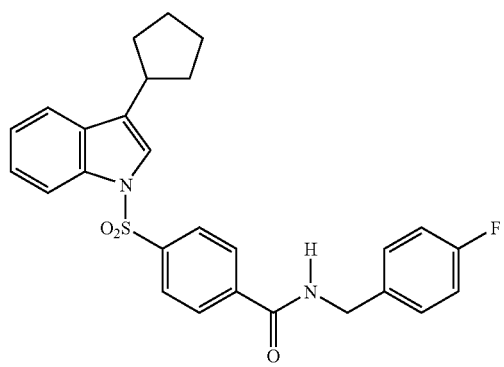

In a 22 L RBF, charge 4-(3-Cyclopentyl-indole-1-sulfonyl)-benzoic acid (435 g, 1.177 mol) and THF (4 L). and cool the solution to 5° C., and add 4-methylmorpholine (131 g, 1.295 mol). Add CDMT (227 g, 1.295 mol) in one portion and stir for 1 hour at 5° C. Add a solution of 4-fluorobenzylamine (162 g, 1.295 mol) and THF (500 ml) drop-wise over a 1 hour period at 5° C. Remove the cooling bath and stir the reaction was for 120 minutes. Cool the solution to 10° C. and quench with 1N HCl (4 L). Add ethyl acetate (3 L), DI water (3 L) and back extract the aqueous layer with ethyl acetate (3 L). Wash the organic layers with saturated sodium bicarbonate (3 L), brine (3 L), dry over sodium sulfate, filter and concentrate under vacuum to give 575 g of an amber oil/foam. Purify the crude material by silica plug filtration and slurry in methanol (2 L) for 17 hours. Cool the slurry to 5° C., stir for 1 hour, filter, rinse with methanol (0.75 L) and dry at 45° C. in a vacuum oven to provide 450 g of a white solid (yield=80.2%) of the title compound having a single melt ranging from 118° C. to 121° C.; 1H NMR (DMSO) d 9.2 (t, 1H), 8.1 (m, 2H), 7.95 (m, 2H), 7.9 (d, 1H), 7.6 (d, 1H), 7.5 (s, 1H), 7.3 (m, 4H), 7.1 (t, 2H), 4.4 (dd, 2H), 3.1 (t, 1H), 2.05 (m, 2H), 1.7 (m, 6H). % Theory C, 68.0484; H, 5.2876; N, 5.8781. % Found C, 68.01; H, 5.13; N, 5.88.

Example 268

4-(3-Cyclopentyl-indole-1-sulfonyl)-N-pyridin-3yl-methyl-benzamide

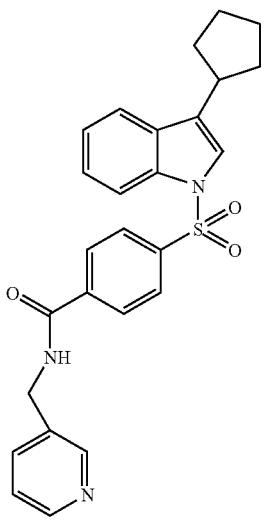

Stir a mixture of 4-(3-Cyclopentyl-indole-1-sulfonyl)-benzoic acid (0.188 g, 0.50 mmol), PyBOP (0.0.288 g, 0.50 m mol), and 3-amino-pyridine (0.063 g, 0.59 mmol) in dry CH$_2$Cl$_2$ (10 mL) under N$_2$ add Hunigs base (0.148 g, 0.200 mL, 1.11 mmol). Stir overnight the reaction at ambient temperature and evaporate on the rotary evaporator. Chromatograph the residue on the ISCO using a 40 g column and a hexane-EtOAc gradient system (0-100%) to give 0.048 g of the title compound as a white foam. Mass spectrum (m/e) (M+H) 460.1697; found 460.1681.

Example 269

4-(3-Cyclopentyl-indole-1-sulfonyl)-n-isobutyl-benzamide

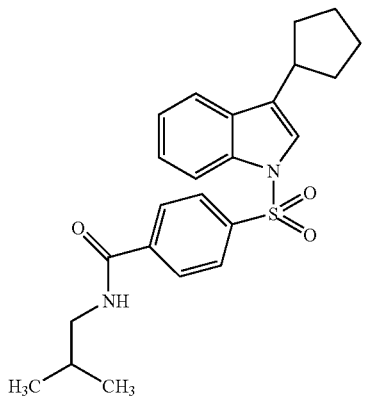

Stir to a mixture of 4-(3-Cyclopentyl-indole-1-sulfonyl)-benzoic acid (0.163 g, 0.44 m mol), PyBOP (0.226 g, 0.51 mmol), and isobutylamine (0.038 g, 0.52 mmol) in dry CH$_2$Cl$_2$ (10 mL) under N$_2$ add Hunigs base (0.148 g, 0.11 mmol). Stir the reaction overnight at ambient temperature and evaporate on the rotary evaporator. Chromatograph the residue on the ISCO using a 40 g column and a hexane-EtOAc gradient system (0-100%) to give 0.10 g of the title compound as a white foam. Mass spectrum (m/e) (M+H) 425.1899; found 460.1925.

Example 270

N-(4-Fluoro-benzyl)-4-(3-isopropyl-indole-1-sulfonyl)-benzamide

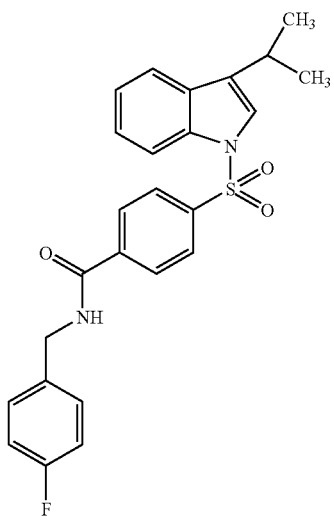

Stir a mixture of 3-isopropyl indole in dry DMF (20 ml) under N$_2$ add potassium t-butoxide 1.0 M (1.2 ml, 1.2 mmol) dropwise. Stir the resulting solution for 30 minutes at ambient temperature. Add 4-(4-Fluoro-benzylcarbamoyl)-benzene-sulfonyl chloride (0.360 g, 1.1 mmol) portionwise and stir the resulting mixture overnight. Pour the reaction mixture into a mixture of EtOAc—H₂O. Separate the EtOAc layer, extract with H₂O wash with brine and dry (MgSO₄). Filter and evaporate to give the crude product. Chromatograph on the ISCO eluting with hexane-EtOAc to give a white solid (0.150 g). Mass spectrum (m/e) (M+H) 451.1492; found 451.1488.

Example 271

N-Cyclopropylmethyl-4-(3-isopropyl-indole-1-sulfonyl)-benzamide

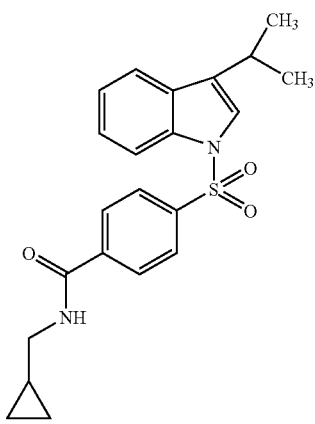

Stir mixture of 4-(3-isopropyl-indole-1-sulfonyl)-benzoic acid (0.181 g, 0.53 mmol), PyBOP (0.243 g, 0.55 mmol) and cyclopropylmethyl amine (0.064 g, 0.59 mmol) in CH₂Cl₂ (20 mL) add Hunigs base (0.28 mL, 1.62 mmol) under N₂. Stir the resulting mixture overnight at ambient temperature. Extract the reaction with H₂O, wash with brine dry (MgSO₄), filter, evaporate and chromatograph using hexane-EtOAc (0-100%) to give 0.183 g of the title compound as an off white solid: Mass spectrum (m/e) (M+H) 397.1593; found 397.1586.

Example 272

4-(3-Cyclopentyl-2,3-dihydro-indole-1-sulfonyl)-N-(4-fluoro-benzyl)-benzamide

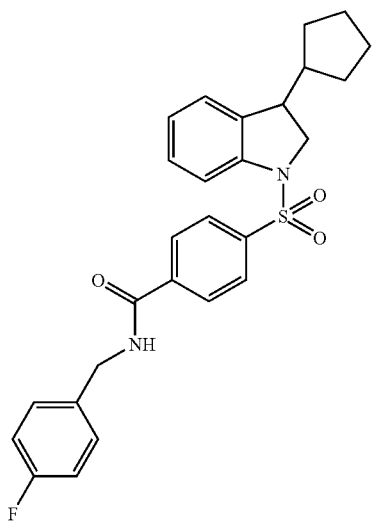

Add 4-(3-cyclopentyl-indole-1-sulfonyl)-N-(4-fluoro-benzyl)-benzamide (0.152 g, 0.319 mmol) portionwise to a stirring mixture of NaCNBH₃ (0.096 g, 1.52 mmol) in TFA at 0 to 5° C. under N₂. Stir the mixture for 15 minutes at 0-5° C., allow to warm to ambient temperature and add an additional 0.096 g NaCNBH₃. Stir the resulting yellow solution for 2 h at ambient temperature, dilute with H₂O (13.0 mL) and stir overnight. Pour the reaction mixture is into EtOAc (100 mL). Separate the EtOAc, extract with H₂O, 5% NaHCO₃ and wash with brine. Separate the EtOAc, dry (MgSO₄), filter and evaporate giving a glass. Chromatograph on the chromatotron eluting with EtOAc-hexane 3:7 to give 0.060 g of the title compound: Mass spectrum (m/e) (M+H) 479.1805; found 479.1788.

Example 273

N-(4-Fluoro-benzyl)-4-(3-methyl-2,3-dihydro-indole-1-sulfonyl)-benzamide

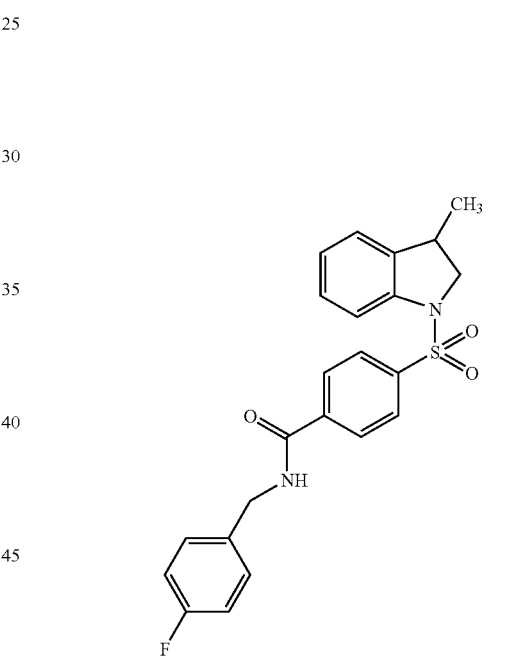

Add N-(4-Fluoro-benzyl)-4-(3-methyl-indole-1-sulfonyl)-benzamide (0.106 g, 0.25 mmol) portionwise to a stirring mixture of NaCNBH₃ (0.074 g, 1.2 mmol, in TFA (5.0 mL) at 0 to 5° C. under N₂. Stir the mixture for 15 minutes at 0-5° C., allow to warm to ambient temperature and stir for 1 h. add NaCNBH₃ (0.074 g, 1.2 mmol) and stir the reaction is for 2 h dilute with H₂O (13.0 mL) and work up as described in the above example. Chromatograph and elute with EtOAc-hexane (0-50%) to give 0.075 g of the title compound: Mass spectrum (m/e) (M+H) 425.1335; found 425.1341.

Example 274

N-(4-Fluoro-benzyl)-4-(3-phenyl-2,3-dihydro-indole-1-sulfonyl)-benzamide

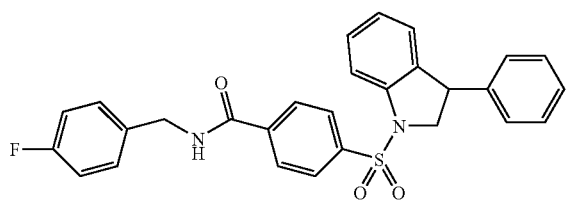

Stir 3-phenyl-2,3-dihydro-1H indole (0.233 g, 1.19 mmol), 4-(4-fluoro-benzylcarbamoyl)-benzenesulfonyl chloride (1 equiv.), Et$_3$N (0.50 mL, 0.36 g, 3.57 mmol), DMA (0.015 g, 0.123 mmol) in CH$_2$Cl$_2$ (45 mL) overnight under N$_2$. Dilute the CH$_2$Cl$_2$ to 150 mL and pour into a saturated solution of NaHCO$_3$ (50 mL) and stir for 15 minutes. Separate the organic layer and wash with H$_2$O (100 mL), extract with 1N HCl (2×75 mL), wash with brine, separate and dry (MgSO$_4$). Filter and evaporate followed by chromatography on the ISCO using a 40 g silica gel column and elute with EtOAc-hexane 90-100%) to give 0.33 g of the racemic compound.

Example 274a

N-(4-Fluoro-benzyl)-4-(3-phenyl-2,3-dihydro-indole-1-sulfonyl)-benzamide Isomer 1

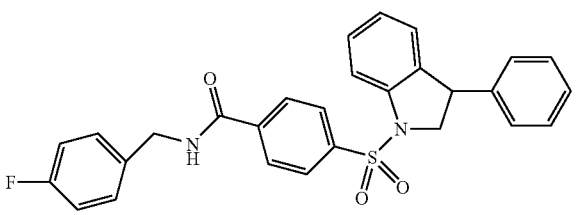

Separate N-(4-Fluoro-benzyl)-4-(3-phenyl-2,3-dihydro-indole-1-sulfonyl)-benzamide via chromatograph separation on chiracel OD (column 90.46×25 cm) (EtOAc-hexane 90-100%) 1.0 mL/min to give (isomer 1) (0.60 g) retention time 5.45 nm in

Example 274b

N-(4-Fluoro-benzyl)-4-(3-phenyl-2,3-dihydro-indole-1-sulfonyl)-benzamide Isomer 2

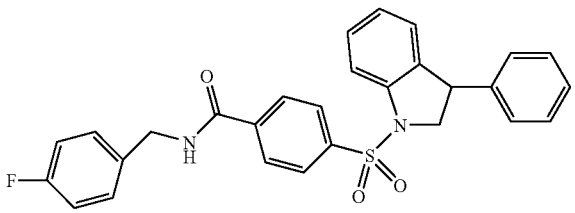

Continue to separate Example 274a via chromatograph separation on chiracel OD (column 90.46×25 cm) (EtOAc-hexane 90-100%) 1.0 mL/min to give (isomer 2) (0.61 g) retention time 7.21 min.

Example 275

4-[3-(3-Cyano-phenyl)-indole-1-sulfonyl]-N-(4-fluoro-benzyl)-benzamide

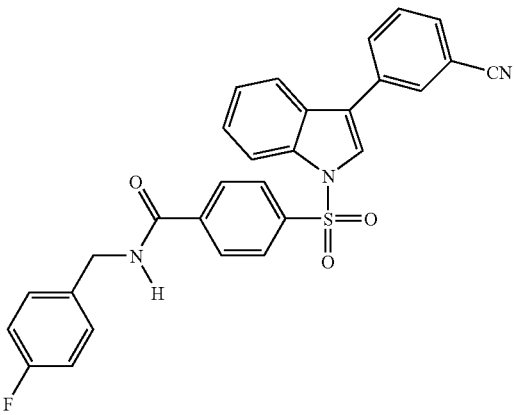

Stir N-(4-Fluoro-benzyl)-4-{3-(4,4,5,5-tetramethyl-[1,3,2]dioxaboralan-2yl)-indole-1-sulfonyl}-benzamide (0.267 g, 0.50 mmol), 3-bromobenzonitrile (0.160 g, 0.55 mmol), PdCl$_2$(dppf).CH$_2$Cl$_2$ (0.032 g, 0.039 mmol) and 2M Na$_2$CO$_3$ (0.50 mL, 1.0 mmol) and heat in dioxane (20 mL) at 81° C. under N$_2$ for 6 h. Concentrate the reaction and chromatograph the residue on the ISCO using a 12 g silica gel column and eluting with hexane-EtOAc (0-100%) to give the title compound as a light tan foam 0.100 g Mass spectrum (m/e) (4+H) 510.1288; found 510.1283.

Example 276

N-(4-Fluoro-benzyl)-4-(3-thiazol-2-yl-indole-1-sulfonyl)-benzamide

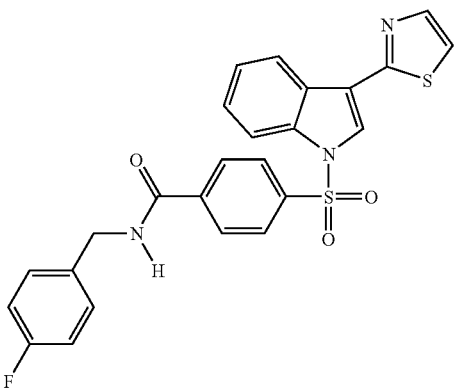

Stir N-(4-Fluoro-benzyl)-4-{3-(4,4,5,5-tetramethyl-[1,3,2]dioxaboralan-2yl)-indole-1-sulfonyl}-benzamide (0.267 g, 0.50 mmol), 2-bromothiazole (0.090 g, 0.55 mmol), PdCl$_2$(dppf).CH$_2$Cl$_2$ (0.032 g, 0.039 mmol) and 2M Na$_2$CO$_3$ (0.25 mL, 0.50 mmol) and heat in dioxane (20 mL) at 99° C. under $N_2$ for 14 h. Concentrate the reaction mixture to dryness and chromatograph the residue on the ISCO, using a 12 g silica gel column and eluting with hexane-EtOAc (5-100%) to give the title compound as a white solid. Mass spectrum (m/e) (M+H) 492.0852; found 492.0848.

Example 277

4-(3-Cyclopentyl-indole-1-sulfonyl)-N-(5-fluoro-pyridin-2-yl-methyl)-benzamide

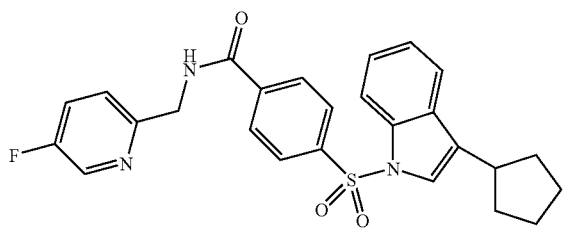

Stir mixture of 4-(3-Cyclopentyl-indole-1-sulfonyl)-benzoic acid (0.767 g, 0.21 m mol), C-(5-fluoro-pyridin-2yl)-methylamine (0.041 g, 0.25 mmol), and EDC (0.063 g, 0.33 mmol) in dry $CH_2Cl_2$ (15 mL) under $N_2$ and add DMAP (0.061 g, 0.50 mmol.). Stir the resulting mixture at ambient temperature for 72 h. Dilute the reaction mixture to 50 mL with $CH_2Cl_2$, wash with $H_2O$, 1N NaOH, and brine sequentially. Dry the organic layer ($MgSO_4$), filter and evaporate to give 0.189 g of crude product. Chromatograph on the ISCO using a 12 g column and eluting with Hexane-EtOAc (0-100%) to gives the title compound 0.60 g as a foam:

Calcd. for: $C_{26}H_{24}FN_3O_3$; C, 65.39; H, 5.066; N, 8.79. Found: C, 65.50; H, 5.26; N, 8.61.

Example

CB1 and CB2 GTPγ$^{35}$S Binding Assays

CB1 and CB2 GTPγ$^{35}$S binding assays were run essentially as described in DeLapp et al. in pH 7.4 buffer containing 20 mM HEPES, 100 mM NaCl and 5 mM $MgCl_2$ (NaCl was omitted from rat brain membrane assay) in a final volume of 200 µl in 96-well Costar plates at 25° C. 100 µl of membrane preparation (25 µg protein per well for CB1 or CB2 Sf9 cell membranes, 15-18 µg per well for rat cerebellar membranes) containing the appropriate concentration of GDP (1 µM GDP for CB1 Sf9 cell membranes, 0.05 µM for CB2 Sf9 cell membranes, 25 µM GDP for rat cerebellar membrane assays) was added to each well followed by the addition of 50 µl of buffer±test compounds or controls and then the plates were incubated for 30 minutes. Next 50 µl of GTPγ$^{35}$S was added to a final concentration of 400 pM in each well and the plates were incubated for another 30 minutes. After that, 20 µl of 0.27% Nonidet P-40 was added with a 30 minute incubation before the addition of 20 µl/well of a 1/400 to 1/100 final dilution anti-Gαl(1-3) antibody (rabbit antibody to BSA-conjugated peptide KNNLKECGLY) with a 60 minute incubation. 50 µl of SPA beads (PVT; anti-rabbit antibody) resuspended in 20 mL assay buffer were then added to each well. After 180 min, plates are centrifuged at 900 g for 10 min and G-protein bound radioactivity was measured using a Wallac plate counter.

DeLapp N W. McKinzie J H. Sawyer B D. Vandergriff A. Falcone J. McClure D. Felder C C. Determination of [$^{35}$S] guanosine-5'-O-(3-thio)triphosphate binding mediated by cholinergic muscarinic receptors in membranes from Chinese hamster ovary cells and rat striatum using an anti-G protein scintillation proximity assay. [Journal Article] *Journal of Pharmacology & Experimental Therapeutics*. 289(2):946-55, 1999 May.

In this test, the IC 50 of the compounds of formula (I) is less than or equal to 5 µM.

The utilities of the present compounds in treating or preventing diseases or disorders may be demonstrated in animal disease models that have been reported in the literature. The following are examples of such animal disease models: a) suppression of food intake and resultant weight loss in rats (Life Sciences 1998, 63, 113-117); b) reduction of sweet food intake in marmosets (Behavioural Pharm. 1998, 9, 179-191); c) reduction of sucrose and ethanol intake in mice (Psychopharm. 1997, 132, 104-106); d) increased motor activity and place conditioning in rats (Psychopharm. 1998, 135, 324-332; Psychopharmacol 2000, 151: 25-30); e) spontaneous locomotor activity in mice (J. Pharm. Exp. Ther. 1996, 277, 586-594); and f) reduction in opiate self-administration in mice (Sci. 1999, 283, 401-404).

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1.0, 2.5, 5.0, 10.0, 15.0, 20.0, 25.0, 30.0, 40.0, 50.0 or 1000.0 milligrams of the active ingredient for the symptomatic adjustment of the dosage to the patient to be treated.

For the treatment of diseases of the eye, ophthalmic preparations for ocular administration comprising 0.001-1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient, preferably present in pharmaceutically effective amounts, and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, suppositories and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids. The compound may be present in crystalline form or may be incorporated into the pharmaceutical composition as an amorphous solid. Alternatively, the compound may be rendered partially or totally amorphous by the manufacturing process.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like. Topical preparations containing the active drug component can be admixed with a variety of carrier materials well known in the art such as, e.g., alcohols, aloe vera gel, allantoin, glycerine, vitamin A and E oils, mineral oil, PPG2 myristyl propionate, and the like. To be administered in the form of a transdermal delivery system, the dosage administration will, of course, be continuous rather than intermittent throughout the dosage regimen.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include polyvinylpyrrolidone, pyran copolymer, polyhydroxypropylmethacrylamide phenol, polyhydroxyethylasparamidepheon, or polyethyleneoxide-polylysine substituted with palmitoyl residues. Furthermore, the compounds of the present invention may be coupled to a class of biodegradable polymers useful in achieving controlled release of a drug, for example, polylactic acid, poly-epsilon caprolactone, polyhydroxybutyric acid, polyorthoesters, polyacetals, polydihydropyrans, polycyanoacrylates and cross-linked or amphipathic block copolymers of hydrogels.

Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

In practical use, the compounds of Formula I can be combined as the active ingredient in intimate admixture with or solubilization in a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, simple oils, fractionated or chemically-modified glycerides, polyoxyethylene-polyoxypropylene co-polymers, alcohols, surface active agents, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. The carrier may possess special properties for controlling or modifying the release and subsequent absorption profile of the drug substance, said properties including but not limited to self-emulsification, or controlled disintegration, dissolution or solubilization in vivo. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Hard or soft gelatin capsules may be prepared by filling either with dry powder or granule formulations or by filling with a liquid formulation compatible with the capsule shell. Desirably, each tablet contains from 0.01 to 500 mg, particularly 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the patient to be treated. And each cachet or capsule contains from about 0.01 to 500 mg, particularly 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the patient to be treated.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration and/or the characteristics of the dosage form (i.e., modified release), the dose may be administered less frequently, e.g., weekly, twice weekly, monthly, etc. The unit dosage may be correspondingly larger for the less frequent administration.

When administered via transdermal routes or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |

Water for injection to a total volume of 1 mL

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule (Dry Fill) | mg/capsule |
|---|---|
| Compound of Formula I | 25 |
| Lactose Powder | 573.5 |
| Magnesium Stearate | 1.5 |
| | 600 |

| Capsule (Liquid Fill) | mg/capsule |
|---|---|
| Compound of Formula I | 25 |
| Peanut oil | 575 |
| | 600 |

| Capsule (Semi-solid Fill, self-emulsifying) | mg/capsule |
|---|---|
| Compound of Formula I | 25 |
| Gelucire 44/14 | 575 |
| | 600 |

| Capsule (Liquid Fill, Self-Emulsifying) | mg/capsule |
|---|---|
| Compound of Formula 1 | 25 |
| Sesame Oil | 125 |
| Cremophor RH40 | 300 |
| Peceol | 150 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

The above dosage form examples are representative. The amount of the compound present in compositions is such that a suitable dosage will be obtained. Preferred compositions and preparations according to the present invention may be determined by a person skilled in the art.

We claim:

1. A method of ameliorating weight gain comprising administering to a mammal in need thereof an effective amount of a compound selected from the group consisting of:
- N-(4-Fluoro-benzyl)-4-(3-phenyl-indole-1-sulfonyl)-benzamide,
- N-(5-Fluoro-pyridin-3-ylmethyl)-4-(3-phenyl-indole-1-sulfonyl)-benzamide,
- 4-(3-Cyclopentyl-indole-1-sulfonyl)-N-(4-fluoro-benzyl)-benzamide,
- N-(4-Fluoro-benzyl)-4-[3-(tetrahydro-pyran-4-yl)-indole-1-sulfonyl]-benzamide,
- N-Cyclopropylmethyl-4-(3-phenyl-indole-1-sulfonyl)-benzamide,
- 4-(3-Cyclopentyl-indole-1-sulfonyl)-N-(tetrahydro-pyran-4-yl)-benzamide, and
- 4-(3-Cyclopentyl-indole-1-sulfonyl)-N-(tetrahydro-pyran-4-ylmethyl)-benzamide.

2. A method for treating obesity comprising administering to a mammal in need thereof an effective amount of a compound selected from the group consisting of:
- N-(4-Fluoro-benzyl)-4-(3-phenyl-indole-1-sulfonyl)-benzamide,
- N-(5-Fluoro-pyridin-3-ylmethyl)-4-(3-phenyl-indole-1-sulfonyl)-benzamide,
- 4-(3-Cyclopentyl-indole-1-sulfonyl)-N-(4-fluoro-benzyl)-benzamide,
- N-(4-Fluoro-benzyl)-4-[3-(tetrahydro-pyran-4-yl)-indole-1-sulfonyl]-benzamide,
- N-Cyclopropylmethyl-4-(3-phenyl-indole-1-sulfonyl)-benzamide,
- 4-(3-Cyclopentyl-indole-1-sulfonyl)-N-(tetrahydro-pyran-4-yl)-benzamide, and
- 4-(3-Cyclopentyl-indole-1-sulfonyl)-N-(tetrahydro-pyran-4-ylmethyl)-benzamide.

* * * * *